(12) United States Patent
Johnson et al.

(10) Patent No.: US 12,042,513 B2
(45) Date of Patent: Jul. 23, 2024

(54) PROTEOLYSIS TARGETING CHIMERIC MOLECULES (PROTACS) WITH FUNCTIONAL HANDLES AND USES THEREOF

(71) Applicants: Massachusetts Institute of Technology, Cambridge, MA (US); Dana-Farber Cancer Institute, Inc., Boston, MA (US)

(72) Inventors: Jeremiah A. Johnson, Boston, MA (US); Hung Vanthanh Nguyen, Braintree, MA (US); Yivan Jiang, Revere, MA (US); Alexandre Detappe, Strasbourg (FR); Michael Agius, Boston, MA (US); Irene Ghobrial, Boston, MA (US); XueZhou Wang, Cambridge, MA (US)

(73) Assignees: Massachusetts Institute of Technology, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 160 days.

(21) Appl. No.: 17/093,832

(22) Filed: Nov. 10, 2020

(65) Prior Publication Data
US 2021/0220391 A1 Jul. 22, 2021

Related U.S. Application Data

(60) Provisional application No. 62/959,539, filed on Jan. 10, 2020.

(51) Int. Cl.
*A61K 31/795* (2006.01)
*A61K 47/55* (2017.01)
(Continued)

(52) U.S. Cl.
CPC ............ *A61K 31/795* (2013.01); *A61K 47/55* (2017.08); *A61K 47/60* (2017.08); *C07D 495/14* (2013.01); *C08G 61/08* (2013.01); *C08G 65/00* (2013.01)

(58) Field of Classification Search
CPC .................................................. A61K 31/795
See application file for complete search history.

(56) References Cited

U.S. PATENT DOCUMENTS

| 3,256,308 A | 6/1966 | Pawloski et al. |
| 3,337,598 A | 8/1967 | Pawloski et al. |

(Continued)

FOREIGN PATENT DOCUMENTS

| CN | 101412792 A | 4/2009 |
| CN | 103819486 A | 5/2014 |

(Continued)

OTHER PUBLICATIONS

Blencowe, J. Am. Chem. Soc. 2013, 135, 5717-5725.*
Wurz, J. Med. Chem. 2018, 61, 453-461.*
Nguyen, ACS Macro Lett. 2018, 7, 472-476.*
Tinworth, Med. Chem. Commun., 2016, 7, 2206.*
Collins, Biochemical Journal (2017) 474 1127-1147.*
Venkatesh, J. Pharm. Sci. 89, 145-154 (2000).*

(Continued)

*Primary Examiner* — Nizal S Chandrakumar
(74) *Attorney, Agent, or Firm* — Wolf, Greenfield & Sacks, P.C.

(57) ABSTRACT

Disclosed multifunctional compounds, conjugates, macromolecules, and polymers that target dysregulated proteins for degradation. Also disclosed are methods of preparation, compositions, kits, and methods of use relating to the degraders.

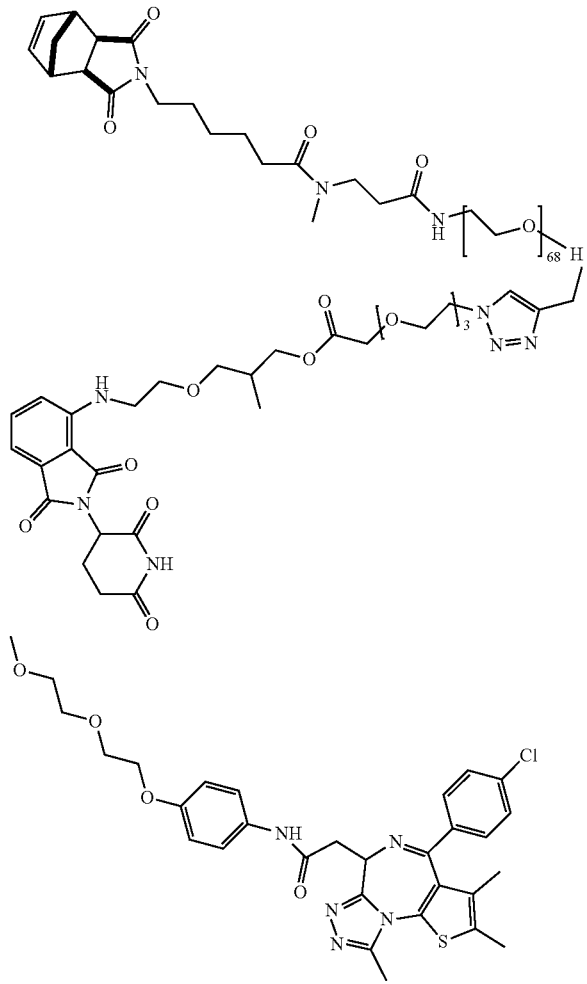

24 Claims, 11 Drawing Sheets

(51) Int. Cl.
*A61K 47/60* (2017.01)
*C07D 495/14* (2006.01)
*C08G 61/08* (2006.01)
*C08G 65/00* (2006.01)

(56) References Cited

U.S. PATENT DOCUMENTS

| | | | |
|---|---|---|---|
| 4,359,425 | A | 11/1982 | Totani et al. |
| 4,510,136 | A | 4/1985 | Moberg et al. |
| 5,811,515 | A | 9/1998 | Grubbs et al. |
| 7,183,059 | B2 | 2/2007 | Verdine et al. |
| 8,067,505 | B2 | 11/2011 | Harris et al. |
| 8,968,920 | B2 | 3/2015 | Lee et al. |
| 9,381,253 | B2 | 7/2016 | Johnson et al. |
| 9,447,129 | B2 | 9/2016 | Johnson et al. |
| 9,822,216 | B2 | 11/2017 | Mahanthappa et al. |
| 10,023,536 | B2 | 7/2018 | Johnson et al. |
| 10,105,449 | B2 | 10/2018 | Johnson et al. |
| 10,153,513 | B2 | 12/2018 | Grubbs et al. |
| 10,159,749 | B2 | 12/2018 | Johnson et al. |
| 10,683,387 | B2 | 6/2020 | Johnson et al. |
| 10,716,858 | B2 | 7/2020 | Johnson et al. |
| 10,792,373 | B2 | 10/2020 | Johnson et al. |
| 10,793,683 | B2 | 10/2020 | Johnson et al. |
| 10,799,594 | B2 | 10/2020 | Johnson et al. |
| 10,961,338 | B2 | 3/2021 | Johnson et al. |
| 10,973,847 | B2 | 4/2021 | Johnson et al. |
| 10,988,491 | B2 | 4/2021 | Johnson et al. |
| 11,752,221 | B2 | 9/2023 | Johnson et al. |
| 2002/0183473 | A1 | 12/2002 | Matyjaszewski et al. |
| 2002/0198328 | A1 | 12/2002 | L'Alloret |
| 2003/0004364 | A1 | 1/2003 | Yaghi et al. |
| 2003/0065023 | A1 | 4/2003 | Swindell et al. |
| 2005/0109976 | A1 | 5/2005 | Fuchs et al. |
| 2008/0063937 | A1 | 3/2008 | Lee et al. |
| 2011/0166128 | A1 | 7/2011 | Remenar et al. |
| 2011/0243848 | A1 | 10/2011 | Appel et al. |
| 2011/0300219 | A1 | 12/2011 | Lippard et al. |
| 2013/0296491 | A1 | 11/2013 | Xia et al. |
| 2013/0324666 | A1 | 12/2013 | Yan et al. |
| 2014/0024137 | A1 | 1/2014 | Arya et al. |
| 2014/0308234 | A1 | 4/2014 | Johnson et al. |
| 2014/0142249 | A1 | 5/2014 | Cho et al. |
| 2015/0225438 | A1 | 8/2015 | Johnson et al. |
| 2015/0291562 | A1* | 10/2015 | Crew ............... A61K 47/555 435/375 |
| 2016/0024246 | A1 | 1/2016 | Mahanthappa et al. |
| 2016/0289392 | A1 | 10/2016 | Grubbs et al. |
| 2016/0296631 | A1 | 10/2016 | Johnson et al. |
| 2016/0361702 | A1 | 12/2016 | Cohen et al. |
| 2017/0000909 | A1 | 1/2017 | Gianneschi et al. |
| 2017/0073311 | A1 | 3/2017 | Johnson et al. |
| 2017/0348431 | A1 | 12/2017 | Johnson et al. |
| 2018/0030213 | A1 | 2/2018 | Johnson et al. |
| 2018/0036415 | A9 | 2/2018 | Johnson et al. |
| 2018/0094099 | A1 | 4/2018 | Johnson et al. |
| 2018/0312634 | A1 | 11/2018 | Chung et al. |
| 2019/0030067 | A1 | 1/2019 | Johnson et al. |
| 2019/0038751 | A1 | 2/2019 | Johnson et al. |
| 2019/0038782 | A1 | 2/2019 | Johnson et al. |
| 2019/0054187 | A1 | 2/2019 | Johnson et al. |
| 2019/0192672 | A1 | 6/2019 | Johnson et al. |
| 2020/0055879 | A1 | 2/2020 | Johnson et al. |
| 2020/0123297 | A1 | 4/2020 | Johnson et al. |
| 2020/0239626 | A1 | 7/2020 | Miyake et al. |
| 2020/0261596 | A1 | 8/2020 | Ali et al. |
| 2020/0362095 | A1 | 11/2020 | Johnson et al. |
| 2020/0369685 | A1 | 11/2020 | Johnson et al. |
| 2021/0023224 | A1 | 1/2021 | Johnson et al. |
| 2021/0113701 | A1 | 4/2021 | Johnson et al. |
| 2021/0147598 | A1 | 5/2021 | Johnson et al. |
| 2021/0284664 | A1 | 9/2021 | Johnson et al. |
| 2021/0317143 | A9 | 10/2021 | Johnson et al. |
| 2021/0386861 | A1 | 12/2021 | Johnson et al. |
| 2022/0370628 | A9 | 11/2022 | Johnson et al. |
| 2023/0068959 | A1 | 3/2023 | Johnson et al. |
| 2023/0192610 | A1 | 6/2023 | Johnson et al. |

FOREIGN PATENT DOCUMENTS

| | | | | |
|---|---|---|---|---|
| CN | 108727581 | A | 11/2018 | |
| DE | 2263509 | A1 | 7/1974 | |
| EP | 3315126 | A1 | 5/2018 | |
| EP | 3584245 | A1 | 12/2019 | |
| JP | H05-112739 | A | 5/1993 | |
| WO | WO 2001/032652 | A2 | 5/2001 | |
| WO | WO 2010/047765 | A1 | 4/2010 | |
| WO | WO 2011/084846 | A1 | 7/2011 | |
| WO | WO 20120113694 | A | 10/2012 | |
| WO | WO 2013/010676 | A2 | 1/2013 | |
| WO | WO 2013/169739 | A1 | 11/2013 | |
| WO | WO 2014/004884 | A1 | 1/2014 | |
| WO | WO 2014/169073 | A1 | 10/2014 | |
| WO | WO 2016/023036 | A1 | 2/2016 | |
| WO | WO 2016/172386 | A1 | 10/2016 | |
| WO | WO 2017/180834 | A1 | 10/2017 | |
| WO | WO 2018/106738 | A1 | 6/2018 | |
| WO | WO 2018/149359 | A1 | 8/2018 | |
| WO | WO 2019/006426 | A2 | 1/2019 | |
| WO | WO 2019006426 | * | 3/2019 | ............. A61P 35/00 |
| WO | WO 2019/200367 | A1 | 10/2019 | |
| WO | WO 2019201123. | * | 10/2019 | ............. A61P 35/00 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Extended European Search Report for EP 14782253.0, mailed Nov. 11, 2016.
International Preliminary Report on Patentability for PCT/US2014/033554, mailed Oct. 22, 2015.
International Search Report and Written Opinion for PCT/US2014/033554, mailed Aug. 29, 2014.
International Search Report for PCT/US2017/036447, mailed Sep. 7, 2017.
International Preliminary Report on Patentability for Application No. PCT/US2017/036447 mailed Dec. 20, 2018.
International Search Report and Written Opinion for PCT/US2017/064784, mailed Mar. 1, 2018.
International Preliminary Report on Patentability for PCT/US2017/064784, mailed Jun. 20, 2019.
International Search Report and Written Opinion for PCT/US2018/040488, mailed Oct. 15, 2018.
International Preliminary Report on Patentability for PCT/US2018/040488, mailed Jan. 9, 2020.
International Search Report and Written Opinion for PCT/US2018/040494, mailed Oct. 10, 2018.
International Preliminary Report on Patentability for PCT/US2018/040494, mailed Jan. 9, 2020.
Invitation to Pay Additional Fees for PCT/US2018/040496, mailed on Nov. 21, 2018.
International Search Report and Written Opinion for Application No. PCT/US2018/040496 mailed Jan. 14, 2019.
International Preliminary Report on Patentability for PCT/US2018/040496, mailed Jan. 9, 2020.
International Search Report and Written Opinion for PCT/US2019/027414, mailed on Sep. 12, 2019.
International Preliminary Report on Patentability for PCT/US2019/027414, mailed on Oct. 22, 2020.
International Search Report and Written Opinion for PCT/US2020/023836, mailed on Jul. 7, 2020.
International Preliminary Report on Patentability for PCT/US2020/023836, mailed on Dec. 2, 2021.
International Preliminary Report on Patentability for PCT/US2020/059827 mailed Jul. 21, 2022.
International Search Report and Written Opinion for PCT/US2020/059827 mailed Mar. 15, 2021.

(56) References Cited

OTHER PUBLICATIONS

Invitation to Pay Additional Fees for PCT/US2020/059827 mailed Feb. 4, 2021.
International Search Report and Written Opinion for PCT/US2020/055862 mailed May 6, 2021.
Invitation to Pay Additional Fees for PCT/US2020/055862, mailed on Feb. 12, 2021.
International Preliminary Report on Patentability for PCT/US2020/055862 mailed Apr. 28, 2022.
Aguirre-Chagala et al., Phenylboronic Acid-Installed Polycarbonates for the ph-Dependent Release of Diol-Containing Molecules. ACS Macro Letters. Nov. 20, 2014;3(12):1249-1253.
Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem. Soc. Rev., 1998;27:19-29.
Aime et al., Pushing the sensitivity envelope of lanthanide-based magnetic resonance imaging (MRI) contrast agents for molecular imaging applications. Acc Chem Res. Jul. 2, 20091;42(7):822-31. doi: 10.1021/ar800192p.
Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.
Altintas et al., Constructing star polymersvia modular ligation strategies. Polym. Chem., 2012;3:34-45. DOI: 10.1039/C1PY00249J.
Alvaradejo et al., Polyoxazoline-Based Bottlebrush and Brush-Arm Star Polymers via ROMP: Syntheses and Applications as Organic Radical Contrast Agents. ACS Macro Lett. Apr. 16, 2019;8(4):473-478. doi: 10.1021/acsmacrolett.9b00016. Epub Apr. 4, 2019. PMID: 31289694.
Amouri et al., Host-guest interactions: design strategy and structure of an unusual cobalt cage that encapsulates a tetrafluoroborate anion. Angew Chem Int Ed Engl. Jul. 18, 2005;44(29):4543-6.
Anderson, Late Transition Metal Complexes of Pentafluorophenylphosphino-Pincer Ligands. Doctoral Thesis. Victoria University of Wellington. 2012:ii, iii, 32.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001; 34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.
Arvizo et al., Modulating pharmacokinetics, tumor uptake and biodistribution by engineered nanoparticles. PLOS One. 2011;6(9):e24374. doi: 10.1371/journal.pone.0024374. Epub Sep. 13, 2011.
Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.
Bapat et al., Dynamic-covalent nanostructures prepared by Diels-Alder reactions of styrene-maleic anhydride-derived copolymers obtained by one-step cascade block copolymerization. Polym. Chem., 2012;3:3112-3120. Doi: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Barbour et al., An intermolecular (H2O)10 cluster in a solid-state supramolecular complex. Nature. 1998;393(6686): 671-673.
Barner-Kowollik et al., Synthesis of core-shell poly(divinylbenzene) microspheres via reversible addition fragmentation chain transfer graft polymerization of styrene. J. Polym. Sci. A Polym. Chem., 2006;42:5067-5076. doi: 10.1002/pola.20328.
Barnes et al., Using an RNAi Signature Assay To Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. Epub Sep. 14, 2016.
Barrett et al., pH-Based Regulation of Hydrogel Mechanical Properties Through Mussel-Inspired Chemistry and Processing. Advanced Functional Materials. Mar. 6, 2013;23(9):1111-1119.
Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Bates et al., Polarity-switching top coats enable orientation of sub-10-nm block copolymer domains. Science. Nov. 9, 2012;338(6108):775-9. doi: 10.1126/science.1226046.
Beck et al., Multistimuli, multiresponsive metallo-supramolecular polymers. J Am Chem Soc. Nov. 19, 2003;125(46):13922-3.
Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.
Blencowe et al., Core cross-linked star polymers via controlled radical polymerisation. Polymer Jan. 2009;50(1):5-32.
Blinco et al., Profluorescent Nitroxides as Sensitive Probes of Oxidative Change and Free Radical Reactions. Australian Journal of Chemistry 2010;64(4):373-389. https://doi.org/10.1071/CH10442.
Boase et al., Molecular imaging with polymers. Polym. Chem., 2012,3, 1384-1389. Doi: 10.1039/C2PY20132A.
Bobko et al., Reversible reduction of nitroxides to hydroxylamines: roles for ascorbate and glutathione. Free Radic Biol Med. Feb. 1, 2007;42(3):404-12. Epub Nov. 10, 2006.
Bohbot-Raviv et al., Discovering new ordered phases of block copolymers. Phys Rev Lett. Oct. 16, 2000;85(16):3428.
Bolton et al., Synthesis and Melt Self-Assembly of PS-PMMA-PLA Triblock Bottlebrush Copolymers. Macromolecules, 2014;47(9):2864-74. DOI: 10.1021/ma500625k.
Brasch et al., Work in progress: nuclear magnetic resonance study of a paramagnetic nitroxide contrast agent for enhancement of renal structures in experimental animals. Radiology. Jun. 1983; 147(3):773-9.
Brasch, Work in progress: methods of contrast enhancement for NMR imaging and potential applications. A subject review. Radiology. Jun. 1983; 147(3):781-8.
Brummelhuis et al., Stimuli-responsive star polymers through thiol-yne core functionalization/crosslinking of block copolymer micelles. Polym. Chem., 2011;2:1180-1184. DOI: 10.1039/C1PY00002K.
Budil et al., Nonlinear-Least-Squares Analysis of Slow-Motion EPR Spectra in One and Two Dimensions Using a Modified Levenberg-Marquardt Algorithm. Elsevier. Journal of Magnetic Resonance, Series A. Jun. 1996; 120(2):155-189.
Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.
Bunzen et al., Self-assembly of M24L48 polyhedra based on empirical prediction. Angew Chem Int Ed Engl. Mar. 26, 2012;51(13):3161-3. doi: 10.1002/anie.201108731.
Burdynska et al., Synthesis of Star Polymers Using ARGET ATRP. Macromolecules, 2010;43(22):9227-9229. DOI: 10.1021/ma101971z.
Burnworth et al., Decoupling Optical Properties in Metallo-Supramolecular Poly (p-phenylene ethynylene)s. Macromolecules. 2008;41(6):2157-2163.
Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.
Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.

(56) References Cited

OTHER PUBLICATIONS

Burts et al., Using EPR To Compare PEG-branch-nitroxide "Bivalent-Brush Polymers" and Traditional PEG Bottle-Brush Polymers: Branching Makes a Difference. Macromolecules. 2012;45(20):8310-18.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.
Caiolfa et al., Polymer-bound camptothecin: initial biodistribution and antitumour activity studies. J Control Release. Mar. 1, 2000;65(1-2):105-19.
Campos-Fernández et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.
Campos-Fernández et al., Fine-tuning the ring-size of metal-lacyclophanes: a rational approach to molecular pentagons. J Am Chem Soc. Jan. 31, 2001;123(4):773-4.
Caravan et al., Gadolinium(III) Chelates as MRI Contrast Agents: Structure, Dynamics, and Applications. Chem Rev. Sep. 8, 1999;99(9):2293-352.
Castilla et al., Stereochemistry in subcomponent self-assembly. Acc Chem Res. Jul. 15, 2014;47(7):2063-73. doi: 10.1021/ar5000924. Epub May 2, 2014.
Chambron et al., Topologically complex molecules obtained by transition metal templation: it is the presentation that determines the synthesis strategy. New Journal of Chemistry. 2013;37(1):49-57.
Chand et al., Self-assembly of a novel macrotricyclic Pd(II) metal-locage encapsulating a nitrate ion. Chem Commun (Camb). Sep. 7, 2001;(17):1652-3.
Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.
Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.
Chen et al., Synthesis of superporous hydrogels: hydrogels with fast swelling and superabsorbent properties. J Biomed Mater Res. Jan. 1999;44(1):53-62.
Cheng et al., Well-defined diblock macromonomer with a norbornene group at block junction: anionic living linking synthesis and ring-opening metathesis polymerization. Macromol. Mar. 4, 2010;43(7):3153-5.
Cheon et al., Synergistically integrated nanoparticles as multimodal probes for nanobiotechnology. Acc Chem Res. Dec. 2008;41(12):1630-40. doi: 10.1021/ar800045c.
Chiang et al., Vitamin D for the prevention and treatment of pancreatic cancer. World J Gastroenterol. Jul. 21, 2009;15(27):3349-54.
Chifotides et al., Anion-π interactions in supramolecular architectures. Acc Chem Res. Apr. 16, 2013;46(4):894-906. doi: 10.1021/ar300251k. Epub Mar. 11, 2013.
Choi et al., Self-confirming "AND" logic nanoparticles for fault-free MRI. J Am Chem Soc. Aug. 18, 2010;132(32):11015-7. doi: 10.1021/ja104503g.
Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.
Clever et al., Inclusion of anionic guests inside a molecular cage with palladium(II) centers as electrostatic anchors. Angew Chem Int Ed Engl. 2009;48(38):7010-2. doi: 10.1002/anie.200902717.
Conrad et al., Tunable, temperature-responsive polynorbornenes with side chains based on an elastin peptide sequence. Angew Chem Int Ed Engl. 2009;48(44):8328-30. doi: 10.1002/anie.200903888.
Cordier et al., Self-healing and thermoreversible rubber from supramolecular assembly. Nature. Feb. 21, 2008;451(7181):977-80. doi: 10.1038/nature06669.

Corey et al., Diisopropylsilyl ditriflate and di-tert-butysilyl ditriflate: new reagents for the protection of diols. Tetrahedron Letters. 1982;23(47):4871-4874.
Dag et al., Three-arm star ring opening metathesis polymers via alkyne-azide click reaction. J. Polym. Sci. A Polym. Chem., 2009;47:2344-2351. doi: 10.1002/pola.23324.
Dalsin et al., Bottlebrush block polymers: Quantitative theory and experiments. ACS Nano. Nov. 6, 2015;9(12):12233-45.
Davies et al., Environmentally responsive MRI contrast agents. Chem Commun (Camb). Oct. 28, 2013;49(84):9704-21. doi: 10.1039/c3cc44268c.
Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.
Davis et al., Atom transfer radical polymerization of tert-butyl acrylate and preparation of block copolymers. Macromol. May 30, 2000;33(11):4039-47.
Davis et al., Nanoparticle therapeutics: an emerging treatment modality for cancer. Nat Rev Drug Discov. Sep. 2008;7(9):771-82. doi: 10.1038/nrd2614.
Desmarets et al., Design, Self-Assembly, and Molecular Structures of 3D Copper(II) Capsules Templated by BF4-Guest Anions. European Journal of Inorganic Chemistry. Oct. 2009;(29-30):4396-4400. doi: 10.1002/ejic.200900606.
Detappe et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.
Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.
Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.
Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.
Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.
Duncan, The dawning era of polymer therapeutics. Nat Rev Drug Discov. May 2003;2(5):347-60.
Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.
Elliott et al., Metabolism of brain tissue slices and suspensions from various mammals. J Neurophysiol. Nov. 1948;11(6):473-84.
Eryazici et al., Two Large-Pore Metal-Organic Frameworks Derived from a Single Polytopic Strut. Crystal Growth & Design. Mar. 7, 2012;12(3):1075-1080.
Feng et al., A metabonomic analysis of organ specific response to USPIO administration. Biomaterials. Sep. 2011;32(27):6558-69. doi: 10.1016/j.biomaterials.2011.05.035.
Fenlon et al., The Thread & Cut Method: Syntheses of Molecular Knot Precursors. Eur J Org Chem. Jun. 2008;2008(18):3065-3068.
Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.
Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.
Fiers et al., Orthogonal Synthesis of Xeno Nucleic Acids. Chemistry. Dec. 12, 2016;22(50): 17945-17948. doi: 10.1002/chem.201604386. Epub Nov. 3, 2016. PMID: 27753151.
Forgan et al., Chemical topology: complex molecular knots, links, and entanglements. Chem Rev. Sep. 14, 2011;111(9):5434-64. doi: 10.1021/cr200034u. Epub Jun. 21, 2011.

(56) References Cited

OTHER PUBLICATIONS

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.
Fox et al., Soluble polymer carriers for the treatment of cancer: the importance of molecular architecture. Acc Chem Res. Aug. 18, 2009;42(8) 1141-51. doi: 10.1021/ar900035f.
Frechet. Functional polymers and dendrimers: reactivity, molecular architecture, and interfacial energy. Science. Mar. 25, 1994;263(5154):1710-5.
Fullenkamp et al., Mussel-Inspired Histidine-Based Transient Network Metal Coordination Hydrogels. Macromolecules. Jan. 18, 2013;46(3):1167-1174.
Gao et al., Development of star polymers as unimolecular containers for nanomaterials. Macromol Rapid Commun. May 14, 2012;33(9):722-34. doi: 10.1002/marc.201200005. Epub Mar. 14, 2012.
Gao et al., Modular Approaches to Star and Miktoarm Star Polymers by ATRP of Cross-Linkers. Macromol. Symp., 291-292: 12-16. doi:10.1002/masy.201050502.
Gao et al., Synthesis of Acid-Labile PEG and PEG-Doxorubicin-Conjugate Nanoparticles via Brush-First Romp. ACS Macro Lett. Sep. 16, 2014;3(9):854-857. Epub Aug. 13, 2014.
Gao et al., Synthesis of functional polymers with controlled architecture by CRP of monomers in the presence of cross-linkers: From stars to gels. Progress in Polymer Science Apr. 2009;34(4):317-350.
Gao et al., Synthesis of Star Polymers by A New "Core-First" Method: Sequential Polymerization of Cross-Linker and Monomer. Macromolecules, 2008;41(4):1118-1125.
Ge et al., A Pyrene-functionalized Polynorbornene for Ratiometric Fluorescence Sensing of Pyrophosphate. Chem. Asian J. 2016;11:687.
Gestwicki et al., Influencing receptor-ligand binding mechanisms with multivalent ligand architecture. J Am Chem Soc. Dec. 18, 2002;124(50):14922-33.
Gilgorich et al., Palladium-catalyzed reductive coupling of styrenes and organostannanes under aerobic conditions. J Am Chem Soc. Nov. 21, 2007;129(46):14193-5. Epub Oct. 27, 2007.
Glunde et al., Magnetic resonance spectroscopy in metabolic and molecular imaging and diagnosis of cancer. Chem Rev. May 12, 2010;110(5):3043-59. doi: 10.1021/cr9004007.
Godugu et al., Abstract 2139: Effect of telmisartan on triple negative breast cancer (TNBC) and lung cancer tumor progression and intratumoral distribution of nanoparticles. Cancer Res. 2013;73(8).
Goh et al., Highly efficient synthesis of low polydispersity core cross-linked star polymers by Ru-catalyzed living radical polymerization. Macromol Rapid Commun. Mar. 2, 2011;32(5):456- 61. doi: 10.1002/marc.201000641. Epub Jan. 7, 2011.
Grahovac et al., Abstract B41: The angiotensin receptor blocker telmisartan inhibits the growth of pancreatic ductal adenocarcinoma and improves survival. Cancer Res. 2016;76(24).
Grason et al., Geometric theory of diblock copolymer phases. Phys Rev Lett. Jul. 31, 2003;91(5):058304.
Greenwald et al., Effective drug delivery by PEGylated drug conjugates. Adv Drug Deliv Rev. Feb. 10, 2003;55(2):217-50.
Gu et al., Mechanism of the reactions of dimethylsilylene with oxetanes. J. Am. Chem. Soc. 1980, 102, 5, 1641-1644.
Gumbley et al., Photoresponsive Polymers Containing Nitrobenzyl Esters via Ring-Opening Metathesis Polymerization. Macromolecules. 2011;44(20):7956-61.
Gupta et al., Cell protective, ABC triblock polymer-based thermoresponsive hydrogels with ROS-triggered degradation and drug release. J Am Chem Soc. Oct. 22, 2014;136(42):14896-902. doi: 10.1021/ja507626y. Epub Oct. 7, 2014. PMID: 25254509.
Hackelbusch et al., Chain Dynamics in Supramolecular Polymer Networks. Macromolecules. 2013;46(15):6273-6286.
Hackelbusch et al., Multiresponsive Polymer Hydrogels by Orthogonal Supramolecular Chain Cross-Linking. Macromolecules. 2014;47(12):4028-4036.
Haddleton et al., Well-defined oligosaccharide-terminated polymers from living radical polymerization. Biomacromolecules. 2000 Summer;1(2):152-6.
Hafkamp et al., Organogel formation and molecular imprinting by functionalized gluconamides and their metal complexes. Chemical Communications. 1997;6:545-546. doi: 10.1039/A608266A.
Hall et al., Platinum(IV) antitumour compounds: their bioinorganic chemistry. Coord Chem Rev. 2002;232:49-67.
Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.
Han et al., Recent Development of Peptide Coupling Reagents in Organic Synthesis. Tetrahedron, 2004;60:2447-2467.
Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.
Hao et al., Dendrimers as scaffolds for multifunctional reversible addition-fragmentation chain transfer agents: Syntheses and polymerization. J. Polym. Sci. A Polym. Chem., 2004;42:5877-5890. doi: 10.1002/pola.20434.
Harrington et al., Holdfast heroics: comparing the molecular and mechanical properties of Mytilus californianus byssal threads. J Exp Biol. Dec. 2007;210(Pt 24):4307-18.
Harrington et al., Iron-clad fibers: a metal-based biological strategy for hard flexible coatings. Science. Apr. 9, 2010;328(5975):216-20. doi: 10.1126/science.1181044. Epub Mar. 4, 2014.
Harris et al., Giant hollow M(n)L(2n) spherical complexes: structure, functionalisation and applications. Chem Commun (Camb). Aug. 4, 2013;49(60):6703-12. doi: 10.1039/c3cc43191f.
Harrison et al., A multimeric MR-optical contrast agent for multimodal imaging. Chem Commun (Camb). Oct. 9, 2014;50(78):11469-71. doi: 10.1039/c4cc05651e.
Harrison et al., Multimeric Near IR-MR Contrast Agent for Multimodal In Vivo Imaging. J Am Chem Soc. Jul. 22, 2015;137(28):9108-16. doi: 10.1021/jacs.5b04509. Epub Jul. 14, 2015.
Harvey et al., Lanthanide Complexes as Paramagnetic Probes for 19F Magnetic Resonance. Eur. J. Inorg. Chem., 2012: 2015-2022. doi:10.1002/ejic.201100894.
Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.
Hawker et al., Preparation of polymers with controlled molecular architecture. A new convergent approach to dendritic macromolecules. J Am Chem Soc. Oct. 1990; 112(21):7638-47.
Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.
Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.
Helms et al., One-Pot Reaction Cascades Using Star Polymers with Core-Confined Catalysts. Angewandte Chemie, 2005;44:6384-6387. doi: 10.1002/ange.200502095.
Heroguez et al., Novel Styrene-Butadiene Copolymers by Ring-Opening Metathesis Polymerization. Macromol. Oct. 3, 2000;33(20):7241-8.
Hirakawa et al., Removal of Perchlorate Anion from an Aqueous Solution by Encapsulation in an Anion-templated Self-assembled Molecular Capsule. Chemistry Letters. 2009;38(3):290- 291.
Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.
Holliday et al., Strategies for the Construction of Supramolecular Compounds through Coordination Chemistry. Angew Chem Int Ed Engl. Jun. 1, 2001;40(11):2022-2043.
Holten-Andersen et al., Metal-coordination: using one of nature's tricks to control soft material mechanics. J. Mater. Chem. B. 2014;2:2467-2472.

(56) References Cited

OTHER PUBLICATIONS

Holten-Andersen et al., pH-induced metal-ligand cross-links inspired by mussel yield self-healing polymer networks with near-covalent elastic moduli. PNAS. Feb. 15, 2011;108:2651-2655.

Hoogenboom et al., 1-Lactide Polymerization Utilizing a Hydroxy-Functionalized 3,6-Bis(2-pyridyl)pyridazine as Supramolecular (Co)initiator: Construction of Polymeric [2 x 2] Grids. Macromolecules, 2003;36(13):4743-9. DOI: 10.1021/ma034119e.

Hoye et al., Silicon tethered ring-closing metathesis reactions for self- and cross-coupling of alkenols. Tetrahedron Letters. Feb. 19, 1999;40(8):1429-1432.

Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.

Huinink et al., Topotecan versus paclitaxel for the treatment of recurrent epithelial ovarian cancer. J Clin Oncol. Jun. 1997;15(6):2183-93.

Huynh, Novel Polymeric Micelles via RAFT Polymerization for Platinum Drug Delivery. Doctoral Thesis. The University of New South Wales. 2012:i, 57-58.

Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.

Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.

Hyodo et al., Probing the intracellular redox status of tumors with magnetic resonance imaging and redox-sensitive contrast agents. Cancer Res. Oct. 15, 2006;66(20):9921-8.

Iha et al., Applications of Orthogonal "Click" Chemistries in the Synthesis of Functional Soft Materials. Chem. Rev., 2009;109(11):5620-5686. DOI: 10.1021/cr900138t.

Inglis et al., Well-defined star shaped polymer-fullerene hybrids via click chemistry. Soft Matter, 2010;6:82-84. DOI: 10.1039/B920806M.

Jackson et al., pH triggered self-assembly of core cross-linked star polymers possessing thermoresponsive cores. Chem. Commun., 2011;47:6807-6809. DOI: 10.1039/C1CC11785H.

Jakubowski et al., Activators regenerated by electron transfer for atom transfer radical polymerization of styrene. Macromol. Jan. 10, 2006;39(1):39-45.

Jamieson et al., Structure, Recognition, and Processing of Cisplatin-DNA Adducts. Chem Rev. Sep. 8, 1999;99(9):2467-98.

Jeong et al., Highly tunable self-assembled nanostructures from a poly (2-vinylpyridine-b-dimethylsiloxane) block copolymer. Nano Lett. Sep. 27, 2011;11(10):4095-101.

Jesberger et al., Hyperbranched polymers as scaffolds for multifunctional reversible addition-fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.

Jiang et al., Morphology and Phase Diagram of Comb Block Copolymer A m+ 1 (BC) m. J Phys Chem B. May 7, 2009;113(21):7462-7.

Johnson et al., Core-clickable PEG-branch-azide bivalent-bottle-brush polymers by ROMP: grafting-through and clicking-to. J Am Chem Soc. Jan. 26, 2011;133(3):559-66. doi: 10.1021/ja108441d. Epub Dec. 13, 2010.

Johnson et al., Drug-loaded, bivalent-bottle-brush polymers by graft-through ROMP. Macromolecules. Dec. 28, 2010;43(24):10326-10335.

Johnson et al., Efficient Synthesis of Doxorubicin Releasing Brush Polymers by Graft-Through Romp. Polymer Preprints. 2010;51(2):96-97.

Jokerst et al., Molecular imaging with theranostic nanoparticles. Acc Chem Res. Oct. 18, 2011;44(10):1050-60. doi: 10.1021/ar200106e. Epub Sep. 15, 2011.

Jokerst et al., Nanoparticle PEGylation for imaging and therapy. Nanomedicine (Lond). Jun. 2011;6(4):715-28. doi: 10.2217/nnm.11.19.

Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.

Jung et al., Orientation-controlled self-assembled nanolithography using a polystyrene- polydimethylsiloxane block copolymer. Nano Lett. Jul. 11, 2007;7(7):2046-50.

Kale et al., Supramolecular assemblies of amphiphilic homopolymers. Langmuir. May 19, 2009;25(17):9660-70.

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kauffman et al., Fluorescence-Based Assays for Measuring oxorubicin in Biological Systems. React Oxyg Species (Apex). 2016;2(6):432-439. doi: 10.20455/ros.2016.873. PMID: 29707647; PMCID: PMC5921830.

Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.

Kawamoto et al., Loops versus branch functionality in model click hydrogels. Macromol. Dec. 1, 2015;48(24):8980-8.

Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.

Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.

Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.

Kim et al., Anion-directed self-assembly of coordination polymer into tunable secondary structure. J Am Chem Soc. Jun. 9, 2004;126(22):7009-14.

Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi20040219_113203.pdf Retrieved Apr. 24, 2015.

Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20, 2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel.2013.03.016. Epub Mar. 2, 2013

Kolishetti et al., Engineering of self-assembled nanoparticle platform for precisely controlled combination drug therapy. Proc Natl Acad Sci U S A. Oct. 19, 2010;107(42): 17939-44. doi: 10.1073/pnas.1011368107. Epub Oct. 4, 2010.

Kreutzer et al., Water-Soluble, Unimolecular Containers Based on Amphiphilic Multiarm Star Block Copolymers. Macromolecules, 2006;39(13):4507-4516. DOI: 10.1021/ma060548b.

(56) References Cited

OTHER PUBLICATIONS

Kumar et al., in the recognition and antagonism of a HIV TAR RNA-TAT assembly using an aminoglycoside benzimidazole scaffold. Org Biomol Chem. Feb. 14, 2016;14(6):2052-6. doi: 10.1039/c5ob02016f. PMID: 26765486; PMCID: PMC4837457.

Kwon et al., Block copolymer micelles as long-circulating drug vehicles. Adv Drug Delivery Rev. 1995;16:295-309.

Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.

Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.

Lee et al., Mussel-Inspired Adhesives and Coatings. Annu Rev Mater Res. Aug. 1, 2011;41:99-132.

Lee et al., Novel phase morphologies in a microphase-separated dendritic polymer melt. Macromol. Jan. 12, 2009;42(3):849-59.

Lee et al., Single-molecule mechanics of mussel adhesion. Proc Natl Acad Sci U S A. Aug. 29, 2006;103(35):12999-3003. Epub Aug. 18, 2006.

Lee et al., Stimuli-responsive molecular brushes. Progress in Polymer Science (Oxford), 35(1-2), 24-44. DOI: 10.1016/j.progpolymsci.2009.11.002.

Leininger et al., Self-assembly of discrete cyclic nanostructures mediated by transition metals. Chem Rev. Mar. 8, 2000;100(3):853-908.

Li et al., Polycatechol Nanoparticle MRI Contrast Agents. Small, 2016;12(5):668-677. https://doi.org/10.1002/smll.201502754.

Li et al., A magnetic switch for spin-catalyzed interconversion of nuclear spin isomers. J Am Chem Soc. Mar. 31, 2010;132(12):4042-3. doi: 10.1021/ja910282p.

Li et al., Crosslinking-induced morphology change of latex nanoparticles: A study of RAFT-mediated polymerization in aqueous dispersed media using amphiphilic double-brush copolymers as reactive surfactants. J Polym Sci Part A: Polym Chem. Nov. 15, 2014;52(22):3250-9.

Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.

Li et al., Dynamic cylindrical assembly of triblock copolymers by a hierarchical process of covalent and supramolecular interactions. J Am Chem Soc. Jan. 4, 2011;133(5):1228-31.

Li et al., Efficient synthesis of narrowly dispersed amphiphilic double-brush copolymers through the polymerization reaction of macromonomer micelle emulsifiers at the oil-water interface. Polym Chem. 2016;7(27):4476-85.

Li et al., Facile syntheses of cylindrical molecular brushes by a sequential RAFT and ROMP "grafting-through" methodology. J Polym Sci A Polym Chem. Oct. 15, 2009;47(20):5557-5563.

Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.

Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.

Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.

Li et al., Surface Properties of Bottlebrush Polymer Thin Films. Macromolecules. 2012;45(17):7118-7127.

Li et al., Synthesis of Hetero-Grafted Amphiphilic Diblock Molecular Brushes and Their Self-Assembly in Aqueous Medium. Macromolecules. 2010;43(3):1182-1184.

Li et al., Well-defined amphiphilic double-brush copolymers and their performance as emulsion surfactants. Macromol. May 18, 2012;45(11):4623-9.

Liang et al., The copper(I)-catalyzed alkyne-azide cycloaddition (CuAAC) "click" reaction and its applications. An overview. Coordination Chemistry Reviews Dec. 2011;255(23-24):2933-2945.

Liao et al., A convergent synthetic platform for single-nanoparticle combination cancer therapy: ratiometric loading and controlled release of cisplatin, doxorubicin, and camptothecin. J Am Chem Soc. Apr. 23, 2014;136(16):5896-9. doi: 10.1021/ja502011g. Epub Apr. 11, 2014.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30): 10209-11. doi: 10.1021/ja105010t.

Liao et al., Two-component control of guest binding in a self-assembled cage molecule. Chem Commun (Camb). Jul. 21, 2010;46(27):4932-4. doi: 10.1039/c0cc00234h. Epub Jun. 2010.

Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.

Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Discrete M2L2 metallacycle and M2L4 cage frameworks and anion competitive reactions of Cu2L4 type receptor. Inorganic Chemistry Communications. Jun. 2009;12(6):457-460.

Liu et al., Nuts and bolts of chemical exchange saturation transfer MRI. NMR Biomed. Jul. 2013;26(7):810-28. doi: 10.1002/nbm.2899. Epub Jan. 10, 2013.

Liu et al., Particles without a Box: Brush-first Synthesis of Photodegradable PEG Star Polymers under Ambient Conditions. J Vis Exp. 2013;80:e50874, doi: 10.3791/50874.

Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.

Lock et al., One-Component Supramolecular Filament Hydrogels as Theranostic Label-Free Magnetic Resonance Imaging Agents. ACS Nano. Jan. 24, 2017;11(1):797-805.

Love et al., A practical and highly active ruthenium-based catalyst that effects the cross metathesis of acrylonitrile. Angew Chem Int Ed Engl. Nov. 4, 2002;41(21):4035-7.

Loveless et al., Chemoresponsive viscosity switching of a metallo-supramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Luo et al., Toroidal structures from brush amphiphiles. Chem Commun. 2014;50(5):536-8.

Ma et al., Hierarchical Responsive Nanoplatform with Two-Photon Aggregation-Induced Emission Imaging for Efficient Cancer Theranostics. ACS Appl Mater Interfaces. Dec. 18, 2019;11(50):47259-47269. doi: 10.1021/acsami.9b17587. Epub Dec. 9, 2019. PMID: 31769279.

Ma et al., Nanoparticles for combination drug therapy. ACS Nano. Nov. 26, 2013;7(11):9518-25. doi: 10.1021/nn405674m.

Machida et al., (2018). Efficient approach to medium-sized cyclic molecules containing (E)-Alkene via z to e photochemical isomeriza-

(56) References Cited

OTHER PUBLICATIONS tion in the presence of AgNO3-impregnated silica gel. Chemistry Letters, 47(2), 186-188. https://doi.org/10.1246/cl.170937.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.

Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.

Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.

Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.

Matsumoto et al., High-resolution mapping of tumor redox status by magnetic resonance imaging using nitroxides as redox-sensitive contrast agents. Clin Cancer Res. Apr. 15, 2006;12(8):2455-62.

Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

Mccammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

Mckenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

Mckenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007; 13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 1, 20123.

Moghimi et al., Long-circulating and target-specific nanoparticles: theory to practice. Pharmacol Rev. Jun. 2001;53(2):283-318.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Mukherjee et al., Oximes as reversible links in polymer chemistry: dynamic macromolecular stars. Polym. Chem., 2014;5:6923-6931. DOI: 10.1039/C4PY01282H.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Na et al., Inorganic Nanoparticles for MRI Contrast Agents. Adv. Mater. 2009;21:2133-2148. doi:10.1002/adma.200802366.

Nair et al., Modulating mechanical properties of self-assembled polymer networks by multi-functional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nguyen et al., Pro-organic radical contrast agents ("pro-ORCAs") for real-time MRI of pro-drug activation in biological systems. Polym Chem. Aug. 7, 2020;11(29):4768-4779. doi: 10.1039/d0py00558d. Epub Jun. 26, 2020. PMID: 33790990; PMCID: PMC8009311.

Nguyen et al., Triply Loaded Nitroxide Brush-Arm Star Polymers Enable Metal-Free Millimetric Tumor Detection by Magnetic Resonance Imaging. ACS Nano. Nov. 27, 2018;12(11):11343-11354. doi: 10.1021/acsnano.8b06160. Epub Nov. 2, 2018. PMID: 30387988; PMCID: PMC6320246.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nishiyama et al., Novel cisplatin-incorporated polymeric micelles can eradicate solid tumors in mice. Cancer Res. Dec. 15, 2003;63(24):8977-83.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer As the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem. 2001;39:2206-2214. doi:10.1002/pola.1197.

Paletta et al., Synthesis and Reduction Kinetics of Sterically Shielded Pyrrolidine Nitroxides. Org. Lett., 2012;14(20):5322-5325. DOI: 10.1021/ol302506f.

Park et al.,Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

(56) References Cited

OTHER PUBLICATIONS

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 1, 20115;104(4):593-8. doi: 10.1038/bjc.2011.6. Epub Feb. 1, 2011.

Prevost et al., Strained organosilacyclic compounds:synthesis of anti-Bredt olefins and trans-dioxasilacyclooctenes. Dalton Trans. Oct. 21, 2010;39(39):9275-81. doi: 10.1039/c003227a. Epub Jul. 8, 2010.

Qiu et al., Efficient and versatile synthesis of star polymers in water and their use as emulsifiers. Chem. Commun., 2011;47:12685-12687. DOI: 10.1039/C1CC15679A.

Qiu et al., Oxidation-Responsive Polymer-Drug Conjugates with a Phenylboronic Ester Linker. Macromol Rapid Commun. Nov. 2015;36(22):2012-8. doi: 10.1002/marc.201500349. Epub Aug. 22, 2015. PMID: 26297612.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Rangadurai et al., Temporal and triggered evolution of host-guest characteristics in amphiphilic polymer assemblies. J Am Chem Soc. Jun. 10, 2016;138(24):7508-11.

Rasmussen et al., Improved numerical algorithm for exploring block copolymer mesophases. J Polym Sci Part B: Poly Phys. Aug. 15, 2002;40(16):1777-83.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Ren et al., Synthetic Strategies towards Well-Defined Complex Polymeric Architectures through Covalent Chemistry. Chemie Ingenieur Technik. 2014;86:2195-2214. doi:10.1002/cite.201400088.

Rizzo et al., In vivo nanotoxicity testing using the zebrafish embryo assay. J. Mater. Chem. B, 2013,1, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic B-Peptoids. Org. Lett., 2008; 10(5):921-924. DOI: 10.1021/ol7030763.

Runge et al., "Synthesis and Self-Assembly of Bottlebrush Block Copolymers" PMSEPreprints, 2005, 92, 5-6.

Rzayev et al., Molecular Bottlebrushes: New Opportunities in Nanomaterials Fabrication. ACS Macro Lett., 2012;1(9):1146-1149. DOI: 10.1021/mz300402x.

Rzayev, Synthesis of polystyrene-polylactide bottlebrush block copolymers and their melt self-assembly into large domain nanostructures. Macromol. Feb. 20, 2009;42(6):2135-41.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Samuni et al., Factors influencing nitroxide reduction and cytotoxicity in vitro. Antioxid Redox Signal. Jun. 2004;6(3):587-95.

Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.

Sanders et al., Metal-free sequential [3 + 2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.

Saunders et al., Synthesis of amphiphilic star block copolymers using ring-opening metathesis polymerization. Macromolecules, 1992;25(7):2055-2057. DOI: 10.1021/ma00033a035.

Schmidt et al., Supramolecular three-armed star polymers via cyclodextrin host-guest self-assembly. Polym. Chem., 2012;3:3139-3145. DOI: 10.1039/C2PY20293J.

Sengupta et al., Temporal targeting of tumour cells and neovasculature with a nanoscale delivery system. Nature. Jul. 28, 2005;436(7050):568-72.

Sheiko et al., Cylindrical molecular brushes: Synthesis, characterization, and properties. Progress in Polymer Science (Oxford), 33(7), 759-785. DOI: 10.1016/j.progpolymsci.2008.05.001.

Shellock et al., Safety of magnetic resonance imaging contrast agents. J Magn Reson Imaging. Sep. 1999; 10(3):477-84.

Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.

Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.

Shin et al., Recent advances in magnetic nanoparticle-based multimodal imaging. Chem Soc Rev. Jul. 21, 2015;44(14):4501-16. doi: 10.1039/c4cs00345d.

Sides et al., Parallel algorithm for numerical self-consistent field theory simulations of block copolymer structure. Polymer. Sep. 1, 2003;44(19):5859-66.

Sinturel et al., High x-low N block polymers: how far can we go ?. ACS Macro Lett. Sep. 2, 2015;4:1044-50.

Skomski et al., Redox-active on-surface assembly of metal-organic chains with single-site Pt(II). J Am Chem Soc. Jul. 16, 2014;136(28):9862-5. doi: 10.1021/ja504850f. Epub Jul. 1, 2014.

Smith et al., Modular synthesis of biologically active phosphatidic acid probes using click chemistry. Mol Biosyst. Sep. 2009;5(9):962-72. doi: 10.1039/b901420a. Epub May 7, 2009. PMID: 19668861; PMCID: PMC5985520.

Smith et al., Nanomaterials for In Vivo Imaging. Chem Rev. Feb. 8, 2017;117(3):901-986. doi: 10.1021/acs.chemrev.6b00073. Epub Jan. 3, 2017.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Sowers et al., Redox-responsive branched-bottlebrush polymers for in vivo MRI and fluorescence imaging. Nature Communications. 2014;5:Article No. 5460.

Spiniello et al., Synthesis and characterization of fluorescently labeled core cross-linked star polymers. J. Polym. Sci. A Polym. Chem., 2008;46:2422-2432. doi:10.1002/pola.22576.

Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.

Su et al., Catechol polymers for pH-responsive, targeted drug delivery to cancer cells. J Am Chem Soc. Aug. 10, 2011;133(31):11850-3. doi: 10.1021/ja203077x. Epub Jul. 19, 2011. PMID: 21751810; PMCID: PMC3149454.

(56) References Cited

OTHER PUBLICATIONS

Su et al., Coordination-directed assembly of trigonal and tetragonal molecular boxes encapsulating anionic guests. Journal of the Chemical Society, Dalton Transactions. 2001:359-361. doi: 10.1039/B0101180.
Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.
Sun et al., Multicomponent metal-ligand self-assembly. Curr Opin Chem Biol. Dec. 2002;6(6):757-64.
Sun et al., Self-assembled M24L48 polyhedra and their sharp structural switch upon subtle ligand variation. Science. May 28, 2010;328(5982): 1144-7. doi:10.1126/science.1188605. Epub Apr. 29, 2010.
Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.
Swaminathan et al., Nephrogenic systemic fibrosis, gadolinium, and iron mobilization. N Engl J Med. Aug. 16, 2007;357(7):720-2.
Takamizu et al., Synthesis of oligo(thiophene)-coated star-shaped ROMP polymers: unique emission properties by the precise integration of functionality. Journal of the American Chemical Society 2012;134(18):7892-7895.
Tam et al., Recent advances in metallogels. Chem Soc Rev. Feb. 21, 2013;42(4):1540-67. doi: 10.1039/c2cs35354g. Epub Jan. 8, 2013.
Tanino et al., Control of Stereochemistry by sigma-Participation of a Silyl Group. A Novel Method for Diastereoselective Polyol Synthesis. J Org Chem. Jun. 27, 1997;62(13):4206-4207. doi: 10.1021/jo9703515. PMID: 11671736.
Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.
Terreno et al., Challenges for molecular magnetic resonance imaging. Chem Rev. May 12, 2010;110(5):3019-42. doi: 10.1021/cr100025t.
Theodorakis et al., Interplay between chain collapse and microphase separation in bottle-brush polymers with two types of side chains. Macromol. May 4, 2010;43(11):5137-48.
Thompson et al., Labelling polymers and micellar nanoparticles via initiation, propagation and termination with ROMP. Polym. Chem., 2014;5:1954-1964.
Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.
Tolmasoff et al., Superoxide dismutase: correlation with life-span and specific metabolic rate in primate species. Proc Natl Acad Sci U S A. May 1980;77(5):2777-81.
Tominaga et al., Finite, spherical coordination networks that self-organize from 36 small components. Angew Chem Int Ed Engl. Oct. 25, 2004;43(42):5621-5.
Tomooka et al., Planar chiral dialkoxysilane:introduction of inherent chirality and high reactivity in conventional achiral alkene. Chemistry. Jun. 16, 2014;20(25):7598-602. doi: 10.1002/chem.201402434. Epub May 6, 2014.
Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.
Tsuji et al., Facile Palladium catalyzed decarboxylative allylation of active methylene compounds under neutral conditions using allylic carbonates. Tetrahedron Letters. 1982;23(46):4809-12.
Tu et al., Multimodal magnetic-resonance/optical-imaging contrast agent sensitive to NADH. Angew Chem Int Ed Engl. 2009;48(35):6547-51. doi: 10.1002/anie.200900984.
Tunca et al., Novel miktofunctional initiator for the preparation of an ABC-type miktoarm star polymer via a combination of controlled polymerization techniques. J. Polym. Sci. A Polym. Chem.; 42: 4228-4236. doi:10.1002/pola.20284.
Valeur et al., Amide bond formation: beyond the myth of coupling reagents. Chem. Soc. Rev., 2009;38:606-631. DOI: 10.1039/B701677H.
Verduzco et al., Correction: Structure, function, self-assembly, and applications of bottlebrush copolymers. Chem Soc Rev. Nov. 7, 2015;44(21):7916. doi: 10.1039/c5cs90099a.
Verduzco et al., Structure, function, self-assembly, and applications of bottlebrush copolymers. Chem. Soc. Rev., 2015;44:2405-20.
Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.
Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.
Wang et al., Advances of cancer therapy by nanotechnology. Cancer Res Treat. Mar. 2009;41(1):1-11. doi: 10.4143/crt.2009.41.1.1. Epub Mar. 31, 2009.
Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol502449r].
Wei et al., Exceedingly small iron oxide nanoparticles as positive MRI contrast agents. Proc. Natl. Acad. Sci. USA 2017;114(9):2325-2330.
Weng et al., Control of Gel Morphology and Properties of a Class of Metallo-Supramolecular Polyers by Good/Poor Solvent Environments. Macromolecules. 2009;42(1):236-246.
Weng et al., Effect of monomer structure on the gelation of a class of metallo-supramolecular polymers. Soft Matter. 2009;5(23):4647-4657.
Weng et al., Structural origin of the thixotropic behavior of a class of metallosupramolecular gels. Tetrahedron. Jul. 30, 2007;63(31):7419-7431.
Weng et al., Understanding the mechanism of gelation and stimuli-responsive nature of a class of metallo-supramolecular gels. J Am Chem Soc. Sep. 6, 2006;128(35):11663-72.
Westhaus et al., Triggered release of calcium from lipid vesicles: a bioinspired strategy for rapid gelation of polysaccharide and protein hydrogels. Biomaterials. Mar. 2001;22(5):453-62.
Wilkinson et al., Electrophilic fluorocyclization of allyl silanes. Angew Chem Int Ed Engl. 2009;48(38):7083-7086. doi:10.1002/anie.200901795.
Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.
Wong et al., Quantitative formation of core cross-linked star polymers via a one-pot two-step single electron transfer-living radical polymerization. Polym. Chem., 2013;4:4562-4565. DOI: 10.1039/C3PY00726J.
Worrell et al., Direct evidence of a dinuclear copper intermediate in Cu(I)-catalyzed azide- alkyne cycloadditions. Science. Apr. 26, 2013;340(6131):457-60. doi: 10.1126/science.1229506. Epub Apr. 4, 2013.
Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.
Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.
Xia et al., EPR study of spin labeled brush polymers in organic solvents. J Am Chem Soc. Dec. 14, 2011;133(49): 19953-9. doi: 10.1021/ja2085349. Epub Nov. 21, 2011.
Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. Epub Aug. 28, 2012.
Xing et al., A stable metal coordination polymer gel based on a calix [4]arene and its 'uptake' of non-ionic organic molecules from the aqueous phase. Chem Commun (Camb). Feb. 21, 2002;(4):362-3.

(56) References Cited

OTHER PUBLICATIONS

Xing et al., Design of coordination polymer as stable catalytic systems. Chemistry. Nov. 4, 2002;8(21):5028-32.
Xing et al., Spontaneous Enrichment of Organic Molecules from Aqueous and Gas Phases into a Stable Metallogel. Langmuir. 2002; 18:9654-9658.
Xu et al., Mechanism of Shear Thickening in Reversibly Cross-linked Supramolecular Polymer Networks. Macromolecules. Apr. 13, 2010;43(7):3556-3565.
Xu et al., Scaling Laws in Supramolecular Polymer Networks. Macromolecules. 2011;44(13):5465-5472.
Xu et al., Strain Hardening and Strain Softening of Reversibly Cross-linked Supramolecular Polymer Networks. Macromolecules. Sep. 27, 2011;44(18):7478-7488.
Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.
Yan et al., Particle carriers for combating multidrug-resistant cancer. ACS Nano. Nov. 26, 2013;7(11):9512-7. doi: 10.1021/nn405632s. Epub Nov. 11, 2013.
Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.
Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas. 1307472110. Epub Sep. 9, 2013.
Yang et al., Luminescent chemodosimeters for bioimaging. Chem Rev. Jan. 9, 2013;113(1):192-270. doi: 10.1021/cr2004103. Epub Jun. 18, 2012.
Yi et al., Telmisartan attenuates hepatic fibrosis in bile ductligated rats. Acta Pharmacol Sin. Dec. 2012;33(12):1518-24. doi: 10.1038/aps.2012.115. Epub Oct. 29, 2012.
Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.
Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.
Yoshizawa et al., Molecular architectures of multi-anthracene assemblies. Chem Soc Rev. Mar. 21, 2014;43(6):1885-98. doi: 10.1039/c3cs60315f.
You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.
Yount et al., Small-molecule dynamics and mechanisms underlying the macroscopic mechanical properties of coordinatively cross-linked polymer networks. J Am Chem Soc. Oct. 19, 2005;127(41):14488-96.
Yount et al., Strong means slow: dynamic contributions to the bulk mechanical properties of supramolecular networks. Angew Chem Int Ed Engl. Apr. 29, 2005;44(18):2746-8.
Yuan et al., One-pot syntheses of amphiphilic centipede-like brush copolymers via combination of ring-opening polymerization and "click" chemistry. Macromol. Jan. 27, 2010;43(4):1739-46.
Yue et al., Macrocyclic and lantern complexes of palladium(II) with bis(amidopyridine) ligands: synthesis, structure, and host-guest chemistry. Inorg Chem. Nov. 29, 2004;43(24):7671-81.
Zhang et al., Active cross-linkers that lead to active gels. Angew Chem Int Ed Engl. Oct. 25, 2013;52(44): 11494-8. doi: 10.1002/anie.201304437. Epub Sep. 12, 2013.
Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.

Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.
Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.
Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.
Zhang et al., Redox-Responsive, Core Cross-Linked Polyester Micelles. ACS Macro Lett., 2013;2(1):40-44. DOI: 10.1021/mz300522n.
Zhao et al., Polystyrene-Polylactide Bottlebrush Block Copolymer at the Air/Water Interface. Macromol. Sep. 28, 2009;42(22):9027-33.
Zhao et al., Rheological Behavor of Shear-Responsive Metallo-Supramolecular Gels. Macromolecules. 2004;37(10):3529-3531.
Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.
Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.
Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.
Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.
Zheng et al., Morphology of ABC triblock copolymers. Macromol. Oct. 1995;28(21):7215-23.
Zhou et al., Counting primary loops in polymer gels. Proc Natl Acad Sci U S A. Nov. 20, 2012;109(47):19119-24. doi: 10.1073/pnas. 1213169109. Epub Nov. 6, 2012.
Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.
Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.
Ohwada et al., Design, synthesis and antifungal activity of a novel water soluble prodrug of antifungal triazole. Bioorg Med Chem Lett. Jan. 20, 2003;13(2):191-6. doi: 10.1016/s0960-894x(02)00892-2. PMID: 12482421.
International Search Report and Written Opinion for PCT/US2017/055145, mailed Jan. 23, 2018.
International Preliminary Report on Patentability for PCT/US2017/055145, mailed Apr. 18, 2019.
International Search Report and Written Opinion for PCT/US2017/48641, mailed Nov. 9, 2017.
International Preliminary Report on Patentability for PCT/US2017/48641 mailed Mar. 7, 2019.
International Search Report and Written Opinion for PCT/US2019/046872, mailed on Oct. 29, 2019.
International Preliminary Report on Patentability for PCT/US2019/046872, mailed on Mar. 4, 2021.
International Search Report and Written Opinion for PCT/US2022/047333 mailed Jan. 25, 2023.
[No Author Listed], 2-Propen-1-amine, 3-(2-methoxyphenyl)-N-2-propyn-1-yl. CAS Registry File RN 1883141-01-2. STN Entry Date Mar. 10, 2016.

(56) References Cited

OTHER PUBLICATIONS

Borke et al., Poly(glyceryl glycerol): A multi-functional hydrophilic polymer for labeling with boronic acids. Polym Chem. Jun. 1, 2017;55(11):1822-30. doi: 10.1002/pola.28497.

Clark et al., Dynamically Restructuring Hydrogel Networks Formed with Reversible Covalent Crosslinks. Advanced Materials. 2007; 19:2503-2507. 10.1002/adma.200602649.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Fu et al., Relay Conjugation of Living Metathesis Polymers. J Am Chem Soc. Sep. 26, 2018;140(38):12181-12188. doi: 10.1021/jacs.8b07315. Epub Sep. 11, 2018.

Manyeruke et al., Synthesis and evaluation of 3-hydroxy-3-phenylpropanoate ester-AZT conjugates as potential dual-action HIV-1 Integrase and Reverse Transcriptase inhibitors. Bioorg Med Chem. Dec. 15, 2015;23(24):7521-8. doi: 10.1016/j.bmc.2015.10.039.

Nishimura et al., Rhodium-Catalyzed Asymmetric Cycloisomerization of 1,6-Ene-ynamides. Adv Synth Catal. May 3, 2013;355(7):1374-82. doi: 10.1002/adsc.201300148.

Pesek et al., Synthesis of bottlebrush copolymers based on poly(dimethylsiloxane) for surface active additives. Polymer. Aug. 19, 2016;98(19):495-504.

Yan et al., The relationship among pKa, pH, and binding constants in the interactions between boronic acids and diols-it is not as simple as it appears. Tetrahedron. Nov. 29, 2004;60(49):11205-11209.

Zhang et al., Convergent Synthesis of Branched Metathesis Polymers with Enyne Reagents. Macromolecules. Sep. 28, 2021;54(18):8435-8442. doi: 10.1021/acs.macromol.1c01051. Epub Sep. 8, 2021.

Vohidov et al., Design of BET Inhibitor Bottlebrush Prodrugs with Superior Efficacy and Devoid of Systemic Toxicities. J Am Chem Soc. Mar. 31, 2021;143(12):4714-4724. doi: 10.1021/jacs.1c00312. Epub Mar. 19, 2021. Author Manuscript, 18 pages.

[No Author Listed], CAS Abstract of S. Masuoka et al., JP 05112739 (1993). CAS Registry File RN 150076-39-4. 2023. 7 pages.

Amass, A.J., Ring-opening metathesis polymerization of cyclic alkenes. In: New Methods of Polymer Synthesis. 1991. J.R. Ebdon, Ed. Blackie & Son Ltd., Glasgow, Scotland. Chapter 3:209 pages.

Baslé et al., Protein chemical modification on endogenous amino acids. Chem Biol. Mar. 26, 2010;17(3):213-27. doi: 10.1016/j.chembiol.2010.02.008.

Beck et al., Strategies and challenges for the next generation of antibody-drug conjugates. Nat Rev Drug Discov. May 2017;16(5):315-337. doi: 10.1038/nrd.2016.268. Epub Mar. 17, 2017.

Dennler et al., Antibody Conjugates: From Heterogeneous Populations to Defined Reagents. Antibodies. Aug. 3, 2015;4(3):197-224. doi: 10.3390/antib4030197.

Dutta et al., Dilute solution structure of bottlebrush polymers. Soft Matter. Apr. 3, 2019;15(14):2928-2941. doi: 10.1039/c9sm00033j.

Ekladious et al., Polymer-drug conjugate therapeutics: advances, insights and prospects. Nat Rev Drug Discov. Apr. 2019;18(4):273-294. doi: 10.1038/s41573-018-0005-0.

Evans, R.A., The Rise of Azide-Alkyne 1,3-Dipolar 'Click' Cycloaddition and its Application to Polymer Science and Surface Modification. Aust J Chem. Jun. 18, 2007;60(6):384-95. doi: 10.1071/CH06457.

Foster et al., Getting into Shape: Reflections on a New Generation of Cylindrical Nanostructures' Self-Assembly Using Polymer Building Blocks. J Am Chem Soc. Feb. 20, 2019;141(7):2742-2753. doi: 10.1021/jacs.8b08648. Epub Feb. 8, 2019.

Furstner et al., Alkyne metathesis: development of a novel molybdenum-based catalyst system and its application to the total synthesis of epothilone A and C. Chem Eur J. Dec. 17, 2001;7(24):5299-317. doi: 10.1002/1521-3765(20011217)7:24<5299::aid-chem5299>3.0.co;2-x.

Furstner et al., Mo[N(t-Bu)(Ar)]$_3$ Complexes As Catalyst Precursors: In Situ Activation and Application to Metathesis Reactions of Alkynes and Diynes. J Am Chem Soc. Sep. 23, 1999;121(40):9453-4. doi: 10.1021/ja991340r.

Gallivan et al., A neutral, water-soluble olefin metathesis catalyst based on an N-heterocyclic carbene ligand. Tetrahedron Lett. Apr. 11, 2005;46(15):2577-80. doi: 10.1016/j.tetlet.2005.02.096.

Grubbs et al., Ring-Closing Metathesis and Related Processes in Organic Synthesis. Acc Chem Res. Nov. 1, 1995;28(11):446-52. doi: 10.1021/ar00059a002.

Hamblett et al., Effects of drug loading on the antitumor activity of a monoclonal antibody drug conjugate. Clin Cancer Res. Oct. 15, 2004;10(20):7063-70. doi: 10.1158/1078-0432.CCR-04-0789.

Knall et al., Inverse electron demand Diels-Alder (iEDDA)-initiated conjugation: a (high) potential click chemistry scheme. Chem Soc Rev. Jun. 21, 2013;42(12):5131-42. doi: 10.1039/c3cs60049a.

Kodger, T., Mechnical Failure in Colloidal Gels. Dissertation. Harvard University. Dec. 2014. 255 pages.

Kolb et al., Click Chemistry: Diverse Chemical Function from a Few Good Reactions. Angew Chem Int Ed Engl. Jun. 1, 2001;40(11):2004-2021. doi: 10.1002/1521-3773(20010601)40:11<2004::AID-ANIE2004>3.0.CO;2-5.

Lambert et al., Ado-trastuzumab Emtansine (T-DM1): an antibody-drug conjugate (ADC) for HER2-positive breast cancer. J Med Chem. Aug. 28, 2014;57(16):6949-64. doi: 10.1021/jm500766w. Epub Jul. 10, 2014.

Li et al., Thermoresponsive PNIPAAM bottlebrush polymers with tailored side-chain length and end-group structure. Soft Matter. Mar. 28, 2014;10(12):2008-15. doi: 10.1039/c3sm52614c.

Luginbuhl et al., One-week glucose control via zero-order release kinetics from an injectable depot of glucagon-like peptide-1 fused to a thermosensitive biopolymer. Nat Biomed Eng. 2017;1:0078. doi: 10.1038/s41551-017-0078. Epub Jun. 5, 2017.

Lyon et al., Reducing hydrophobicity of homogeneous antibody-drug conjugates improves pharmacokinetics and therapeutic index. Nat Biotechnol. Jul. 2015;33(7):733-5. doi: 10.1038/nbt.3212. Epub Jun. 15, 2015.

Panchamoorthy et al., Targeting the human MUC1-C oncoprotein with an antibody-drug conjugate. JCI Insight. Jun. 21, 2018;3(12):e99880. doi: 10.1172/jci.insight.99880.

Qi et al., A brush-polymer conjugate of exendin-4 reduces blood glucose for up to five days and eliminates poly(ethylene glycol) antigenicity. Nat Biomed Eng. 2016;1:0002. doi: 10.1038/s41551-016-0002. Epub Nov. 28, 2016.

Qiu et al., ROMP synthesis of benzaldehyde-containing amphiphilic block polynorbornenes used to conjugate drugs for pH-responsive release. React Func Polym. Jul. 2018; 128:1-15. doi: 10.1016/j.reactfunctpolym.2018.03.010.

Sakamoto et al., Protacs: chimeric molecules that target proteins to the Skp1-Cullin-F box complex for ubiquitination and degradation. Proc Natl Acad Sci U S A. Jul. 17, 2001;98(15):8554-9. doi: 10.1073/pnas.141230798. Epub Jul. 3, 2001.

Schrock et al., Tungsten(VI) neopentylidyne complexes. Organometallics. Dec. 1, 1982;1(12):1645-51. doi: 10.1021/om00072a018.

Shibuya et al., Mikto-Brush-Arm Star Polymers via Cross-Linking of Dissimilar Bottlebrushes: Synthesis and Solution Morphologies. ACS Macro Lett. Sep. 19, 2017;6(9):963- 968. doi: 10.1021/acsmacrolett.7b00529. Epub Aug. 21, 2017.

Shieh et al., Tailored silyl ether monomers enable backbone-degradable polynorbornene-based linear, bottlebrush and star copolymers through ROMP. Nat Chem. Dec. 2019;11(12):1124-1132. doi: 10.1038/s41557-019-0352-4. Epub Oct. 28, 2019.

Sowers et al., Redox-responsive branched-bottlebrush polymers for in vivo MRI and fluorescence imaging. Nat Commun. Nov. 18, 2014;5:5460. doi: 10.1038/ncomms6460.

Tolcher et al., Randomized phase II study of BR96-doxorubicin conjugate in patients with metastatic breast cancer. J Clin Oncol. Feb. 1999; 17(2):478-84. doi: 10.1200/JCO.1999.17.2.478.

Trail et al., Cure of xenografted human carcinomas by BR96-doxorubicin immunoconjugates. Science. Jul. 9, 1993;261(5118):212-5. doi: 10.1126/science.8327892. Erratum in: Science Feb. 25, 1994;263(5150):1076.

(56) References Cited

OTHER PUBLICATIONS

Tu et al., Recent advances towards applications of molecular bottlebrushes and their conjugates. Curr Opin Solid State Mater Sci. Feb. 2019;23(1):50-61. doi: 10.1016/j.cossms.2019.01.003.

Xiao et al., Precision glycocalyx editing as a strategy for cancer immunotherapy. Proc Natl Acad Sci U S A. Sep. 13, 2016;113(37):10304-9. doi: 10.1073/pnas.1608069113. Epub Aug. 22, 2016.

Xu et al., Site-specific labeling of an anti-MUC1 antibody: probing the effects of conjugation and linker chemistry on the internalization process. RSC Adv. Jan. 15, 2019;9(4):1909-1917. doi: 10.1039/c8ra09902b.

Yurkovetskiy et al., A Polymer-Based Antibody-Vinca Drug Conjugate Platform: Characterization and Preclinical Efficacy. Cancer Res. Aug. 15, 2015;75(16):3365-72. doi: 10.1158/0008-5472.CAN-15-0129. Epub Jun. 25, 2015.

Yurkovetskiy et al., Fully degradable hydrophilic polyals for protein modification. Biomacromolecules. Sep.-Oct. 2005;6(5):2648-58. doi: 10.1021/bm049210k.

Zhang et al., Practical Synthesis of Functional Metathesis Initiators Using Enynes. Macromol. Aug. 16, 2018;51(16):6497-503. doi: 10.1021/acs.macromol.8b00866.

\* cited by examiner

PROTEOLYSIS TARGETING CHIMERIC MOLECULES (PROTACS) WITH FUNCTIONAL HANDLES AND USES THEREOF

RELATED APPLICATIONS

This application claims priority under 35 U.S.C. § 119(e) to U.S. Provisional Application, U.S. Ser. No. 62/959,539, filed Jan. 10, 2020, which is incorporated herein by reference.

GOVERNMENT SUPPORT

This invention was made with Government support under Grant No. R01 CA220468 awarded by the National Institutes of Health. The Government has certain rights in the invention.

BACKGROUND OF THE INVENTION

Proteolysis targeting chimeras or proteolysis targeting chimeric molecules (PROTACs) are typically hetero-bifunctional molecules capable of removing targeted proteins by inducing selective intracellular proteolysis. PROTACs typically contain an ubiquitin ligase (E3 ligase, E3 ubiquitin ligase) binding moiety (binder). The ubiquitin ligase binder may be an analog of thalidomide, which binds the E3 ubiquinase known as cereblon. The ubiquitin ligase binder may also be a ligand that binds the von Hippel-Lindau tumor suppressor (VHL) protein, which is attached via a linker to another small molecule (target-moiety) that binds a target protein (see, e.g., Lai et al., Angew. Chem. Int. Ed. Engl. 55(22):807-810 (2016)). Targeted protein degradation refers to small molecule (e.g., protein-binding small molecule) induced ubiquitination and degradation of disease targets, in which the small molecule may simultaneously recruit both a ubiquitin ligase and the target protein into close proximity of each other, which may lead to ubiquitination of the target protein. Progress has recently been made towards chemically induced targeted protein degradation using PROTACs (see, e.g., Bondeson et al., Cell Chem. Biol., 25(1):78-87 (2018); Neklesa et al., Pharmacol. Ther., 174:138-144 (2017); Gadd et al., Nat. Chem. Biol., 13:514-521 (2017); Buckley et al., ACS Chem. Biol., 10:1831-1837 (2015); J. Lu et al., Chem. Biol., 22:755-763 (2015); Winter et al., Science, 348:1376-1381 (2015)). Although PROTACs open up a wide spectrum of applications, however, they often show poor biodistribution and pharmacokinetics (see, e.g., Lai et al., Nat. Rev. Drug Discov., 16(2):101-114 (2017); Coleman et al., Annu. Rev. Cancer Biol., 2:41-58 (2018)). There is a need to improve the PROTACs.

SUMMARY OF THE INVENTION

In one aspect, the present disclosure provides compounds (e.g., compounds of Formula (I)) comprising a protein-binding small molecule, a ubiquitin ligase binder, and a first reaction handle. The protein-binding small molecule and the ubiquitin ligase binder may act as a PROTAC. The first reaction handle may react with a second reaction handle. For example, the first reaction handle may react with a second reaction handle of a delivery vehicle (e.g., to form a conjugate (e.g., a conjugate of Formula (II))). The first reaction handle may also react with a second reaction handle of a monomer (e.g., to form a macromonomer (e.g., a macromonomer of Formula (III-A) or (III-B))). The same type of macromonomers may polymerize to form polymers. Two or more different types of macromonomers may also polymerize to form polymers. The conjugates and the polymers may improve the delivery of the compound, or a fragment thereof that includes the protein-binding small molecule and ubiquitin ligase binder, to a subject, cell, tissue, or biological sample. The conjugates and the polymers may also be useful in treating or preventing diseases (e.g., proliferative diseases). The conjugates and the polymers may be advantageous over known PROTACs (e.g., PROTACs that are not part of a conjugate or polymer) for treating the diseases (e.g., in part because of the improved delivery). In another aspect, the present disclosure provides compositions, kits, methods of preparing the conjugates, methods of preparing the polymers, methods of delivering a PROTAC, methods of treating a disease, methods of preventing a disease, and methods of diagnosing a disease.

A first aspect of the present invention is directed to compounds of the formula:

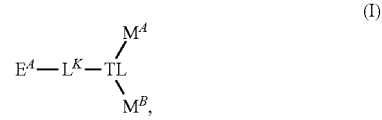
(I)

and salts thereof, wherein $E^A$, $L^K$, TL, $L^E$, $M^A$, and $M^B$ are as described herein.

In another aspect, the disclosure is directed to conjugates of the formula:

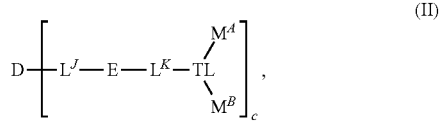
(II)

and salts thereof, wherein D, c, $L^J$, E, $L^K$, TL, $L^E$, V, $M^A$, and $M^B$ are as defined herein.

Further provided are macromonomers of Formula (III-A) or (III-B):

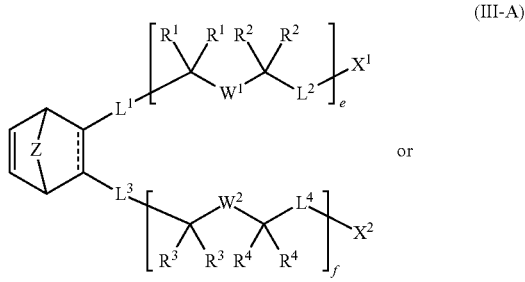
(III-A)

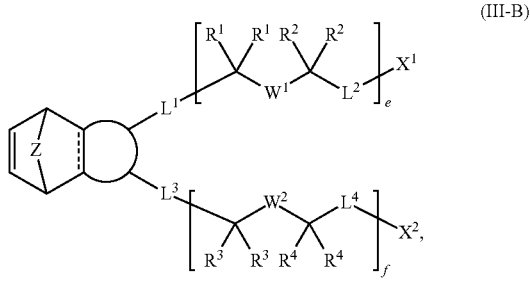
(III-B)

or a salt thereof, wherein Z, $L^1$, $L^2$, $L^3$, $L^4$, $R^1$, $R^2$, $R^3$, $R^4$, $W^1$, $W^2$, e, f, $X^1$, and $X^2$ are as defined herein.

An exemplary macromonomer is of the formula:

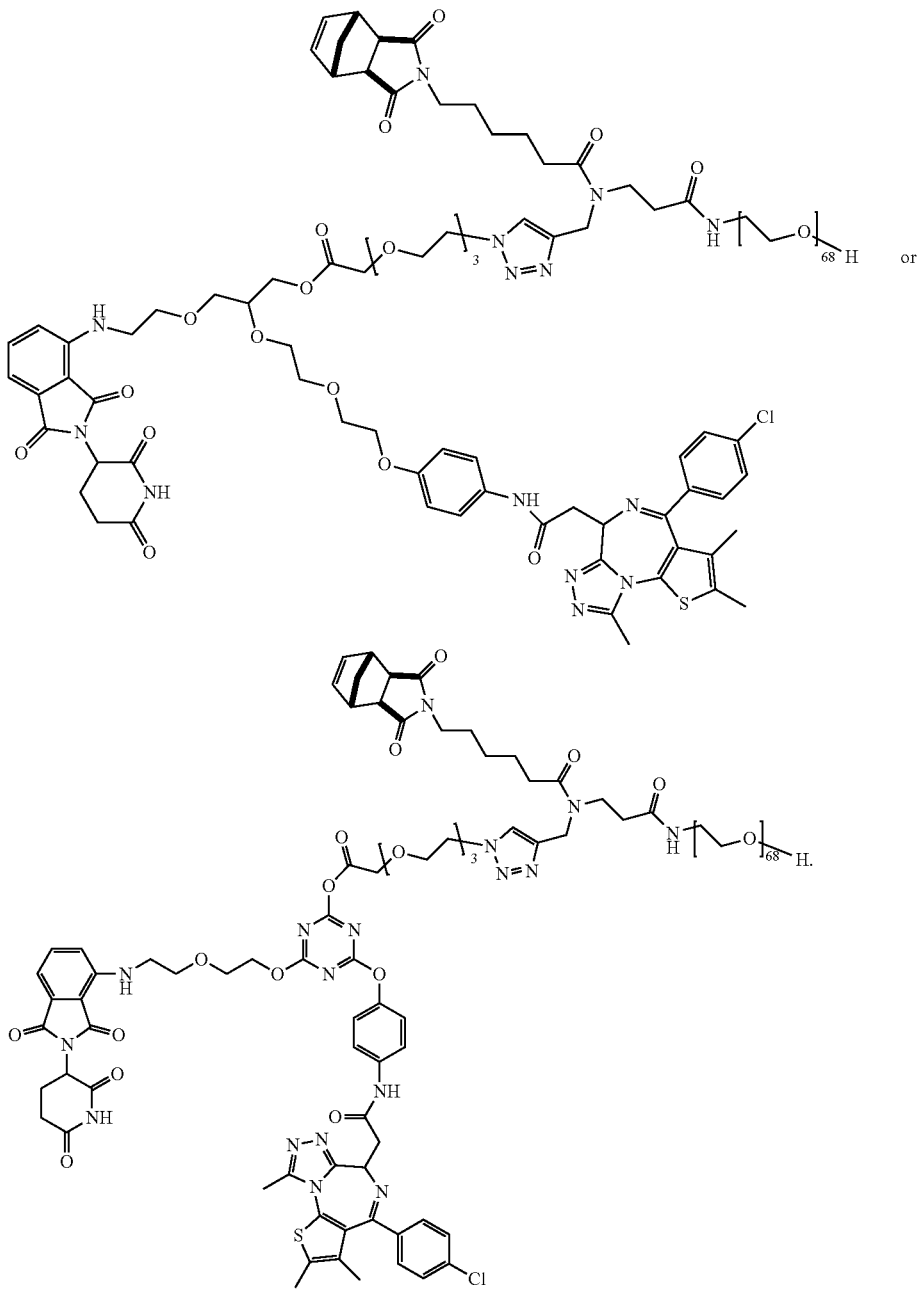

Also provided herein are polymers prepared by polymerizing macromonomers of Formula (III-A) and/or (III-B), and/or salts thereof.

Also provided herein are methods of polymerizing macromonomers of Formula (III-A) and/or (III-B), and/or salts thereof.

Further, the present disclosure describes methods of preparing a conjugate via reacting a compound of the formula:

D-L$^J$-E$^B$     (IV), or salt thereof, with a compound of the formula (I) or (I-A), or salt thereof.

In certain aspects, the disclosure provides compositions comprising a conjugate as described herein, or a salt thereof, or a polymer as described herein; and optionally an excipient.

Further provided are kits comprising a compound, macromonomer, or conjugate as described herein, or a salt thereof, a polymer as described herein, or composition as described herein; and instructions for using the compound, macromonomer, conjugate, or a salt thereof, the polymer, or the composition.

The present disclosure further provides methods of treating a disease in a subject in need thereof, the method comprising administering to the subject in need thereof a therapeutically effective amount of a conjugate as described herein, or a salt thereof, a polymer as described herein, or a composition as described herein.

The present disclosure further provides methods of preventing a disease in a subject in need thereof, the method comprising administering to the subject in need thereof a prophylactically effective amount of a conjugate as described herein, or a salt thereof, a polymer as described herein, or a composition as described herein.

The present disclosure further provides methods of diagnosing a disease in a subject in need thereof, the method comprising administering to the subject in need thereof a diagnostically effective amount of a conjugate as described herein, or a salt thereof, a polymer as described herein, or a composition as described herein.

Further provided in the present disclosure are methods of delivering a PROTAC to a subject in need thereof, the method comprising administering to the subject a conjugate as described herein, or a salt thereof, a polymer as described herein, or a composition as described herein.

In certain aspects, the present disclosure provides methods of delivering a PROTAC to a biological sample, tissue, or cell, the method comprising contacting the biological sample, tissue, or cell a conjugate as described herein, or a salt thereof, a polymer as described herein, or a composition as described herein.

In certain embodiments, the PROTAC is a compound described herein, or a salt or fragment thereof, wherein the fragment comprises the protein-binding small molecule and the ubiquitin ligase binder.

The details of certain embodiments of the invention are set forth in the Detailed Description of Certain Embodiments, as described below. Other features, objects, and advantages of the invention will be apparent from the Definitions, Figures, Examples, and Claims. It should be understood that the aspects described herein are not limited to specific embodiments, methods, or configurations, and as such can, of course, vary. It is also to be understood that the terminology used herein is for the purpose of describing particular aspects only and, unless specifically defined herein, is not intended to be limiting.

DEFINITIONS

Figure 1:
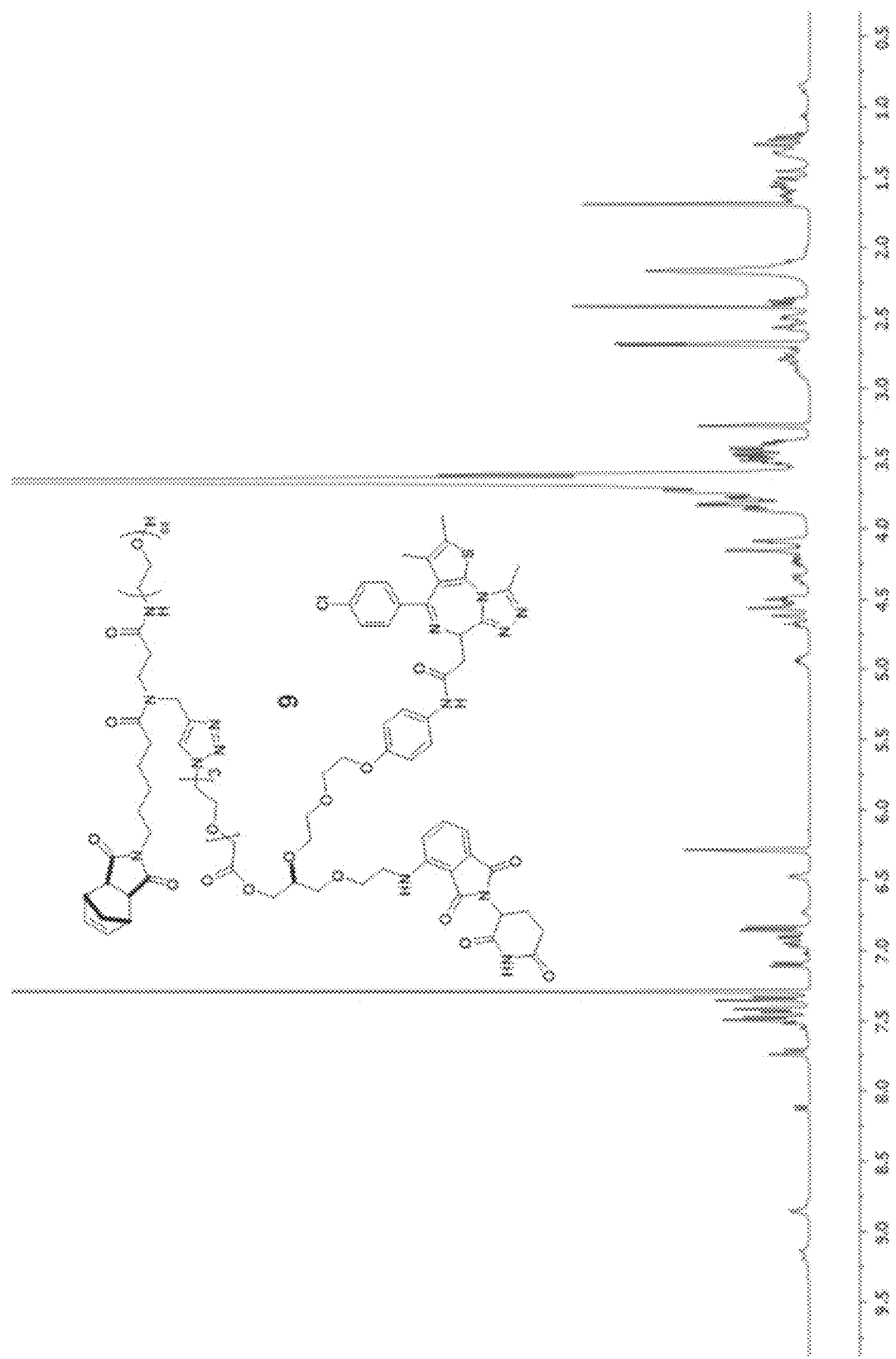
FIG. 1 shows a $^1$H NMR spectrum of macromonomer A13 (compound 9) in $CDCl_3$.
Figure 2:
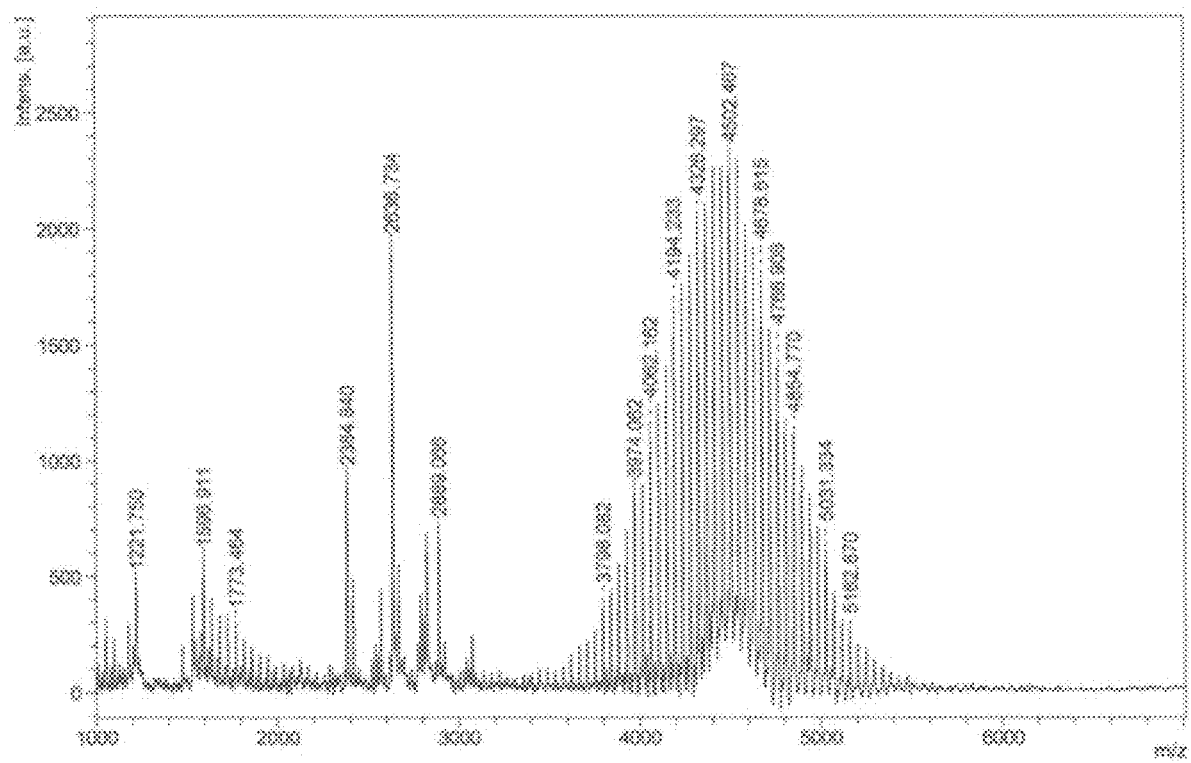
FIG. 2 shows a mass spectrum (MALDI) of macromonomer A13 (compound 9).
Figure 3A:
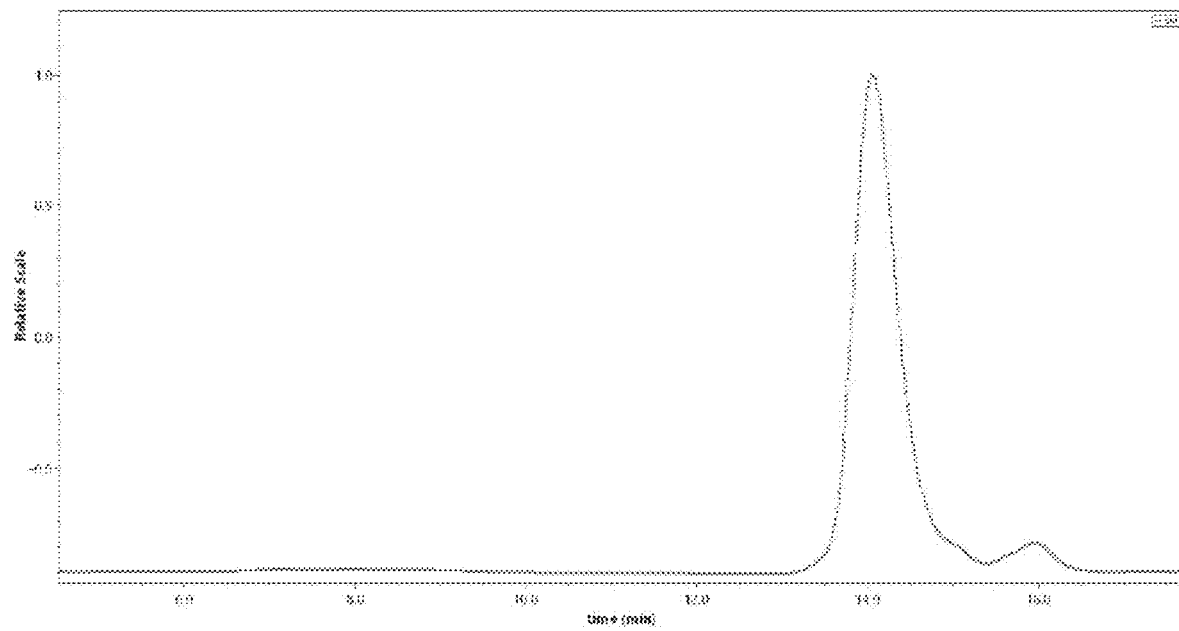
FIG. 3A shows a gel permeation chromatography (GPC) trace of a bottlebrush polymer (BBP) generated from macromonomer A13/compound 9 (referred to herein as BBP-10, see example 1.10).
Figure 3B:
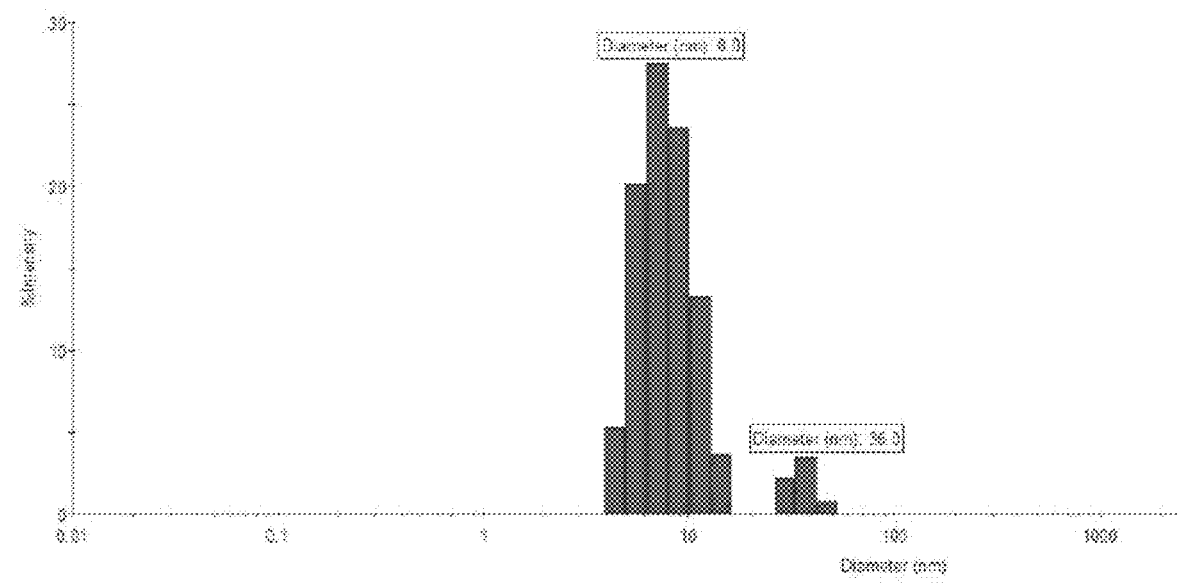
FIG. 3B shows a dynamic light scattering (DLS) of a BBP generated from macromonomer A13/compound 9 (referred to herein as BBP-10, see example 1.10).
Figure 4A:
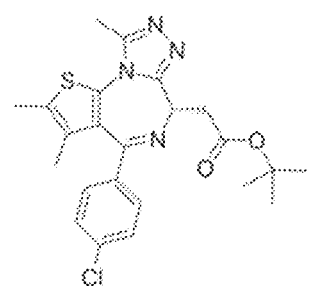
FIG. 4A shows the formula of compound JQ1.
Figure 4B:
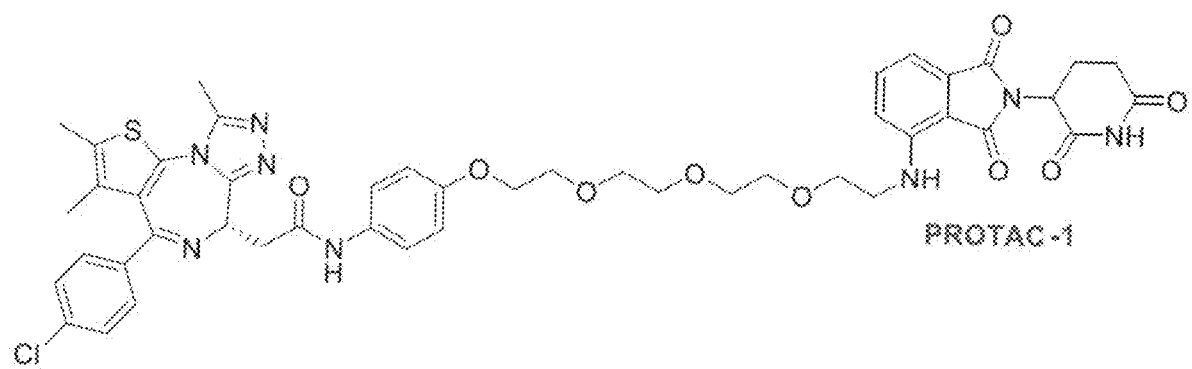
FIG. 4B shows the formula of a PROTAC compound comprising JQ1 and POM (referred to herein as "PROTAC-1").
Figure 4C:
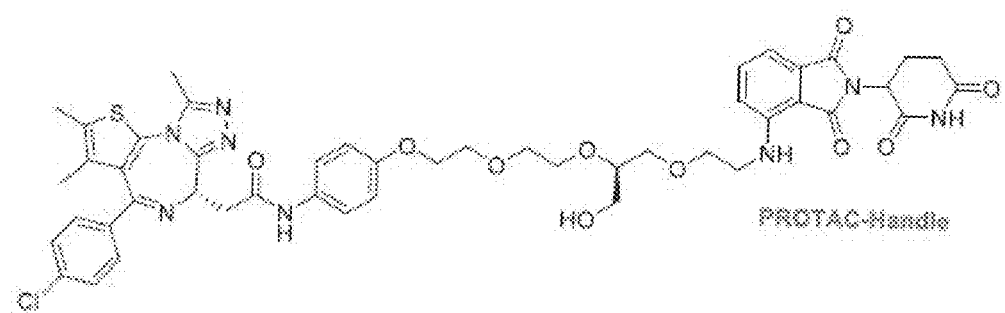
FIG. 4C shows the formula of an exemplary PROTAC compound comprising a reaction handle (referred to herein at "PROTAC-handle").
Figure 4D:
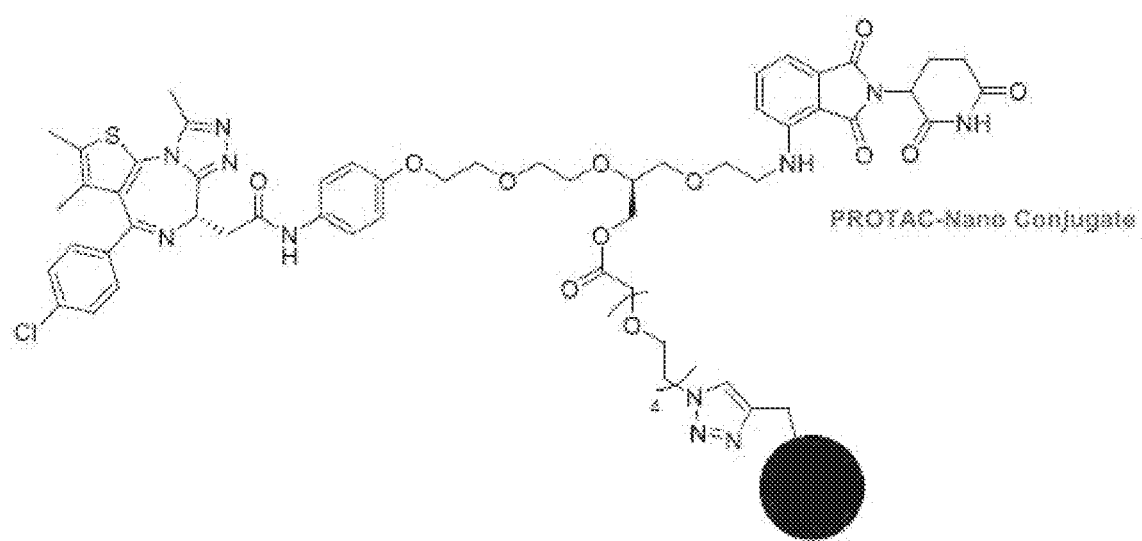
FIG. 4D shows the formula of an exemplary PROTAC delivery vehicle comprising a BBP of macromonomer A13/compound 9 (referred to herein as "PROTAC-Conjugate").
Figure 5A:
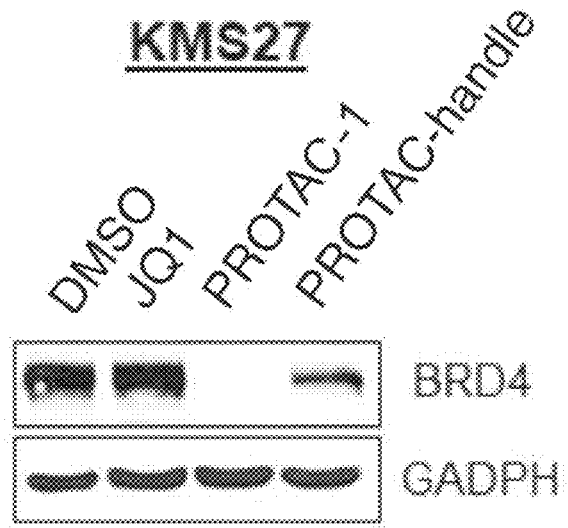
FIG. 5A shows an immunoblot depicting the degradation of BRD4 in KMS27 cells by JQ1, PROTAC-1, and PROTAC-handle with DMSO as a negative control.
Figure 5B:
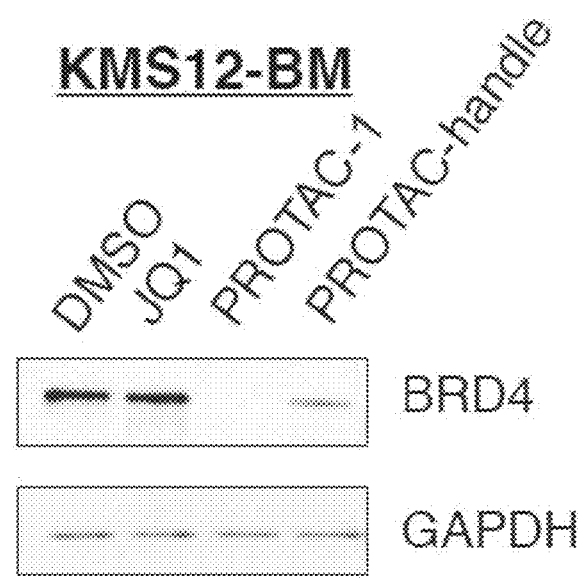
FIG. 5B shows an immunoblot depicting the degradation of BRD4 in KMS12BM cells by JQ1, PROTAC-1, and PROTAC-handle with DMSO as a negative control.
Figure 5C:
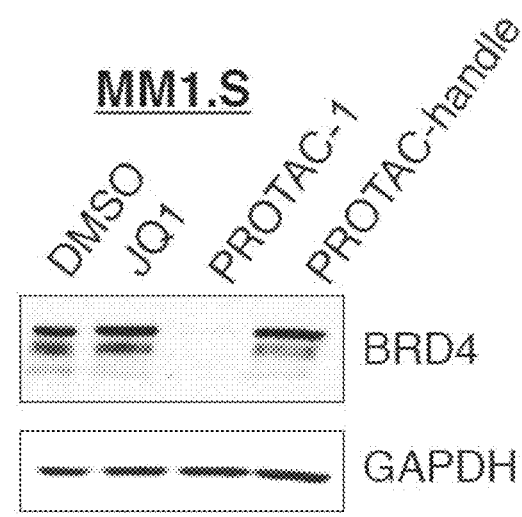
FIG. 5C shows an immunoblot depicting the degradation of BRD4 in MM1S cells by JQ1, PROTAC-1, and PROTAC-handle with DMSO as a negative control.
Figure 5D:
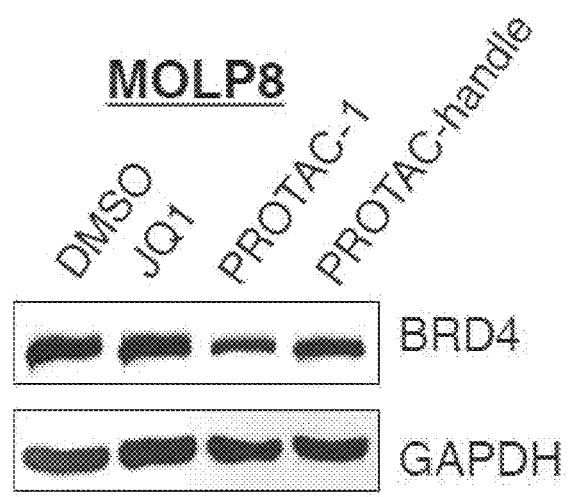
FIG. 5D shows an immunoblot depicting the degradation of BRD4 in MOLP8 cells by JQ1, PROTAC-1, and PROTAC-handle with DMSO as a negative control.
Figure 6A:
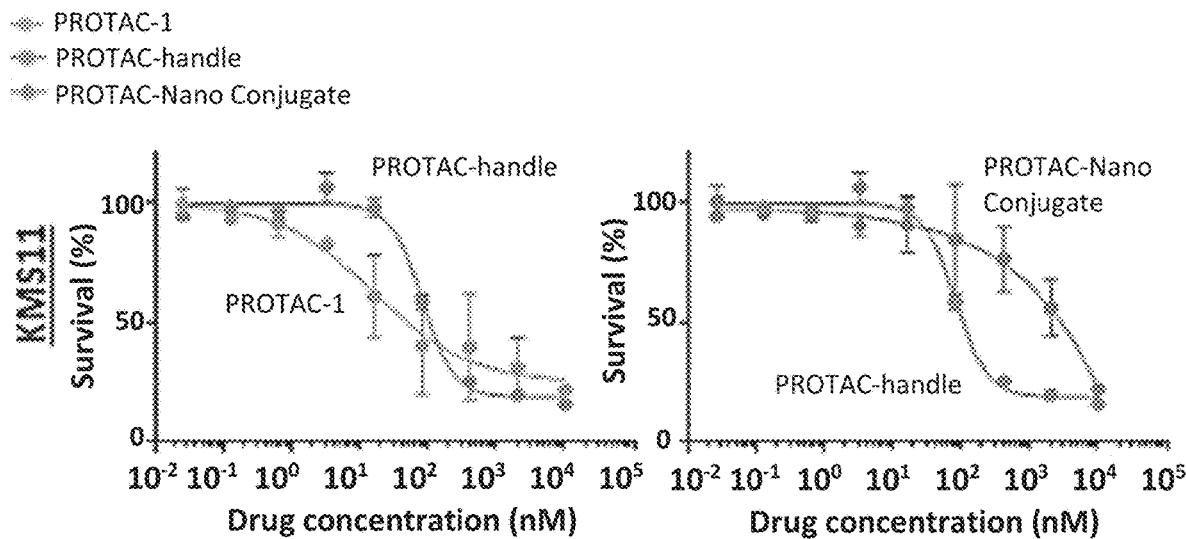
FIG. 6A shows an example of cellular degradation of BRD4 in KMS11 cells with increasing concentrations of PROTAC-1 and PROTAC-handle, and PROTAC-handle and PROTAC-Conjugate.
Figure 6B:
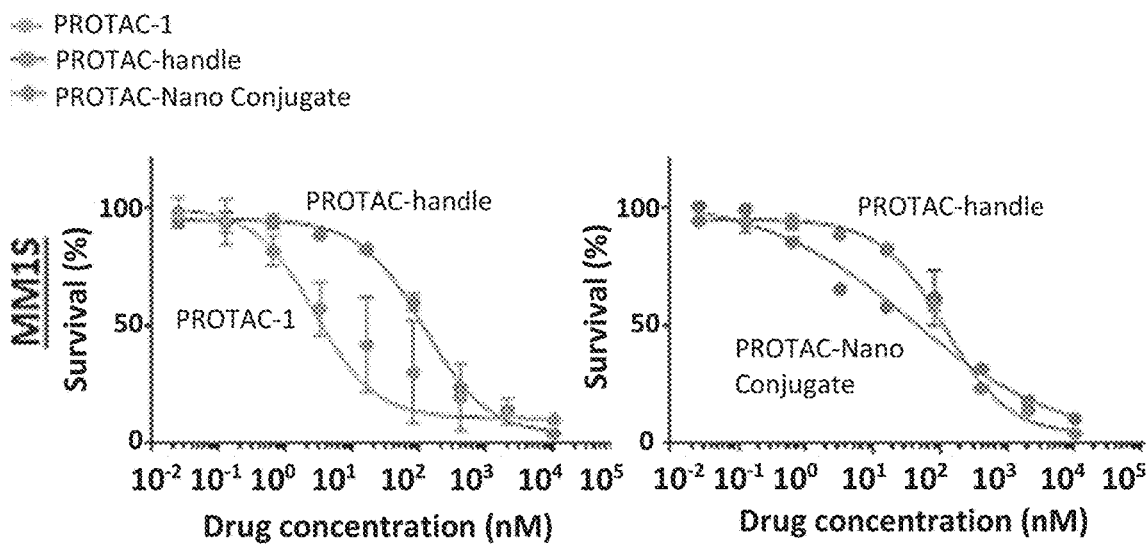
FIG. 6B shows an example of cellular degradation of BRD4 in MMiS cells with increasing concentrations of PROTAC-1 and PROTAC-handle, and PROTAC-handle and PROTAC-Conjugate.
Figure 6C:
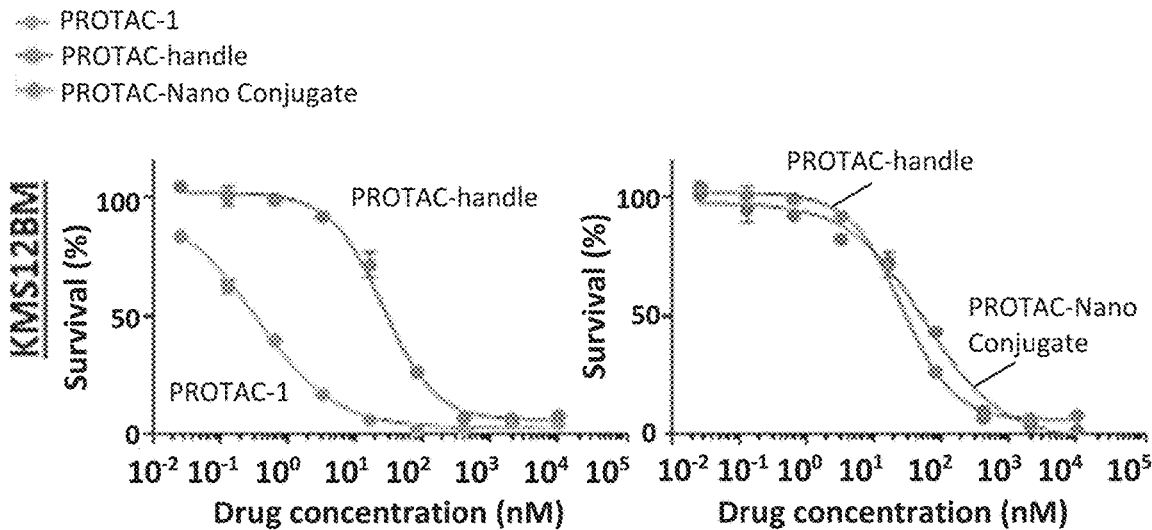
FIG. 6C shows an example of cellular degradation of BRD4 in KMS12BM cells with increasing concentrations of PROTAC-1 and PROTAC-handle, and PROTAC-handle and PROTAC-Conjugate.
Figure 6D:
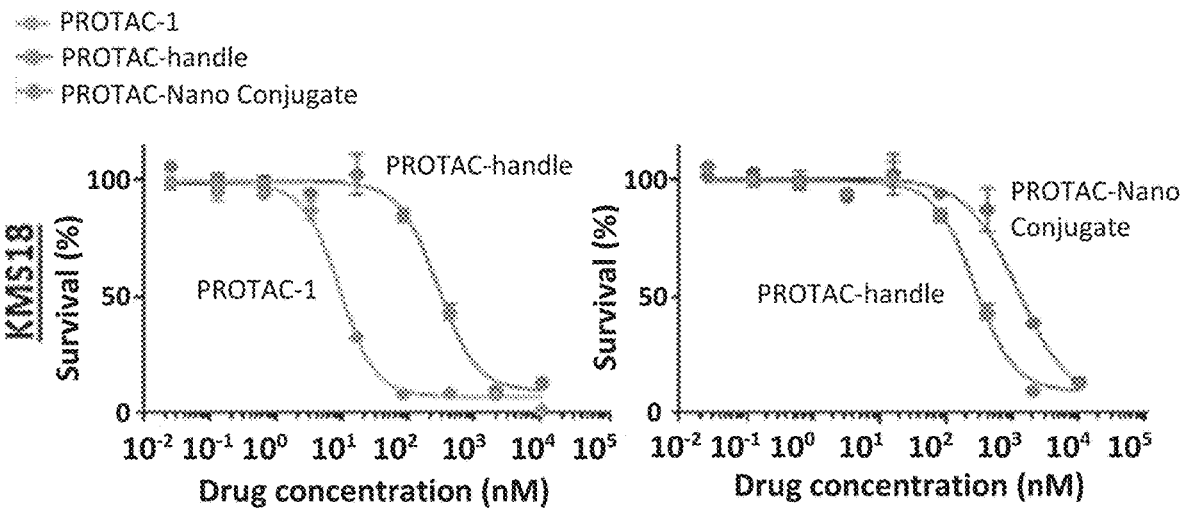
FIG. 6D shows an example of cellular degradation of BRD4 in KMS18 cells with increasing concentrations of PROTAC-1 and PROTAC-handle, and PROTAC-handle and PROTAC-Conjugate.
Figure 6E:
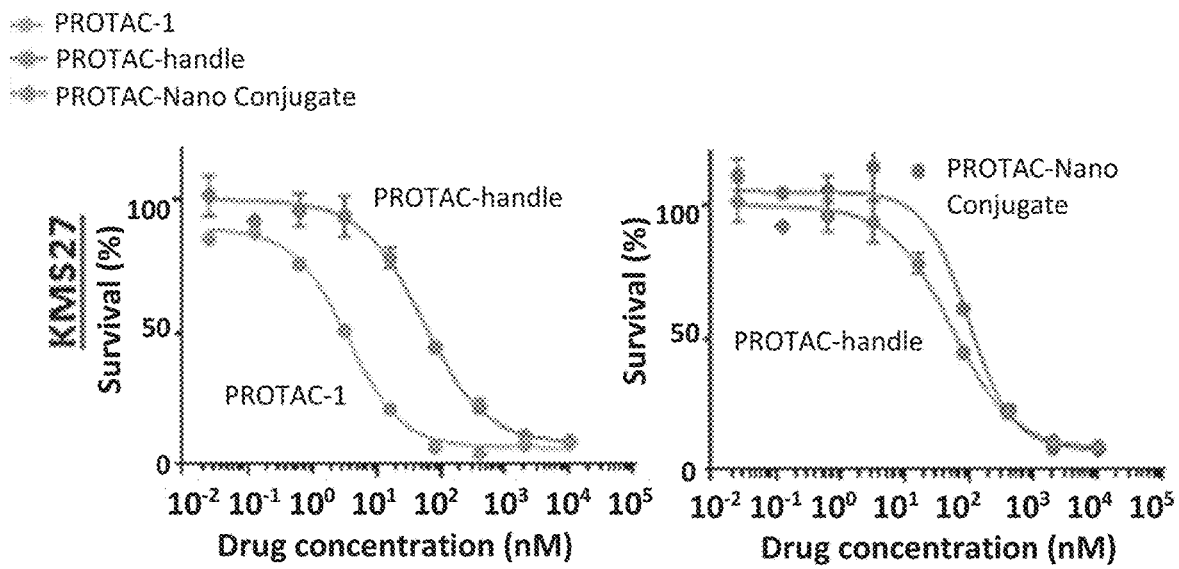
FIG. 6E shows an example of cellular degradation of BRD4 in KMS27 cells with increasing concentrations of PROTAC-1 and PROTAC-handle, and PROTAC-handle and PROTAC-Conjugate.
Figure 6F:
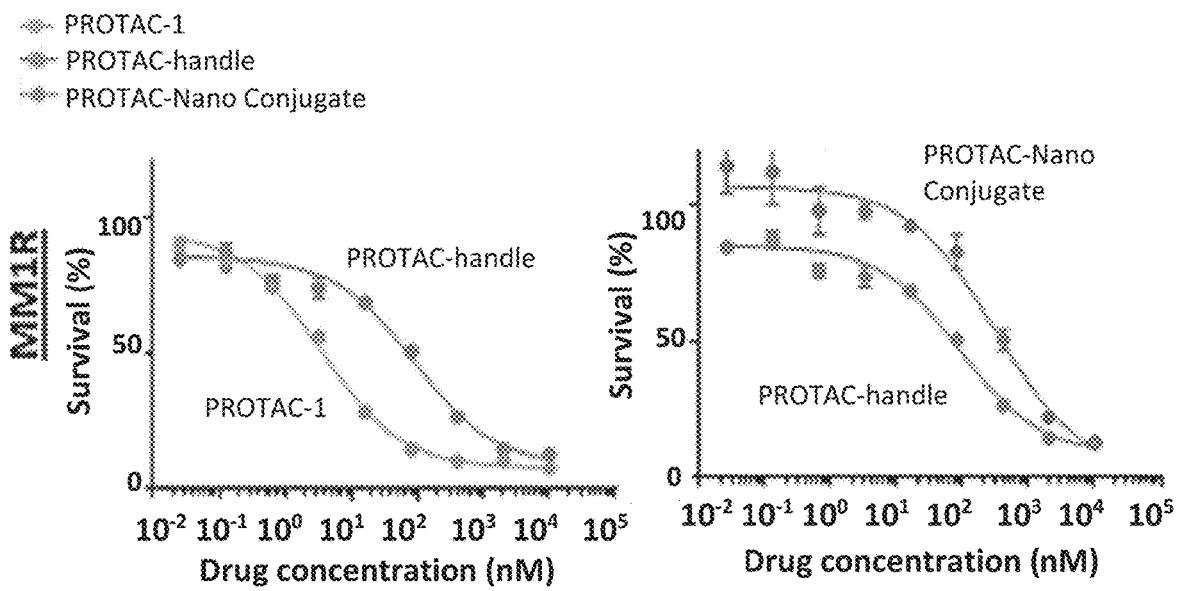
FIG. 6F shows an example of cellular degradation of BRD4 in MM1R cells with increasing concentrations of PROTAC-1 and PROTAC-handle, and PROTAC-handle and PROTAC-Conjugate.
Figure 6G:
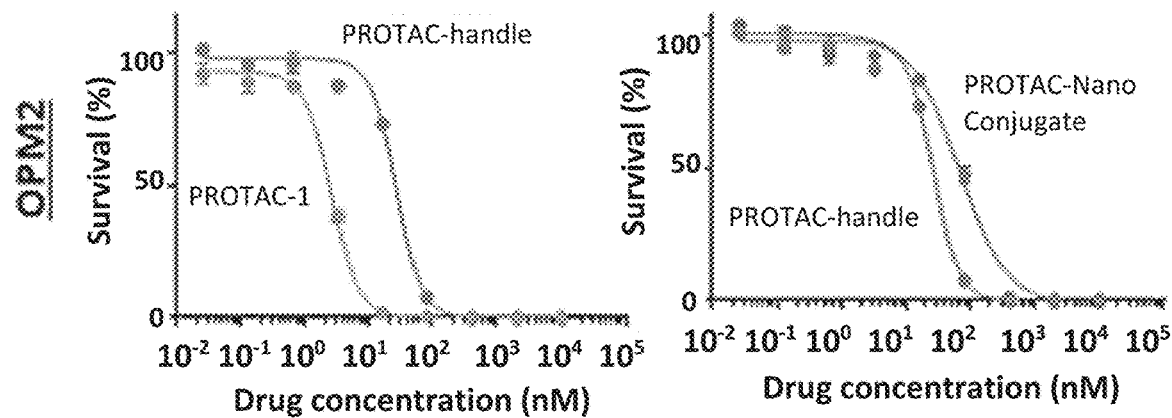
FIG. 6G shows an example of cellular degradation of BRD4 in OPM2 cells with increasing concentrations of PROTAC-1 and PROTAC-handle, and PROTAC-handle and PROTAC-Conjugate.
Figure 6H:
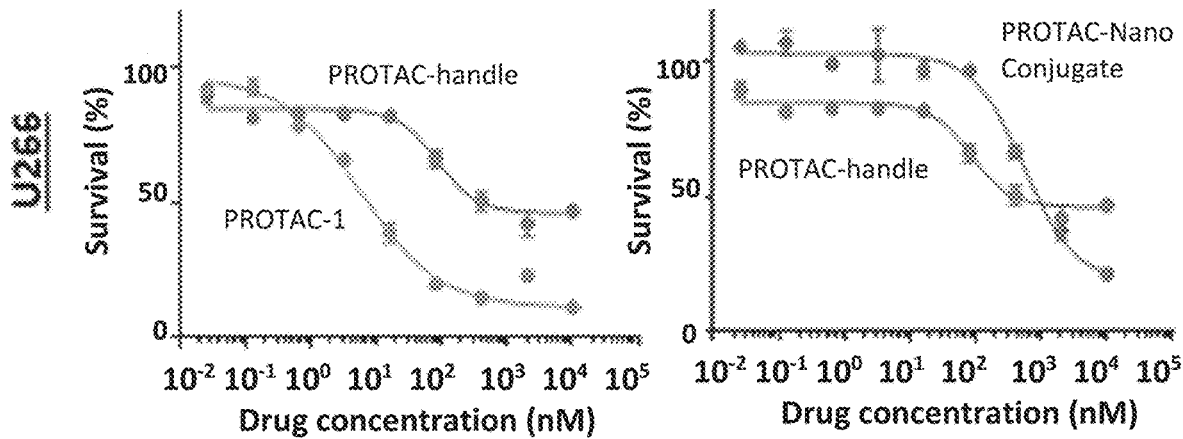
FIG. 6H shows an example of cellular degradation of BRD4 in U266 cells with increasing concentrations of PROTAC-1 and PROTAC-handle, and PROTAC-handle and PROTAC-Conjugate.

For convenience, certain terms employed herein, in the specification, examples and appended claims are collected herein.

Unless otherwise required by context, singular terms shall include pluralities, and plural terms shall include the singular.

The following definitions are more general terms used throughout the present application:

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, Some Modem Methods of Organic Synthesis, 3$^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The disclosure additionally encompasses compounds as individual isomers substantially free of other isomers, and alternatively, as mixtures of various isomers.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The term "alkyl" refers to a radical of a straight-chain or branched saturated hydrocarbon group. In some embodiments, an alkyl group has 1 to 1000 carbon atoms ("$C_1$-$C_{1000}$ alkyl"), 1 to 900 carbon atoms ("$C_1$-$C_{900}$ alkyl"), 1 to 800 carbon atoms ("$C_1$-$C_{800}$ alkyl"), 1 to 700 carbon atoms ("$C_1$-$C_{700}$ alkyl"), 1 to 600 carbon atoms ("$C_1$-$C_{600}$ alkyl"), 1 to 500 carbon atoms ("$C_1$-$C_{500}$ alkyl"), 1 to 400 carbon atoms ("$C_1$-$C_{400}$ alkyl"), 1 to 300 carbon atoms ("$C_1$-$C_{300}$ alkyl"), 1 to 200 carbon atoms ("$C_1$-$C_{200}$ alkyl"), 1 to 100 carbon atom ("$C_1$-$C_{100}$ alkyl"). In some embodiments, an alkyl group has 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents.

The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 1000 carbon atoms ("$C_2$-$C_{1000}$ alkenyl"), 2 to 900 carbon atoms ("$C_2$-$C_{900}$ alkenyl"), 2 to 800 carbon atoms ("$C_2$-$C_{800}$ alkenyl"), 2 to 700 carbon atoms ("$C_2$-$C_{700}$ alkenyl"), 2 to 600 carbon atoms ("$C_2$-$C_{600}$ alkenyl"), 2 to 500 carbon atoms ("$C_2$-$C_{500}$ alkenyl"), 2 to 400 carbon atoms ("$C_2$-$C_{400}$ alkenyl"), 2 to 300 carbon atoms ("$C_2$-$C_{300}$ alkenyl"), 2 to 200 carbon atoms ("$C_2$-$C_{200}$ alkenyl"), 2 to 100 carbon atom ("$C_2$-$C_{100}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently unsubstituted (an "unsubstituted alkenyl") or substituted (a "substituted alkenyl") with one or more substituents. In an alkenyl group, a C═C double bond for which the stereochemistry is not specified (e.g., —CH═CHCH$_3$,

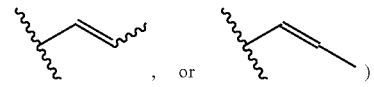

, or )

may be in the (E)- or (Z)-configuration.

The term "alkynyl" refers to a radical of a straight-chain or branched hydrocarbon group having from 2 to 1000 carbon atoms and one or more carbon-carbon triple bonds (e.g., 1, 2, 3, or 4 triple bonds). In some embodiments, an alkynyl group has 2 to 1000 carbon atoms ("$C_2$-$C_{1000}$ alkynyl"), 2 to 900 carbon atoms ("$C_2$-$C_{900}$ alkynyl"), 2 to 800 carbon atoms ("$C_2$-$C_{800}$ alkynyl"), 2 to 700 carbon atoms ("$C_2$-$C_{700}$ alkynyl"), 2 to 600 carbon atoms ("$C_2$-$C_{600}$ alkynyl"), 2 to 500 carbon atoms ("$C_2$-$C_{500}$ alkynyl"), 2 to 400 carbon atoms ("$C_2$-$C_{400}$ alkynyl"), 2 to 300 carbon atoms ("$C_2$-$C_{300}$ alkynyl"), 2 to 200 carbon atoms ("$C_2$-$C_{200}$ alkynyl"), 2 to 100 carbon atom ("$C_2$-$C_{100}$ alkynyl"). In some embodiments, an alkynyl group has 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_{2-6}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Unless otherwise specified, each instance of an alkynyl group is independently unsubstituted (an "unsubstituted alkynyl") or substituted (a "substituted alkynyl") with one or more substituents.

The term "heteroalkyl" refers to an alkyl group which further includes at least one heteroatom (e.g., 1, 2, 3, or 4 heteroatoms) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{1000}$ heteroalkyl"), 1 to 900 carbon atoms and 1 or more heteroatoms within the parent chain ("$C_1$-$C_{900}$ heteroalkyl"), 1 to 800 carbon atoms and 1 or more heteroatoms within the parent chain ("$C_1$-$C_{800}$ heteroalkyl"), 1 to 700 carbon atoms and 1 or more heteroatoms within the parent chain ("$C_1$-$C_{700}$ heteroalkyl"), 1 to 600 carbon atoms and 1 or more heteroatoms within the parent chain ("$C_1$-$C_{600}$ heteroalkyl"), 1 to 500 carbon atoms and 1 or more heteroatoms within the parent chain ("$C_1$-$C_{500}$ heteroalkyl"), 1 to 400 carbon atoms and 1 or more heteroatoms within the parent chain ("$C_1$-$C_{400}$ heteroalkyl"), 1 to 300 carbon atoms and 1 or more heteroatoms within the parent chain ("$C_1$-$C_{300}$ heteroalkyl"), 1 to 200 carbon atoms and 1 or more heteroatoms within the parent chain ("$C_1$-$C_{200}$ heteroalkyl"), or 1 to 100 carbon atoms and 1 or more heteroatoms within the parent chain ("$C_1$-$C_{100}$ heteroalkyl"). In certain embodiments, a heteroalkyl group refers to a saturated group having from 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and 1 or more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl"). Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a saturated group having from 1 to 1000 carbon atoms and 1 or more heteroatoms within the parent chain ("hetero$C_1$-$C_{1000}$ alkenyl"), 1 to 900 carbon atoms and 1 or more heteroatoms within the parent chain ("hetero$C_1$-$C_{900}$ alkenyl"), 1 to 800 carbon atoms and 1 or more heteroatoms within the parent chain ("hetero$C_1$-$C_{800}$ alkenyl"), 1 to 700 carbon atoms and 1 or more heteroatoms within the parent chain ("hetero$C_1$-$C_{700}$ alkenyl"), 1 to 600 carbon atoms and 1 or more heteroatoms within the parent chain ("hetero$C_1$-$C_{600}$ alkenyl"), 1 to 500 carbon atoms and 1 or more heteroatoms within the parent chain ("hetero$C_1$-$C_{500}$ alkenyl"), 1 to 400 carbon atoms and 1 or more heteroatoms within the parent chain ("hetero$C_1$-$C_{400}$ alkenyl"), 1 to 300 carbon atoms and 1 or more heteroatoms within the parent chain ("hetero$C_1$-$C_{300}$ alkenyl"), 1 to 200 carbon atoms and 1 or more heteroatoms within the parent chain ("hetero$C_1$-$C_{200}$ alkenyl"), or 1 to 100 carbon atoms and 1 or more heteroatoms within the parent chain ("hetero$C_1$-$C_{100}$ alkenyl"). In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a saturated group having from 1 to 1000 carbon atoms and 1 or more heteroatoms within the parent chain ("hetero$C_{1-1000}$ alkynyl"), 1 to 900 carbon atoms and 1 or more heteroatoms within the parent chain ("hetero$C_1$-$C_{900}$ alkynyl"), 1 to 800 carbon atoms and 1 or more heteroatoms within the parent chain ("hetero$C_1$-$C_{800}$ alkynyl"), 1 to 700 carbon atoms and 1 or more heteroatoms within the parent chain ("hetero$C_1$-$C_{700}$ alkynyl), 1 to 600 carbon atoms and 1 or more heteroatoms within the parent chain ("hetero$C_1$-$C_{600}$ alkynyl"), 1 to 500 carbon atoms and 1 or more heteroatoms within the parent chain ("hetero$C_1$-$C_{500}$ alkynyl"), 1 to 400 carbon atoms and 1 or more heteroatoms within the parent chain ("hetero$C_1$-$C_{400}$ alkynyl"), 1 to 300 carbon atoms and 1 or more heteroatoms within the parent chain ("hetero$C_1$-$C_{300}$ alkynyl"), 1 to 200 carbon atoms and 1 or more heteroatoms within the parent chain ("hetero$C_1$-$C_{200}$ alkynyl"), or 1 to 100 carbon atoms and 1 or more heteroatoms within the parent chain ("hetero$C_1$-$C_{100}$ alkynyl"). In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"), 3 to 7 ring carbon atoms ("C$_{3-7}$ carbocyclyl"), 3 to 6 ring carbon atoms ("C$_{3-6}$ carbocyclyl"), 4 to 6 ring carbon atoms ("C$_{4-6}$ carbocyclyl"), 5 to 6 ring carbon atoms ("C$_{5-6}$ carbocyclyl"), or 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ s carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" refers to a radical of a 5-14 membered monocyclic or polycyclic (e.g., bicyclic, tricyclic) 4n+2 aromatic ring system (e.g., having 6, 10, or 14 n electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$alkynyl, heteroC$_{1-10}$ alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_2$-10 alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_6$-14 aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, or —NO$_2$.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{aa}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9 (2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyl-eneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{bb}$)$_3$$^+$X$^-$, —P(OR$^{cc}$)$_2$, —P(OR$^{cc}$)$_3$$^+$X$^-$, —P(=O) (R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or —$NH_2$.

As used herein, the term "polyethylene glycol" or "PEG" refers to an ethylene glycol polymer that contains about 20 to about 2,000,000 linked monomers, typically about 50-1,000 linked monomers, usually about 100-300. Polyethylene glycols include ethylene glycol polymer containing various numbers of linked monomers, e.g., PEG20, PEG30, PEG40, PEG60, PEG80, PEG100, PEG115, PEG200, PEG300, PEG400, PEG500, PEG600, PEG1000, PEG1500, PEG2000, PEG3350, PEG4000, PEG4600, PEG5000, PEG6000, PEG8000, PEG 11000, PEG12000, PEG2000000, and any mixtures thereof.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C^{1-4} alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Click chemistry" refers to a chemical approach to conjugation introduced by Sharpless in 2001 and describes chemistry tailored to generate substances quickly and reliably by joining units together. See, e.g., Kolb, Finn and Sharpless *Angewandte Chemie International Edition* 2001 40, 2004-2021; Evans, *Australian Journal of Chemistry* 2007 60, 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition reactions); and Diels-Alder reactions (e.g., tetrazine [4+2] cycloaddition). Examples of click chemistry reactions and click-chemistry handles can be found in, e.g., Kolb, H. C.; Finn, M. G. and Sharpless, K. B. *Angew. Chem. Int. Ed.* 2001, 40, 2004-2021. Kolb, H. C. and Sharless, K. B. *Drug Disc. Today*, 2003, 8, 112-1137; Rostovtsev, V. V.; Green L. G.; Fokin, V. V. and Shrapless, K. B. *Angew. Chem. Int. Ed.* 2002, 41, 2596-2599; Tomoe, C. W.; Christensen, C. and Meldal, M. *J. Org. Chem.* 2002, 67, 3057-3064. Wang, Q. et al. *J. Am. Chem. Soc.* 2003, 125, 3192-3193; Lee, L. V. et al. *J. Am. Chem. Soc.* 2003 125, 9588-9589; Lewis, W. G. et al. *Angew. Chem. Int. Ed.* 2002, 41, 1053-41057; Manetsch, R. et al., *J. Am. Chem. Soc.* 2004, 126, 12809-12818; Mocharla, V. P. et al. *Angew. Chem., Int. Ed.* 2005, 44, 116-120. Any methods known in the art of bioconjugation can be used (e.g., click chemistry reactions). For example, the nanoparticle may comprise a click chemistry handle on its outer shell, which can react with a click chemistry handle on a targeting agent, thereby covalently linking the nanoparticle with the targeting agent. In certain embodiments, the one or more nanoparticles are conjugated to the targeting agent via click chemistry, and therefore the linker comprises a moiety derived from a click chemistry reaction (e.g., triazole, diazole, diazine, sulfide bond, maleimide ring, succinimide ring, ester, amide).

The term "average molecular weight" may encompass the number average molecular weight ($M_n$), weight average molecular weight ($M_w$), higher average molecular weight ($M_z$ or $M_z+1$), GPC/SEC (gel permeation chromatography/size-exclusion chromatography)-determined average molecular weight ($M_p$), and viscosity average molecular weight ($M_v$).

The term "average hydrodynamic diameter" ($D_H$) as used herein refers to the average size of a conjugate or particle. The average hydrodynamic diameter may or may not encompass the solvation layers of conjugate or particle, and may be determined through a number of methods including dynamic light scattering, electron microscopy (e.g., scanning electron microscopy, transmission electron microscopy), atomic force microscopy, and X-ray diffraction. The hydrodynamic diameter measured by dynamic light scattering (DLS) is defined as "the size of a hypothetical hard sphere that diffuses in the same fashion as that of the particle being measured". In practice though, particles or macromolecules in solution are non-spherical, dynamic (tumbling), and solvated. Because of this, the diameter calculated from the diffusional properties of the particle will be indicative of the apparent size of the dynamic hydrated/solvated particle. Hence the terminology, Hydrodynamic diameter. The hydrodynamic diameter, or Stokes diameter, therefore is that of a sphere that has the same translational diffusion coefficient as the particle being measured, assuming a hydration layer surrounding the particle or molecule. The measured data in a dynamic light scattering (DLS) experiment is the correlation curve which should be a smooth, single exponential decay function for a mono-size particle dispersion (Chu, B., *Annual Review of Physical Chemistry*, 1970, 21, 145-174). Embodied within the correlation curve is all of the information regarding the diffusion of particles within the sample being measured. By fitting the correlation curve to an exponential function, the diffusion coefficient (D) can be calculated (D is proportional to the lifetime of the exponential decay). With the diffusion coefficient (D) now known, the hydrodynamic diameter can be calculated by using a variation of the Stokes-Einstein equation. For a polydisperse sample this curve is a sum of exponential decays.

The term "degree of polymerization" (DP) refers to the number of repeating units in a polymer. In certain embodiments, the DP is determined by a chromatographic method, such as gel permeation chromatography. For a homopolymer, the DP refers to the number of repeating units included in the homopolymer. For a copolymer of two types of monomers (e.g., a first monomer and a second monomer) wherein the molar ratio of the two types of monomers is about 1:1, the DP refers to the number of repeating units of either one of the two type of monomers included in the copolymer. For a copolymer of two types of monomers (e.g., a first monomer and a second monomer) wherein the molar ratio of the two types of monomers is not about 1:1, two DPs may be used. A first DP refers to the number of repeating units of the first monomer included in the copolymer, and a second DP refers to the number of repeating units of the second monomer included in the copolymer. Unless provided otherwise, a DP of "xx", wherein xx is an integer, refers to the number of repeating units of either one of the two types of monomers of a copolymer of two types of monomers (e.g., a first monomer and a second monomer) wherein the molar ratio of the two types of monomers is about 1:1. Unless provided otherwise, a DP of "xx-yy", wherein xx and yy are integers, refers to xx being the number of repeating units of the first monomer, and yy being the number of repeating units of the second monomer, of a copolymer of two types of monomers (e.g., a first monomer and a second monomer) wherein the molar ratio of the two types of monomers is not about 1:1.

As used herein, the term "agent" means a molecule, group of molecules, complex or substance administered to an organism for diagnostic, therapeutic, preventative medical, or veterinary purposes. In certain embodiments, the agent is an agent (e.g., a therapeutic agent, a diagnostic agent, or a prophylactic agent). In certain embodiments, the monomers, conjugates, or particles disclosed herein comprise an agent (s), e.g., a first therapeutic agent (e.g., at least one (including, e.g., at least two, at least three). In some embodiments, the compositions (e.g., monomers, conjugates, or particles) can further comprise a second therapeutic agent, a targeting moiety, a diagnostic moiety, e.g., as described herein. The agent(s) can be coupled to the conjugate or particle. In other embodiments, the agent(s) can be associated with a conjugate or particle. In some embodiments, a first agent can be coupled to the conjugate or particle, and a second agent, targeting moiety, and/or diagnostic moiety can be non-covalently associated with the conjugate or particle. Any of the agents disclosed herein can be used in the monomers, conjugates, particles and other compositions and methods disclosed herein.

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent, e.g., a therapeutic agent, can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refer to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the conjugate or particle described herein incorporates one therapeutic agent or prodrug thereof. In some embodiments, the conjugate or particle described herein incorporates more than one therapeutic agents or prodrugs.

In some embodiments, the agent, e.g., a therapeutic agent, a small molecule. The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than 2,000 g/mol. In certain embodiments, the molecular weight of a small molecule is not more than 1,500 g/mol. In certain embodiments, the molecular weight of a small molecule is not more than 1,000 g/mol, not more than 900 g/mol, not more than 800 g/mol, not more than 700 g/mol, not more than 600 g/mol, not more than 500 g/mol, not more than 400 g/mol, not more than 300 g/mol, not more than 200 g/mol, or not more than 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and not more than 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present disclosure.

Exemplary agents, e.g., a therapeutic agents, in the compounds, conjugates, macromonomers, polymers, and compositions include, but are not limited to, those found in *Harrison's Principles of Internal Medicine,* 13th Edition, Eds. T. R. Harrison et al. McGraw-Hill N.Y., NY; *Physicians' Desk Reference,* 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In some embodiments, exemplary therapeutic agents in the compounds, conjugates, macromonomers, polymers, and compositions include, but are not limited to, one or more of the agents listed in Paragraph [0148] of U.S. Pat. No. 9,381,253, incorporated by reference herein.

In other embodiments, exemplary therapeutic agents in the compounds, conjugates, macromonomers, polymers, and compositions include, but are not limited to, one or more of the therapeutic agents listed in WO 2013/169739, including the anti-hypertensive and/or a collagen modifying agents ("AHCM") disclosed, e.g., in Paragraphs 40-49, 283, 286-295; the microenviroment modulators disclosed, e.g., in Paragraphs 113-121, of WO 2013/169739, incorporated herein by reference. In some embodiments, the compounds, conjugates, macromonomers, polymers, and compositions comprising the AHCM and/or the microenvironment modulator causes one or more of: reduces solid stress (e.g., growth-induced solid stress in tumors); decreases tumor fibrosis; reduces interstitial hypertension or interstitial fluid pressure (IFP); increases interstitial tumor transport; increases tumor or vessel perfusion; increases vascular diameters and/or enlarges compressed or collapsed blood vessels; reduces or depletes one or more of: cancer cells, or stromal cells (e.g., tumor associated fibroblasts or immune cells); decreases the level or production of extracellular matrix components, such as fibers (e.g., collagen, procollagen), and/or polysaccharides (e.g., glycosaminoglycans such as hyaluronan or hyaluronic acid); decreases the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases the production of cancer stem cells (also referred to herein as tumor-initiating cells); or enhances the efficacy (e.g., penetration or diffusion), of the therapy, e.g., the cancer therapy (e.g., radiation, photodynamic therapy, chemotherapeutics, and immunotherapies) in a tumor or tumor vasculature, in the subject.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anti-convulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antialrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain instances, the diagnostic agent is an imaging agent or contrast agent. The terms "imaging agent" and "contrast agent" refer to a substance used to enhance the contrast of structures or fluids within the body in medical imaging. It is commonly used to enhance the visibility of blood vessels and the gastrointestinal tract in medical imaging.

The term "crosslinker" refers to a compound that allows for two or more polymers (e.g., brush polymers) to be joined by covalent bonds. In certain embodiments, the crosslinker results in a covalent attachment between two polymers.

The term "ring-opening metathesis polymerization (ROMP)" refers to a type of olefin metathesis chain-growth polymerization that is driven by the relief of ring strain in cyclic olefins (e.g., norbornene or cyclopentene). The catalysts used in the ROMP reaction ("metathesis catalyst") include $RuCl_3$/alcohol mixture, bis(cyclopentadienyl)dimethylzirconium(IV), dichloro[1,3-bis(2,6-isopropylphenyl)-2-imidazolidinylidene](benzylidene)(tricyclohexylphosphine)ruthenium(II), dichloro[1,3-Bis(2-methylphenyl)-2-imidazolidinylidene](benzylidene)(tricyclohexylphosphine) ruthenium(II), dichloro[1,3-bis(2,4,6-trimethylphenyl)-2-imidazolidinylidene][3-(2-pyridinyl)propylidene]ruthenium (II), dichloro(3-methyl-2-butenylidene)bis (tricyclopentylphosphine)ruthenium(II), dichloro[1,3-bis(2-methylphenyl)-2-imidazolidinylidene](2-isopropoxyphenylmethylene)ruthenium(II) (Grubbs C571), dichloro(benzylidene)bis(tricyclohexylphosphine)ruthenium(II) (Grubbs I), dichloro[1,3-bis(2,4,6-trimethylphenyl)-2-imidazolidinylidene](benzylidene)(tricyclohexylphosphine) ruthenium(II) (Grubbs II), and dichloro[1,3-bis(2,4,6-trimethylphenyl)-2-imidazolidinylidene](benzylidene)bis(3-bromopyridine)ruthenium(II) (Grubbs III).

A "protein," "peptide," or "polypeptide" comprises a polymer of amino acid residues linked together by peptide bonds. The term refers to proteins, polypeptides, and peptides of any size, structure, or function. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. One or more of the amino acids in a protein may be protected. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these. In certain embodiments, a protein comprises between 2 and 10, between 10 and 30, between 30 and 100, between 100 and 300, or between 300 and 1,000, inclusive, amino acids. In certain embodiments, the amino acids in a protein are natural amino acids. In certain embodiments, the amino acids in a protein are unnatural amino acids. In certain embodiments, the amino acids in a protein are a combination of natural amino acids and unnatural amino acids.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKal, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK1, SIK2, SIK3, skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6psl, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2psl, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The disclosure is not intended to be limited in any manner by the above exemplary listing of substituents. Additional terms may be defined in other sections of this disclosure.

DETAILED DESCRIPTION OF CERTAIN EMBODIMENTS

The present disclosure provides compounds, conjugates, macromonomers, and polymers. The present disclosure also provides compositions and kits, each of which comprises the conjugates or polymers. The compounds, conjugates, and macromonomers include a PROTAC moiety (e.g., a moiety that comprises a protein-binding small molecule and a ubiquitin ligase binder), which may degrade a protein (e.g., BET protein). The protein may be involved in the genesis and/or progression of diseases via the cell's ubiquitin/proteasome system, whose function is to routinely identify and remove damaged proteins. The compounds include a first reaction handle. The first reaction handle may react with a second reaction handle (e.g., a second reaction handle of a delivery vehicle or of a monomer). The delivery vehicle, which may be a nanoparticle or antibody, may facilitate delivery (e.g., endocytotic delivery) of the PROTAC, may improve bioavailability, and may reduce cell toxicity (e.g., by lowering the effective amount of the PROTAC). The ubiquitin ligase binder, $M^B$, may recruit the E3 ubiquitin ligase to tag the protein (which is bound by the protein-binding small molecule, $M^A$) for ubiquitination and degradation through the proteasome. After destruction of the protein, the ubiquitin ligase binder may be released from the binding to the protein and may continue to be active. Thus, the compounds, conjugates, macromonomers, polymers, compositions, and kits described herein may be advantageous over known protein-binding small molecules and/or PROTACs thereof in the treatment of diseases, such as diseases that are difficult to treat by known protein-binding small molecules and/or PROTACs thereof.

Also provided are methods of preparing the conjugates, methods of preparing the polymers, methods of delivering a PROTAC, methods of treating a disease, methods of preventing a disease, and methods of diagnosing a disease.

Compounds, Conjugates, Macromonomers, and Polymers

In one aspect, provided here are compounds of Formula (I):

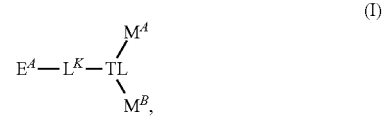

and salts thereof, wherein
$E^A$ is a first reaction handle;
$L^K$ is a first linker;
TL is a trivalent linker;
$M^A$ is a protein-binding small molecule; and
$M^B$ is a ubiquitin ligase binder.

In certain aspects, a compound of Formula (I) is of Formula (I-A):

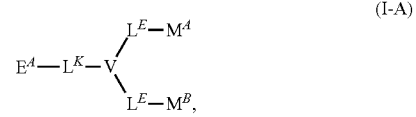

or a salt thereof, wherein:
$E^A$ is a first reaction handle;
$L^K$ is a first linker;
V is N, B, P, $C(R^J)$, $Si(R^J)$, $P(=O)$, substituted or unsubstituted carbocyclyl, substituted or unsubstituted heterocyclyl, substituted or unsubstituted aryl, or substituted or unsubstituted heteroaryl, wherein $R^J$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^A$;

R$^A$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

each instance of L$^E$ is a second linker;

M$^A$ is a protein-binding small molecule;

M$^B$ is a ubiquitin ligase binder, and the protein-binding small molecule is different from the ubiquitin ligase binder.

In compounds, conjugates, macromonomers, or polymers, wherein more than one instance of a particular variable (e.g., L$^E$, A, B) is present, each instance of the variable is independent from one another (i.e., each instance of the variable is independently selected from the definition of the variable as described herein). In certain embodiments, at least two instances of a variable are different from each other. In certain embodiments, all instances of a variable are different from each other. In certain embodiments, all instances of a variable are the same.

TL is a trivalent linker. In certain embodiments, TL provides a covalent attachment of M$^A$ to M$^B$. In certain embodiments, TL provides a covalent attachment of the BET targeting ligand to the Degron. The structure of TL may not be critical, provided it does not substantially interfere with the activity of the targeting ligand or the M$^B$. In certain aspects, TL is substituted or unsubstituted carbocyclyl, substituted or unsubstituted heterocyclyl, substituted or unsubstituted aryl, or substituted or unsubstituted heteroaryl. In certain aspects, TL comprises

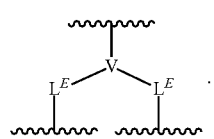

In some aspects, TL comprises

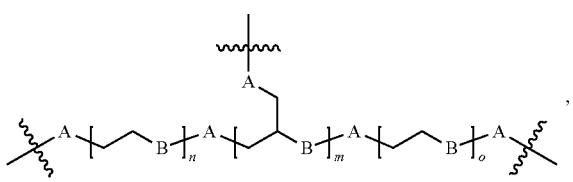

wherein A, B, n, m, and o are described herein. In some aspects, TL comprise

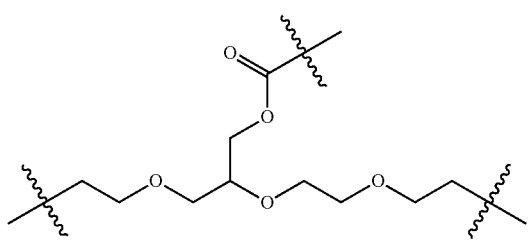

In some aspects, TL comprises

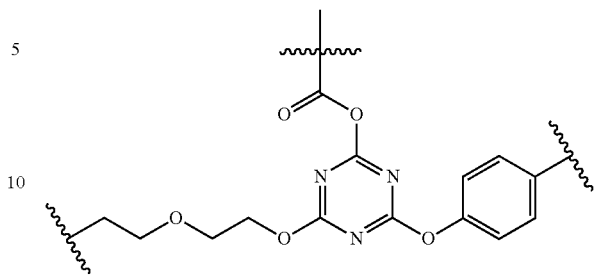

E$^A$ is a first reaction handle. E$^A$ may react with a second reaction handle included in a delivery vehicle to form a conjugate. In some embodiments, E$^A$ is a nucleophile, an electrophile, a leaving group, —OH, —SH, —NHR$^A$, —N$_3$, —C(=O)OH, —C(=NR$^A$)OH, —S(=O)OH, —S(=O)$_2$OH, —C(=O)-(a leaving group), —C(=NR$^A$)-(a leaving group), —S(=O)-(a leaving group), or —S(=O)$_2$-(a leaving group), wherein each instance of R$^A$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom. In some embodiments, E$^A$ is a nucleophile. In certain embodiments, E$^A$ is an electrophile. In some embodiments, E$^A$ is a leaving group. In some embodiments, E$^A$ is —OH or —SH. In some embodiments, E$^A$ is —C(=O)OH, —S(=O)OH, or —S(=O)$_2$OH. In certain embodiment, E$^A$ is —NHR$^A$. In certain embodiments, E$^A$ is an addition polymerization handle. In some embodiments, E$^A$ is alkenyl or alkynyl. In certain embodiments, E$^A$ is a vinyl halide. In some embodiments, E$^A$ is —C≡CH. In some embodiments, E$^A$ is a condensation polymerization handle. In some embodiments E$^A$ is —NH$_2$, —C(=O)OH, or —C(=O)H. In some embodiments E$^A$ is —NH$_2$. In certain embodiments, E$^A$ is a metathesis polymerization handle. In certain embodiments, X is a ring-opening metathesis polymerization handle. In some embodiments, X comprises substituted or unsubstituted, partially unsaturated carbocyclyl. In some embodiments, X comprises substituted or unsubstituted, partially unsaturated heterocyclyl. In some embodiments, E$^A$ is a first click-chemistry handle. In certain embodiments, E$^A$ is a first click-chemistry handle, wherein the first click-chemistry handle is —N$_3$. In certain embodiments, E$^A$ is a first click-chemistry handle, wherein the first click-chemistry handle is —C≡CH. In some embodiments E$^A$ is —OH.

L$^K$ is a first linker. In certain embodiments, L$^K$ is Cleavable. In some embodiments L$^K$ is cleavable by ultraviolet irradiation, hydrolysis, reduction, oxidation, or contacting with an enzyme. In certain embodiments, L$^K$ is cleavable by hydrolysis. In some embodiments, L$^K$ is cleavable by contacting with an enzyme. In some embodiments, L$^K$ is more cleavable than each instance of L$^E$. In some embodiments, L$^K$ is a bond. In some embodiments, L$^K$ is a single bond. In certain embodiments, L$^K$ is a double bond. In certain embodiments, L$^K$ is a substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene, wherein: optionally one or more backbone carbon atoms of each instance of the substituted or unsubstituted alkylene, substituted or unsubstituted alkenylene, substituted or unsubstituted alkynylene, substituted or unsubstituted heteroalkylene, substituted or unsubstituted heteroalkenylene, and substituted or unsubstituted heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more backbone heteroatoms of each instance of the substituted or unsubstituted heteroalkylene, substituted or unsubstituted heteroalkenylene, and substituted or unsubstituted heteroalkynylene are independently replaced with substituted or unsubstituted carbocyclylene, substituted or unsubstituted heterocyclylene, substituted or unsubstituted arylene, or substituted or unsubstituted heteroarylene. In some embodiments, $L^K$ comprises —C(=O)O—, —OC(=O)—, —OC(=O)O—, —S(=O)O—, —OS(=O)—, —OS(=O)O—, —S(=O)$_2$O—, —OS(=O)$_2$—, or —OS(=O)$_2$O—. In certain embodiments, $L^K$ comprises —C(=O)O— or —OC(=O)—. In some embodiments, $L^K$ comprises a polymer. In certain embodiments, $L^K$ comprises a biodegradable polymer. In some embodiments, $L^K$ comprises a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester. In some embodiments, at least one instance of the polymer is polyethylene glycol (PEG). In some embodiments, $L^K$ comprises substituted or unsubstituted polyethylene. In some embodiments, $L^K$ comprises unsubstituted polyethylene. In some embodiments, $L^K$ comprises substituted or unsubstituted polystyrene. In some embodiments, $L^K$ comprises PEG. In some embodiments, $L^K$ comprises

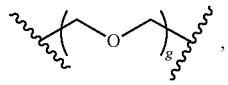

wherein each instance of g is independently an integer from 1 to 200. In certain embodiments, $L^K$ comprises a polymer (e.g., PEG) with a weight-average molecular weight between 200 and 500, between 500 and 1,000, between 1,000 and 2,000, between 2,000 and 5,000, between 5,000 and 10,000, or between 10,000 and 50,000, inclusive, g/mol. In some embodiments, $L^K$ comprises a polymer (e.g., PEG) with the weight average molecular weight between 1,000 and 5,000, inclusive, g/mol. In some embodiments, $L^K$ comprises a polymer (e.g., PEG) with the weight average molecular weight between 2,000 and 5,000, inclusive, g/mol.

In certain embodiments, $L^K$ comprises

wherein:
each instance of q is independently an integer from 1 to 12, inclusive;
each instance of g is independently an integer from 0 to 12, inclusive;

each instance of s is independently 0 or 1;
each instance of t is independently an integer from 0 to 10, inclusive;
each instance of -$L^B$-$L^A$- is independently —C(=O)O—, —OC(=O)—, —OC(=O)O—, —S(=O)O—, —OS(=O)—, —OS(=O)O—, —S(=O)$_2$O—, —OS(=O)$_2$—, or —OS(=O)$_2$O—, a single bond, or —C(=O)NR$^E$—, —NR$^E$C(=O)— wherein each instance of R$^E$ is independently hydrogen, substituted or unsubstituted, C$_{1-6}$ alkyl, or a nitrogen protecting group;
each instance of r is independently an integer from 0 to 12 inclusive;
"**" is attached closer to E$^A$ than V; and
"***" is attached closer to V than E$^A$.

In some embodiments, q is 1. In some embodiments, q is 2, 3, or 4. In certain embodiments q is 5 or 6.

In some embodiments, g is 0. In certain embodiments, g is 1. In some embodiments, g is 2, 3, or 4. In certain embodiments g is 3.

In some embodiments, s is 0. In certain embodiments, s is 1.

In some embodiments, t is 0. In certain embodiments, t is 1. In some embodiments, t is 2, 3, or 4.

In some embodiments r is 0. In certain embodiments, r is 1. In some embodiments, r is 2, 3, or 4.

In certain embodiments, each instance of -$L^B$-$L^A$- is the same. In some embodiments, each instance of -$L^B$-$L^A$- is different. In certain embodiments, some instances of -$L^B$-$L^A$- are the same. In certain embodiments, -$L^B$-$L^A$- is —C(=O)O—, —OC(=O)—, —OC(=O)O—, —S(=O)O—, —OS(=O)—, —OS(=O)O—, —S(=O)$_2$O—, —OS(=O)$_2$—, or —OS(=O)$_2$O—. In certain embodiments, -$L^B$-$L^A$- is independently —C(=O)O—, —OC(=O)—, —C(=O)NR$^E$—, —NR$^E$C(=O)—, or a single bond, wherein each instance of R$^E$ is independently hydrogen, substituted or unsubstituted, C$_{1-6}$ alkyl, or a nitrogen protecting group. In some embodiments -$L^B$-$L^A$- is —C(=O)O—, —OC(=O)—, or —OC(=O)O—. In some embodiments -$L^B$-$L^A$- is a single bond. In some embodiments -$L^B$-$L^A$- is —C(=O)NR$^E$— or —NR$^E$C(=O), wherein each instance of R$^E$ is independently hydrogen, substituted or unsubstituted, C$_{1-6}$ alkyl, or a nitrogen protecting group. In some embodiments -$L^B$-$L^A$- is —C(=O)NR$^E$— or —NR$^E$C(=O), wherein each instance of R$^E$ is hydrogen. In some embodiments -$L^B$-$L^A$- is —C(=O)NR$^E$— or —NR$^E$C(=O), wherein each instance of R$^E$ is methyl, ethyl, or propyl. In some embodiments -$L^B$-$L^A$- is —C(=O)NR$^E$— or —NR$^E$C(=O), wherein each instance of R$^E$ is a nitrogen protecting group.

In some embodiments, -$L^B$-$L^A$- is C(=O)O—, —OC(=O)—, —OC(=O)O—, —S(=O)O—, —OS(=O)—, —OS(=O)O—, —S(=O)$_2$O—, —OS(=O)$_2$—, —OS(=O)$_2$O—, —C(=O)NR$^E$—, —NR$^E$C(=O)—, or a single bond, r is 1, s is 0, g is 3, t is 0, and q is 1.

In certain embodiments, $L^K$ comprises

In some embodiments, r is 1, s is 0, g is 3, t is 0, and q is 1. In certain embodiments, r is 1, s is 0, g is 3, 4, or 5, t is 0, and q is 1. In some embodiments, r is 2, s is 0, g is 3, t is 0, and q is 1. In some embodiments, r is 2, s is 0, g is 3, t is 2, and q is 1.

In certain embodiments, $L^K$ comprises

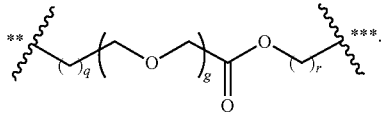

In some embodiments, r is 0, 1, 2, or 3, g is 0, 1, 2, 3, or 4, and q is 0, 1, 2, or 3. In certain embodiments, r is 1, g is 3, and q is 1.

In some embodiments, compounds of the disclosure contain V. In some embodiments, V is N, B, P, $C(R^J)$, $Si(R^J)$, P(=O), substituted or unsubstituted carbocyclyl, substituted or unsubstituted heterocyclyl, substituted or unsubstituted aryl, or substituted or unsubstituted heteroaryl. In some embodiments V is N, B, P, or P(=O). In certain embodiments, V is substituted or unsubstituted carbocyclyl, substituted or unsubstituted heterocyclyl, substituted or unsubstituted aryl, or substituted or unsubstituted heteroaryl. In some embodiments, V is substituted or unsubstituted aryl or substituted or unsubstituted heteroaryl. In some embodiments, V is substituted or unsubstituted aryl selected from the group consisting of substituted or unsubstituted phenyl and substituted or unsubstituted naphthyl. In certain embodiments, V is

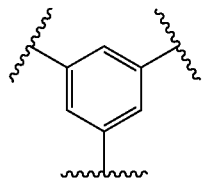

In certain embodiments, V is substituted or unsubstituted pyridinyl, substituted or unsubstituted pyridazinyl, substituted or unsubstituted pyrimidinyl, substituted or unsubstituted pyrazinyl, and substituted or unsubstituted triazinyl (e.g., 1,2,4-triazinyl, 1,3,5-triazinyl). In certain embodiments, V is

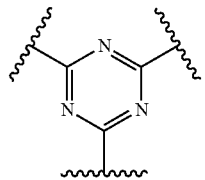

In certain embodiments, $R^J$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or —$OR^A$.

In certain embodiments, V is $C(R^J)$ and $R^J$ is hydrogen. In certain embodiments, V is $C(R^J)$ and $R^J$ is methyl. In certain embodiments, V is $C(R^J)$ and $R^J$ is halogen. In certain embodiments, V is $C(R^J)$ and $R^J$ is —$OR^A$.

In some embodiments, $R^A$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom. In certain embodiments, $R^A$ is hydrogen. In some embodiments, $R^A$ is $C_{1-6}$ alkyl (e.g., methyl, ethyl, propyl, butyl, pentyl, or hexyl). In certain embodiments, $R^A$ is an oxygen protecting group. In certain embodiments, $R^A$ is a nitrogen protecting group.

In certain embodiments, V is $C(R^J)$ and $R^J$ is —$OR^A$ and $R^A$ is hydrogen. In certain embodiments, V is $C(R^J)$ and $R^J$ is —$OR^A$ and $R^A$ is methyl. In certain embodiments, V is $C(R^J)$ and $R^J$ is —$OR^A$ and $R^A$ is halogen.

In some embodiments, compounds of the disclosure contain $L^E$, a second linker. In certain embodiments, $L^E$ is cleavable. In some embodiments, $L^E$ is no cleavable. In certain embodiments, $L^E$ is different than $L^K$. In certain embodiments, each instance of $L^E$ is different than $L^K$. In certain embodiments, each instance of $L^E$ is different. In some embodiments, each instance of $L^E$ is the same.

In certain embodiments, $L^E$ comprises

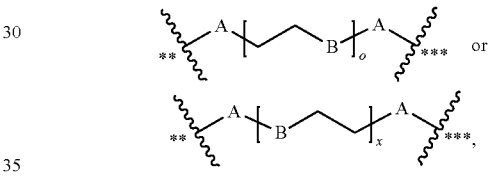

wherein: each instance of A is independently a bond, substituted or unsubstituted alkylene, substituted or unsubstituted alkenylene, substituted or unsubstituted alkynylene, substituted or unsubstituted alkoxylene, substituted or unsubstituted heteroalkylene, substituted or unsubstituted heteroalkenylene, substituted or unsubstituted heteroalkynylene, substituted or unsubstituted carbocyclylene, substituted or unsubstituted heterocyclylene, substituted or unsubstituted aryloxylene, substituted or unsubstituted arylene, substituted or unsubstituted heteroarylene,

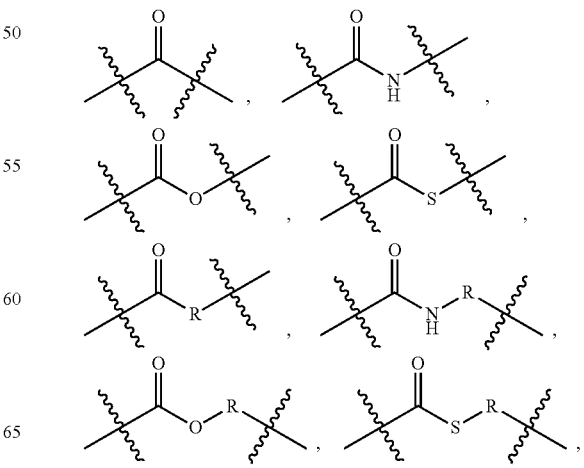

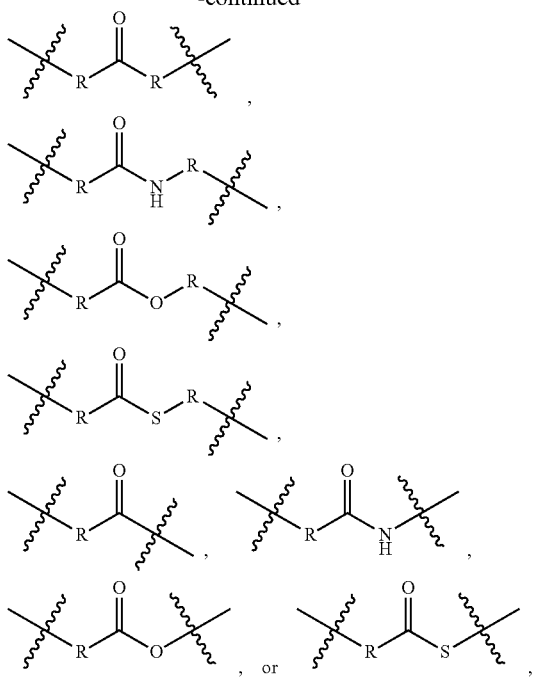

wherein R is an alkylene chain, or an alkylene chain optionally interrupted by —O—, —S—, —N(R')—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclyl, 3- to 12-membered heterocyclyl, 5- to 12-membered aryl, 5- to 12-membered heteroaryl or any combination thereof, wherein R' is H or $C_1$-$C_6$ alkyl;

each instance of B is a bond, optionally substituted C, O, S, optionally substituted N, optionally substituted P, Si, independently substituted or unsubstituted alkylene, substituted or unsubstituted alkenylene, substituted or unsubstituted alkynylene, substituted or unsubstituted alkoxylene, substituted or unsubstituted heteroalkylene, substituted or unsubstituted heteroalkenylene, substituted or unsubstituted heteroalkynylene, substituted or unsubstituted carbocyclylene, substituted or unsubstituted heterocyclylene, substituted or unsubstituted aryloxylene, substituted or unsubstituted arylene, or substituted or unsubstituted heteroarylene;

is an integer between 0 and 100 inclusive;
x is an integer between 0 and 100 inclusive;
"**" is attached closer to V than $M^A$ or $M^B$; and
"***" is attached closer to $M^A$ or $M^B$ than V.

In certain embodiments, each instance of $L^E$ independently comprises

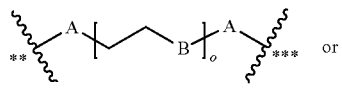  or

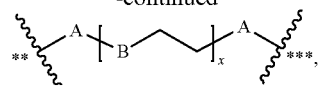

wherein: each instance of A independently is a single bond, C(RD)$_2$, NR$^D$, O, S, substituted or unsubstituted alkoxylene, substituted or unsubstituted aryloxylene, substituted or unsubstituted carbocyclylene, substituted or unsubstituted heterocyclylene, substituted or unsubstituted arylene, or substituted or unsubstituted heteroarylene;

each instance of RD is hydrogen, halogen, substituted or unsubstituted $C_{1-6}$ alkyl, or substituted or unsubstituted $C_{1-6}$ alkoxy;

each instance of B independently is a single bond, C(RD)$_2$, NR$^D$, O, S, substituted or unsubstituted alkoxylene, substituted or unsubstituted aryloxylene, substituted or unsubstituted carbocyclylene, substituted or unsubstituted heterocyclylene, substituted or unsubstituted arylene, or substituted or unsubstituted heteroarylene;

o is an integer between 0 and 30 inclusive;
x is an integer between 0 and 30 inclusive;
"**" is attached closer to V than $M^A$ or $M^B$; and
"***" is attached closer to $M^A$ or $M^B$ than V.

In some embodiments, each instance of $L^E$ independently comprises

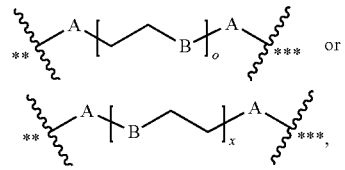

wherein:
each instance of A independently is a single bond, CH$_2$, NH, O, S, substituted or unsubstituted alkoxylene, substituted or unsubstituted aryloxylene;

each instance of B independently is a single bond, CH$_2$, NH, O, S;

o and x are as defined herein;
"**" is attached closer to V than $M^A$ or $M^B$; and
"***" is attached closer to $M^A$ or $M^B$ than V.

In certain embodiments, each instance of A is different. In some embodiments, each instance of A is different. In some embodiments, some instances of the A are the same and some are different. In certain embodiments, A is a bond. In certain embodiments A is a single bond. In some embodiments, A is substituted or unsubstituted alkylene. In some embodiments, A is

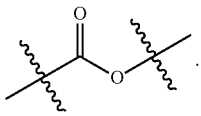 [SMILES: *OC(*)=O]

In certain embodiments, A is

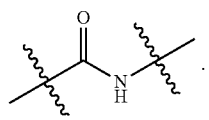 [SMILES: *NC(*)=O]

In some embodiments, A is

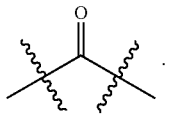 [SMILES: *C(*)=O]

In certain embodiments, A is substituted or unsubstituted arylene. In some embodiments, A is C(R$^D$)$_2$. In some embodiments, A is CH$_2$. In certain embodiments, A is NR$^D$. In some embodiments, A is NH. In some embodiments, A is O. In certain embodiments, A is substituted or unsubstituted alkoxylene. In some embodiments, A is substituted or unsubstituted aryloxylene. In certain embodiments, A is substituted or unsubstituted phenoxylene. In some embodiments, A is

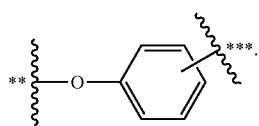

In certain embodiments, A is

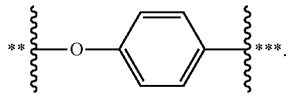 [SMILES: *Oc1ccc(*)cc1]

In some embodiments, R is an alkylene chain. In certain embodiments, R is an alkylene chain interrupted by —O—. In certain embodiments, R is an alkylene chain interrupted by —N(R')—. In certain embodiments, R is an alkylene chain interrupted by —C(O)—, —C(O)O—, or —OC(O)—. In some embodiments, R is an alkylene chain interrupted by a 5- to 12-membered aryl, 5- to 12-membered heteroaryl.

In certain embodiments, R' is hydrogen. In some embodiments, R' is methyl. In certain embodiments, R' is ethyl.

In certain embodiments, each instance of B is different. In some embodiments, each instance of B is different. In some embodiments, some instances of the B are the same and some are different. In certain embodiments, B is a single bond. In some embodiments, B is substituted or unsubstituted alkylene. In some embodiments, B is optionally substituted c. In certain embodiments, B is C(R$^D$)$_2$. In some embodiments, B is CH$_2$. In certain embodiments, B is NR$^D$. In some embodiments, B is NH. In some embodiments, B is O. In some embodiments, B is S.

In certain embodiments, o is 0. In some embodiments, o is 1. In certain embodiments, o is 2, 3, or 4.

In some embodiments, x is 0. In certain embodiments, x is 1. In some embodiments, x is 2, 3, or 4.

In certain embodiments, each instance of L$^E$ independently comprises

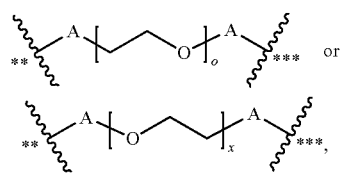

wherein:
each instance of A independently is a single bond, CH$_2$, substituted or unsubstituted phenoxylene;
o and x are as defined herein;
"**" is attached closer to V than M$^A$ or M$^B$; and
"***" is attached closer to M$^A$ or M$^B$ than V.

In certain embodiments, each instance of L$^E$ independently comprises

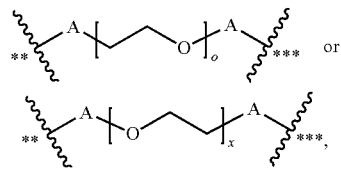

and A is a single bond, CH$_2$,

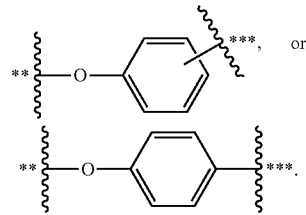

In certain embodiments, each instance of L$^E$ independently comprises

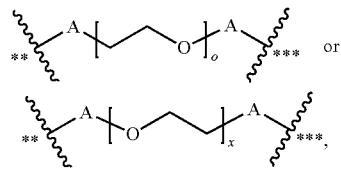

A is a single bond, CH$_2$,

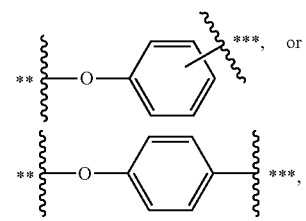

and o or x are 1, 2, or 3.

In some embodiments,

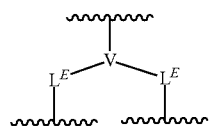

is

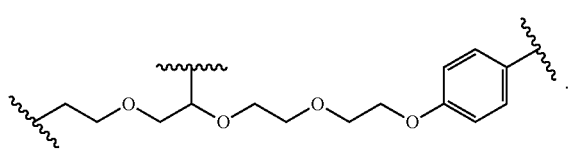 [SMILES: *CCOCC(*)OCCOCCOc1ccc(*)cc1]

In some embodiments,

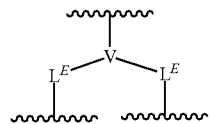

is

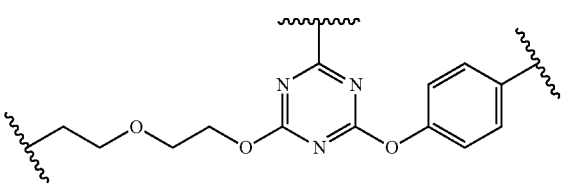

In certain embodiments,

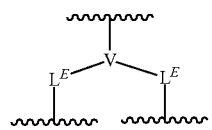

provides a covalent attachment of $M^A$ to $M^B$. In certain embodiments,

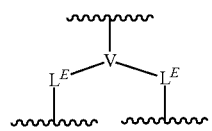

provides a covalent attachment of the BET targeting ligand to the Degron. The structure of

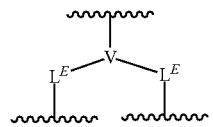

may not be critical, provided it does not substantially interfere with the activity of the targeting ligand or the $M^B$. In some embodiments,

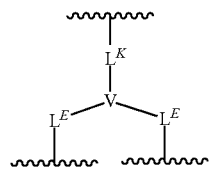

comprises

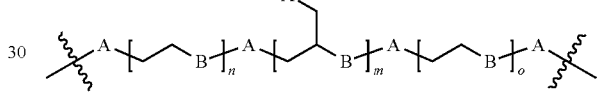

wherein m represents an integer from 1 to 100, inclusive. In certain embodiments,

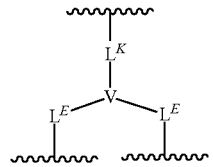

comprises

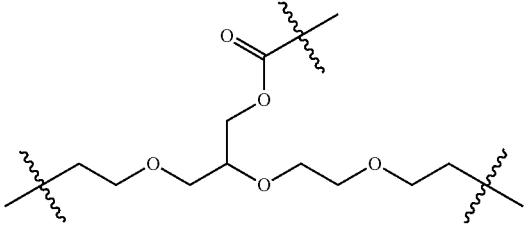

In certain embodiments,

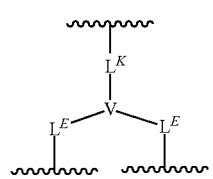

comprises

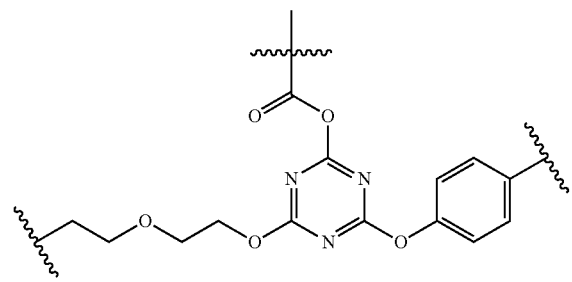

In some embodiments,

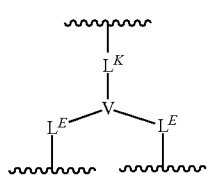

comprises

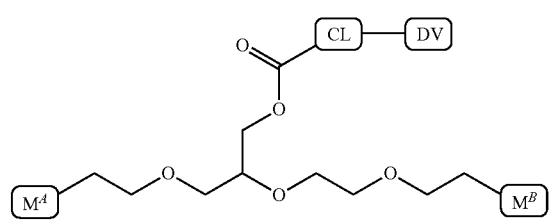

In some embodiments,

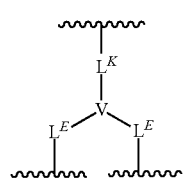

comprises

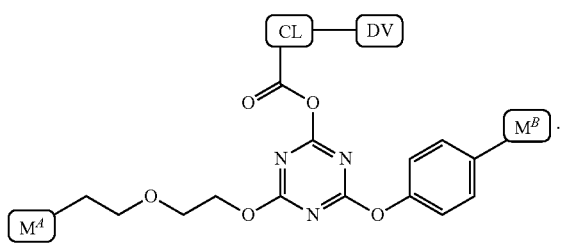

In some embodiments,

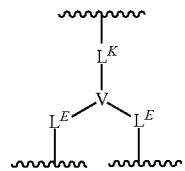

comprises

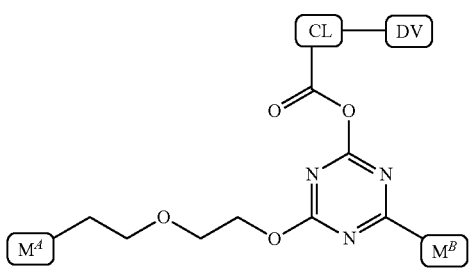

$M^A$ is a protein-binding small molecule (protein binder, e.g., a targeting ligand). In certain embodiments, $M^A$ is a protein-kinase binder. In certain embodiments, $M^A$ is a bromodomain and extra-terminal domain (BET) protein binder. In certain embodiments, $M^A$ is a Bromodomain and Extra-Terminal Domain (BET) protein inhibitor. In certain embodiments, $M^A$ is a BET protein inhibitor, which is a bromodomain protein (BRD) 4 inhibitor. In some embodiments, $M^A$ is a bromodomain protein (BRD) 4 binder. In certain embodiments, $M^A$ is of the formula:

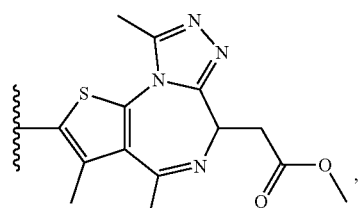

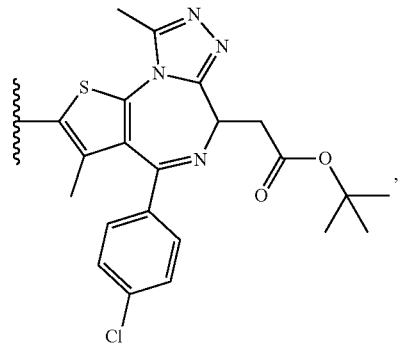

-continued

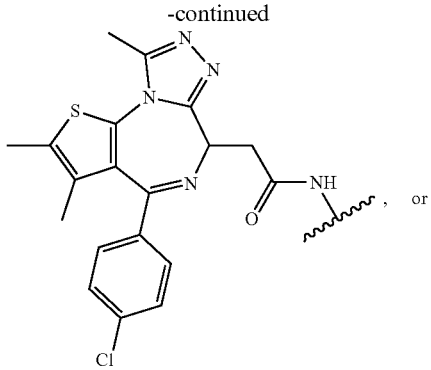

In certain embodiments, $M^A$ is of the formula:

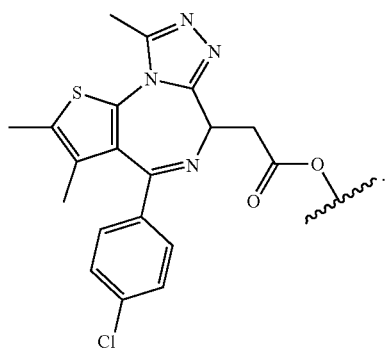

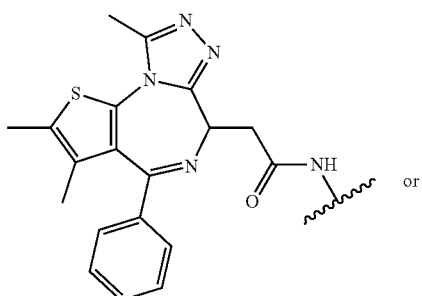

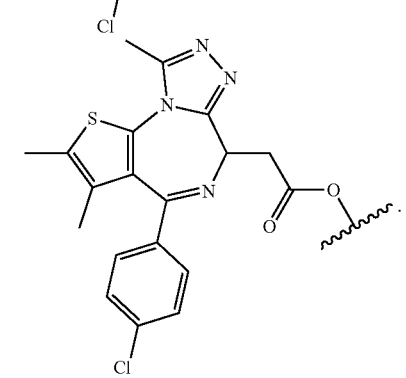

In certain embodiments, $M^A$ is a radical of a compound disclosed in U.S. Patent Application Publication, US 2018/0327419 A1. In certain embodiments, $M^A$ is of Formula TL-I:

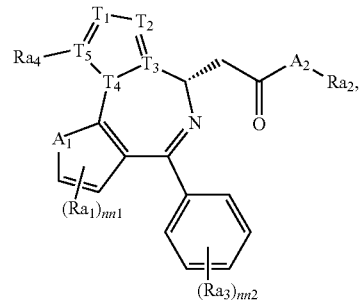

wherein:

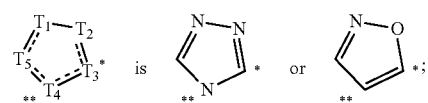

$A_1$ is S or C=C;

$A_2$ is $NRa_5$ or O;

nn1 is 0, 1, or 2;

each $Ra_1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, $C(O)NRa_5L$, OL, $NRa_5L$, or L;

$Ra_2$ is H, $C_1$-$C_6$ alkyl, $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is optionally substituted with $C_1$-$C_3$ alkyl, L, or C(O)L, and wherein the phenyl is optionally substituted with $C_1$-$C_3$ alkyl, CN, halogen, OH, $C_1$-$C_3$ alkoxy, or L;

nn2 is 0, 1, 2, or 3;

each $Ra_3$ is independently $C_1$-$C_3$ alkyl, $(CH_2)_{0-3}$—CN, $(CH_2)_{0-3}$-halogen, L, or $C(O)NRa_5L$;

$Ra_4$ is $C_1$-$C_3$ alkyl or hydrogen;

$Ra_5$ is H or $C_1$-$C_3$ alkyl; and

L is a Linker of Formula L0:

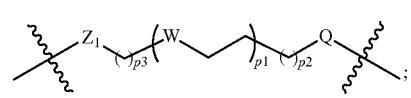

p1 is an integer selected from 0 to 12;

p2 is an integer selected from 0 to 12;

p3 is an integer selected from 1 to 6;

each W is independently absent, $CH_2$, O, S, NH, or $NR_{19}$;

$Z_1$ is absent, $CH_2C(O)NH$, $OCH_2C(O)NH$, $OCH_2C(O)NR_{19}$, $C(O)NH$, $C(O)NR_{19}$, $NHC(O)$, $NR_{19}C(O)$, $CH_2$, O, NH, or $NR_{19}$;

each $R_{19}$ is independently $C_1$-$C_3$ alkyl;

Q is absent or $NHC(O)CH_2$; and the Linker of Formula L0 is covalently bonded to an instance of $L^E$ via the

next to Q;

provided that Formula TL-I comprises only one L.

In certain embodiments, $M^A$ is of Formula TL-I1:

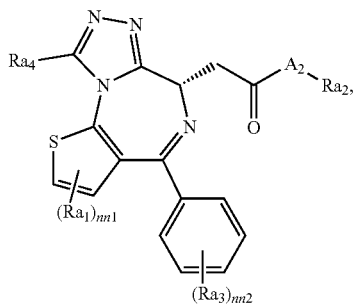

(TL-I1)

or a pharmaceutically acceptable salt thereof, wherein $A_2$, $Ra_1$, $Ra_2$, $Ra_3$, $Ra_4$, $Ra_5$, nn1, and nn2 are each as defined above in Formula TL-I.

The term "binding," "binder," "bind," or "binds" as it relates to interaction between a protein-binding small molecule and a protein, typically refers to an inter-molecular interaction that is substantially specific in that binding of the targeting ligand with other proteinaceous entities present in the cell is functionally insignificant. Binding of the targeting ligand to a bromodomain of a BET protein target may be selective with respect to BET proteins and preferential with respect to various bromodomains contained in a target BET protein. By way of example, JQ1 or an analog thereof, which is disclosed herein as a targeting ligand, exhibits selective binding to bromodomains and preferential binding to BRD4, and less preferential binding to two other members of the BET subfamily of BRD proteins, namely BRD2 and BRD3.

In some embodiments, $M^B$ is referred to as a degron or degrader. In some embodiments, $M^B$ is a functional moiety or ligand that binds an E3 ubiquitin ligase. In some embodiments, $M^B$ binds cereblon (CRBN). In certain embodiments, $M^B$ is of the formula:

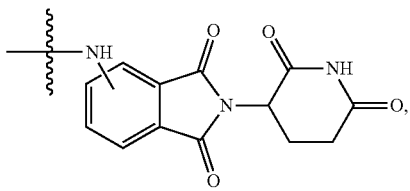

-continued

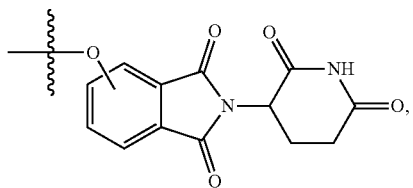

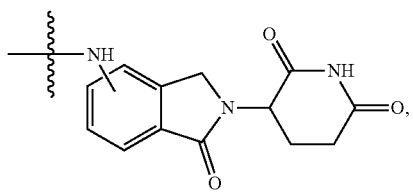

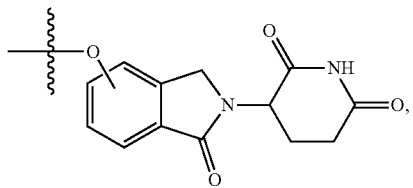

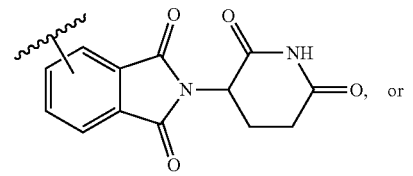
or

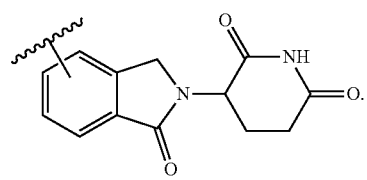

In some embodiments, M$^B$ binds von Hippel Landau tumor suppressor (VHL). In certain embodiments, M$^B$ is of the formula:

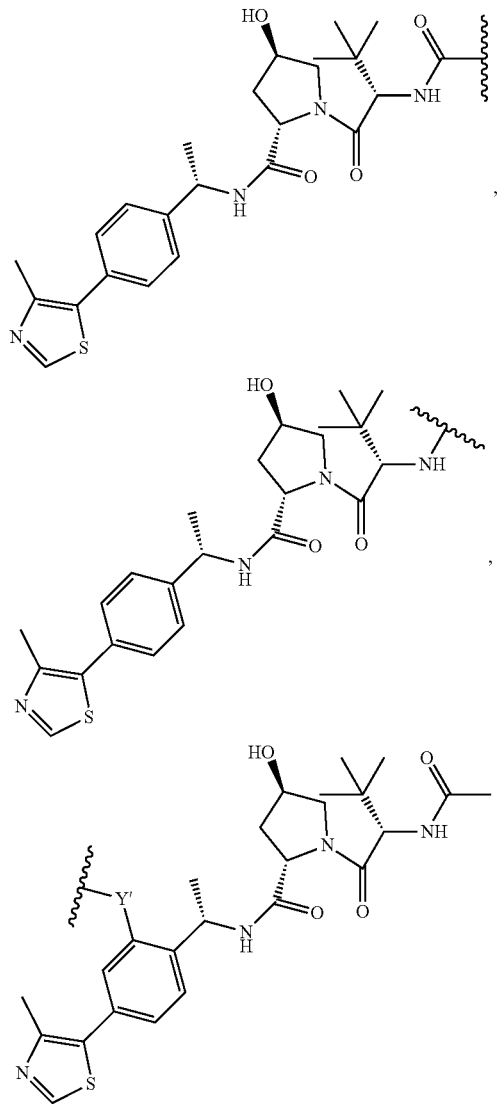

wherein Y' is a single bond, NH, O or CH$_2$,

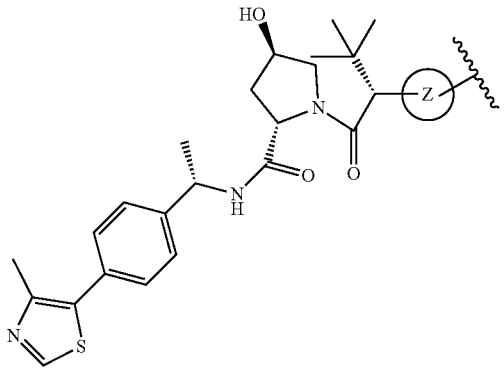

wherein

is a cyclic group, and

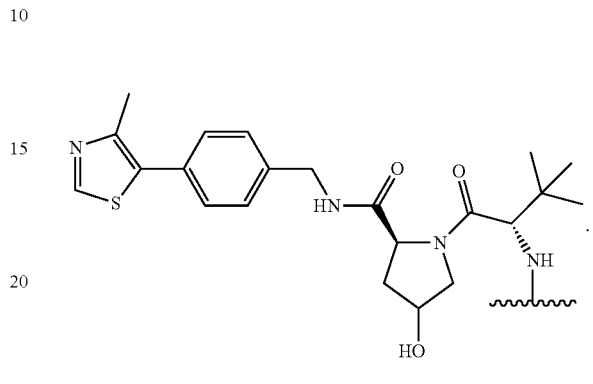

In certain embodiments, Y' is a single bond. In some embodiments, Y' is NH. In some embodiments, Y' is O. In certain embodiments, Y' is CH$_2$. In certain embodiments,

is a substituted or unsubstituted carbocyclylene, substituted or unsubstituted heterocyclylene, substituted or unsubstituted arylene, or substituted or unsubstituted heteroarylene. In certain embodiments,

is a substituted or unsubstituted arylene. Yet other examples of M$^B$ that bind VHL and which may be suitable for use in the present invention are disclosed in U.S. Patent Application Publication 2017/0121321 A1. In some embodiments, the compound of formula (I), or salt thereof, includes M$^B$ that binds cereblon. Representative examples of M$^B$ that bind cereblon are described in U.S. Patent Application Publication 2018/0015085 (e.g., the indolinones such as isoindolinones and isoindoline-1,3-diones embraced by formulae IA ad IA' therein, the bridged cycloalkyl compounds embraced by formulae IB and IB' therein).

The term "binding," "binder," "bind," or "binds" as it relates to interaction between M$^B$ and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

In certain embodiments, a compound of Formula (I) or (I-A), or salt thereof, is of the formula:
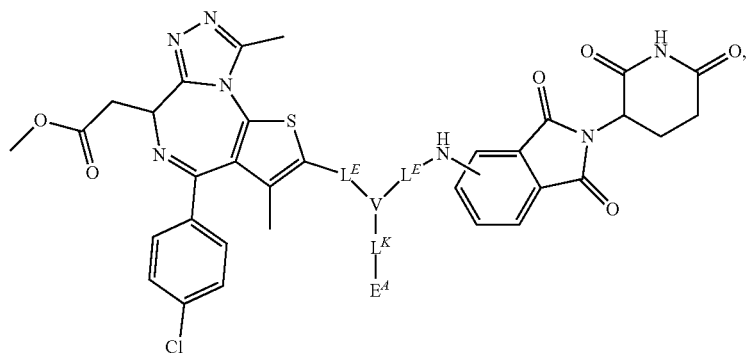
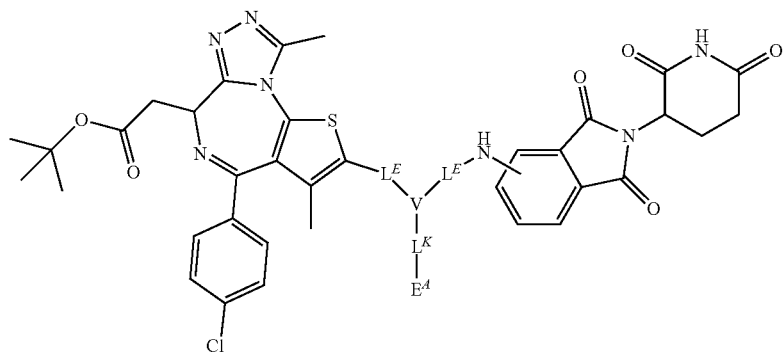
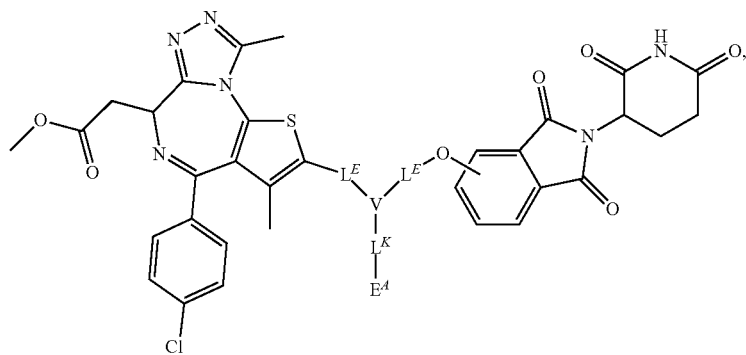
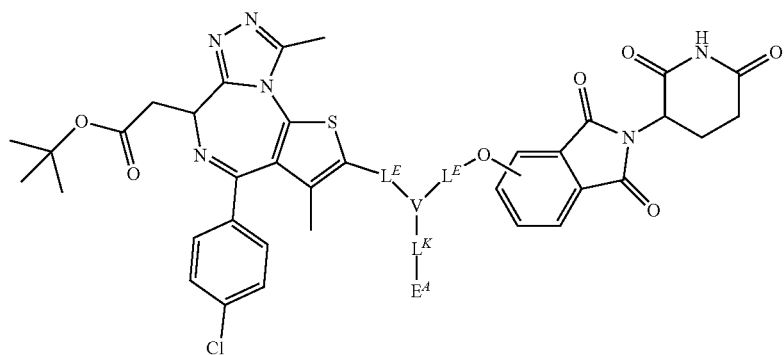

-continued
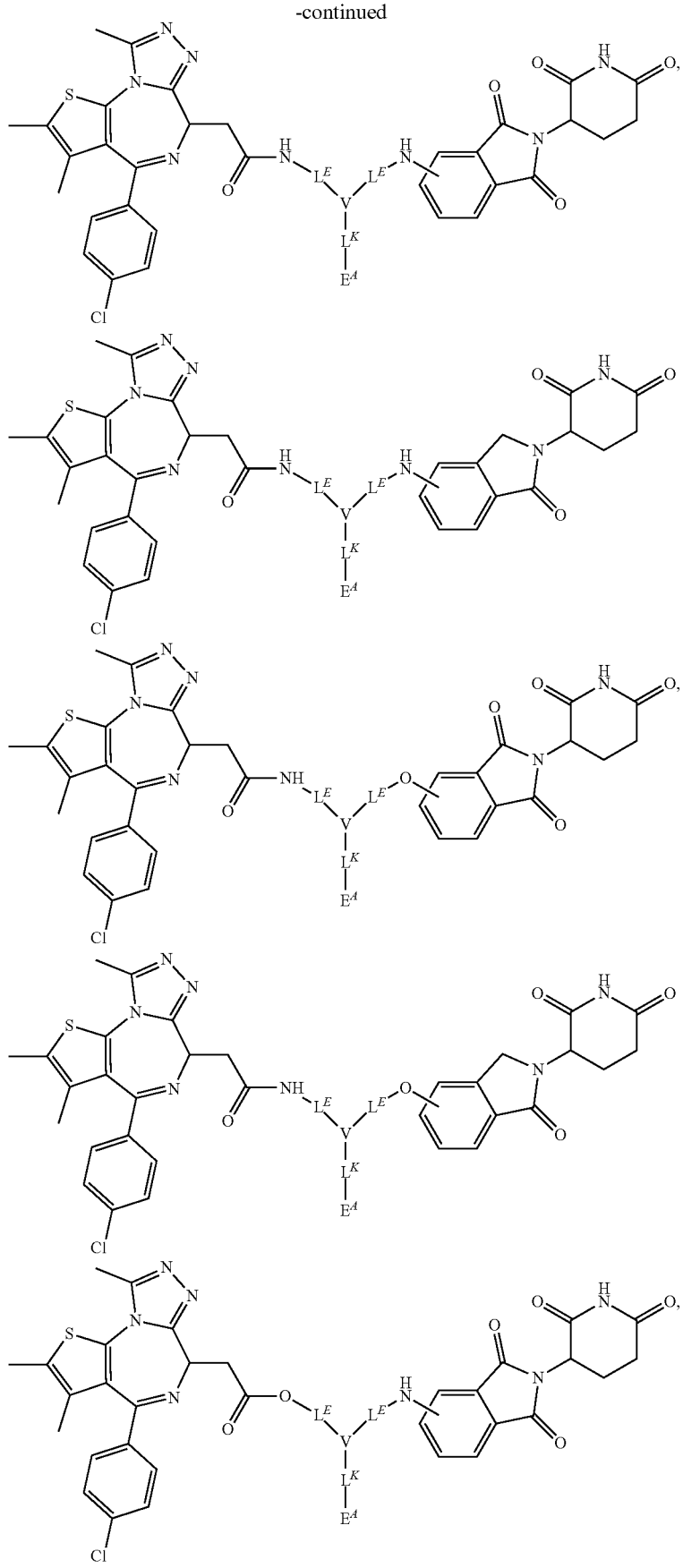

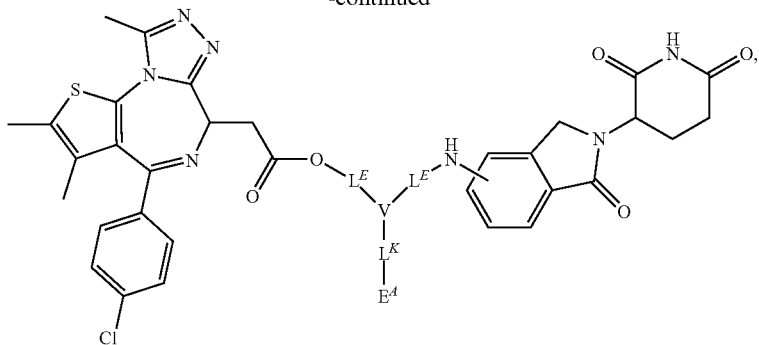
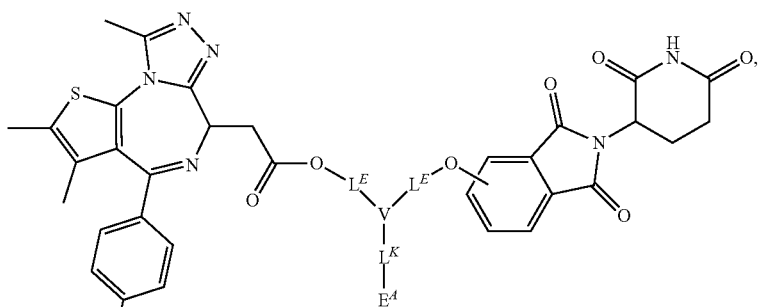
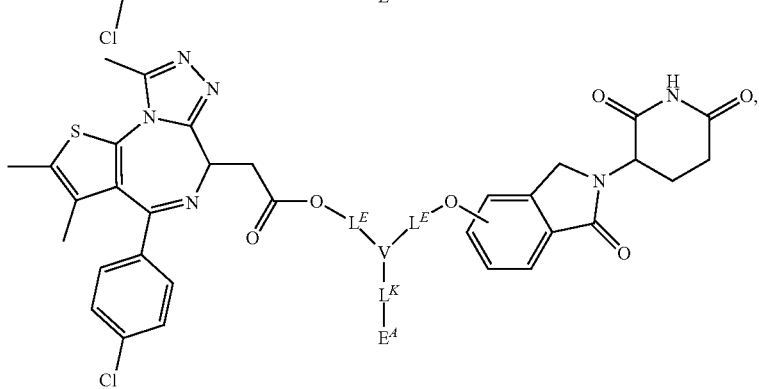
or a pharmaceutically acceptable salt thereof.
In certain embodiments, a compound of Formula (I) or (I-A), or salt thereof, is of the formula:
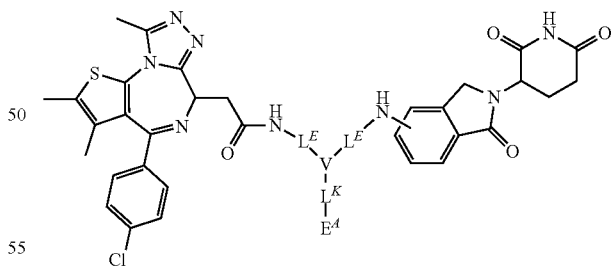
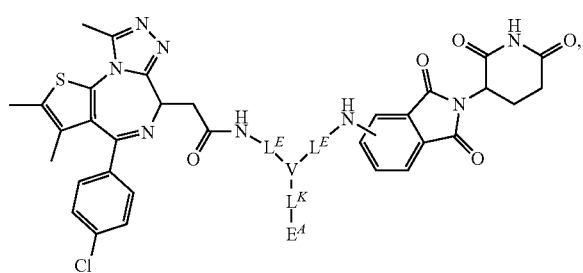
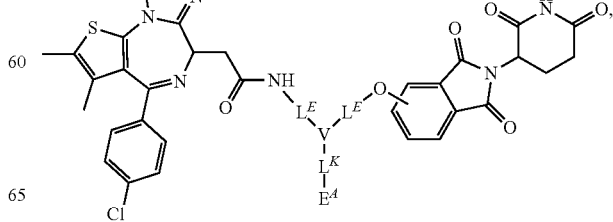

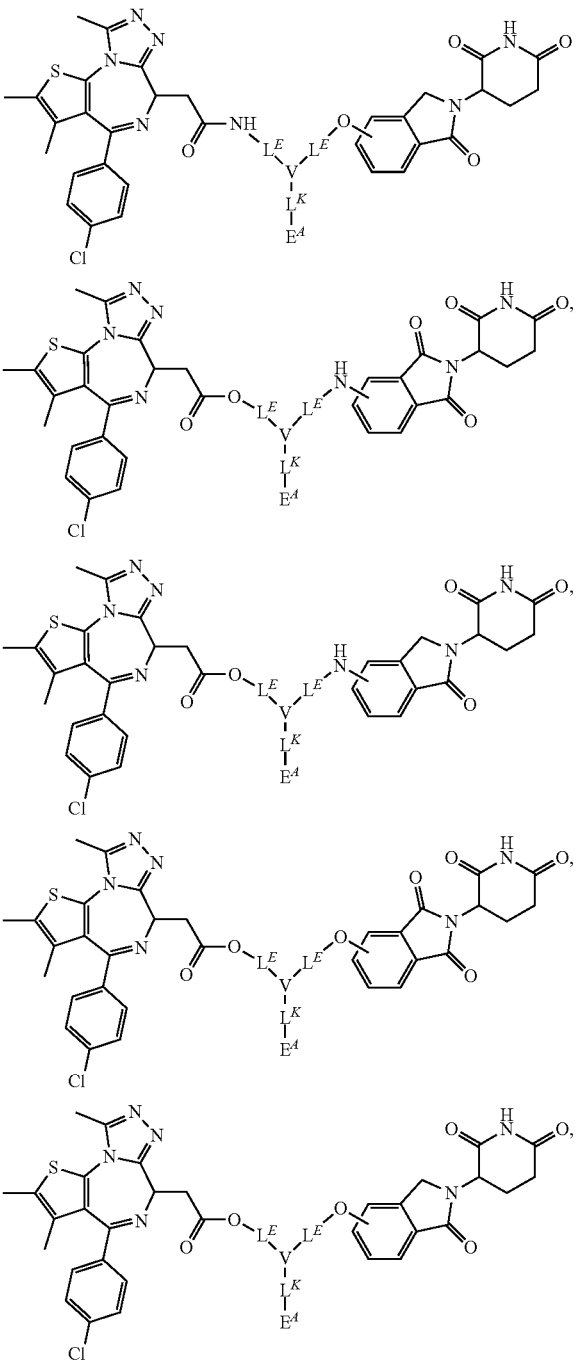

or a pharmaceutically acceptable salt thereof.

In some embodiments, the present disclosure provides conjugates of Formula (II):

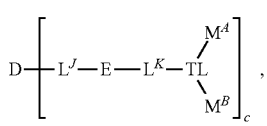

(II)

or a salt thereof, wherein:
D is a polymeric moiety, dendrimeric moiety, antibody, particle, bead, nanostructure, liposome, micelle, or vesicle;
c is an integer between 1 and 1000, inclusive;
L is a third linker;
E is a moiety formed by reacting $E^A$ with $E^B$;
$E^B$ is a second reaction handle, wherein the second reaction handle is able to react with $E^A$; and
$E^A$, $R^A$, $L^K$, V, $L^E$, $M^A$, and $M^B$ are as defined herein.

In certain embodiments, the present disclosure provides conjugates of Formula (II-A):

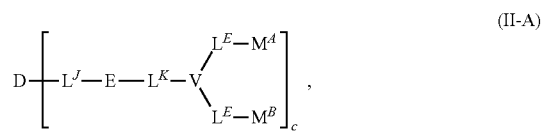

(II-A)

or a salt thereof, wherein:
D is a polymeric moiety, dendrimeric moiety, antibody, particle, bead, nanostructure, liposome, micelle, or vesicle;
c is an integer between 1 and 1000, inclusive;
$L^J$ is a third linker;
E is a moiety formed by reacting $E^A$ with $E^B$;
$E^B$ is a second reaction handle, wherein the second reaction handle is able to react with $E^A$; and
$E^A$, $R^A$, $L^K$, V, $L^E$, $M^A$, and $M^B$ are as defined herein.

In some embodiments, D is a polymeric moiety, dendrimeric moiety, antibody, nanostructure, liposome, micelle, or vesicle. In certain embodiments, D is a polymeric moiety. In some embodiments, D is a brush polymeric moiety. In certain embodiments D is a brush-arm start polymeric moiety. In some embodiments, D is a dendrimeric moiety In some embodiments, D is a particle or bead. In certain embodiments, D is nanostructure (e.g., nanoparticle, nanoflake). In some embodiments, D is a microparticle. In certain embodiments, D is a supraparticle. In some embodiments, D is liposome, micelle, or vesicle. In some embodiments, D is an antibody. In certain embodiments, D is not an antibody. In some embodiments, D facilitates endocytosis delivery of $M^B$, improves bioavailability, and reduces cell toxicity by lowering the concentration of $M^B$ needed for treatment.

In some embodiments, c is 1. In certain embodiments, c is 2. In some embodiments, c is 3, 4, or 5.

In some embodiments, E is a moiety formed by reacting a first click-chemistry handle with a second click-chemistry handle. In some embodiments, E is a triazolyl. In certain embodiments, E is a bond, —O—, —S—, —NR$^A$—, —C(=O)O—, —C(=NR$^A$)O—, —S(=O)O—, —S(=O)$_2$O—, —C(=O)NR$^A$—, —C(=NR$^A$)NR$^A$—, —S(=O) NR$^A$—, —S(=O)$_2$NR$^A$—, —OC(=O)—, —OC (=NR$^A$)—, —OS(=O)—, —OS(=O)$_2$—, —NR$^A$C (=O)—, —NR$^A$C(=NR$^A$)—, —NR$^A$S(=O)—, —NR$^A$S (=O)$_2$—, —OC(=O)O—, —OC(=NR$^A$)O—, —OS(=O) O—, —OS(=O)$_2$O—, —NR$^A$C(=O)O—, —NR$^A$C (=NR$^A$)O—, —NR$^A$S(=O)O—, —NR$^A$S(=O)$_2$O—, —OC(=O)NR$^A$—, —OC(=NR$^A$)NR$^A$—, —OS(=O) NR$^A$—, —OS(=O)$_2$NR$^A$—, —NR$^A$C(=O)NR$^A$—, —NR$^A$C(=NR$^A$)NR$^A$—, —NR$^A$S(=O)NR$^A$—, —NR$^A$S (=O)$_2$NR$^A$—, —C(=O)—, —C(=NR$^A$)—, —S(=O)—, or —S(=O)$_2$—. In some embodiments, E is a bond. In certain embodiments, E is —C(=O)O— or —OC(=O)—. In some embodiments, E is —C(=O)NR$^A$— or —NR$^A$C (=O)—, wherein R$^A$ is hydrogen or methyl.

In certain embodiments, $E^B$ is a second click-chemistry handle. In some embodiments, $E^B$ is —$N_3$. In certain embodiments, $E^B$ is —C≡CH. In some embodiments, $E^B$ is a nucleophile, an electrophile, a leaving group, an alkyne, an alkene, —OH, —SH, —$NHR^B$, —$N_3$, —C(=O)OH, —C(=O)N($R^B$)$_2$, —C(=$NR^B$)OH, —S(=O)OH, —S(=O)$_{20}$H, —C(=O)-(a leaving group), —C(=$NR^B$)-a leaving group), —S(=O)-(a leaving group), or —S(=O)$_{24}$a leaving group); wherein each instance of $R^B$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom. In certain embodiments, $E^B$ is a nucleophile. In some embodiments, $E^B$ is an electrophile. In certain embodiments, $E^B$ is a leaving group. In some embodiments, $E^B$ is —C(=O)OH.

In certain embodiments, $L^J$ is cleavable. In some embodiments $L^J$ is cleavable by ultraviolet irradiation, hydrolysis, reduction, oxidation, or contacting with an enzyme. In certain embodiments, $L^J$ is cleavable by hydrolysis. In some embodiments, $L^K$ is Cleavable by contacting with an enzyme. In some embodiments, $L^J$ is more cleavable than each instance of $L^E$. In some embodiments, $L^J$ is a bond. In some embodiments, $L^J$ is a single bond. In certain embodiments, $L^J$ is a double bond. In some embodiments, $L^J$ is a substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene, wherein: optionally one or more backbone carbon atoms of each instance of the substituted or unsubstituted alkylene, substituted or unsubstituted alkenylene, substituted or unsubstituted alkynylene, substituted or unsubstituted heteroalkylene, substituted or unsubstituted heteroalkenylene, and substituted or unsubstituted heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more backbone heteroatoms of each instance of the substituted or unsubstituted heteroalkylene, substituted or unsubstituted heteroalkenylene, and substituted or unsubstituted heteroalkynylene are independently replaced with substituted or unsubstituted carbocyclylene, substituted or unsubstituted heterocyclylene, substituted or unsubstituted arylene, or substituted or unsubstituted heteroarylene. In some embodiments $L^J$ is a bond, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene. In some embodiments, $L^J$ is a substituted or unsubstituted alkylene. In some embodiments, $L^J$ is a substituted or unsubstituted $C_1$-$C_6$alkylene. In certain embodiments, $L^J$ is $CH_2$. In some embodiments, $L^J$ is a substituted or unsubstituted heteroalkylene. In some embodiments, $L^J$ is a substituted or unsubstituted $C_1$-$C_6$ heteroalkylene. In some embodiments, $L^J$ is a substituted or unsubstituted $C_1$-$C_6$heteroalkylene comprising oxygen. In some embodiments, $L^J$ is $OCH_2$ or $CH_2O$.

In some embodiments, the delivery of the conjugate, or a salt thereof, to a subject, biological sample, tissue, or cell is increased as compared to the delivery of a compound of the formula:

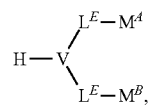

or a salt thereof, to the subject, biological sample, tissue, or cell. In some embodiments, the amount of conjugated delivered is increased. In some embodiments, the amount of conjugated delivered is increased by >1, 1.5, 2, 3, 4, 10, 100, or 1000 fold. In some embodiments, the amount of conjugated delivered over time is increased. In some embodiments, the amount of conjugated delivered over time is increased by >1, 1.5, 2, 3, 4, 10, 100, or 1000 fold.

In some aspects, the present disclosure provides macromonomers of Formula (III-A) or (III-B):

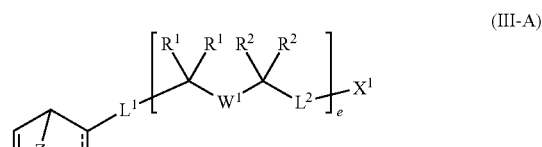
(III-A)

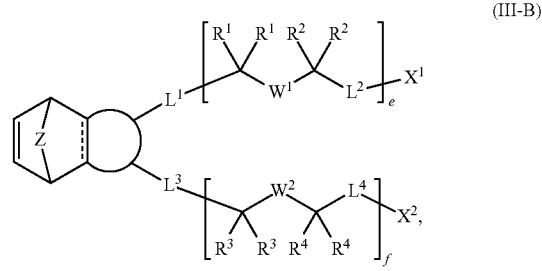
(III-B)

or a salt thereof, wherein:

each instance of
is Ring B, wherein each instance of Ring B is independently a substituted or unsubstituted, monocyclic carbocyclic ring, substituted or unsubstituted, monocyclic heterocyclic ring, substituted or unsubstituted, monocyclic aryl ring, or substituted or unsubstituted, monocyclic heteroaryl ring;

each instance of Z is independently $C(R^P)_2$ or O;

each instance of $R^P$ is independently hydrogen, halogen, or substituted or unsubstituted alkyl;

each instance of ===== is independently a single bond or double bond;

each instance of $L^1$, $L^2$, $L^3$, and $L^4$ is independently a single bond, substituted or unsubstituted alkylene, substituted or unsubstituted alkenylene, substituted or unsubstituted alkynylene, substituted or unsubstituted heteroalkylene, substituted or unsubstituted heteroalkenylene, or $C_{2-200}$ heteroalkynylene;

each instance of $R^1$, $R^2$, $R^3$, and $R^4$ is independently hydrogen, halogen, or substituted or unsubstituted alkyl, or two instances of $R^1$ attached to the same carbon atom are taken together to form oxo, or two instances of $R^2$ attached to the same carbon atom are taken together to form oxo, or two instances of $R^3$ attached to the same carbon atom are taken together to form oxo, or two instances of $R^4$ attached to the same carbon atom are taken together to form oxo;

each instance of $W^1$ and $W^2$ is independently a single bond,

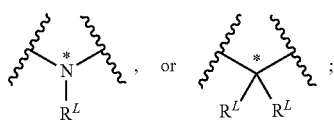

each instance of $R^L$ is independently hydrogen, a nitrogen protecting group when attached to a nitrogen atom, or

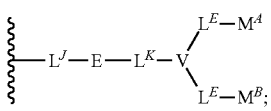

each instance of e and f is independently an integer between 0 and 10, inclusive;

each instance of $X^1$ and $X^2$ is independently hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, —$OR^C$, —$N(R^C)_2$, —$C(\!=\!O)R^C$, —$C(\!=\!O)OR^C$, —$C(\!=\!O)N(R^C)_2$, —$NR^CC(\!=\!O)R^C$, —$NR^CC(\!=\!O)OR^C$, —$NR^CC(\!=\!O)N(R^C)_2$, —$OC(\!=\!O)R^C$, —$OC(\!=\!O)OR^C$, or —$OC(\!=\!O)N(R^C)_2$;

each instance of $R^C$ is independently hydrogen, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, a leaving group, an oxygen protecting group when attached to an oxygen atom, a nitrogen protecting group when attached to a nitrogen atom,

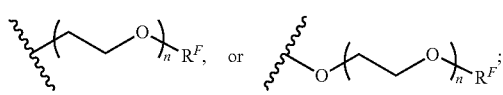

each instance of n is independently an integer between 1 and 300, inclusive; and each instance of $R^F$ is independently hydrogen, substituted or unsubstituted alkyl, or an oxygen protecting group;

or

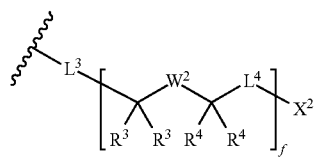

is hydrogen or absent, as valency permits;

provided that at least one instance of $R^L$ is

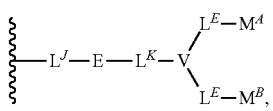

wherein $L^J$, E, $R^A$, $L^K$, V, $L^E$, $M^A$, and $M^B$ are as defined herein.

In some embodiments, $L^3$ is a single bond, f is 0 and $X^2$ is hydrogen in a macromonomer of Formula (III-A) or (III-B).

In certain embodiments, a macromonomer of Formula (III-A) or (III-B) is of formula:

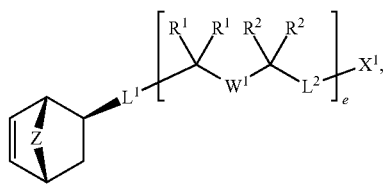

or salt thereof. In some embodiments, a macromonomer of Formula (III-A) or (III-B) is of formula:

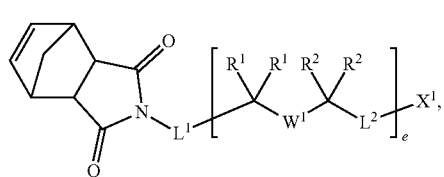

or salt thereof.

In certain embodiments, a macromonomer of Formula (III-A) or (III-B) is of formula:

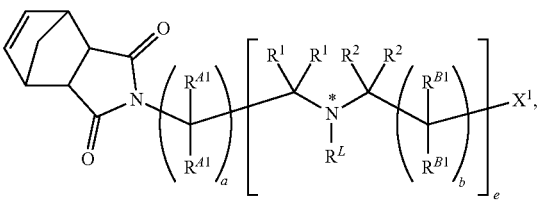

or a salt thereof, wherein: each instance of $R^{A1}$ is independently hydrogen, halogen, or substituted or unsubstituted, $C_{1-6}$ alkyl; a is an integer between 1 and 20, inclusive; each instance of $R^{B1}$ is independently hydrogen, halogen, or substituted or unsubstituted, $C_{1-6}$ alkyl; each instance of b is independently an integer between 1 and 20, inclusive; and e is an integer between 1 and 10, inclusive.

In some embodiments, a macromonomer of Formula (III-A) or (III-B) is of formula:

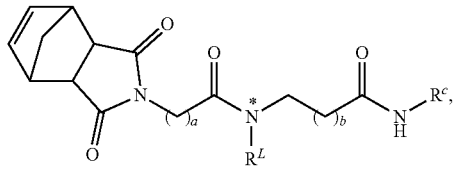

or salt thereof. In some embodiments a is an integer from 1 to 7, inclusive and b is an integer from 1 to 3, inclusive.

In certain embodiments, a macromonomer of Formula (III-A) or (III-B) is of formula:

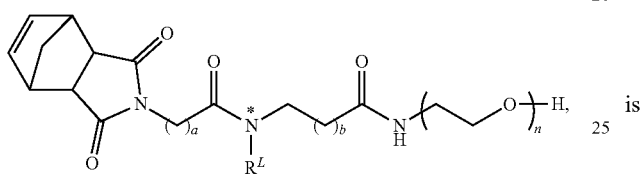

or salt thereof. In some embodiments a is an integer from 1 to 7, inclusive, b is an integer from 1 to 3, inclusive, and n is an integer from 50 to 75 inclusive.

In certain embodiments, n is an integer from 10 to 200, 20 to 150, 20 to 100, 30 to 100, or 50 to 75, inclusive.

In some embodiments, a macromonomer of Formula (III-A) or (III-B) is of formula:

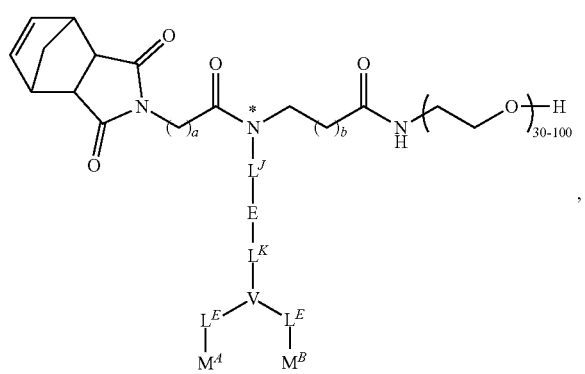

or salt thereof.

In certain embodiments, each instance

is Ring B, wherein each instance of Ring B is independently unsubstituted, monocyclic aryl ring, or substituted or unsubstituted, monocyclic heteroaryl ring. In certain embodiments, at least one instance of Ring B is a substituted or unsubstituted, monocyclic heterocyclic ring. In certain embodiments, at least one instances of Ring B is a substituted or unsubstituted, 5-membered monocyclic heterocyclic ring. In certain embodiments, at least one instance of Ring B is

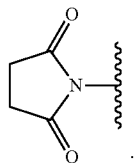 [SMILES: *N1C(=O)CCC1=O]

In certain embodiments, at least one instance of

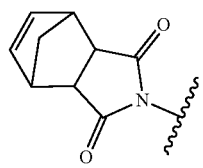 [SMILES: *N1C(=O)C2C3C=CC(C3)C2C1=O]

is

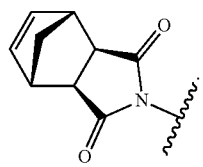

In certain embodiments, each instance of

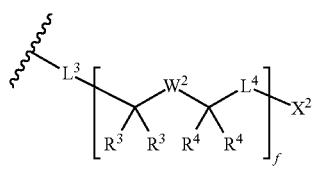

is hydrogen or absent, as valency permits.

In certain embodiments, at least one instance of Z is $C(R^P)_2$. In certain embodiments at least one instance of Z is $CH_2$. In certain embodiments, at least one instance of Z is O.

In certain embodiments, each instance of $R^P$ is hydrogen. In certain embodiments, at least one instance of $R^P$ is hydrogen. In certain embodiments, at least one instance of $R^P$ is halogen. In certain embodiments, at least one instance of $R^P$ is unsubstituted, $C_{1-6}$ alkyl or $C_{1-6}$ alkyl substituted with one or more halogen. In certain embodiments, at least one instance of $R^P$ is unsubstituted methyl.

In certain embodiments, at least one instance of ==== is a single bond. In certain embodiments, at least one instance of ==== is a double bond.

In certain embodiments, at least one instance of $L^1$, $L^2$, $L^3$, and $L^4$ is a single bond. In certain embodiments, at least one instance of $L^1$ is substituted or unsubstituted, $C_{1-20}$ alkylene. In certain embodiments, at least one instance of $L^2$ is substituted or unsubstituted, $C_{1-20}$ alkylene. In certain embodiments, at least one instance of $L^1$ is substituted or unsubstituted, $C_{2-20}$ heteroalkylene. In certain embodiments, at least one instance of $L^2$ is substituted or unsubstituted, $C_{2-20}$ heteroalkylene. In certain embodiments, at least one instance of $L^3$ is hydrogen. In certain embodiments, at least one instance of $L^4$ is hydrogen.

In certain embodiments, each instance of $R^1$, $R^2$, $R^3$, and $R^4$ is hydrogen. In certain embodiments, at least two instances of $R^1$ attached to the same carbon atom are taken together to form oxo. In certain embodiments, at least two instances of $R^2$ attached to the same carbon atom are taken together to form oxo. In certain embodiments, at least two instances of $R^3$ attached to the same carbon atom are taken together to form oxo. In certain embodiments, at least two instances of $R^4$ attached to the same carbon atom are taken together to form oxo. In certain embodiments, at least one instance of $R^1$, $R^2$, $R^3$, and $R^4$ is hydrogen. In certain embodiments, at least two instances of $R^1$ attached to the same carbon atom are each hydrogen. In certain embodiments, at least two instances of $R^2$ attached to the same carbon atom are each hydrogen. In certain embodiments, at least two instances of $R^1$ attached to the same carbon atom are taken together to form oxo, and at least two instances of $R^2$ attached to the same carbon atom are each hydrogen. In certain embodiments, at least two instances of $R^2$ attached to the same carbon atom are taken together to form oxo, and at least two instances of $R^1$ attached to the same carbon atom are each hydrogen. In certain embodiments, at least one instance of $R^1$, $R^2$, $R^3$, and $R^4$ is halogen (e.g., F). In certain embodiments, at least one instance of $R^1$, $R^2$, $R^3$, and $R^4$ is unsubstituted $C_{1-6}$ alkyl. In certain embodiments, at least one instance of $R^1$, $R^2$, $R^3$, and $R^4$ is substituted $C_{1-6}$ alkyl.

In certain embodiments, at least one instance of $W^1$ or $W^2$ is a single bond. In certain embodiments, at least one instance of $W^1$ or $W^2$ is

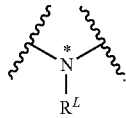

In certain embodiments, each instance of $W^1$ is

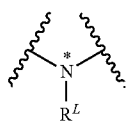

In certain embodiments, at least one instance of $W^1$ or $W^2$ is

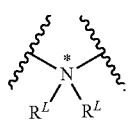

In certain embodiments, at least one instance of $R^L$ is hydrogen. In certain embodiments, at least one instance of $R^L$ is a nitrogen protecting group when attached to a nitrogen atom. In certain embodiments, at least one instance of $R^L$ is

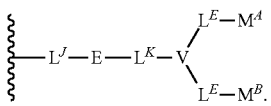

In certain embodiments, each instance of $R^L$ is

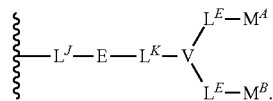

In certain embodiments, wherein at least one instance of $R^L$ comprises one or more reacted click-chemistry handles. In certain embodiments, wherein at least one instance of $R^L$ comprises one or more instances of reacted —C≡CH. In certain embodiments, wherein each instance of $R^L$ comprises one or more (e.g., 2 or 3) instances of reacted —C≡CH. In certain embodiments, wherein at least one instance of $R^L$ comprises an amino acid or a peptide. In certain embodiments, wherein at least one instance of $R^L$ is cleavable by ultraviolet irradiation, hydrolysis, reduction, oxidation, or contacting with an enzyme. In certain embodiments, wherein each instance of $R^L$ is cleavable by hydrolysis or contacting with an enzyme.

In certain embodiments, wherein at least one instance of -$L^J$-E-$L^K$- comprises substituted or unsubstituted, $C_{2-50}$ heteroalkylene, wherein: one or more carbon atoms and/or one or more heteroatoms, of the substituted or unsubstituted, $C_{2-50}$ heteroalkylene are replaced with

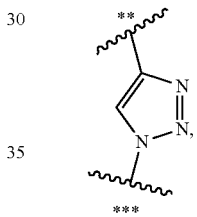

wherein "**" is attached closer to the nitrogen atom labeled "*" than V, and "***" is attached closer to V than the nitrogen atom labeled "*"; and optionally one or more carbon atoms and/or one or more heteroatoms, of the $C_{2-50}$ heteroalkylene are independently replaced with substituted or unsubstituted phenylene.

In certain embodiments, wherein at least one instance of -$L^J$-E-$L^K$- comprises $C_{2-50}$ heteroalkylene, wherein: the $C_{2-50}$ heteroalkylene is unsubstituted or substituted with one or more substituents independently selected from the group consisting of halogen, unsubstituted $C_{1-6}$ alkyl, and oxo; one or more carbon atoms and/or one or more heteroatoms, of the $C_{2-50}$ heteroalkylene are replaced with

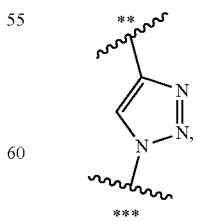

wherein "**" is attached closer to the nitrogen atom labeled "*" than V, and "***" is attached closer to V than the nitrogen atom labeled "*"; and optionally one or more carbon atoms and/or one or more heteroatoms, of the $C_{2-50}$ heteroalkylene are independently replaced with substituted or unsubstituted phenylene.

In certain embodiments, at least one instance of $-L^J-E-L^K-$ comprises a substituted or unsubstituted, $C_{2-200}$ alkynylene. In certain embodiments, at least one instance of $-L^J-E-L^K-$ comprises a substituted or unsubstituted, $C_{2-200}$ heteroalkynylene. In certain embodiments, at least one instance of $-L^J-E-L^K-$ comprises a substituted or unsubstituted, $C_{2-200}$ heteroalkylene, wherein one or more carbons and/or one or more heteroatoms, of the substituted or unsubstituted, $C_{2-200}$ heteroalkylene, are independently replaced with substituted or unsubstituted heteroarylene. In certain embodiments, at least one instance of $-L^J-E-L^K-$ comprises a substituted or unsubstituted, $C_{2-200}$ heteroalkylene, wherein one or more carbons and/or one or more heteroatoms, of the substituted or unsubstituted, $C_{2-200}$ heteroalkylene, are independently replaced with

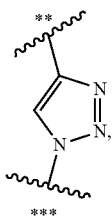 [SMILES: *c1cn(*)nn1]

wherein "**" is attached closer to the nitrogen atom labeled "*" than V, and "***" is attached closer to V than the nitrogen atom labeled "*". In certain embodiments, at least one instance of $-L^J-E-L^K-$ comprises a substituted or unsubstituted, $C_{2-200}$ heteroalkylene, wherein one carbon or one heteroatom, of the substituted or unsubstituted, $C_{2-200}$ heteroalkylene, is replaced with

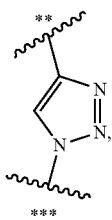

wherein the nitrogen atom labeled with "*" is closer to the attachment point labeled with "" than the attachment point labeled with "*".

In certain embodiments, at least one instance of $-L^J-E-L^K-$ comprises

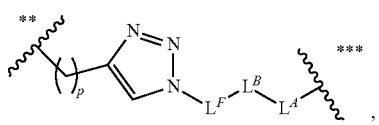

wherein: each instance of p is independently an integer from 1 to 10, inclusive; each instance of $L^F$ is independently substituted or unsubstituted, $C_{2-180}$ heteroalkylene; each instance of $-L^B-L^A-$ is independently $-C(=O)O-$, $-OC(=O)-$, $-C(=O)NR^E-$, $-NR^EC(=O)-$, or a single bond wherein each instance of $R^E$ is independently hydrogen, substituted or unsubstituted, $C_{1-6}$ alkyl, or a nitrogen protecting group; wherein "**" is attached closer to the nitrogen atom labeled "*" than V, and "***" is attached closer to V than the nitrogen atom labeled "*". In certain embodiments, $-L^J-E-L^K-$ is

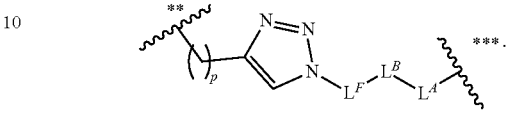

In certain embodiments, at least one instance of $-L^J-E-L^K-$ comprises

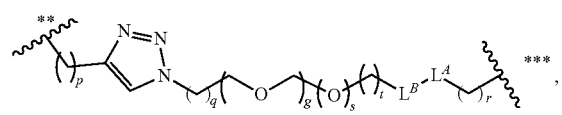

each instance of p is independently an integer from 1 to 12, inclusive; each instance of q is independently an integer from 1 to 12, inclusive; each instance of g is independently an integer from 0 to 12, inclusive; each instance of s is independently 0 or 1; each instance of t is independently an integer from 0 to 10, inclusive; each instance of $-L^B-L^A-$ is independently $-C(=O)O-$, $-OC(=O)-$, $-C(=O)NR^E-$, $-NR^EC(=O)-$, or a single bond, wherein each instance of $R^E$ is independently hydrogen, substituted or unsubstituted, $C_{1-6}$ alkyl, or a nitrogen protecting group; each instance of r is independently an integer from 0 to 12 inclusive; "**" is attached closer to the nitrogen atom labeled "*" than V and "***" is attached closer to V than the nitrogen atom labeled "*". In certain embodiments, $-L^J-E-L^K-$ is

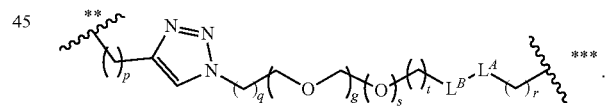

In certain embodiments, at least one instance of $-L^J-E-L^K-$ comprises

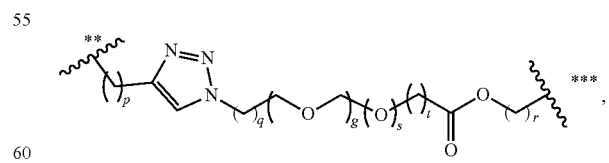

wherein: p, q, g, s, t, and r are as defined herein; "**" is attached closer to the nitrogen atom labeled "*" than V, and "***" is attached closer to V than the nitrogen atom labeled "*". In certain embodiments, $-L^J-E-L^K-$ is

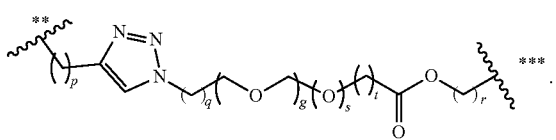

In certain embodiments, at least one instance of -L$^J$-E-L$^K$- comprises

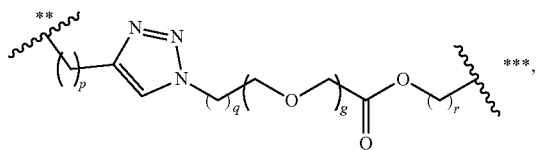

wherein: p, q, g, and r are as defined herein; "*" is attached closer to the nitrogen atom labeled "" than V, and "*" is attached closer to V than the nitrogen atom labeled "*". In certain embodiments, -L$^J$-E-L$^K$- is

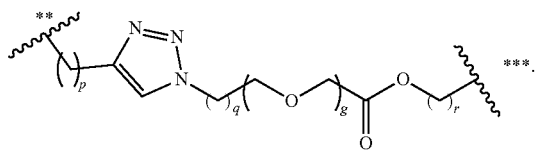

In certain embodiments p is 1. In certain embodiments, p is 2. In some embodiments, p is 3. In some embodiments, p is 4.

In certain embodiments q is 1. In certain embodiments, q is 2. In certain embodiments, q is 3. In some embodiments, q is 4.

In some embodiments, g is 2. In certain embodiments, g is 3. In certain embodiments, g is 4. In certain embodiments, g is 5.

In certain embodiments r is 0. In certain embodiments r is 1. In certain embodiments, r is 2. In some embodiments, r is 3. In some embodiments, r is 4.

In some embodiments, p is 1 and q is 1. In certain embodiments, p is 1, q is 1, and g is 3. In some embodiments, p is 1, q is 1, and r is 1. In certain embodiments, p is 1, q is 1, g is 3, and r is 1.

In certain embodiments, at least two instances of -L$^J$-E-L$^K$- are different from each other. In certain embodiments, all instances of -L$^J$-E-L$^K$- are different from each other. In certain embodiments, all instances of -L$^J$-E-L$^K$- are the same.

In certain embodiments, at least one instance of -L$^J$-E-L$^K$- comprises a polymer chain. In some embodiments, at least one instance of the polymer chain is a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester. In some embodiments, at least one instance of the polymer chain is polyethylene glycol (PEG). In some embodiments, the PEG has a molecular weight of between about 100 and about 6000 g/mol (e.g., PEG$_{100}$, PEG$_{200}$, PEG$_{300}$, PEG$_{600}$, PEG$_{800}$, PEG$_{1000}$, PEG$_{1500}$, PEG$_{2000}$, PEG$_{3000}$, PEG$_{4000}$, or PEG$_{6000}$). In some embodiments, the PEG is PEG$_{100}$. In some embodiments, the PEG is PEG200. In some embodiments, the PEG is PEG$_{400}$. In some embodiments, the PEG is PEG$_{600}$. In some embodiments, the PEG is PEG$_{800}$. In some embodiments, the PEG is PEG$_{1000}$. In some embodiments, the PEG is PEG$_{2000}$. In some embodiments, the PEG is PEG$_{3000}$. In some embodiments, the PEG is PEG$_{4000}$. In some embodiments, the PEG is PEG$_{6000}$.

In some embodiments, L$^J$ comprises a cleavable linker. In some embodiments, L$^K$ comprises a cleavable linker. In some embodiments, L$^E$ comprises a cleavable linker. In some embodiments, L$^J$ is a cleavable linker. In some embodiments, L$^K$ is a cleavable linker. In some embodiments, L$^E$ is a cleavable linker. In certain embodiments, "the cleavable linker" refers to any of L$^J$, L$^K$, and L$^E$.

In some embodiments, the cleavable linker (e.g., L, L$^K$, L$^E$) is cleavable by or is sensitive to an enzyme (e.g., an esterase or a protease), pH (e.g., acidic pH, basic pH), light (e.g., ultraviolet light), a nucleophile, reduction, or oxidation. In some embodiments, the cleavable linker is cleavable by or is sensitive to an enzyme (e.g., an esterase or a protease) or pH (e.g., acidic pH, basic pH). In some embodiments, the cleavable linker is not cleavable by light (e.g., ultraviolet light).

In some embodiments, the cleavable linker comprises an ester, an acetal, a ketal, a phosphoramidite, a hydrazone, an imine, an oxime, a disulfide, or a silyl moiety, a combination of acetal or ketal with ester group, an oligo-acetal or oligo-ketal group, a combination of the oligo-ketal and silyl ether group, or a combination of the oligo-ketal and vinyl ether group. In some embodiments, the cleavable linker comprises an ester. In some embodiments, the cleavable linker comprises an acetal. In some embodiments, the cleavable linker comprises a phosphoramidite. In some embodiments, the cleavable linker comprises a hydrazine. In some embodiments, the cleavable linker comprises an imine. In some embodiments, the cleavable linker comprises an oxime. In some embodiments, the cleavable linker comprises a silyl moiety. In some embodiments, the cleavable linker comprises a disulfide.

In other embodiments, the cleavable linker is chosen from a combination of acetal or ketal with cis-aconityl, hydrazine, oxime, imidazole, or trityl groups. Any of the aforesaid groups or combination of groups can modified to enhance the pH sensitivity of the cleavable linker, e.g., as described herein.

In some embodiments, the cleavable linker is an amide, urea, carbamate, carbonate, or disulfide.

In some embodiments, the cleavable linker comprises: —OC(O)—, —C(O)O—,

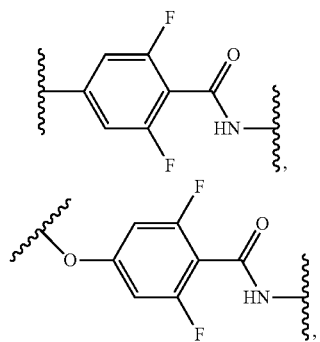

-continued

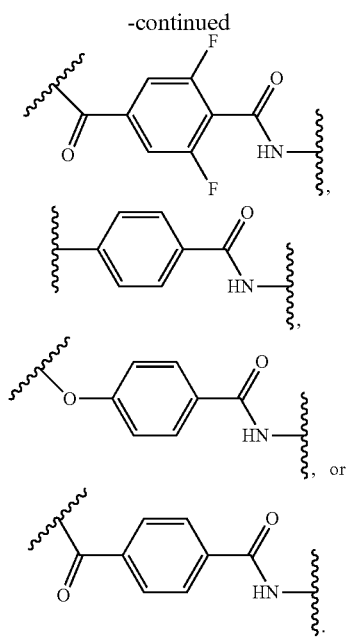

The cleavable linker may include an atom or a part of a moiety that is derived in part from the agent (e.g., a therapeutic agent).

In some embodiments, the cleavable linker is cleaved or degraded, e.g., preferentially cleaved or degraded, upon exposure to a first set of conditions relative to a second set of conditions. For example, the cleavable linker can be "preferentially cleaved" or "preferentially degraded" in a first set of conditions relative to a second set of conditions if at least 10%, 20%, 30%, 40%, 50%, 60%, 70%, 80%, 90%, 95%, or more of a bond or bonds of the cleavable linker are broken, or the agent is released, in the first set of conditions relative to the second set of conditions.

In some embodiments, the cleavable linker is degraded or hydrolyzed at physiological conditions. In some embodiments, the linker is pH sensitive or cleaved at a certain pH. In some embodiments, the linker is degraded or hydrolyzed through the action of an enzyme (e.g., a protease or esterase). For example, in some embodiments, the cleavable linker is preferentially cleaved in a tissue microenvironment, e.g., a tumor microenvironment, which is referred to herein as a "tissue microenvironment cleavable linker." In embodiments, the tissue (e.g., tumor) microenvironment cleavable linker is preferentially cleaved or degraded upon exposure to a first desired tissue or tumor microenvironment relative to a second tissue or non-tumor tissue. A tissue (e.g., tumor) microenvironment cleavable linker can be preferentially cleaved if at least 10%, 20%, 30%, 40%, 50%, 60%, 70%, 80%, 90%, 95% or more of a bond or bonds of the linker are broken, or the agent is released, in a desired tissue or tumor microenvironment relative to another tissue or non-tumor tissue. In one embodiments, the tissue (e.g., tumor) microenvironment cleavable linker is preferentially cleaved or degraded if one or more of the bonds of the linker are broken, or the agent is released, at least 2, 5, 10, 20, 30, 40, 50, 60, 70, 80, or 100 times faster upon exposure to a first desired tissue or tumor microenvironment relative to a second tissue or non-tumor tissue. The tissue (e.g., tumor) microenvironment can have a particular set of conditions, e.g., pH, enzymes, that cause the cleavage or degradation of the linker.

In some embodiments, the cleavable linker is a peptide. In some embodiments, the linker is a peptide, and the peptide sequence is comprised of naturally occurring amino acids. In some embodiments, the linker is a peptide, and the peptide sequence comprises at least one synthetically derived amino acids, e.g., at least 2, at least 3, at least 4, at least 5, at least 8, at least 10, at least 15, at least 20, or more synthetically derived amino acids (unnatural amino acid). In some embodiments, the peptide has a linear structure. In some embodiments, the peptide has a branched structure. In some embodiments, the peptide has a branched structure with, e.g., at least 2, at least 3, at least 4, at least 5, at least 6, at least 7, or at least 8 branching points. In some embodiments, the peptide has a cyclic structure.

In some embodiments, the cleavable linker is a peptide, and the peptide sequence comprises at least 2 amino acid residues. In some embodiments, the peptide sequence comprises at least 3, at least 4, at least 5, at least 6, at least 7, at least 8, at least 9, or at least 10 amino acid residues. In some embodiments, the peptide sequence is from about 1 to about 10 amino acid residues. In some embodiments, the peptide sequence is from about 1 to about 15, about 20, about 25, about 30, about 40, about 50, about 60, about 70, about 80, about 90, or about 100 amino acid residues. In some embodiments, the peptide sequence is from about 10 to about 100 amino acid residues. In some embodiments, the peptide sequence is from about 25 to about 100 amino acid residues. In some embodiments, the peptide sequence is from about 50 to about 100 amino acid residues.

In some embodiments, the cleavable linker comprises a substrate peptide that is cleaved, e.g., activated, by a matrix metalloprotease (MMP) selected from a sequence disclosed in U.S. Patent Application No. 2015/0087810 with a publication date of Mar. 26, 2015. In some embodiments, the substrate peptide comprises a protease substrate comprising an amino acid sequence selected from the group consisting of SEQ ID NOs: 353-363, 372-375, 376-378, 395-401, 411-419, 426-433, 437-449, 454-456, 459-469, 475-482, 487-495, 318-323, 325-327, 330-335, 341-347, 14-33, and 159, e.g., as described in U.S. Patent Application No. 2015/0087810. In some embodiments, the linker comprises a substrate peptide derived from a sequence disclosed in U.S. Pat. No. 8,541,203, e.g., a substrate peptide chosen from an enzyme selected from the group consisting of MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the linker comprises a sequence disclosed in U.S. Pat. No. 8,513,390. In some embodiments, the linker comprises a sequence disclosed in International Patent Publication No. WO2003/079972. In some embodiments, the linker comprises a sequence disclosed in U.S. Pat. No. 7,495,099. In some embodiments, the linker comprises a sequence disclosed in U.S. Pat. No. 8,580,244. In some embodiments, the linker comprises a sequence disclosed in one of the following articles: van Kempen, et al. *Eur Cancer* (2006) 42:728-734; Desnoyers, L. R. et al. *Sci Transl Med* (2013) 5:207ra144; Rice, J. J. et al. *Protein Sci* (2006) 15:825-836; Boulware, K. T. and Daugherty, P. S. *Proc Natl Acad Sci USA* (2006) 103:7583-7588; Deperthes, D. *Biol Chem* (2002) 383:1107-1112; Harris, J. L. *Proc Natl Acad Sci USA* (2000) 97:7754-7759; Salmaso S. and Caliceti, P. J *Drug Deliv* (2013) 2013:1-19; and Eckhard, U et al. *Matrix Biol* (2015) doi: 10.1016/j.matbio.2015.09.003 (epub ahead of print). The contents of any of the publications referenced herein are hereby expressly incorporated by reference.

In some embodiments, the cleavable linker comprises a substrate peptide that is cleaved, e.g., activated, by a protease, e.g., a protease present in a tumor or fibrotic microenvironment (e.g, a matrix metalloprotease (MMP), e.g., as described by Desnoyers, L. R. et al. *Sci Transl Med* (2013) 5:207ra144; Eckhard, U et al *Matrix Biol* (2015) doi: 10.1016/j.matbio.2015.09.003 (epub ahead of print); and van Kempen, et al. *Eur Cancer* (2006) 42:728-734. In one embodiments, the linker includes the amino acid sequence of a substrate for uPA, e.g., comprises the amino acid sequence LSGRSDNH (SEQ ID NO:1), e.g., as described in U.S. Pat. No. 8,513,390. In some embodiments, the linker sequence further includes a Gly-Ser- containing peptide linker, at either end, or both ends to the substrate peptide. Additional exemplary proteases that may be upregulated in a tumor microenvironment include, but are not limited to, urokinase-type plasminogen activator (uPA), which is upregulated in human carcinomas (S. Ulisse, et al. *Curr. Cancer Drug Targets* 9, 32-71 (2009)), membrane-type serine protease 1 (MT-SP1/matriptase) (K. Uhland *Cell. Mol. Life Sci.* 63, 2968-2978 (2006); A. M. LeBeau, et al. *Proc. Natl. Acad. Sci. U.S.A.* 110, 93-98 (2013)), and legumain, a lysosomal protease found to be released and active in the acidic extracellular tumor microenvironment (C. Liu, et al. *Cancer Res.* 63, 2957-2964 (2003)). In some embodiments, the protease is produced by an inflammatory cell, e.g., a tumor infiltrating leukocyte (e.g., a leukocyte-derived MMP), e.g., as described by van Kempen, et al. *Eur Cancer* (2006) 42:728-734. In other embodiments, the MMP is chosen from MMP1, MMP2, MMP3, MMP7, MMP8, MMP9, MMP12, MMP13 or MMP14, e.g., as described by Eckhard, U et al. supra.

In some embodiments, the substrate peptide is derived from a CLiPS library (as described in, e.g., K. T. Boulware, P. S. Daugherty, *Proc. Natl. Acad. Sci. U.S.A.* 103, 7583-7588 (2006)). In other embodiments, the substrate peptide specificity is evaluated using combinatorial fluorogenic substrate libraries, e.g., as described by Harris, J. L. *Proc Natl Acad Sci USA* (2000) 97:7754-7759. In other embodiments, the substrate peptide is derived from a phage display library (e.g., it is a phage display substrate), e.g., as described by Deperthes, D. *Biol Chem* (2002) 383:1107-1112. For example, a phage display substrate is exposed to a plurality of proteases; peptides released through specific cleavage can be amplified in an expression system. In other embodiments, the substrate peptide is derived from a bacterial display library, e.g., as described by Rice, J. J. et al. *Protein Sci* (2006) 15:825-836.

In one embodiments, the tissue (e.g., tumor) microenvironment cleavable linker is cleavable by an enzyme. In some embodiments, the enzyme comprises an esterase or a protease. Exemplary proteases include MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, or TACE.

In other embodiments, the tissue microenvironment cleavable linker is cleavable at a particular pH. In some embodiments, the tissue microenvironment cleavable linker is cleavable at a pH between about 5.0 and about 7.4, between 5.0 and 7.0, between 5.0 and 6.5, between 5.0 and 5.5, or between 5.9 and 6.2. In one embodiment, the tissue microenvironment cleavable linker is cleavable at a pH between about 6.0 and about 7.0, between about 6.2 and about 6.9, between about 6.5 and about 6.8, or between about 6.5 and about 6.7. In one embodiment, the tissue microenvironment cleavable linker is cleavable at a pH between about 5.5 and about 6.5, e.g., between 5.9 and 6.2. In one embodiment, the tissue microenvironment cleavable linker is cleavable at a hypoxic pH, e.g., a pH about 6.7 to 6.9, e.g., compared to a physiological pH of about 7.4.

In some embodiments, the tissue microenvironment cleavable linker is cleavable is cleaved at a pH of no more than 7.4, no more than 7.0, no more than 6.9, no more than 6.8, no more than 6.7, no more than 6.6, no more than 6.5, no more than 6.4, no more than 6.3, no more than 6.2, no more than 6.1, no more than 6.0, no more than 5.5 or lower.

In one embodiment, the tissue microenvironment cleavable linker is preferentially cleaved or degraded upon exposure to a first pH relative to a second pH. In one embodiment, the tissue microenvironment cleavable linker is cleaved or degraded at least 2, 5, 10, 20, 30, 40, 50, 60, 70, 80, or 100 times faster upon exposure to a first pH relative to a second pH. In other embodiments, the tissue microenvironment cleavable linker shows a greater release or degradation rate at a first acidic pH (e.g., pH=6.7) relative to a second more basic pH (e.g., pH=7.4). In one embodiment, ratio of release or degradation rate of the tissue microenvironment cleavable linker at pH=6.7 relative to pH=7.4 is greater than 1, 1.2, 1.4, 1.6, 1.8, 2, 2.2, 2.4, 2.6, 2.8, 3 or higher. In one embodiment, ratio of release or degradation rate of the tissue microenvironment cleavable linker at pH=6.7 relative to pH=7.4 is greater than 2.

In one embodiment, the tissue microenvironment cleavable linker shows increased pH-sensitivity in a hypoxic microenvironment, e.g., in a tumor, or fibrotic tissue.

In some embodiments, the tissue microenvironment cleavable linker exhibits an increased release rate or increased release yield of the agent at a desired site (e.g., a tumor), e.g., relative to the release rate or release yield at another site. In one embodiment, the tissue microenvironment cleavable linker comprises an electron withdrawing group (e.g., an electron withdrawing group that enhances the cleavage rate or yield.

In certain embodiments, the rate of cleavage of at least one instance of Si—O bond in the backbone of the polymer is slower (e.g., at least 3-fold, at least 10-fold, at least 30-fold, at least 100-fold, at least 300-fold, at least 1,000-fold, or at least 10,000-fold slower) than that of at least one instance of L under the same conditions. In certain embodiments, the rate of cleavage of at least one instance of Si—O bond in the backbone of the polymer is faster (e.g., at least 3-fold, at least 10-fold, at least 30-fold, at least 100-fold, at least 300-fold, at least 1,000-fold, or at least 10,000-fold faster) than that of at least one instance of L under the same conditions.

In certain embodiments, at least one instance of e is 0. In certain embodiments, each instance of e is 0. In certain embodiments, at least one instance of e is 1, 2, 3, 4, 5, 6, 7, 8, 9, and 10. In certain embodiments, each instance of e is 1, 2, 3, 4, 5, 6, 7, 8, 9, and 10. In certain embodiments, at least one instance of e is 1. In certain embodiments, each instance of e is 1. In certain embodiments, at least one instance of e is 2, 3, or 4. In certain embodiments, at least one instance of e is 5, 6, 7, 8, 9, or 10.

In certain embodiments, at least one instance of f is 0. In certain embodiments, each instance of f is 0. In certain embodiments, at least one instance of f is 1, 2, 3, 4, 5, 6, 7, 8, 9, and 10. In certain embodiments, each instance of f is 1, 2, 3, 4, 5, 6, 7, 8, 9, and 10. In certain embodiments, at least one instance of f is 1. In certain embodiments, each instance of f is 1. In certain embodiments, at least one instance of f is 2, 3, or 4. In certain embodiments, at least one instance of f is 5, 6, 7, 8, 9, or 10.

In certain embodiments at least one instance of $X^1$ and $X^2$ is —OH, C(=O)$R^C$, —C(=O)O$R^C$, or —C(=O)N($R^C$)$_2$. In certain embodiments at least one instance of $X^1$ and $X^2$ is —O$R^C$, —N($R^C$)$_2$, —N$R^C$C(=O)$R^C$, —N$R^C$C(=O)O$R^C$, —N$R^C$C(=O)N($R^C$)$_2$, —OC(=O)$R^C$, —OC(=O)O$R^C$, or —OC(=O)N($R^C$)$_2$. In certain embodiments, at least one instance of $X^1$ and $X^2$ is O$R^C$ or N($R^C$)$_2$. In certain embodiments, at least one instance of $X^1$ and $X^2$ is hydrogen or $C_{1-6}$ alkyl. In certain embodiments, at least one instance of $X^1$ and $X^2$ is substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl.

In certain embodiments, at least one instance of $X^1$ is —O$R^C$, —N($R^C$)$_2$, —C(=O)$R^C$, —C(=O)O$R^C$, —C(=O)N($R^C$)$_2$, —N$R^C$C(=O)$R^C$, —N$R^C$C(=O)O$R^C$, —N$R^C$C(=O)N($R^C$)$_2$, —OC(=O)$R^C$, —OC(=O)O$R^C$, or —OC(=O)N($R^C$)$_2$. In certain embodiments, each instance of $X^1$ is independently —O$R^C$, —N($R^C$)$_2$, —C(=O)$R^C$, —C(=O)O$R^C$, —C(=O)N($R^C$)$_2$, —N$R^C$C(=O)$R^C$, —N$R^C$C(=O)O$R^C$, —N$R^C$C(=O)N($R^C$)$_2$, —OC(=O)$R^C$, —OC(=O)O$R^C$, or —OC(=O)N($R^C$)$_2$. In certain embodiments, at least one instance of $X^1$ is —O$R^C$, —N($R^C$)$_2$, —C(=O)$R^C$, —C(=O)N($R^C$)$_2$, —N$R^C$C(=O)$R^C$, or —N$R^C$C(=O)N($R^C$)$_2$. In certain embodiments, each instance of $X^1$ is —O$R^C$, —N($R^C$)$_2$, —C(=O)$R^C$, —C(=O)N($R^C$)$_2$, —N$R^C$C(=O)$R^C$, or —N$R^C$C(=O)N($R^C$)$_2$.

In certain embodiments, at least one instance of $R^C$ is hydrogen, substituted or unsubstituted, $C_{1-6}$ alkyl, an oxygen protecting group, or a leaving group. In certain embodiments, at least one instance of $R^C$ is substituted or unsubstituted, $C_{50-1000}$ heteroalkyl. In certain embodiments, at least one instance of $R^C$ is substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl. In certain embodiments, at least one instance of $R^C$ is

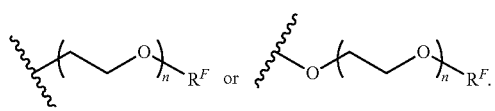

In certain embodiments, each instance of $R^C$ is independently

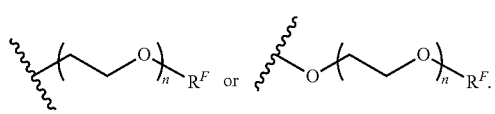

In certain embodiments, at least one instance of $R^C$ is

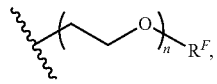

wherein: n is an integer from 1 to 300 (e.g., from 10 to 200, or from 20 to 100), inclusive; and $R^F$ is hydrogen, substituted or unsubstituted, $C_{1-6}$ alkyl (e.g., —CH$_3$), or an oxygen protecting group. In certain embodiments, $R^C$ is

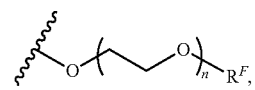

wherein: n is an integer from 1 to 300 (e.g., from 10 to 200, or from 20 to 100), inclusive; and $R^F$ is hydrogen, substituted or unsubstituted, $C_{1-6}$ alkyl (e.g., —CH$_3$), or an oxygen protecting group.

In certain embodiments, wherein at least one instance of $R^C$ is

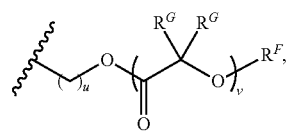

wherein: u is 1, 2, 3, 4, 5, or 6; each instance of $R^G$ is independently hydrogen, halogen, or substituted or unsubstituted, $C_{1-6}$ alkyl(e.g., —CH$_3$); v is an integer from 1 to 300 (e.g., from 10 to 200, or from 20 to 100), inclusive; and $R^F$ is hydrogen, substituted or unsubstituted, $C_{1-6}$ alkyl (e.g., —CH$_3$), or an oxygen protecting group. In certain embodiments, the first monomer does not comprise —O—O—.

In some embodiments, the molecular weight of at least one instance of the first monomer is between about 1 kDa and about 10 kDa, e.g., between about 2 kDa and about 8 kDa or about 3 kDa and about 6 kDa, e.g., as detected by mass spectrometry. In some embodiments, the molecular weight of at least one instance of the first monomer is between about 3 kDa and about 6 kDa. In some embodiments, the molecular weight of at least one instance of the first monomer is about 2 kDa, about 3 kDa, about 4 kDa, about 5 kDa, or about 6 kDa. In some embodiments, the hydrodynamic diameter of at least one instance of the first monomer is between about 0.5 nm and about 3 nm, e.g., about 1 nm and about 2 nm, e.g., as detected by dynamic light scattering.

In certain embodiments, $X^1$ is —C(=O)N($R^C$)$_2$ wherein one instance of $R^C$ is hydrogen. In certain embodiments, $X^1$ is —C(=O)N($R^C$)$_2$ wherein one instance of $R^C$ is

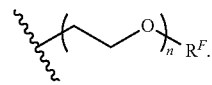

In certain embodiments, $X^1$ is —C(=O)N($R^C$)$_2$ wherein one instance of $R^C$ is

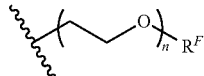

and the other instance of $R^C$ is hydrogen. In certain embodiments, $X^1$ is —C(=O)N($R^C$)$_2$ wherein one instance of $R^C$ is

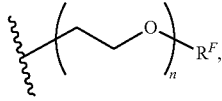

wherein n is an integer 30-100 (e.g., 50-75), and the other instance of $R^C$ is hydrogen.

In some embodiments, each instance of $R^A$ is the same. In some embodiments, each instance of $R^A$ is different. In some embodiments, some instances of $R^A$ are the same and some are different. In certain embodiments, each instance of $R^A$ is hydrogen. In certain embodiments, at least one instance of $R^A$ is hydrogen. In certain embodiments, each instance of $R^A$ is halogen. In certain embodiments, at least one instance of $R^A$ is halogen. In certain embodiments, each instance of $R^A$ is unsubstituted $C_{1-6}$ alkyl. In certain embodiments, at least one instance of $R^A$ is unsubstituted $C_{1-6}$ alkyl. In certain embodiments, each instance of $R^A$ is substituted $C_{1-6}$ alkyl. In certain embodiments, at least one instance of $R^A$ is substituted $C_{1-6}$ alkyl. In certain embodiments, some $R^{A1}$ are methyl. In certain embodiments, some $R^{A1}$ are halogen.

In certain embodiments, a is 1. In some embodiments, a is 2. In certain embodiments, a is 3. In some embodiments, a is 4. In certain embodiments, a is 5. In some embodiments, a is 6. In certain embodiments, at least one instance of a is 2, 3, 4, 5, or 6. In certain embodiments, each instance of a is independently 2, 3, 4, 5, or 6. In certain embodiments, at least one instance of a is 3, 4, or 5. In certain embodiments, each instance of a is independently 3, 4, or 5.

In certain embodiments, each instance of $R^B$ is hydrogen. In certain embodiments, at least one instance of $R^B$ is hydrogen. In certain embodiments, each instance of $R^B$ is halogen. In certain embodiments, at least one instance of $R^B$ is halogen. In certain embodiments, each instance of $R^B$ is unsubstituted $C_{1-6}$ alkyl. In certain embodiments, at least one instance of $R^B$ is unsubstituted $C_{1-6}$ alkyl. In certain embodiments, each instance of $R^B$ is substituted $C_{1-6}$ alkyl. In certain embodiments, at least one instance of $R^B$ is substituted $C_{1-6}$ alkyl. In certain embodiments, some $R^{B1}$ are hydrogen. In certain embodiments, some $R^{B1}$ are methyl. In certain embodiments, some $R^{B1}$ are halogen.

In certain embodiments, at least one instance of b is 1, 2, 3, 4, 5, or 6. In certain embodiments, each instance of b is independently 1, 2, 3, 4, 5, or 6. In certain embodiments, at least one instance of b is 1, 2, or 3. In certain embodiments, each instance of b is independently 1, 2, or 3. In certain embodiments, b is 1. In some embodiments, b is 2. In certain embodiments, b is 3. In some embodiments, b is 4. In certain embodiments, b is 5. In some embodiments, b is 6.

In certain embodiments, e is 1. In some embodiments, e is 2. In certain embodiments, e is 3. In some embodiments, e is 4. In certain embodiments, e is 5. In some embodiments, e is 6.

In some embodiments, the macromonomer is of the formula:

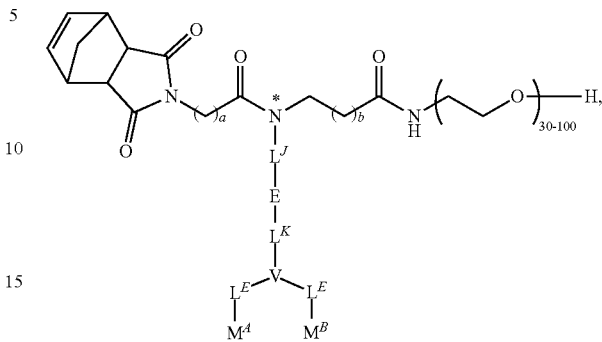

or salt thereof, wherein -$L^J$-E-$L^K$- comprises

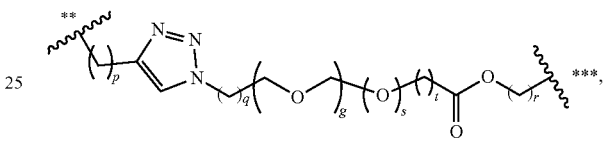

V is C($R^J$), $R^J$ is hydrogen, and each instance of $L^E$ independently comprises

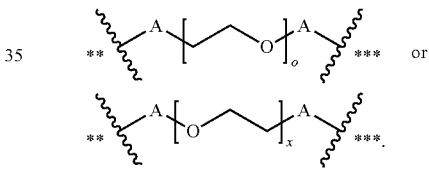

In some embodiments, the macromonomer is of the formula:

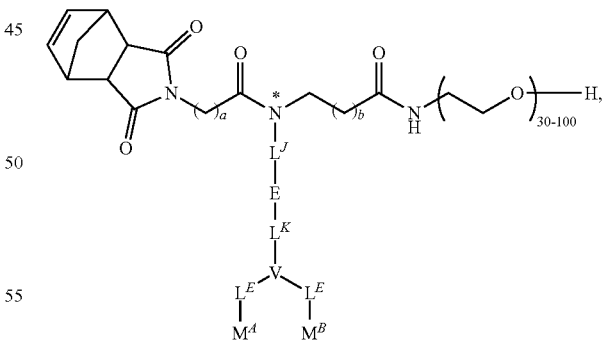

or salt thereof, wherein -$L^J$-E-$L^K$- comprises

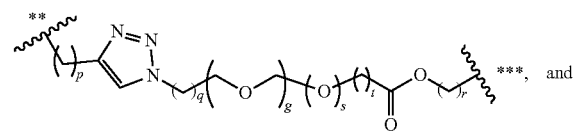

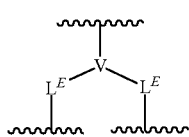
comprises
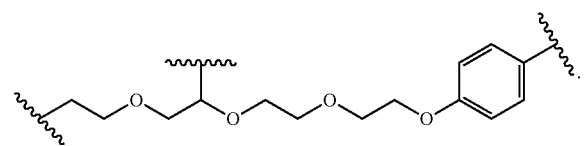 [SMILES: *CCOCC(*)OCCOCCOc1ccc(*)cc1]
In some embodiments, the macromonomer is of the formula:
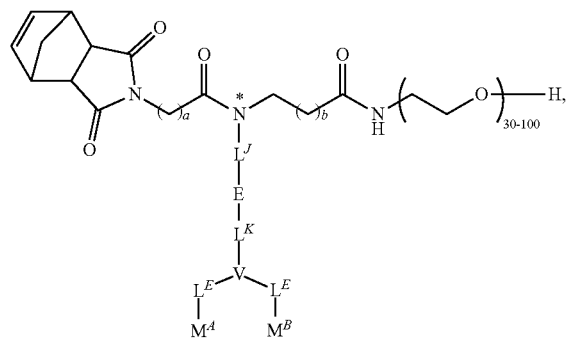
or salt thereof, wherein -L$^J$-E-L$^K$- comprises
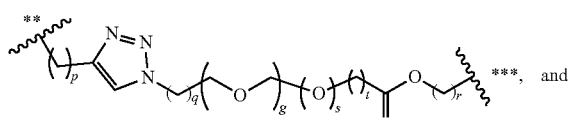, and
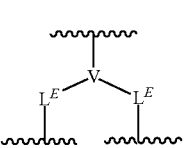
comprises
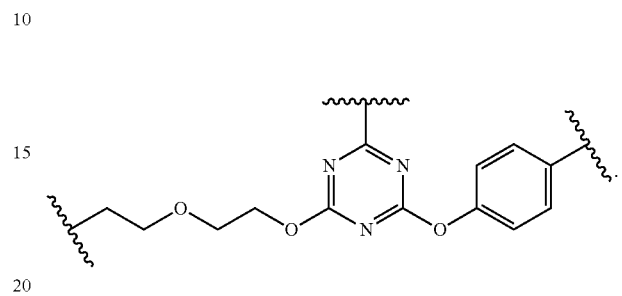
In some embodiments, a compound of Formula (I), I-A), (II), (II-A), (III-A), or (III-B) comprises:
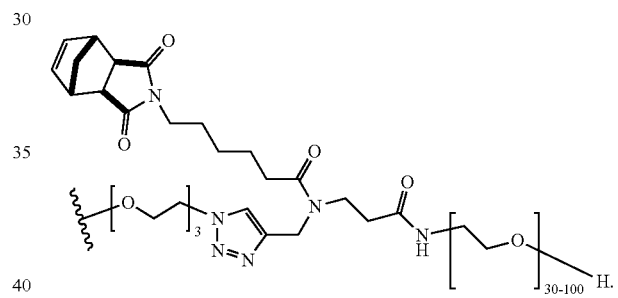
In certain embodiments, a macromonomer is of the formula:
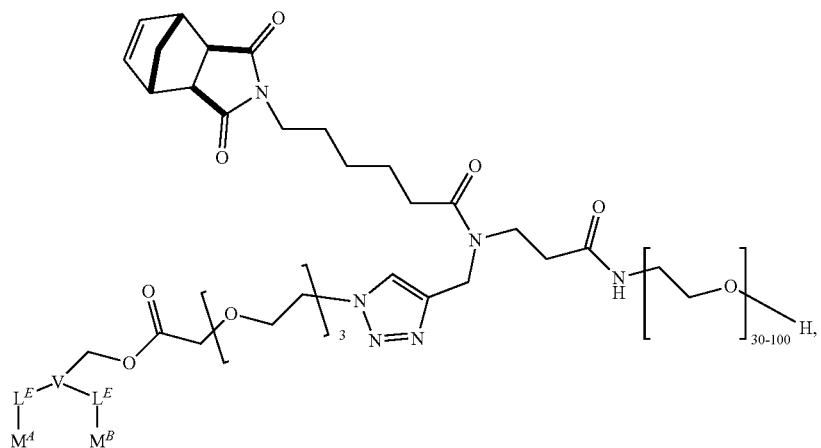

or salt thereof. In some embodiments, a macromonomer is of the formula:
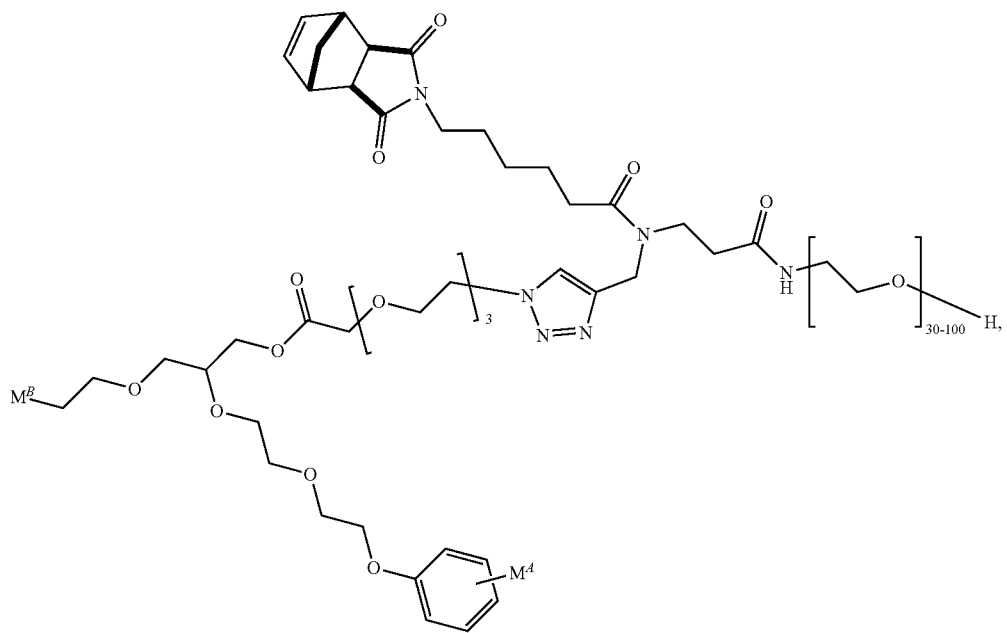
or salt thereof.
In certain embodiments, a macromonomer is of the formula:
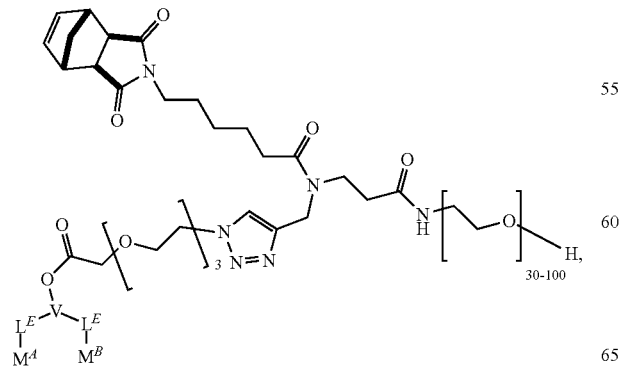

or salt thereof. In some embodiments, a macromonomer is of the formula:
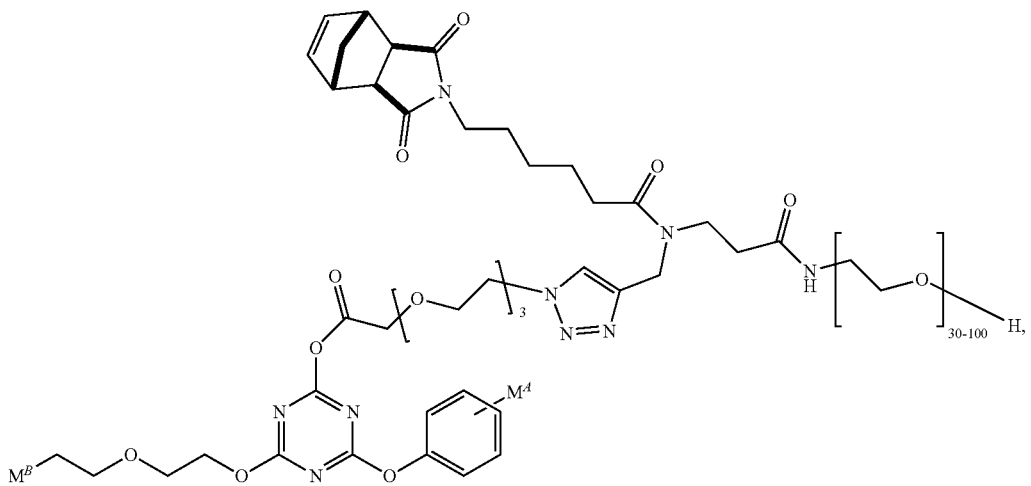
or salt thereof.
In some embodiments, $M^A$ is of the formula:
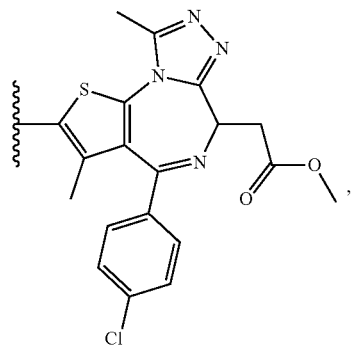
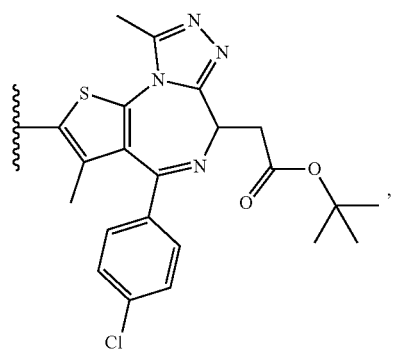
-continued
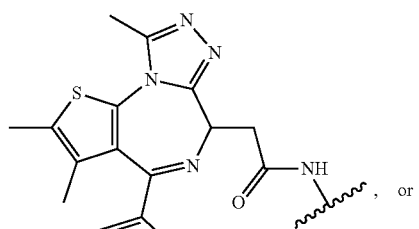
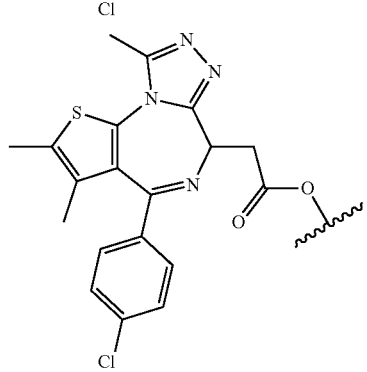
and $M^B$ is of the formula:
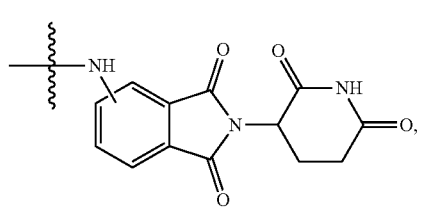

87
-continued
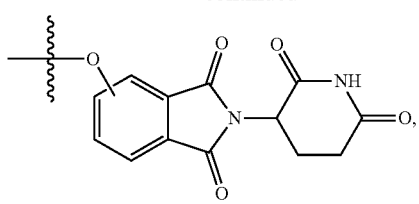
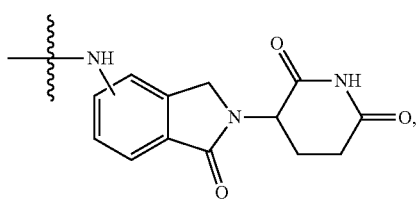
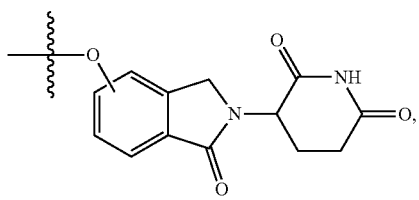
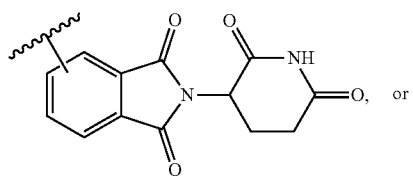, or
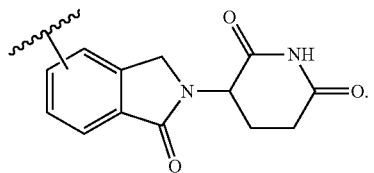
In some embodiments, $M^A$ is of the formula:
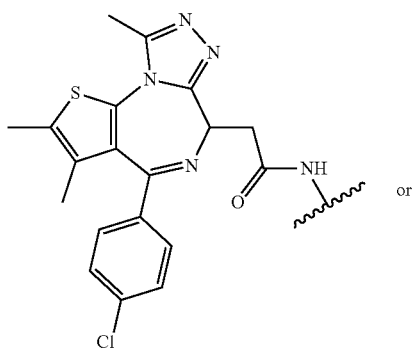 or
88
-continued
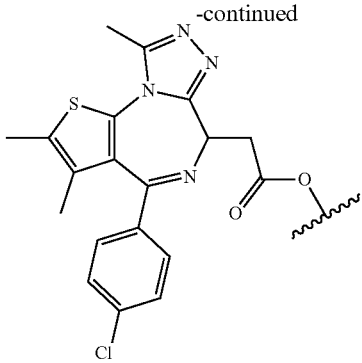
and $M^B$ is of the formula:
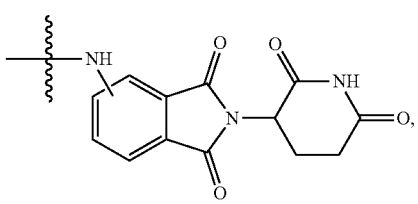
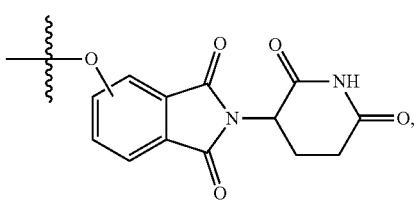
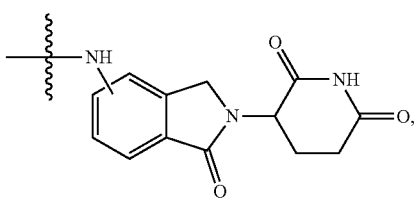
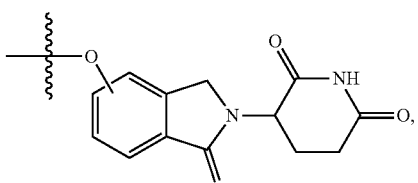
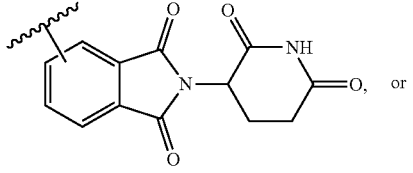, or
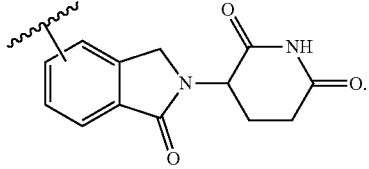

In certain embodiments, a macromonomer is of the formula:
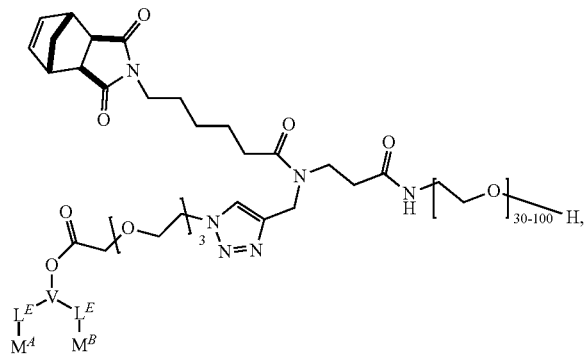
or salt thereof, wherein $M^A$ is of the formula:
and $M^B$ is of the formula:
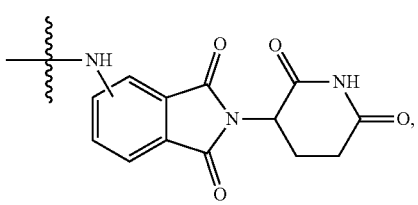
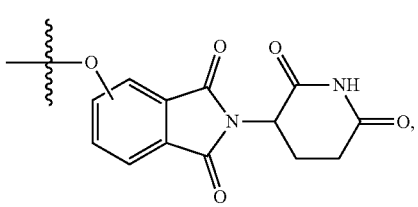
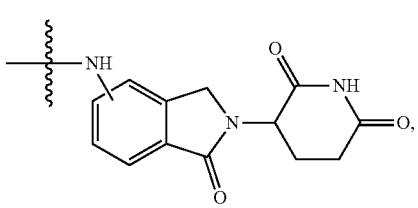
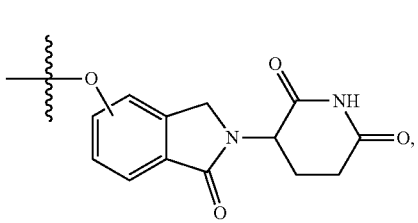

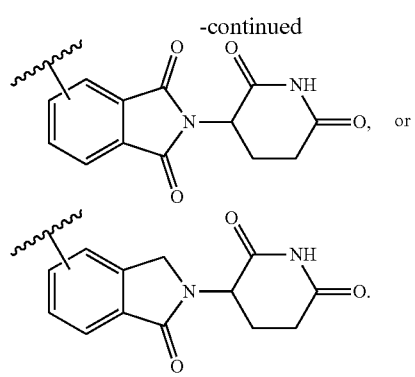
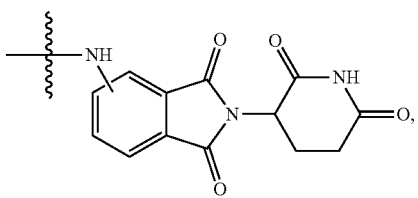
In certain embodiments, a macromonomer is of the formula:
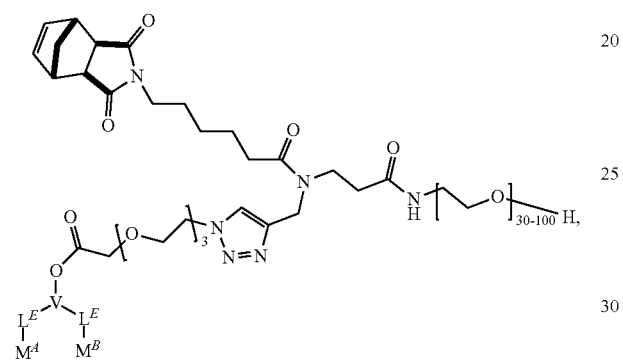
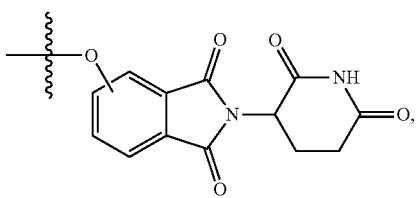
or salt thereof, wherein $M^A$ is of the formula:
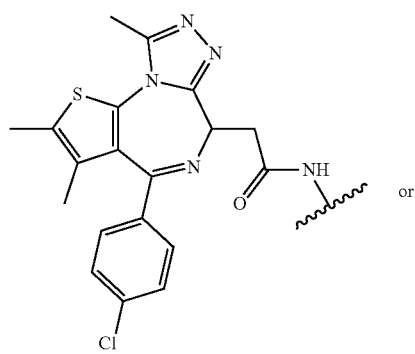
or
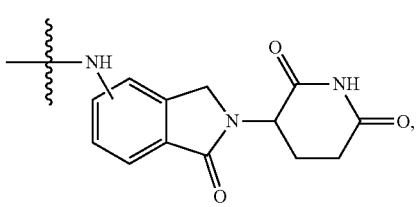
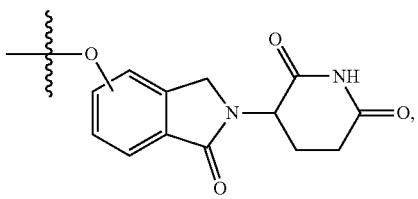
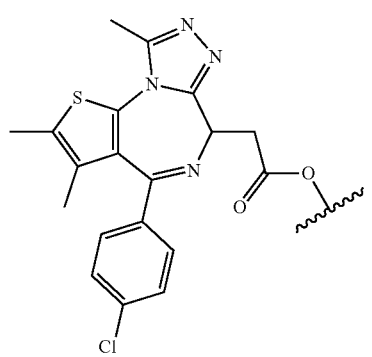
and $M^B$ is of the formula:
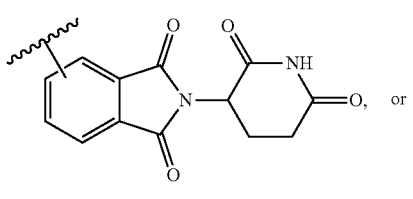
or In certain embodiments, a macromonomer is of the formula:
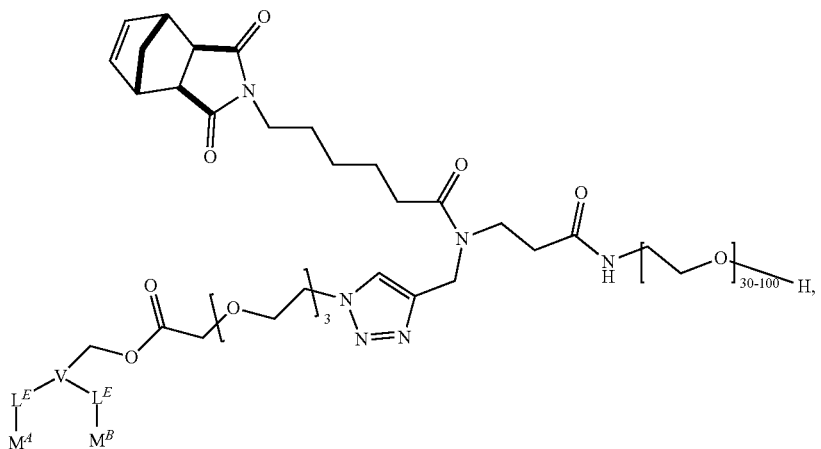
or salt thereof, wherein $M^A$ is of the formula:
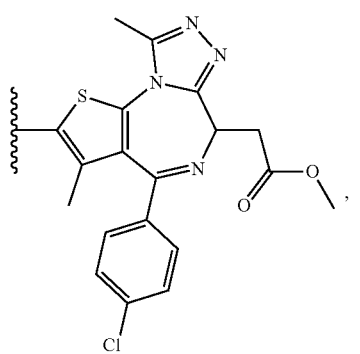
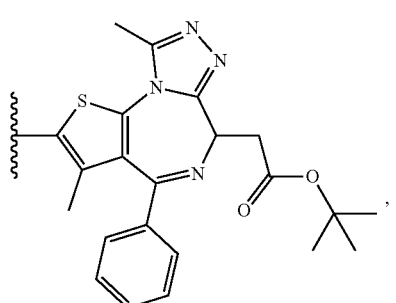
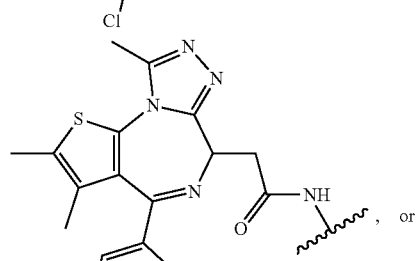
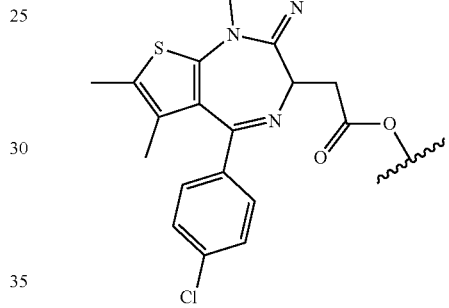
and $M^B$ is of the formula:
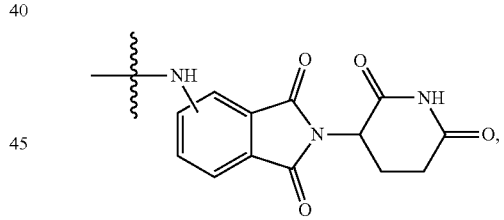
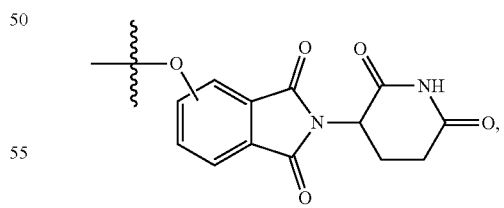
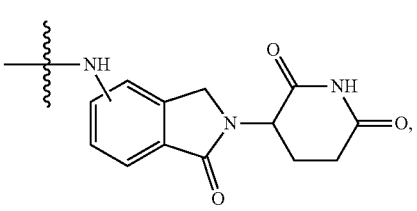

95
-continued
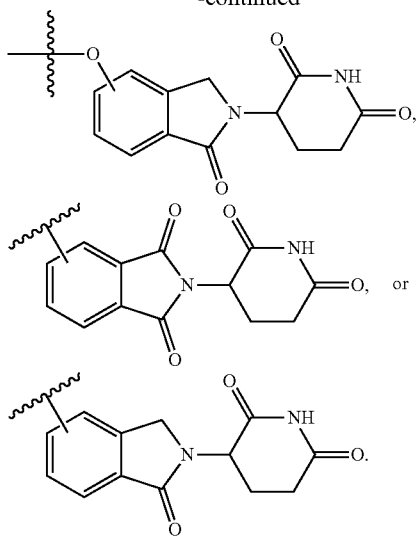
96
-continued
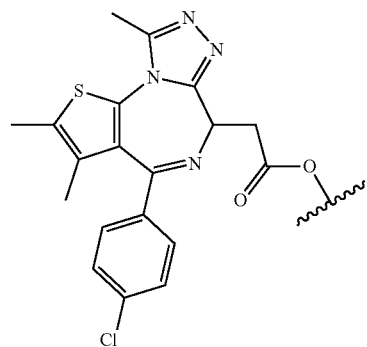
In certain embodiments, a macromonomer is of the formula: and $M^B$ is of the formula:
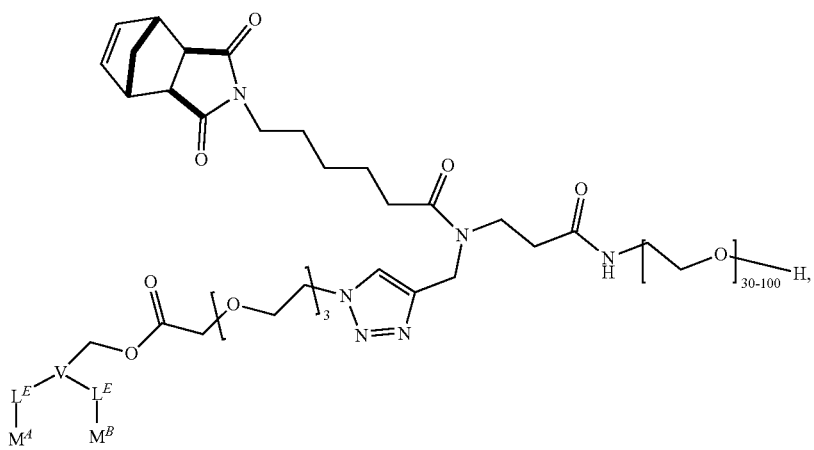
or salt thereof, wherein $M^A$ is of the formula:
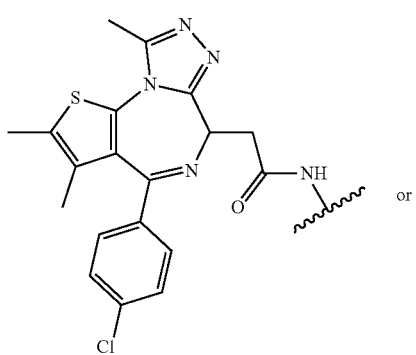
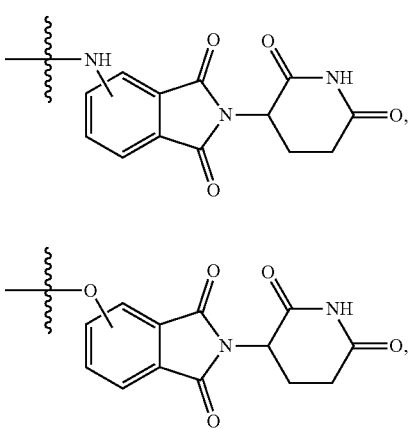

-continued
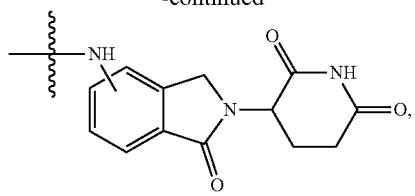
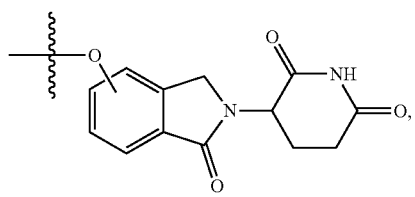
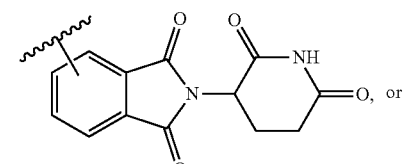
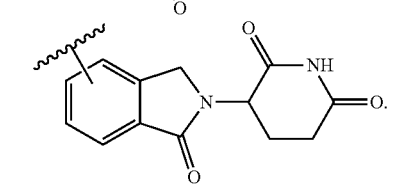
or salt thereof, wherein $M^A$ is of the formula:
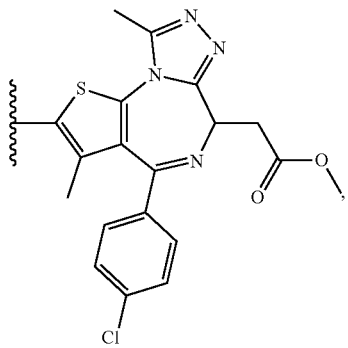
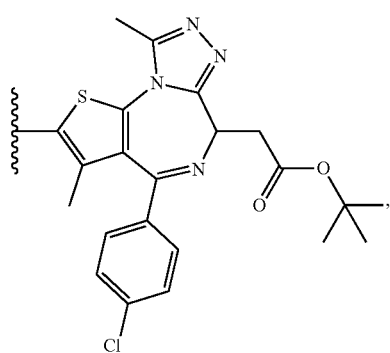
In some embodiments, a macromonomer is of the formula:
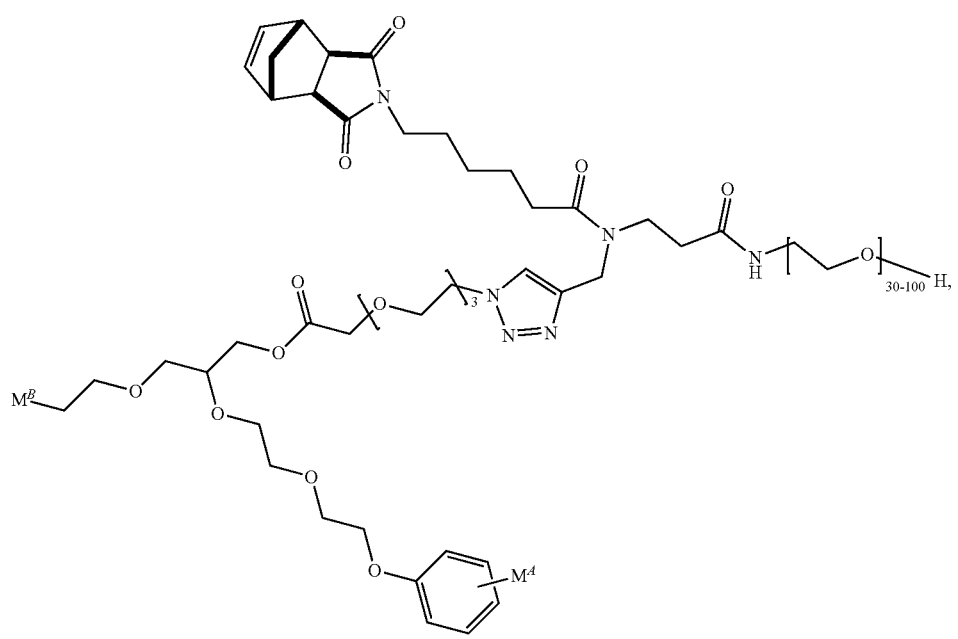

99
-continued
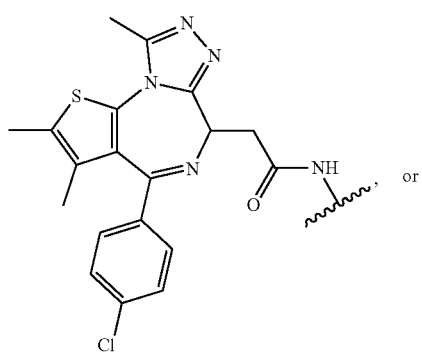
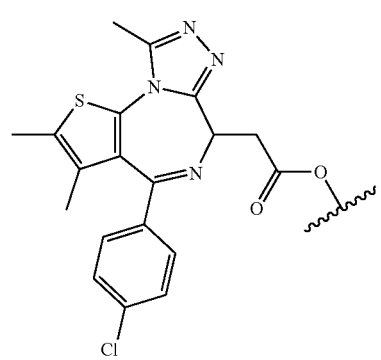
and M$^B$ is of the formula:
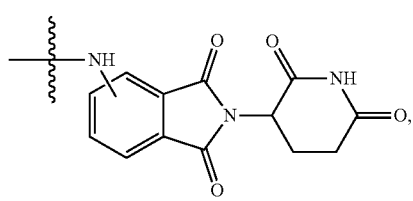
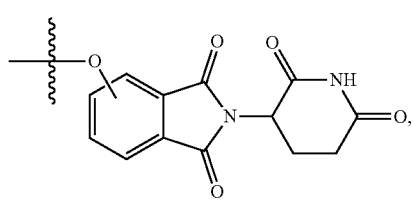
100
-continued
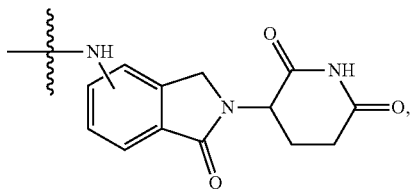
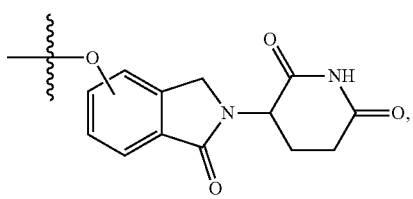
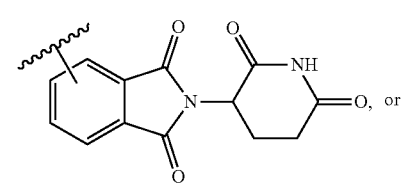
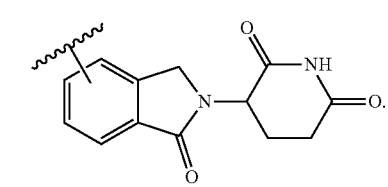

In some embodiments, a macromonomer is of the formula:
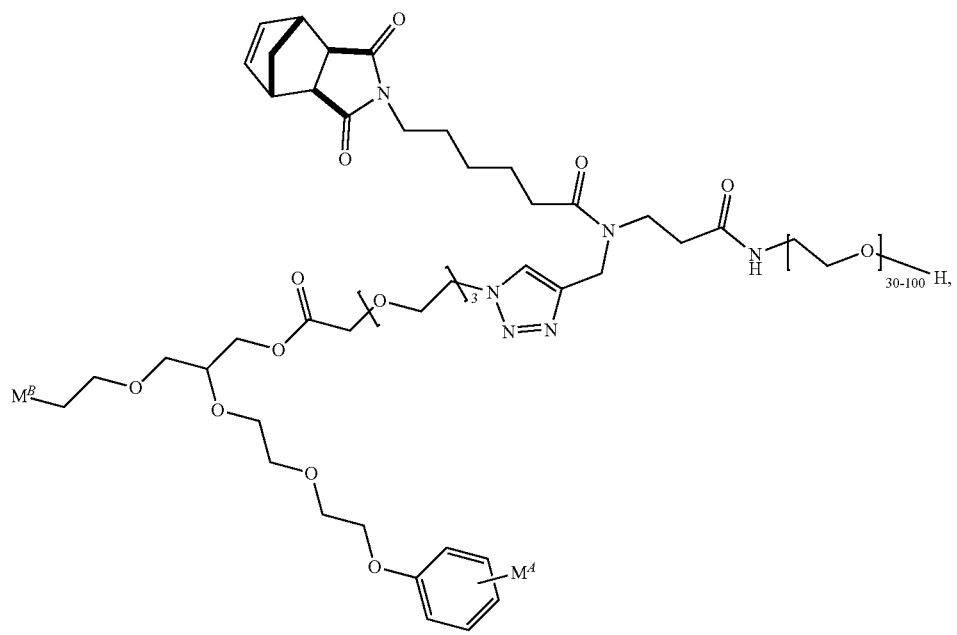
or salt thereof, wherein $M^A$ is of the formula:
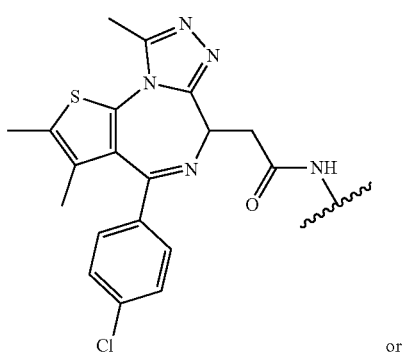
or
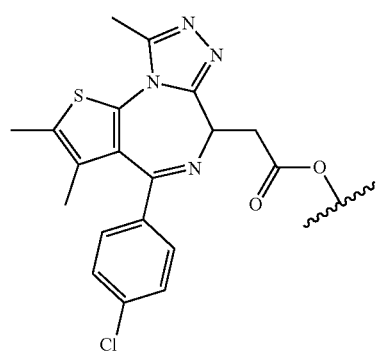
and $M^B$ is of the formula:
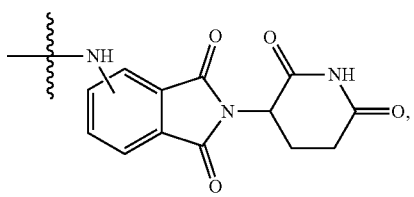
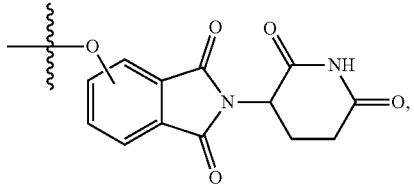
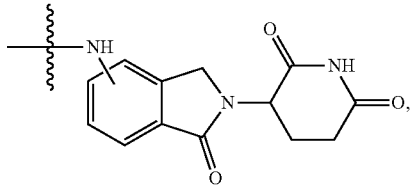
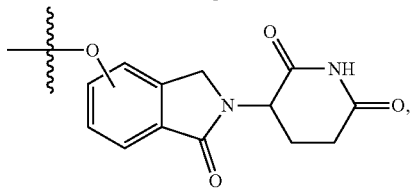
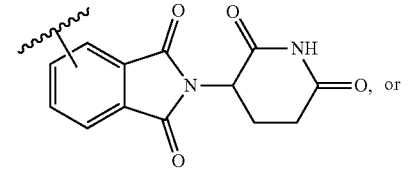
or

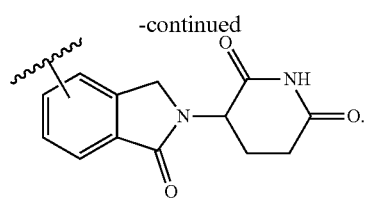
In some embodiments, a macromonomer is of the formula:
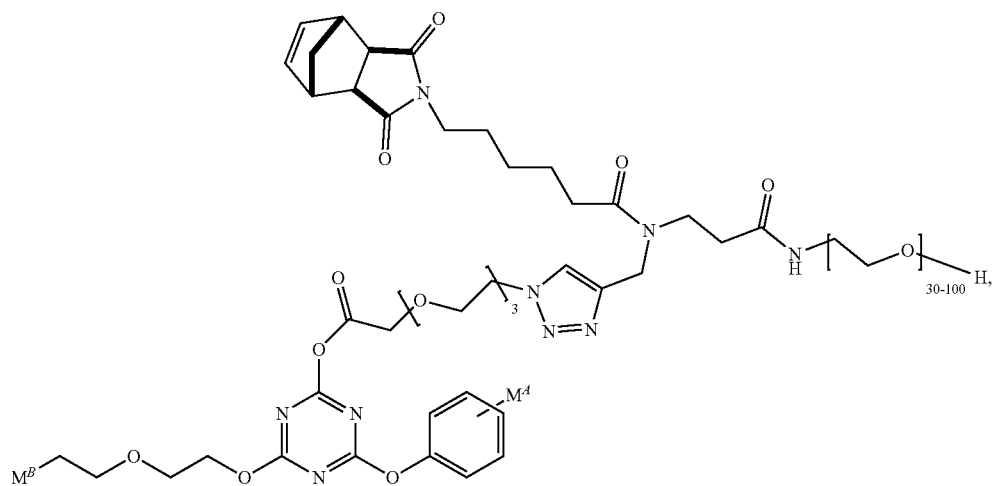
or salt thereof, wherein $M^A$ is of the formula:
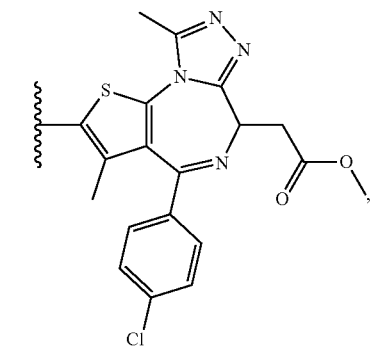
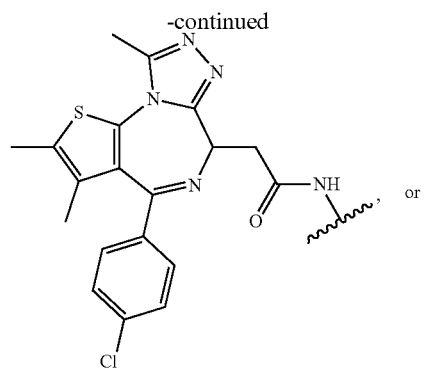
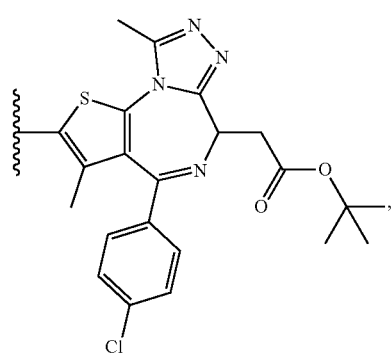
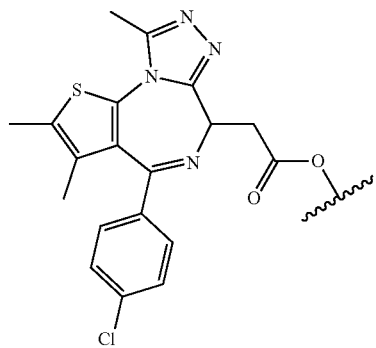

and $M^B$ is of the formula:
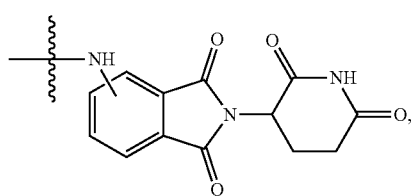
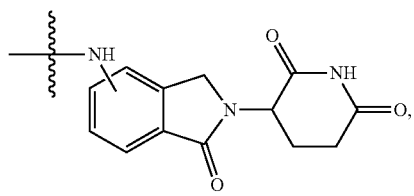
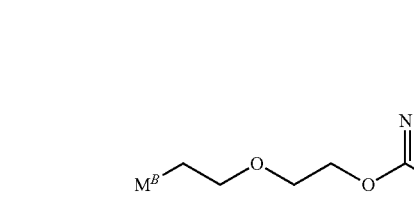
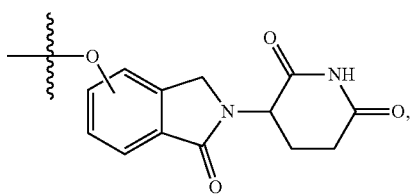
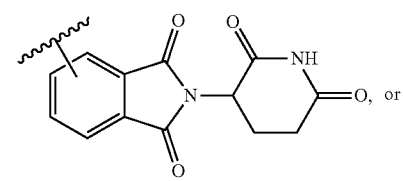
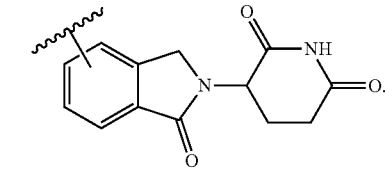, or
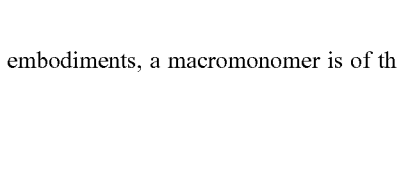
In some embodiments, a macromonomer is of the formula:
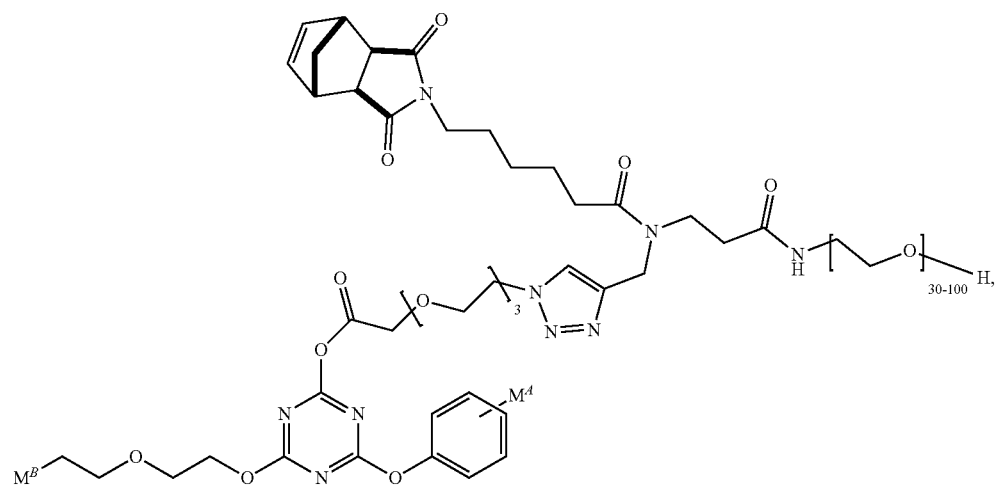

or salt thereof, wherein M^A is of the formula:
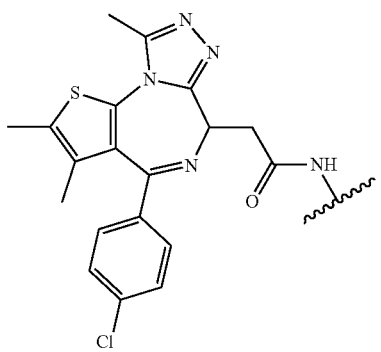
or
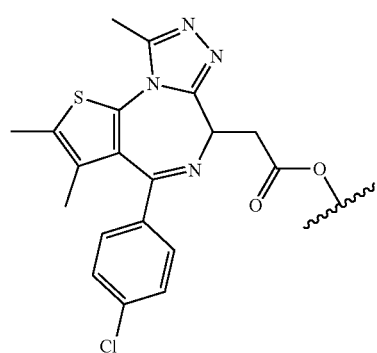
and M^B is of the formula:
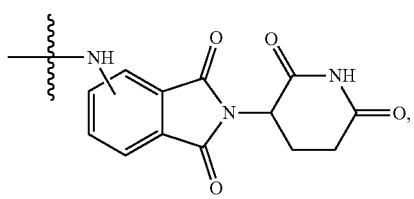
-continued
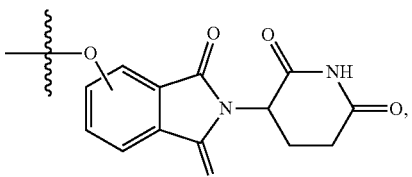
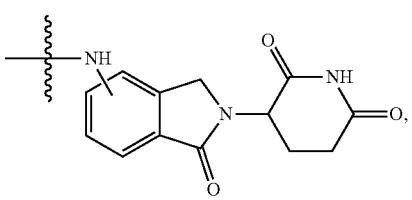
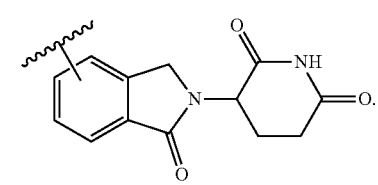
In certain embodiments, the macromonomer is of the formula:
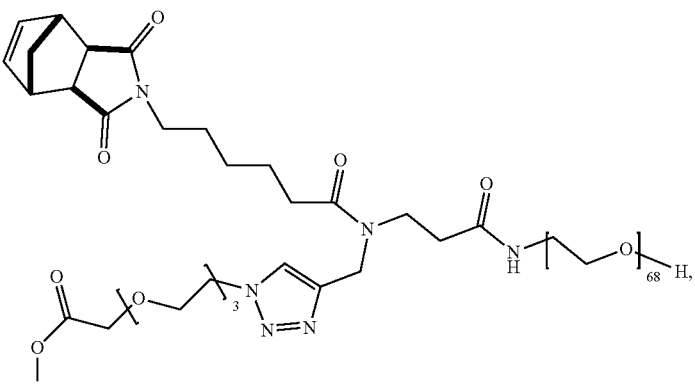

-continued
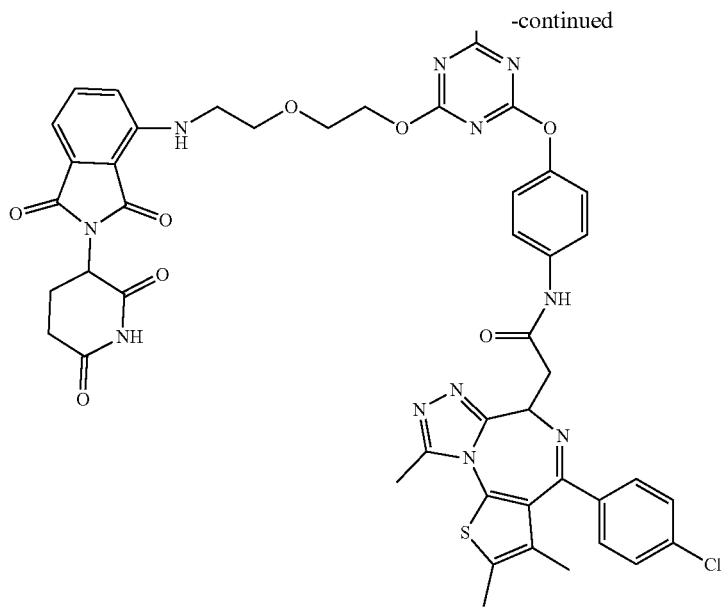
or salt thereof.
In certain embodiments, the macromonomer is of the formula:
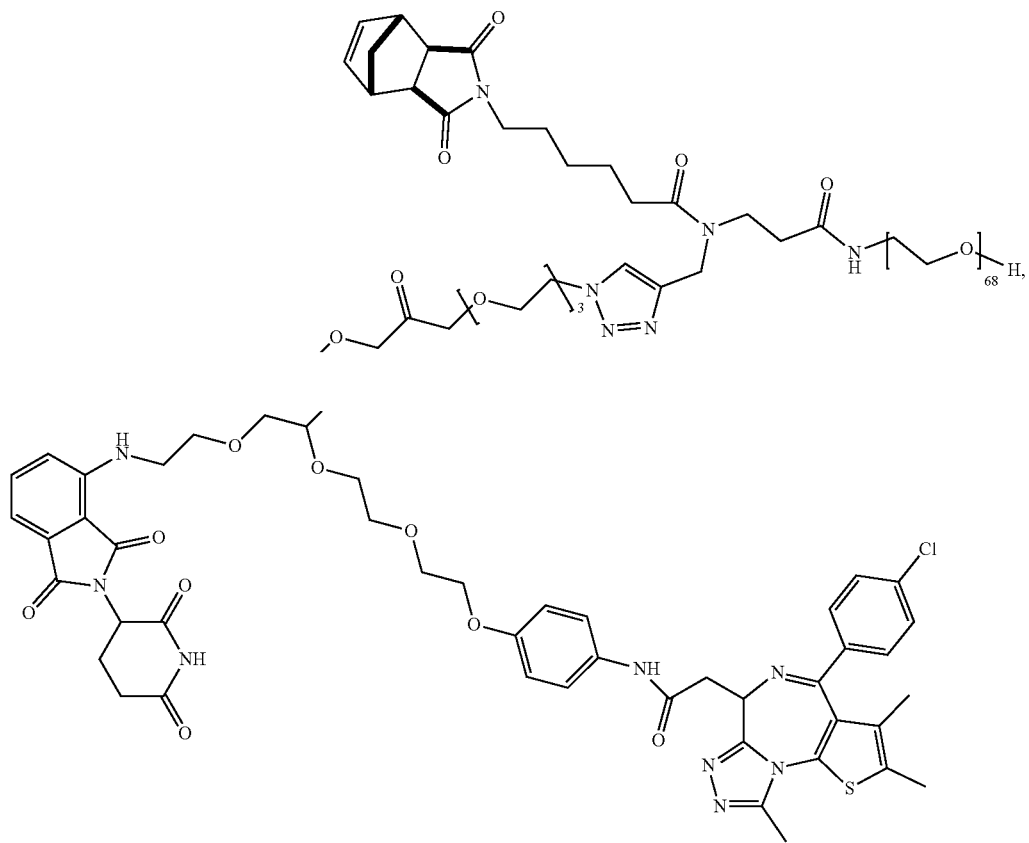
or salt thereof.

In certain embodiments, a conjugate is of the formula:

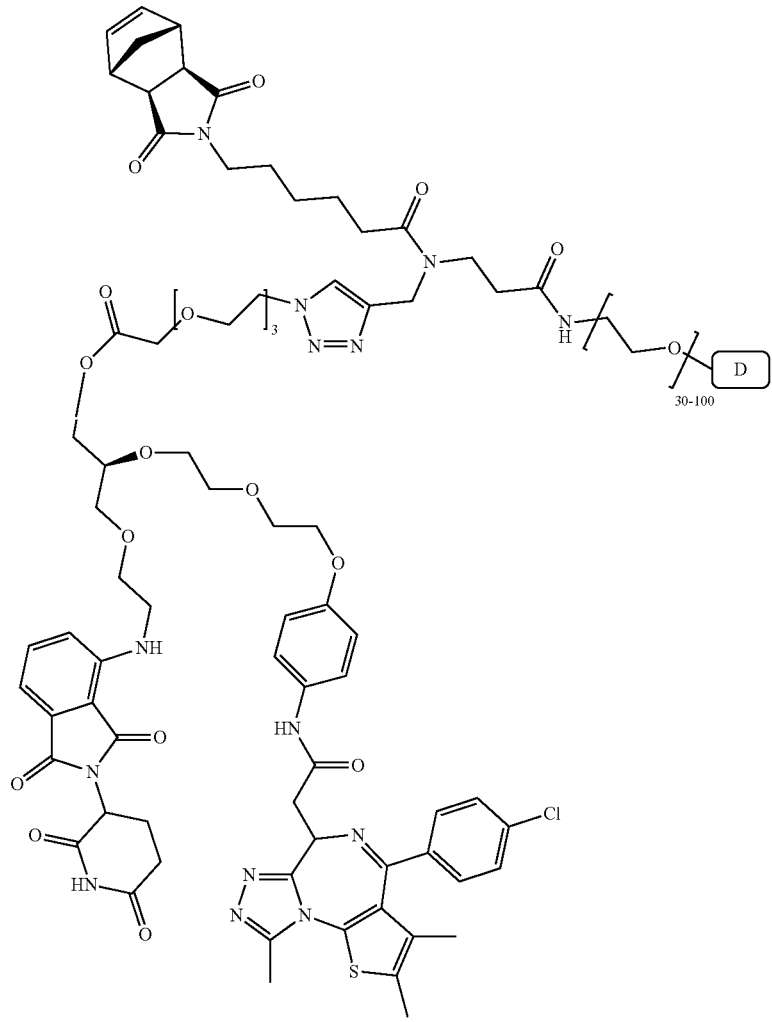

and pharmaceutically acceptable salts and stereoisomers thereof.

In certain embodiments, the conjugate is a polymer, or salt thereof. In certain embodiments, the conjugate is a polymer prepared by a method comprising polymerizing a macromonomer of Formula (III-A) or (III-B). In certain embodiments, the conjugate is a polymer prepared by a method comprising polymerizing a macromonomer of Formula (III-A) or (III-B) and a second monomer. In certain embodiments, the conjugate is a polymer prepared by a method comprising polymerizing a macromonomer of Formula (III-A) or (III-B) with a second and third monomer. In certain embodiments, the conjugate is a polymer prepared by a method comprising polymerizing a macromonomer of formula:

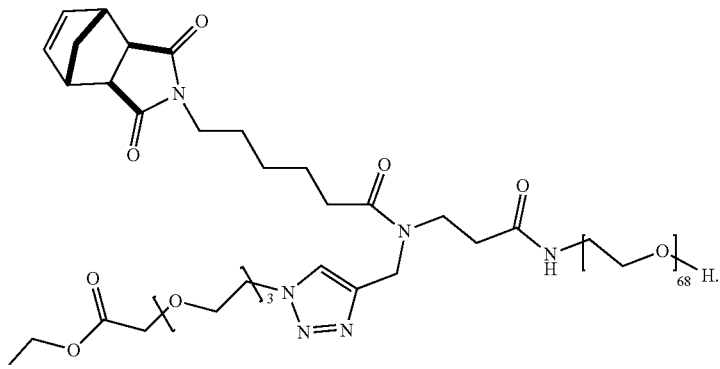

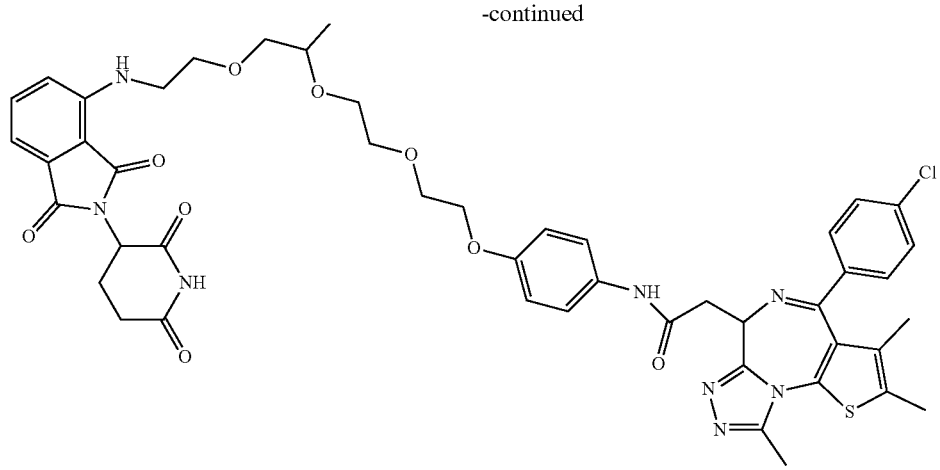
20
In some embodiments, a conjugate is brush polymeric moiety (a brush polymer) of the formula:
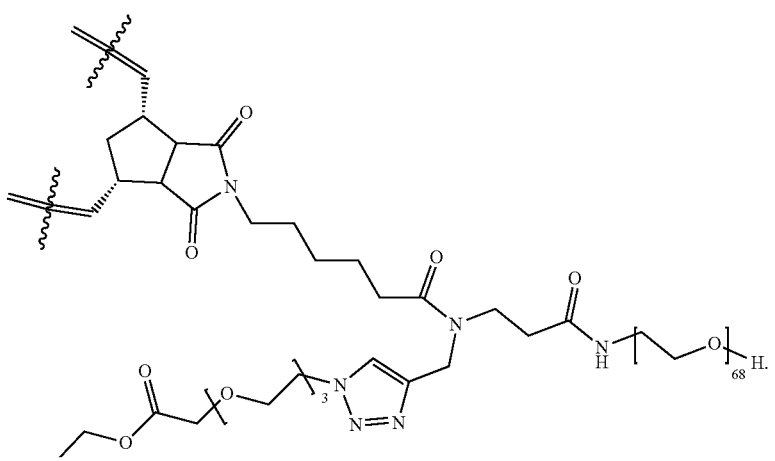
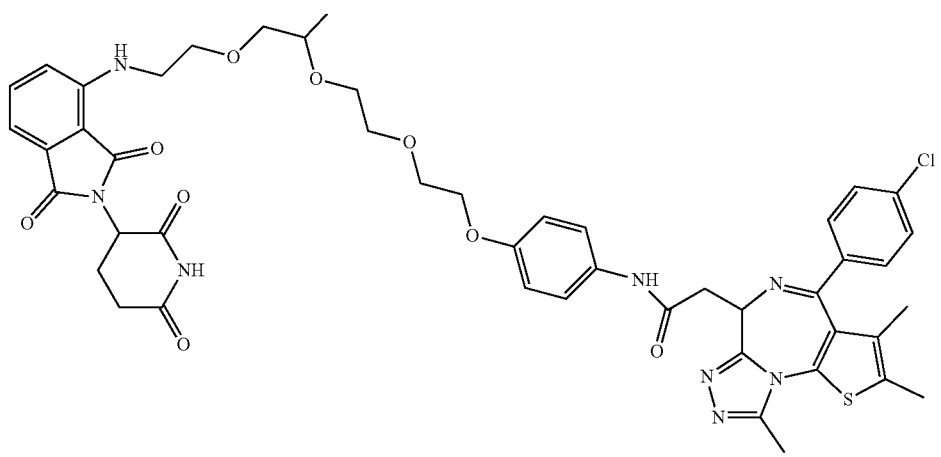

In some embodiments, a conjugate is brush polymeric moiety (a brush polymer) of the formula:

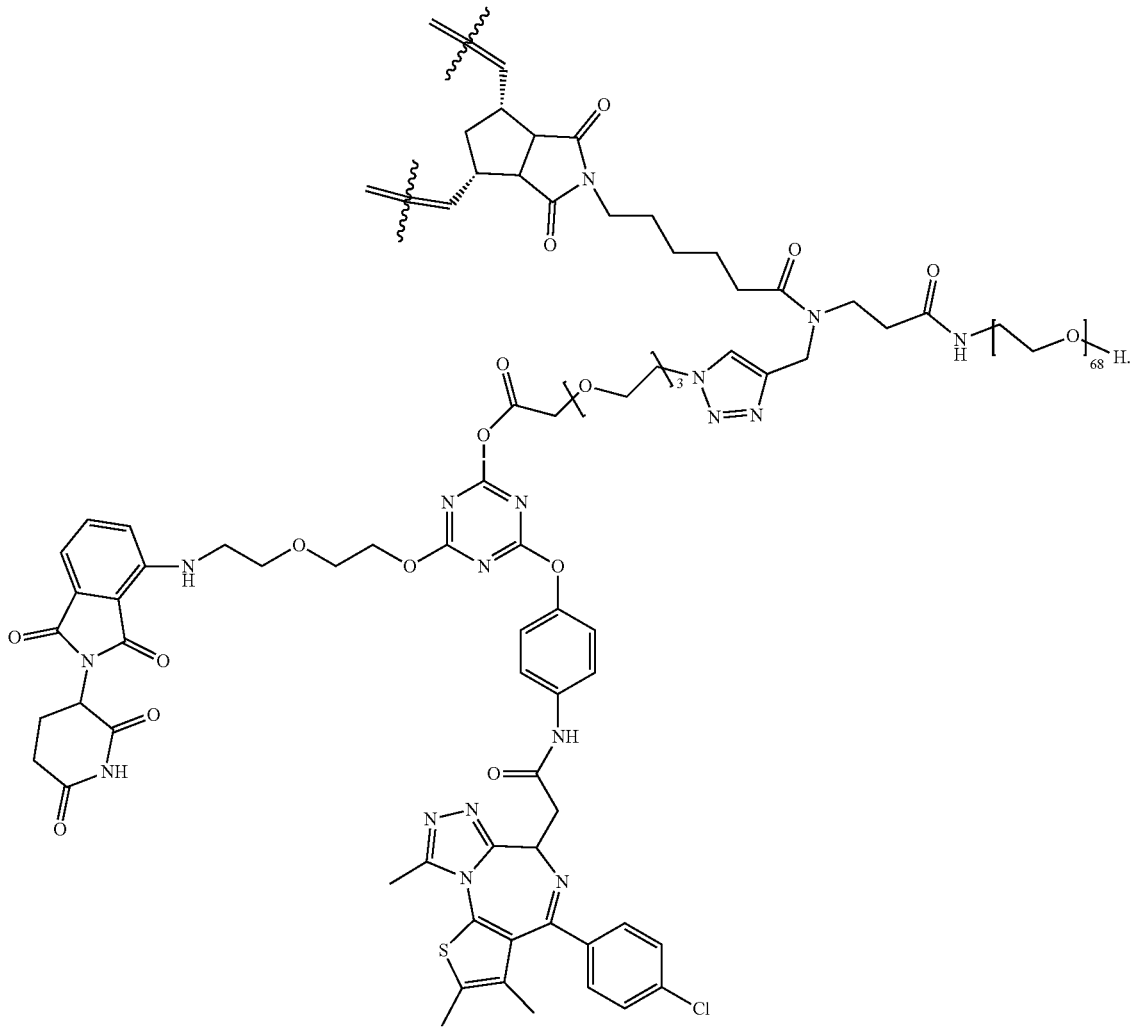

In certain embodiments, the conjugate is a polymer prepared by a method comprising polymerizing a macromonomer of Formula (III-A) or (III-B), and then adding in a cross-linker.

In some embodiments, a conjugate is the brush-arm star polymer comprising a cross linker and the bottlebrush of formula:

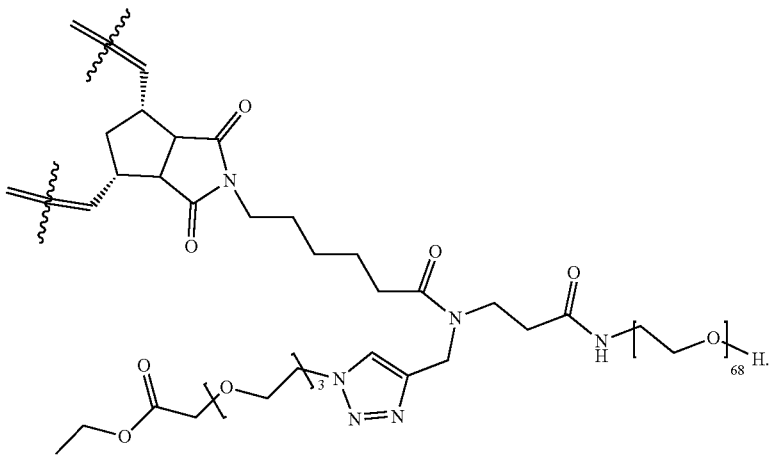

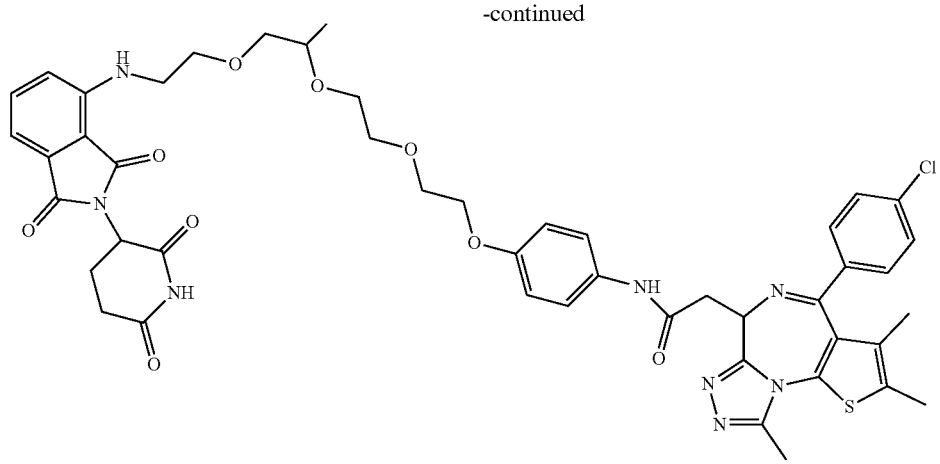

Compounds, macromonomers, conjugates, or polymers of the present invention may be in the form of a free acid or free base, or a pharmaceutically acceptable salt or ester. As used herein, the term "pharmaceutically acceptable" in the context of a salt or ester refers to a salt or ester of the compound, macromonomer, conjugate, or polymer that does not abrogate the biological activity or properties of the compound, and is relatively non-toxic, i.e., the compound, macromonomer, conjugate, or polymer in salt form may be administered to a subject without causing undesirable biological effects (such as dizziness or gastric upset) or interacting in a deleterious manner with any of the other components of the composition in which it is contained. The term "pharmaceutically acceptable salt or ester" refers to a product obtained by reaction of the compound, macromonomer, conjugate, or polymer of the present invention with a suitable acid or a base. Examples of pharmaceutically acceptable salts of the compounds, macromonomers, conjugates, or polymers of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain aspects of the invention can form pharmaceutically acceptable salts with various organic bases such as lysine, arginine, guanidine, diethanolamine or metformin. Suitable base salts include aluminum, calcium, lithium, magnesium, potassium, sodium, or zinc, salts. Representative examples of pharmaceutically acceptable esters include (e.g., methyl, ethyl, isopropyl and tert-butyl esters).

In some embodiments, the compounds, macromonomers, conjugates, or polymers of the present invention is an isotopic derivative in that it has at least one desired isotopic substitution of an atom, at an amount above the natural abundance of the isotope, i.e., enriched. In one embodiment, the compound, macromonomer, conjugate, or polymer includes deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances. For example, in compound, macromonomer, conjugate, or polymer comprising formula (I) that target BRD4, a JQ1 moiety may be deuterated in order to increase half-life.

Compounds, macromonomers, conjugates, or polymers of the present invention may have at least one chiral center and thus may be in the form of a stereoisomer, which as used herein, embraces all isomers of individual compounds, macromonomers, conjugates, or polymers that differ only in the orientation of their atoms in space. The term stereoisomer includes mirror image isomers (enantiomers which include the (R-) or (S-) configurations), mixtures of mirror image isomers (physical mixtures of the enantiomers, and racemates or racemic mixtures), geometric (cis/trans or E/Z, R/S) isomers and isomers with more than one chiral center that are not mirror images of one another (diastereoisomers). The chiral centers of the compounds, macromonomers, conjugates, or polymers may undergo epimerization in vivo; thus, for these, administration of the (R-) form is considered equivalent to administration of the compound in its (S-) form. Accordingly, the compounds, macromonomers, conjugates, and polymers of the present invention may be made and used in the form of individual isomers and substantially free of other isomers, or in the form of a mixture of various isomers, e.g., racemic mixtures of stereoisomers.

In addition, the compounds, macromonomers, conjugates, and polymers of the present invention embrace the use of N-oxides, crystalline forms (also known as polymorphs), active metabolites having the same type of activity, tautomers, and unsolvated as well as solvated forms with pharmaceutically acceptable solvents such as water, ethanol, and the like, of the compounds. The solvated forms are also considered to be disclosed herein.

Methods of Preparation

In another aspect, the present disclosure provides methods of preparing a conjugate. In some embodiments, the conjugate is prepared via a reaction between two formula as described herein. In certain embodiments, the two formula are the same. In some embodiments, the two formula are different.

In some aspects, the present disclosure provides methods of preparing a conjugate comprising reacting a compound of formula: D-L'-E$^B$ (IV), or salt thereof, with a compound of the formula:

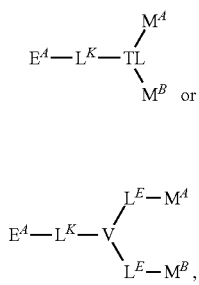

(I)

(I-A)

thereof, in the presence of the metathesis catalyst. In another aspect, the present disclosure provides methods of preparing a brush polymeric moiety (a brush polymer), the method comprises polymerizing a macromonomer of Formula (III-A) or (III-B), or salt thereof, in the presence of the metathesis catalyst. In another aspect, the present disclosure provides methods of preparing a brush-arm star polymeric moiety (a BASP), the method comprises polymerizing a macromonomer of Formula (III-A) or (III-B), or salt thereof, in the presence of the metathesis catalyst. In certain embodiments, a compound of Formula (III-A) or (III-B) is of the formula:

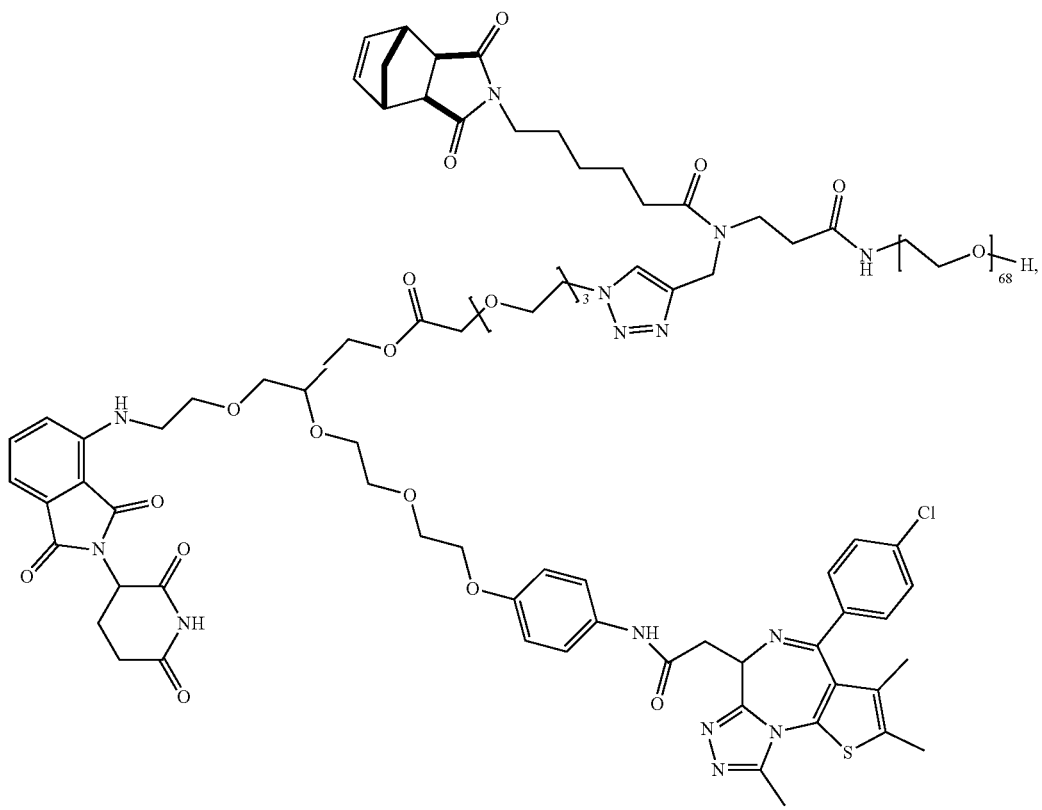

or salt thereof, wherein $E^B$, $E^A$, $L^K$, V, $L^E$, $M^A$, and $M^B$ are as defined herein. In certain embodiments, $E^A$ and $E^B$ react to form E. In certain embodiments, $E^A$ and $E^B$ react via a click-chemistry reaction to form E. In certain embodiments, $E^A$ and $E^B$ react via a condensation reaction to form E. In certain embodiments, $E^A$ and $E^B$ react via a nucleophilic substitution reaction to form E. In certain embodiments, $E^A$ and $E^B$ react via an addition reaction to form E. In certain embodiments, $E^A$ and $E^B$ react via an elimination reaction to form E. In certain embodiments, $E^A$ and $E^B$ react via a substitution reaction to form E. In certain embodiments, $E^A$ and $E^B$ react via a rearrangement reaction to form E. In certain embodiments, $E^A$ and $E^B$ react via a photochemical reaction to form E. In certain embodiments, $E^A$ and $E^B$ react via a redox reaction to form E.

In another aspect, the present disclosure provides methods of preparing a polymer, the method comprises polymerizing a macromonomer of Formula (III-A) or (III-B), or salt or salt thereof.

In another aspect, the present disclosure provides methods of preparing a BASP, the method comprises crosslinking one or more instances of the brush polymer in the presence of a crosslinker and the metathesis catalyst.

The preparation of the polymers may involve a metathesis reaction. In certain embodiments, the metathesis reaction is a ring-opening metathesis polymerization (ROMP) (see, e.g., Liu et al. *J. Am. Chem. Soc.* 2012, 134, 16337; Liu, J.; Gao, A. X.; Johnson, J. A. *J Vis Exp* 2013, e50874).

In certain embodiments, the metathesis catalyst (e.g., ROMP catalyst) is a tungsten (W), molybdenum (Mo), or ruthenium (Ru) catalyst. In certain embodiments, the metathesis catalyst is a ruthenium catalyst. metathesis catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-

2580; Furstner et al., *J. Am. Chem. Soc.* (1999) 121:9453; and *Chem. Eur. J.* (2001) 7:5299; the entire contents of each of which are incorporated herein by reference.

In certain embodiments, the metathesis catalyst is a Grubbs catalyst. In certain embodiments, the Grubbs catalyst is selected from the group consisting of:

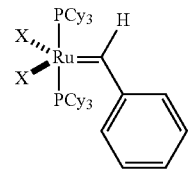

X = Cl; Br; I
Cy = cyclohexyl

Benzylidenebis-(tricyclohexylphosphine)-dichlororuthenium (X=Cl); Benzylidenebis-(tricyclohexylphosphine)-dibromoruthenium (X=Br); Benzylidenebis-(tricyclohexylphosphine)-diiodoruthenium (X=I);

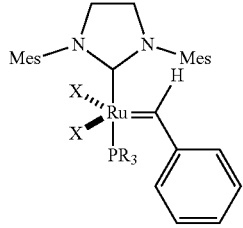

X = Cl; Br; I
R = cyclohexyl (Cy); phenyl (Ph); benzyl (Bn)

1,3-(Bis(mesityl)-2-imidazolidinylidene)dichloro-(phenylmethylene) (tricyclohexyl-phosphine)ruthenium (X=Cl; R=cyclohexyl); 1,3-(Bis(mesityl)-2-imidazolidinylidene)dibromo-(phenylmethylene) (tricyclohexyl-phosphine)ruthenium (X=Br; R=cyclohexyl); 1,3-(Bis(mesityl)-2-imidazolidinylidene)diiodo-(phenylmethylene) (tricyclohexyl-phosphine)ruthenium (X=I; R=cyclohexyl); 1,3-(Bis(mesityl)-2-imidazolidinylidene)dichloro-(phenylmethylene) (triphenylphosphine)ruthenium (X=Cl; R=phenyl); 1,3-(Bis(mesityl)-2-imidazolidinylidene)dichloro-(phenylmethylene) (tribenzylphosphine)ruthenium (X=Cl; R=benzyl);

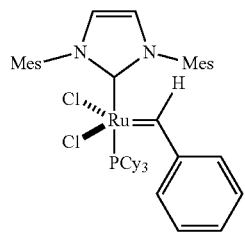

R = cyclohexyl (Cy); phenyl (Ph)
R' = methyl; phenyl

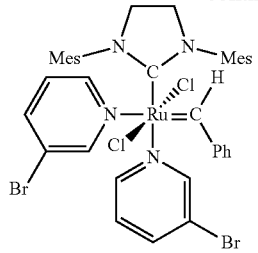

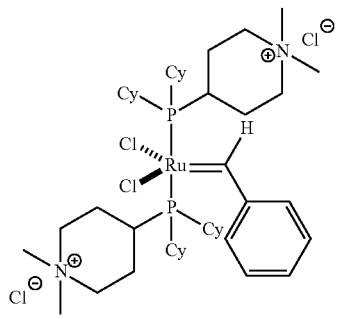

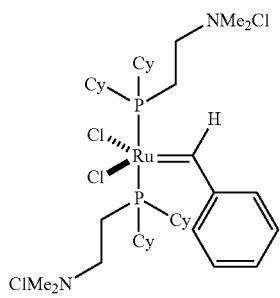

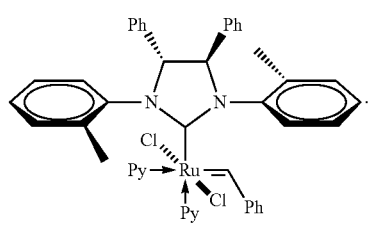

Py = pyridine
Ph = phenyl

In certain embodiments, the metathesis catalyst is a Grubbs-Hoveyda catalyst. In certain embodiments, the Grubbs-Hoveyda catalyst is selected from the group consisting of:

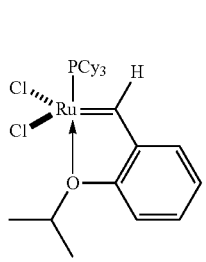 and 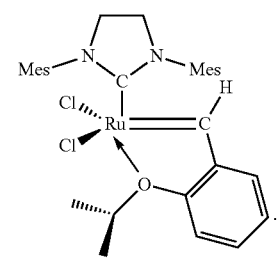.

In certain embodiments, the metathesis catalyst is selected from the group consisting of:

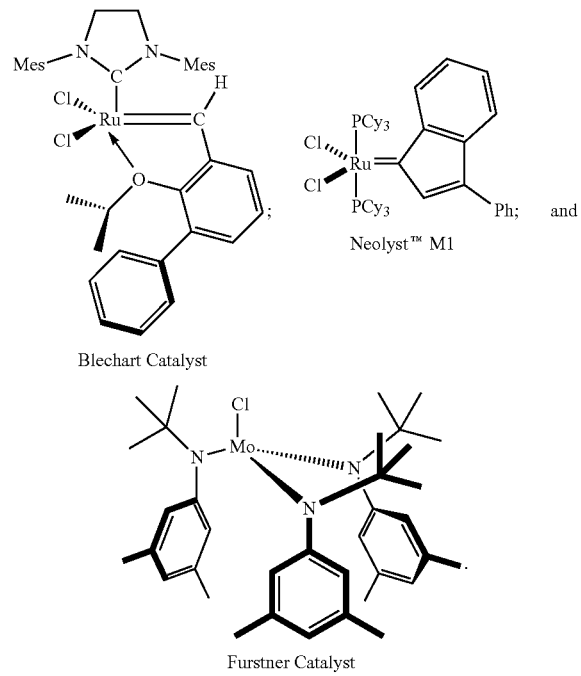

Blechart Catalyst

Furstner Catalyst

In certain embodiments, the metathesis catalyst is of the formula:

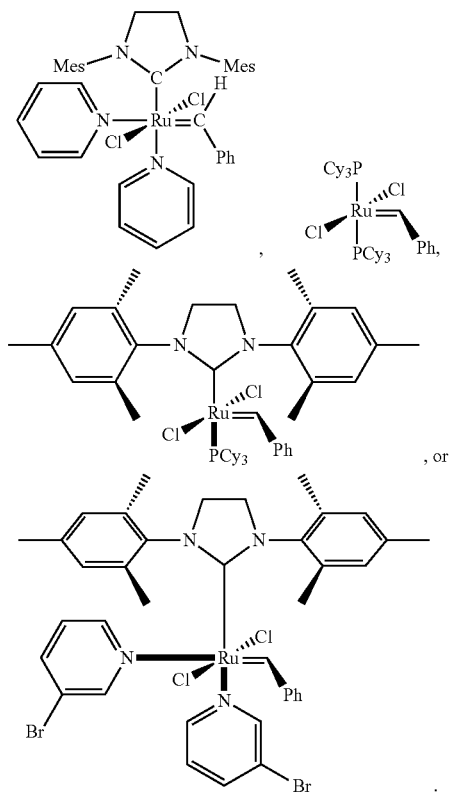

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula $$R^{V1}-O-C(R^{V2})=C(R^{V3})(R^{V4})$$

Each of $R^{V1}$, $R^{V2}$, $R^{V3}$, and $R^{V4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{V1}$ is optionally substituted alkyl, and $R^{V2}$, $R^{V3}$, and $R^{V4}$ are hydrogen. In certain embodiments, $R^{V1}$ is unsubstituted alkyl, and $R^{V2}$, $R^{V3}$, and $R^{V4}$ are hydrogen. In certain embodiments, $R^{V1}$ is substituted alkyl, and $R^{V2}$, $R^{V3}$, and $R^{V4}$ are hydrogen. In certain embodiments, $R^{V1}$ is methyl, and $R^{V2}$, $R^{V3}$, and $R^{V4}$ are hydrogen. In certain embodiments, $R^{V1}$ is ethyl, and $R^{V2}$, $R^{V3}$, and $R^{V4}$ are hydrogen. In certain embodiments, $R^{V1}$ is propyl, and $R^{V2}$, $R^{V3}$, and $R^{V4}$ are hydrogen. In certain embodiments, $R^{V1}$ is optionally substituted alkenyl, and $R^{V2}$, $R^{V3}$, and $R^{V4}$ are hydrogen. In certain embodiments, $R^{V1}$ is unsubstituted alkenyl, and $R^{V2}$, $R^{V3}$, and $R^{V4}$ are hydrogen. In certain embodiments, $R^{V1}$ is vinyl, and $R^{V2}$, $R^{V3}$, and $R^{V4}$ are hydrogen. In certain embodiments, at least one of $R^{V1}$, $R^{V2}$, $R^{V3}$, and $R^{V4}$ is conjugated with a diagnostic agent as defined herein. In certain embodiments, the ROMP is quenched by ethyl vinyl ether. Excess ethyl vinyl ether can be removed from the polymers by vacuum.

Compositions and Kits

In certain aspects, the present disclosure presents compositions. In certain embodiments, the composition is a pharmaceutical composition. In certain embodiments, the composition is a cosmetic composition. In certain embodiments, the composition is a nutraceutical composition. In some embodiments, the composition comprises a compound, macromonomer, conjugate, or polymer as described herein and optionally, an excipient. In certain embodiments, the excipient is a pharmaceutically acceptable excipient. In certain embodiments, the excipient is a cosmetically acceptable excipient. In certain embodiments, the excipient is a nutraceutically acceptable excipient.

In certain embodiments, the pharmaceutical compositions are useful for treating a disease in a subject in need thereof. In certain embodiments, the pharmaceutical compositions are useful for preventing a disease in a subject. In certain embodiments, the pharmaceutical compositions are useful for diagnosing a disease in a subject. In certain embodiments, the pharmaceutical compositions are useful for delivering an agent (e.g., to a subject or cell).

In certain embodiments, a compound, macromonomer, conjugate, or polymer described herein is provided in an effective amount in the composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In some embodiments, the proliferative disease is cancer. In some embodiments, the cancer is nuclear protein of the testis (NUT) midline carcinoma, treatment-refractory acute myeloid leukemia, myelodysplastic syndrome, multiple myeloma, triple negative- and estrogen receptor-positive breast cancers, small cell and non-small cell lung cancers, castration resistant prostate cancer, pancreatic ductal adenocarcinoma, colorectal cancer, neuroblastoma and N-Myc Proto-Oncogene Protein (MYCN)-driven solid tumors, acute myeloid leukemia (AML), Ewing sarcomas, anaplastic thyroid carcinoma (ATC), ovarian cancer, medulloblastoma, or uveal melanoma. In certain embodiments, the effective amount is an amount effective for treating multiple myeloma in a subject in need thereof. In certain embodiments, the effective amount is an amount effective for preventing multiple myeloma in a subject in need thereof. In certain embodiments, the effective amount is an amount effective for treating a hematological disease in a subject in need thereof. In certain embodiments, the effective amount is an amount effective for preventing a hematological disease in a subject in need thereof. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a in a painful condition subject in need thereof. In certain embodiments, the effective amount is an amount effective for preventing a painful condition in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for reducing the risk of developing a disease (e.g., proliferative disease, hematological disease, neurological disease, painful condition, psychiatric disorder, or metabolic disorder) in a subject in need thereof. In certain embodiments, the effective amount is an amount effective for inhibiting the activity (e.g., aberrant activity, such as increased activity) of a protein kinase in a subject or cell. In certain embodiments, the effective amount is an amount effective for treating a disease mediated by dysregulated or dysfunctional BET protein activity in a subject in need thereof. In certain embodiments, the effective amount is an amount effective for preventing a disease mediated by dysregulated or dysfunctional BET protein activity in a subject in need thereof. In certain embodiments, the effective amount is an amount effective for inhibiting BET protein activity in a subject or cell.

In certain embodiments, the pharmaceutical compositions are useful for delivering an agent (e.g., to a subject or cell). In some embodiments, the agent is delivered to a biological sample. In certain embodiments, the agent is delivered to a tissues. In some embodiments, the agent is delivered to a cell. In certain embodiments, the cell is in vitro. In certain embodiments, the cell is in vivo. In certain embodiments, the cell is a malignant cell. In certain embodiments, the cell is a premalignant cell.

An agent can be a molecule, group of molecules, complex or substance administered to an organism for diagnostic, therapeutic, preventative medical, or veterinary purposes. In certain embodiments, at least one instance of the agent is a pharmaceutical agent. In certain embodiments, at least one instance of the agent is a therapeutic agent. In certain embodiments, at least one instance of the agent is a diagnostic agent or a prophylactic agent. In certain embodiments, at least one instance of the agent or therapeutic agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF), and antibodies (e.g., Herceptin (trastuzumab), T-DM1, AVASTIN (bevacizumab), ERBITUX (cetuximab), Vectibix (panitumumab), Rituxan (rituximab), Bexxar (tositumomab)). Exemplary chemotherapeutic agents include, but are not limited to, anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL, BMS-354825), erlotinib (TARCEVA®), gefitinib (IRESSA®), imatinib (Gleeveco, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the anti-cancer agent is paclitaxel. In certain embodiments, the agent is an anti-hypertension agent. Exemplary anti-hypertension agents include, but are not limited to, amiloride, amlodipine, atenolol, azilsartan, benazepril, bendroflumethiazide, betaxolol, bisoprolol, bucindolol, bumetanide, candesartan, captopril, carteolol, carvedilol, chlorothiazide, chlorthalidone, cilnidipine, clevidipine, diltiazem, doxazosin, enalapril, epitizide, eplerenone, eprosartan, ethacrynic acid, felodipine, Fimasartan, fosinopril, furosemide, hydrochlorothiazide, indapamide, indoramin, irbesartan, isradipine, labetalol, lercanidipine, levamlodipine, lisinopril, losartan, methyclothiazide, metolazone, metoprolol, moexipril, nadolol, nebivolol, nicardipine, nifedipine, nimodipine, nisoldipine, nitrendipine, olmesartan, oxprenolol, penbutolol, perindopril, pindolol, phenoxybenzamine, phentolamine, polythiazide, prazosin, propranolol, quinapril, ramipril, spironolactone, telmisartan, terazosin, timolol, tolazoline, torsemide, trandolapril, triamterene, valsartan, and verapamil. In certain embodiments, the agent is telmisartan.

Exemplary diagnostic agents include, but are not limited to, fluorescent molecules; gases; metals; imaging agents, such as commercially available imaging agents used in positron emissions tomography (PET), computer assisted tomography (CAT), single photon emission computerized tomography, x-ray, fluoroscopy, and magnetic resonance imaging (MRI); and contrast agents, such as magnetic-resonance signal enhancing agents, X-ray attenuating agents, ultrasound scattering agent, and ultrasound frequency shifting agents. Examples of suitable materials for use as contrast agents in MRI include gadolinium chelates, as well as iron, magnesium, manganese, copper, and chromium. Examples of materials useful for CAT and x-ray imaging include iodine-based materials. In certain embodiments, the diagnostic agent is used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al. (Chemical Society Reviews (1998), 27:19-29), the entire teachings of which are incorporated herein by reference.

In certain embodiments, the diagnostic agent is a metal, inorganic compound, organometallic compound, organic compound, or salt thereof. In certain embodiments, the imaging agent contains a metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, gadolinium, gallium, thallium, and barium. In certain embodiments, the diagnostic agent is an organic compound. In certain embodiments, the diagnostic agent is metal-free. In certain embodiments, the diagnostic agent is a metal-free organic compound.

In certain embodiments, the imaging agent is a magnetic resonance imaging (MRI) agent. In certain embodiments, the MRI agent is gadolinium. In certain embodiments, the MRI agent is a nitroxide radical-containing compound.

In certain embodiments, the imaging agent is a nuclear medicine imaging agent. In certain embodiments, the nuclear medicine imaging agent is selected from the group consisting of $^{64}Cu$ diacetyl-bis($N^4$-methylthiosemicarbazone) ($^{64}Cu$-ASTM), $^{18}F$-fluorodeoxyglucose (FDG), $^{18}F$-fluoride, 3'-deoxy-3'-[$^{18}F$]fluorothymidine (FLT), $^{18}F$-fluoromisonidazole (FMISO), gallium, technetium-99m, and thallium.

In certain embodiments, the imaging agent is radiographic imaging agent. In certain embodiments, the radiographic imaging agent is selected from the group consisting of barium, gastrografin, and iodine contrast agent.

In certain embodiments, the imaging agent is a radical-containing compound. In certain embodiments, the imaging agent is a nitroxide radical-containing compound. In certain embodiments, the imaging agent or diagnostic agent is of the formula:

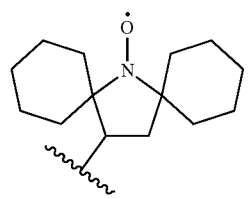

In certain embodiments, the imaging agent or diagnostic agent is an organic compound. In certain embodiments, the imaging agent is a salt of an organic compound. In certain embodiments, the imaging agent or diagnostic agent is of the formula:

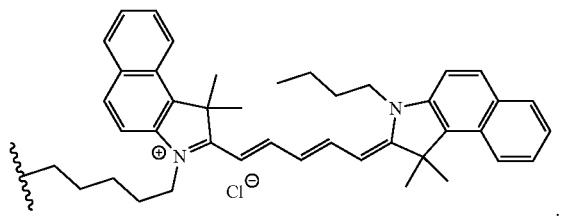 [SMILES: *CCCCC[N+]1=C(/C=C/C=C/C=C2\N(CCCC)c3ccc4ccccc4c3C2(C)C)C(C)(C)c2c1ccc1ccccc21 ; [Cl-]]

In certain embodiments, the diagnostic agent may comprise a fluorescent molecule, a metal chelate, a contrast agent, a radionuclide, or a positron emission tomography (PET) imaging agent, an infrared imaging agent, a near-IR imaging agent, a computer assisted tomography (CAT) imaging agent, a photon emission computerized tomography imaging agent, an X-ray imaging agent, or a magnetic resonance imaging (MRI) agent.

In some embodiments, the diagnostic agent is a fluorescent molecule. In some embodiments, the fluorescent molecule comprises an acridine dye, a cyanine dye, a rhodamine dye, a BODIPY dye, a fluorescein dye, a dansyl dye, an Alexa dye, an atto dye, a quantum dot, or a fluorescent protein. In some embodiments, the fluorescent molecule is a cyanine dye (e.g., Cy3, Cy 3.5, Cy5, Cy5.5, Cy7, or Cy7.5).

In some embodiments, the diagnostic agent is an MRI agent (e.g., a contrast agent). Examples of suitable materials for use as MRI agents (e.g., contrast agents) include gadolinium chelates, as well as iron, magnesium, manganese, copper, and chromium.

In some embodiments, the diagnostic agent is a CAT imaging agent or an X-ray imaging agent. Examples of materials useful for CAT and X-ray imaging include iodine-based materials.

In some embodiments, the diagnostic agent is a PET imaging agent. Examples of suitable PET imaging agents include compounds and compositions comprising the positron emitting radioisotopoes $^{18}$F, $^{15}$O, $^{13}$N, $^{11}$C, $^{82}$Rb, $^{64}$Cu, and $^{68}$Ga, e.g., fludeoxyglucose ($^{18}$F-FDG), $^{68}$Ga-DOTA-psuedopeptides (e.g., $^{68}$Ga-DOTA-TOC), $^{11}$C-metomidate, $^{11}$C-acetate, $^{11}$C-methionine, $^{11}$C-choline, $^{18}$F-fluciclovine, $^{18}$F-fluorocholine, $^{18}$F-fluorodeoxysorbitol, $^{18}$F-3'-fluoro-3'-deoxythymidine, $^{11}$C-raclopride, and $^{18}$F-desmethoxyfallypride.

In some embodiments, the diagnostic agent is a near-IR imaging agent. Examples of near-IR imaging agents include Pz 247, DyLight 750, DyLight 800, cyanine dyes (e.g., Cy5, Cy5.5, Cy7), AlexaFluor 680, AlexaFluor 750, IRDye 680, IRDye 800CW, and Kodak X-SIGHT dyes.

In some embodiments, the agent can be a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present disclosure include, but are not limited to, $^{123}$I, $^{125}$I, $^{130}$I, $^{131}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, or $^{18}$F.

Prophylactic agents that can be included in the conjugates of the disclosure include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant.

In certain embodiments, at least one instance of the agent is a cosmetic agent. In certain embodiments, at least one instance of the agent is a nutraceutical agent. In certain embodiments, at least one instance of the agent is a small molecule. In certain embodiments, at least one instance of the agent is a peptide or protein.

Pharmaceutical compositions described herein can be prepared by any method known in the art of pharmacology. In general, such preparatory methods include bringing a compound, macromonomer, conjugate, or polymer described herein (which may include a therapeutic agent (the "active ingredient")) into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients, such as cocoa butter and suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound, macromonomer, conjugate, or polymer described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the a compound, macromonomer, conjugate, or polymer in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

A compound, macromonomer, conjugate, or polymer provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds, macromonomers, conjugates, polymers, and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound, macromonomer, conjugate, or polymer required to achieve an effective amount will vary from subject to subject, depending, for example, on species, age, and general condition of a subject, severity of the side effects or disorder, identity of the particular compound, macromonomer, conjugate, or polymer, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound, macromonomer, conjugate, or polymer described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound, macromonomer, conjugate, or polymer described herein. In certain embodiments, a dose described herein includes independently between 1 mg and 3 mg, inclusive, of a compound, macromonomer, conjugate, or polymer described herein. In certain embodiments, a dose described herein includes independently between 3 mg and 10 mg, inclusive, of a compound, macromonomer, conjugate, or polymer described herein. In certain embodiments, a dose described herein includes independently between 10 mg and 30 mg, inclusive, of a compound, macromonomer, conjugate, or polymer described herein. In certain embodiments, a dose described herein includes independently between 30 mg and 100 mg, inclusive, of a compound, macromonomer, conjugate, or polymer described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A compound, macromonomer, conjugate, polymer or composition as described herein, can be administered in combination with one or more additional pharmaceutical agents (e.g., therapeutically and/or prophylactically active agents). The compound, macromonomer, conjugate, polymer or composition can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in diagnosing a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound, macromonomer, conjugate, or polymer described herein and an additional pharmaceutical agent shows a synergistic effect that is absent in a pharmaceutical composition including one of the compound, macromonomer, conjugate, or polymer and the additional pharmaceutical agent, but not both.

The compound, macromonomer, conjugate, polymer or compositions can be administered concurrently with, prior to, or subsequent to one or more additional pharmaceutical agents, which are different from the compound, macromonomer, conjugate, polymer or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the a compound, macromonomer, conjugate, polymer or composition described herein in a single dose or administered separately in different doses. The particular combination to employ in a regimen will take into account compatibility of the compound, macromonomer, conjugate, or polymer described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation.

In certain embodiments, the compounds, macromonomers, conjugates, or polymers described herein or pharmaceutical compositions can be administered in combination with an additional therapy. In certain embodiments, the compounds, macromonomers, conjugates, or polymers described herein or pharmaceutical compositions can be administered in combination with an anti-cancer therapy including surgery, radiation therapy, transplantation (e.g., stemcell transplantation, bone marrow transplantation), immunotherapy, chemotherapy, targeted therapy or any combination thereof. In certain embodiments, the compounds, macromonomers, conjugates, or polymers described herein or pharmaceutical compositions can be administered in combination with an additional therapy. In some embodiments, the compounds, macromonomers, conjugates, or polymers described herein or pharmaceutical compositions can be administered in combination with radiation therapy.

Also encompassed by the disclosure are kits (e.g., pharmaceutical packs). The kits provided may comprise a pharmaceutical composition, compound, macromonomer, conjugate, or polymer described herein and instructions for use. The kits may further comprise a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition, compound, macromonomer, conjugate, or polymer described herein. In some embodiments, the pharmaceutical composition, compound, macromonomer, conjugate, or polymer described herein provided in the first container and the second container are combined to form one unit dosage form.

In some embodiments, the percentage of a compound, macromonomer, conjugate, or polymer that comprise an agent is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the compound, macromonomer, conjugate, or polymer that comprise an agent is less than about 50%, e.g., less than about 40%, less than about 35%, less than about 30%, less than about 25%, less than about 20%, less than about 15%, or less than about 10%. In some embodiments, the percentage of the compound, macromonomer, conjugate, or polymer that comprise an agent is between about 5% and about 50%, about 5% and about 40%, about 5% and about 30%, about 5% and about 25%, or about 5% and about 20%. In some embodiments, the percentage of the compound, macromonomer, conjugate, or polymer that comprise an agent is between about 5% and 90%. In some embodiments, the percentage of the compound, macromonomer, conjugate, or polymer that comprise an agent is between about 5% and about 75%. In the some embodiments, the compound, macromonomer, conjugate, or polymer that comprise an agent is between about 5% and about 50%. In the some embodiments, the percentage of the compound, macromonomer, conjugate, or polymer that comprise an agent is between about 10% and about 25%.

In some embodiments, the total amount of the agent present in the compound, macromonomer, conjugate, or polymer is greater than about 5% (e.g., about 6%, about 7%, about 8%, about 9%, about 10%, about 12%, about 15%, about 20%, about 25%, about 30%, or more) of the total size or weight of the polymer. In some embodiments, the total amount of the agent present in the compound, macromonomer, conjugate, or polymer is greater than about 10% (e.g., about 12%, about 15%, about 20%, about 25%, about 30%, or more) of the total size or weight of the polymer.

Without being bound by theory, the compound, macromonomer, conjugate, or polymer disclosed herein may improve the efficiency of an agent by one or more of increasing the localization and/or release (e.g., preferential release) of the agent to a target cell (e.g., a cancer cell), or increasing the half-life of the agent, thus resulting in a significantly higher amount of a released agent at a target site (e.g., a tumor). According, the compounds, macromonomers, conjugates, or polymers disclosed herein can be more effective therapeutically than the free agent (e.g., due to enhanced drug uptake in the target) and/or allow for a lower therapeutic dose of the agent, e.g., without substantially compromising the resulting drug concentration at a target tissue. In some embodiments, the compounds, macromonomers, conjugates, or polymers disclosed herein can reduce the adverse effect associated with systemic administration of an agent in free form (e.g., not coupled to polymer, conjugate or particle described herein).

Without being bound by theory, due to the localized delivery of the compound, macromonomer, conjugate, or polymer (e.g., bottle brush polymer or brush-arm star polymer) or compositions described herein, a lower dose or amount of the agent in the particles can be administered (e.g., through local sustained delivery) compared to the agent in free form. In other embodiments, the agent-containing particles are administered at a dose or amount of the agent that is less than the dose or amount of said agent in free form to have a desired effect (e.g., a desired therapeutic effect).

In some embodiments, the agent is incorporated into a compound, macromonomer, conjugate, or polymer at a dose that is less than the dose or amount of said agent in free form to have a desired effect (e.g., a desired therapeutic effect), e.g., the standard of care dose for the intended use of the free agent. In one embodiment, the agent is incorporated into the particles at a dose or amount of the agent that is less than the standard of care dose of the agent for a desired therapy (e.g., a dose that is less than about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 0.95 that of the standard of care dose of the agent).

In some embodiments, the agent is incorporated into a compound, macromonomer, conjugate, or polymer at a dose equivalent to the dose or amount of said agent in free form to have a desired effect (e.g., a desired therapeutic effect), e.g., the standard of care dose for the intended use of the free agent. In these embodiments, the compound, macromonomer, conjugate, or polymer produces a greater therapeutic effect and/or a less adverse effect than the free agent. In certain embodiments, the compound, macromonomer, conjugate, or polymer increases the amount of the agent delivered to a tissue or cell in need thereof and reduces the amount of the agent exposed to a non-target tissue or cell, as compared to the free agent.

In some embodiments, the agent is incorporated into a compound, macromonomer, conjugate, or polymer at a dose higher than the dose or amount of said agent in free form to have a desired effect (e.g., a desired therapeutic effect), e.g., the standard of care dose for the intended use of the free agent. In some embodiments, the agent is incorporated into a compound, macromonomer, conjugate, or polymer at a dose higher than the dose or amount of said agent in free form that would produce an adverse effect by systemic administration (e.g., a reduction in blood pressure). In some embodiments, since the compound, macromonomer, conjugate, or polymer described herein releases the agent at a target site based on pH microenvironment, other non-target sites (e.g., blood vessels) with different pH would be less likely to be exposed to the agent.

In another aspect, provided are kits including a first container comprising a compound, macromonomer, conjugate, polymer or pharmaceutical composition described herein. In certain embodiments, the kits are useful for delivering an agent (e.g., to a subject or cell). In certain embodiments, the kits are useful for treating a disease (e.g., proliferative disease, hematological disease, neurological disease, painful condition, psychiatric disorder, or metabolic disorder) in a subject in need thereof. In certain embodiments, the kits are useful for preventing a disease (e.g., proliferative disease, hematological disease, neurological disease, painful condition, psychiatric disorder, or metabolic disorder) in a subject in need thereof. In certain embodiments, the kits are useful for reducing the risk of developing a disease (e.g., proliferative disease, hematological disease, neurological disease, painful condition, psychiatric disorder, or metabolic disorder) in a subject in need thereof. In certain embodiments, the kits are useful for treating cancer in a subject in need thereof. In certain embodiments, the kits are useful for preventing cancer in a subject in need thereof. In certain embodiments, the kits are useful for reducing the risk of developing cancer in a subject in need thereof. In certain embodiments, the kits are useful for inhibiting the activity (e.g., aberrant activity, such as increased activity) of a protein kinase in a subject or cell. In some embodiments, the disease is mediated by dysregulated or dysfunctional BET protein activity. In certain embodiments, the kits are useful for diagnosing a disease in a subject or cell.

In certain embodiments, a kit described herein further includes instructions for using the kit. A kit described herein may also include information as required by a regulatory agency such as the U.S. Food and Drug Administration (FDA). In some embodiments, a kit comprises a polymer or composition as described herein and instructions for using the polymer or composition. In certain embodiments, the information included in the kits is prescribing information. In certain embodiments, the kits and instructions provide for delivering an agent. In certain embodiments, the kits and instructions provide for treating a disease (e.g., proliferative disease, hematological disease, neurological disease, painful condition, psychiatric disorder, or metabolic disorder) in a subject in need thereof. In certain embodiments, the kits and instructions provide for preventing a disease (e.g., proliferative disease, hematological disease, neurological disease, painful condition, psychiatric disorder, or metabolic disorder) in a subject in need thereof. In certain embodiments, the kits and instructions provide for reducing the risk of developing a disease (e.g., proliferative disease, hematological disease, neurological disease, painful condition, psychiatric disorder, or metabolic disorder) in a subject in need thereof. In certain embodiments, the kits and instructions provide for inhibiting the activity (e.g., aberrant activity, such as increased activity) of a protein kinase in a subject or cell. A kit described herein may include one or more additional pharmaceutical agents described herein as a separate composition.

The compounds of the present invention may be formulated into several different types of pharmaceutical compositions that contain a therapeutically effective amount of the compound, and a pharmaceutically acceptable carrier. Generally, the inventive compounds may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral), parenteral (e.g., subcutaneous (s.c.), intravenous (i.v.), intramuscular (i.m.), and intrasternal injection, or infusion techniques, intra-arterial, intramedullary, intrathecal, intraventricular, transdermal, interdermal, rectal, intravaginal, intraperitoneal, topical mucosal, nasal, buccal, sublingual, intratracheal instillation, bronchial instillation, and/or inhalation. In some embodiments, the compositions are formulated for oral or intravenous administration (e.g., systemic intravenous injection. In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration).

The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Accordingly, compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

The compounds may be formulated as solutions for parenteral and oral delivery, particularly to the extent that they are water-soluble. Parenteral administration may also be advantageous in that the compound may be administered relatively quickly such as in the case of a single-dose treatment and/or an acute condition.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of the present invention may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery vehicle, for example, in a liposome coated with organ-specific antibody. In such embodiments, the liposomes are targeted to and taken up selectively by the organ.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

The compositions may be formulated for buccal or sublingual administration, examples of which include tablets, lozenges and gels.

The compositions may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

In some embodiments, the compounds may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, and cetyl or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

In certain embodiments, a therapeutically effective amount is an amount of a compound, macromonomer, conjugate, polymer, or a pharmaceutically acceptable salt or a stereoisomer thereof, effective in producing the desired therapeutic response in a particular patient suffering from a disease or disorder. The term "therapeutically effective amount" includes the amount of the compound, macromonomer, conjugate, or polymer of the application or a pharmaceutically acceptable salt or a stereoisomer thereof, when administered, may induce a positive modification in the disease or disorder to be treated (e.g., to inhibit and/or reduce expression of BRD4, BRD2, or BRD3), or is sufficient to prevent development or progression of the disease or disorder, or alleviate to some extent, one or more of the symptoms of the disease or disorder being treated in a subject, or which simply kills or inhibits the growth of diseased cells, or reduces the amount of BRD4, BRD2, or BRD3 in diseased cells. In respect of the therapeutic amount of the compound, macromonomer, conjugate, or polymer, the amount of the compound used for the treatment of a subject is low enough to avoid undue or severe side effects, within the scope of sound medical judgment can also be considered.

The total daily dosage of the compounds, macromonomers, conjugates, or polymers and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs that may be used in combination or coincidental with the specific compound employed; and like factors well known in the medical arts (see, for example, Goodman and Gilman's, "The Pharmacological Basis of Therapeutics," 10th Edition, A. Gilman, J. Hardman and L. Limbird, eds., McGraw-Hill Press, 155-173, 2001).

Compounds, macromonomers, conjugates, or polymers of the present invention may be effective over a wide dosage range. In some embodiments, the total daily dosage (e.g., for adult humans) may range from about 0.001 to about 1000 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day, and in yet other embodiments from about 50 to about 100 mg per day. Individual dosages may be formulated to contain the desired dosage amount depending upon the number of times the compound is administered per day. By way of example, capsules may be formulated with from about 5 to about 25 mg of compound (e.g., 1, 2, 2.5, 3, 4, 5, 10, 15, 20, 25, 50, 100, 150, and 200 mg).

In some embodiments, dosages range from about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, the dosage levels below the lower limit of the aforesaid range may be more than adequate, while in other cases still larger doses may be used without causing any harmful side effect.

Methods of Use

The present disclosure also provides methods of using the compounds, conjugates, macromonomers, and polymers described herein, or a pharmaceutical composition thereof, for delivering PROTAC. The present disclosure also provides methods of using the compounds, conjugates, macromonomers, and polymers described herein, or a pharmaceutical composition thereof, for the treatment, prevention, or diagnosis of a disease or condition.

The present disclosure provides methods of treating a disease in a subject in need thereof. In certain embodiments, the methods described herein comprise administering to a subject in need thereof a therapeutically effective amount of a compound, conjugate, macromonomer, polymer or composition. In some embodiments, the methods described herein comprise administering to a subject in need thereof a therapeutically effective amount of a compound, conjugate, macromonomer, polymer or composition comprising $M^A$ and $M^B$. In certain embodiments, the disease is a proliferative disease. In some embodiments, the disease is cancer. In some embodiments, the cancer is multiple myeloma. In certain embodiments, the disease is nuclear protein of the testis (NUT) midline carcinoma, treatment-refractory acute myeloid leukemia, myelodysplastic syndrome, multiple myeloma, triple negative- and estrogen receptor-positive breast cancers, small cell and non-small cell lung cancers, castration resistant prostate cancer, pancreatic ductal adenocarcinoma, colorectal cancer, neuroblastoma and N-Myc Proto-Oncogene Protein (MYCN)-driven solid tumors, acute myeloid leukemia (AML), Ewing sarcomas, anaplastic thyroid carcinoma (ATC), ovarian cancer, medulloblastoma, or uveal melanoma.

In certain embodiments, the methods described herein include administering to a subject an effective amount of a compound, conjugate, macromonomer, or polymer described herein, or a pharmaceutical composition thereof. In certain embodiments, the methods described herein include administering to a subject an effective amount of a compound, conjugate, macromonomer, or polymer described herein, or a pharmaceutical composition thereof. In certain embodiments, the methods described herein comprise treating a disease or condition in a subject in need thereof by administering to in the subject a therapeutically effective amount of: a compound, conjugate, macromonomer, or polymer described herein; or a pharmaceutical composition thereof. In certain embodiments, the methods described herein comprise preventing a disease or condition in a subject in need thereof by administering to the subject a prophylactically effective amount of: a compound, conjugate, macromonomer, or polymer described herein; or a pharmaceutical composition thereof.

In certain embodiments, the disease or condition is a proliferative disease, hematological disease, neurological disease, painful condition, psychiatric disorder, metabolic disorder, or a long-term medical condition. In certain embodiments, the disease is cancer (e.g., nuclear protein of the testis (NUT) midline carcinoma, treatment-refractory acute myeloid leukemia, myelodysplastic syndrome, multiple myeloma, triple negative- and estrogen receptor-positive breast cancers, small cell and non-small cell lung cancers, castration resistant prostate cancer, pancreatic ductal adenocarcinoma, colorectal cancer, neuroblastoma and N-Myc Proto-Oncogene Protein (MYCN)-driven solid tumors, acute myeloid leukemia (AML), Ewing sarcomas, anaplastic thyroid carcinoma (ATC), ovarian cancer, medulloblastoma, or uveal melanoma), benign neoplasm, angiogenesis, inflammatory disease, autoinflammatory disease, or autoimmune disease. In certain embodiments, the long-term medical condition is hypertension.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) including leukemia, lymphoma and multiple myeloma. Adult tumors/cancers and pediatric tumors/cancers are included. The cancers may be vascularized, or not yet substantially vascularized, or non-vascularized tumors.

In some embodiments, the compounds, conjugates, macromonomers, or polymers described herein, or a pharmaceutical composition thereof are useful in treating a cancer. In some embodiments, the compounds, conjugates, macromonomers, or polymers described herein, or a pharmaceutical composition thereof, are useful to delay the onset of, slow the progression of, or ameliorate the symptoms of cancer. In some embodiments, the compounds, conjugates, macromonomers, or polymers described herein, or a pharmaceutical composition thereof, are administered in combination with other compounds, drugs, or therapeutics to treat cancer. In some embodiments, the compounds, conjugates, macromonomers, or polymers described herein, or a pharmaceutical composition thereof, are administered in combination with an additional therapy. In certain embodiments, the compounds, conjugates, macromonomers, or polymers described herein, or a pharmaceutical composition thereof, are administered in combination with an radiation therapy.

In some embodiments, the compounds, conjugates, macromonomers, or polymers described herein, or a pharmaceutical composition thereof are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLUSLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Representative examples of cancers includes adenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (nonmelanoma), biliary cancer, extrahepatic bile duct cancer, intrahepatic bile duct cancer, bladder cancer, urinary bladder cancer, brain cancer (e.g., gliomas and glioblastomas such as brain stem glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, gestational trophoblastic tumor glioma, head and neck cancer, Hodgkin's lymphoma, leukemia, lymphoma, multiple myeloma, hypopharyngeal cancer, ocular cancer, islet cell tumors (endocrine pancreas), renal cancer (e.g., Wilm's Tumor, clear cell renal cell carcinoma), liver cancer, lung cancer (e.g., non-small cell lung cancer and small cell lung cancer), Waldenstrom's macroglobulinema, uveal melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm/multiple myeloma, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, transitional cell cancer of the renal pelvis and ureter and other urinary organs, urethral cancer, gestational trophoblastic tumor, vaginal cancer and vulvar cancer.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, the compounds, conjugates, macromonomers, or polymers described herein, or a pharmaceutical composition thereof are useful for treating a cancer including, but not limited to, nuclear protein of the testis (NUT) midline carcinoma, treatment-refractory acute myeloid leukemia, myelodysplastic syndrome, multiple myeloma, triple negative- and estrogen receptor-positive breast cancers, small cell and non-small cell lung cancers, castration resistant prostate cancer, pancreatic ductal adenocarcinoma, colorectal cancer, neuroblastoma and N-Myc Proto-Oncogene Protein (MYCN)-driven solid tumors, acute myeloid leukemia (AML), Ewing sarcomas, anaplastic thyroid carcinoma (ATC), ovarian cancer, medulloblastoma, or uveal melanoma.

In some embodiments, the proliferative disease is a benign neoplasm. All types of benign neoplasms disclosed herein or known in the art are contemplated as being within the scope of the disclosure. In some embodiments, the proliferative disease is associated with angiogenesis. All types of angiogenesis disclosed herein or known in the art are contemplated as being within the scope of the disclosure. In certain embodiments, the proliferative disease is an inflammatory disease. All types of inflammatory diseases disclosed herein or known in the art are contemplated as being within the scope of the disclosure. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the disclosure. In some embodiments, the proliferative disease is an autoimmune disease. All types of autoimmune diseases disclosed herein or known in the art are contemplated as being within the scope of the disclosure.

In some embodiments, the compounds, conjugates, macromonomers, or polymers herein, or a pharmaceutical composition thereof contain at least one therapeutic agent useful in treating cancer. In some embodiments, the compounds, conjugates, macromonomers, or polymers herein, or a pharmaceutical composition thereof are administer with a therapeutic agent. In certain embodiments, the therapeutic agent is an anti-cancer agent. In some embodiments, the anti-cancer agent is bortezomib. In some embodiments, the anti-cancer agent is selected from the group consisting of abiraterone acetate, ABVD, ABVE, ABVE-PC, AC, AC-T, ADE, ado-trastuzumab emtansine, afatinib dimaleate, aldesleukin, alemtuzumab, anastrozole, arsenic trioxide, asparaginase *Erwinia chrysanthemi*, axitinib, azacitidine, BEACOPP, belinostat, bendamustine hydrochloride, BEP, bevacizumab, bicalutamide, bleomycin, blinatumomab, bortezomib, bosutinib, brentuximab vedotin, busulfan, cabazitaxel, cabozantinib-s-malate, CAF, capecitabine, CAPOX, carboplatin, carboplatin-taxol, carfilzomibcarmustine, carmustine implant, ceritinib, cetuximab, chlorambucil, chlorambucil-prednisone, CHOP, cisplatin, clofarabine, CMF, COPP, COPP-ABV, crizotinib, CVP, cyclophosphamide, cytarabine, dabrafenib, dacarbazine, dactinomycin, dasatinib, daunorubicin hydrochloride, decitabine, degarelix, denileukin diftitox, denosumab, Dinutuximab, docetaxel, doxorubicin hydrochloride, doxorubicin hydrochloride liposome, enzalutamide, epirubicin hydrochloride, EPOCH, erlotinib hydrochloride, etoposide, etoposide phosphate, everolimus, exemestane, FEC, fludarabine phosphate, fluorouracil, FOLFIRI, FOLFIRI-BEVACIZUMAB, FOLFIRI-CETUXIMAB, FOLFIRINOX, FOLFOX, FU-LV, fulvestrant, gefitinib, gemcitabine hydrochloride, gemcitabine-cisplatin, gemcitabine-oxaliplatin, goserelin acetate, Hyper-CVAD, ibritumomab tiuxetan, ibrutinib, ICE, idelalisib, ifosfamide, imatinib mesylate, imiquimod, ipilimumab, irinotecan hydrochloride, ixabepilone, lanreotide acetate, lapatinib ditosylate, lenalidomide, lenvatinib, letrozole, leucovorin calcium, leuprolide acetate, liposomal cytarabine, lomustine, mechlorethamine hydrochloride, megestrol acetate, mercaptopurine, methotrexate, mitomycin c, mitoxantrone hydrochloride, MOPP, nelarabine, nilotinib, nivolumab, obinutuzumab, OEPA, ofatumumab, OFF, olaparib, omacetaxine mepesuccinate, OPPA, oxaliplatin, paclitaxel, paclitaxel albumin-stabilized nanoparticle formulation, PAD, palbociclib, pamidronate disodium, panitumumab, panobinostat, pazopanib hydrochloride, pegaspargase, peginterferon alfa-2b, peginterferon alfa-2b, pembrolizumab, pemetrexed disodium, pertuzumab, plerixafor, pomalidomide, ponatinib hydrochloride, pralatrexate, prednisone, procarbazine hydrochloride, radium 223 dichloride, raloxifene hydrochloride, ramucirumab, R-CHOP, recombinant HPV bivalent vaccine, recombinant human papillomavirus, nonavalent vaccine, recombinant human papillomavirus, quadrivalent vaccine, recombinant interferon alfa-2b, regorafenib, rituximab, romidepsin, ruxolitinib phosphate, siltuximab, sipuleucel-t, sorafenib tosylate, STANFORD V, sunitinib malate, TAC, tamoxifen citrate, temozolomide, temsirolimus, thalidomide, thiotepa, topotecan hydrochloride, toremifene, tositumomab and iodine I 131, tositumomab, TPF, trametinib, trastuzumab, VAMP, vandetanib, VEIP, vemurafenib, vinblastine sulfate, vincristine sulfate, vincristine sulfate liposome, vinorelbine tartrate, vismodegib, vorinostat, XELIRI, XELOX, ziv-aflibercept, and zoledronic acid. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin (BPD-M$^A$), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), Ca2+ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the methods provided herein comprise administering a conjugate, or a salt thereof, a polymer, or a composition to a subject in need thereof. In certain embodiments, the methods provided herein comprise contacting a biological sample, tissue, or cell with a conjugate, or a salt thereof, a polymer, or a composition. In certain embodiments, the biological sample or cell is in vitro. In some embodiments, the biological sample or cell is in vivo. In some embodiments, the cell is a malignant cell. In certain embodiments the cell is a premalignant cell. In some embodiments, the pharmaceutical agent is delivered to a biological sample or cell to treat a disease. In some embodiments, the pharmaceutical agent is delivered to a biological sample or cell to prevent a disease. In some embodiments, the pharmaceutical agent is delivered to a biological sample or cell to diagnose a disease.

In some aspects, the present invention is directed to treating diseases and disorders mediated or characterized by dysfunctional or dysregulated BET protein activity. As used herein, the terms "characterized by" or "mediated by", refer to BET activity that may include participation in the inception, manifestation of one or more symptoms or markers, or the severity or progression of the disease or disorder. The diseases or disorders may be said to be characterized or mediated by dysfunctional or dysregulated protein activity (e.g., elevated protein levels or otherwise abnormal protein activity compared to a non-pathological state). A "disease" is generally regarded as a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. In some embodiments, compounds of the application may be useful in the treatment of non-cancerous proliferative diseases and disorders. In some embodiments, compounds of the application may be useful in the treatment of proliferative diseases and disorders (e.g., cancer or benign neoplasms). As used herein, the term "cell proliferative disease or disorder" refers to the conditions characterized by unregulated or abnormal cell growth, or both. Cell proliferative disorders include noncancerous conditions, precancerous conditions, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" the treatment may be suffering from or suspected of suffering from a specific disease or disorder may have been positively diagnosed or otherwise presents with a sufficient number of risk factors, or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

The modes of administration (e.g., oral, parenteral) may be determined in accordance with the standard medical practice.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, obesity, metabolic diseases, and allergic and genetic diseases Representative examples of specific non-cancerous diseases and disorders include rheumatoid arthritis, lymphoproliferative conditions, acromegaly, rheumatoid spondylitis, osteoarthritis, gout, sepsis, septic shock, endotoxic shock, gram-negative sepsis, toxic shock syndrome, asthma, adult respiratory distress syndrome, chronic obstructive pulmonary disease, chronic pulmonary inflammation, inflammatory bowel disease, Crohn's disease, systemic lupus erythematosus, multiple sclerosis, juvenile-onset diabetes, autoimmune uveoretinitis, autoimmune vasculitis, bullous pemphigus, myasthenia gravis, autoimmune thyroditis or Hashimoto's disease, Sjogren's syndrome, granulomatous orchitis, autoimmune oophoritis, sarcoidosis, rheumatic carditis, ankylosing spondylitis, Grave's disease, autoimmune thrombocytopenic purpura, psoriasis, eczema, ulcerative colitis, pancreatic fibrosis, hepatic fibrosis, acute and chronic renal disease, irritable bowel syndrome, pyresis, restenosis, cerebral malaria, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, thrombosis, restenosis, silicosis, pulmonary sarcosis, bone resorption diseases, such as osteoporosis, graft-versus-host reaction, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sudden infant death syndrome, sickle cell disease, Tay-Sachs disease, Turner syndrome, urea cycle disorders, thalassemia, cystic fibrosis, uveitis, polymyositis, and dermatomyositis, arteriosclerosis, amyotrophic lateral sclerosis, asocality, immune response, varicosis, vaginitis, including chronic recurrent yeast vaginitis, depression, Sudden Infant Death Syndrome, and varicosis.

In some embodiments, methods of the present invention entail treatment of subjects having cell proliferative diseases or disorders of the hematological system, liver (hepatocellular), brain, lung, colorectal (e.g., colon), pancreas, prostate, skin, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the long, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, anaplastic thyroid carcinoma, giant cell carcinoma, spindle cell carcinoma, and large cell neuroendocrine carcinoma. Lung cancer also includes lung neoplasms having histologic and ultrastructural heterogeneity (e.g., mixed cell types).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

In some embodiments, wherein the method entails use of a multifunctional compound that targets a BRD protein, the subject may have a cancer e.g., NUT midline carcinoma, treatment-refractory acute myeloid leukemia, myelodysplastic syndrome, multiple myeloma, triple negative- and estrogen receptor-positive breast cancers, small cell and non-small cell lung cancers, castration resistant prostate cancer, pancreatic ductal adenocarcinoma, colorectal cancer, neuroblastoma and N-Myc Proto-Oncogene Protein (MYCN)-driven solid tumors.

The compounds of the present application may be administered to a patient, e.g., a cancer patient, as a monotherapy or by way of combination therapy, and as a front-line therapy or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present invention may entail administration of compounds of the invention or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of five days.

The compounds, conjugates, macromonomers, and polymers of the present invention may be used in combination or concurrently with at least one other active agent, e.g., anti-cancer agent or regimen, in treating diseases and disorders. The terms "in combination" and "concurrently in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second component, the first of the two components is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound, conjugate, macromonomer, or polymer of the invention in combination with one or more additional therapeutics known for use in treating the disease or condition (e.g., cancer). The dosage of the additional anticancer therapeutic may be the same or even lower than known or recommended doses. See, Hardman et al., eds., Goodman & Gilman's The Pharmacological Basis Of Basis Of Therapeutics, 10th ed., McGraw-Hill, New York, 2001; Physician's Desk Reference 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound, conjugate, macromonomer, or polymer of the invention and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

When the active components of the combination are not administered in the same pharmaceutical composition, it is understood that they can be administered in any order to a subject in need thereof. For example, a compound, conjugate, macromonomer, or polymer of the present application can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various aspects, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the anticancer therapeutics are administered within the same office visit. In another example, the combination anticancer therapeutics may be administered at 1 minute to 24 hours apart.

In some embodiments, the compound, conjugate, macromonomer, or polymer of the present invention and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1.1. Synthesis of Compound A3

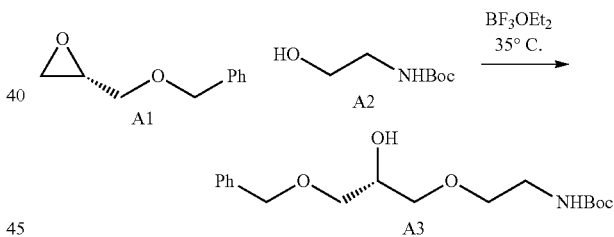

To a solution of compound A1 (340 mg, 6.0 mmol) and A2 (2.0 g, 12 mmol) was added BF$_3$ dietherate (86 mg, 0.61 mmol). The reaction was stirred overnight, after which the crude mixture was purified via column chromatography to yield compound A3 (950 mg, 3.0 mmol). LRMS-ESI: Calcd for C$_{17}$H$_{28}$NO$_5$: m/z=326.2 [M+H]$^+$; Found: 326.1 [M+H]$^+$. $^1$H NMR (400 MHz, CDCl$_3$, ppm) $\delta_H$ 7.34-7.28 (overlap, 5H), 4.88 (br, 1H), 4.52 (m, 2H), 3.40-3.36 (overlap, 5H), 3.25-3.21 (overlap, 4H), 1.16 (s, 9H).

Example 1.2. Synthesis of Compound A5

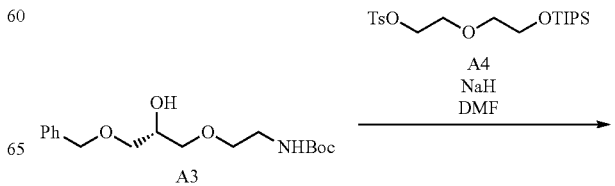

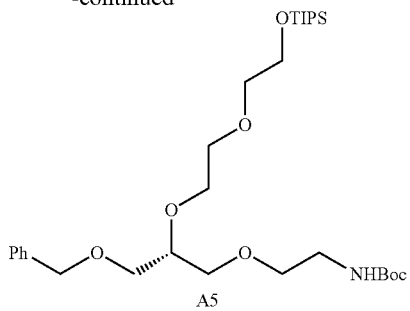

Compound A3 (900 mg, 2.8 mmol) was mixed with compound A4 (1.5 g, 3.6 mmol) and dry DMF (10 mL). After cooling to 0° C., NaH (60 wt % dispersion in mineral oil, 130 mg, 3.1 mmol) was added. The reaction was stirred overnight, after which the crude mixture was mixed with 50 mL EtOAc and extracted 3 times with 50 mL of 1% LiCl solution. The organic layer was concentrated under reduced pressure and the crude mixture was purified by column chromatography to yield compound A5 (920 mg, 1.6 mmol). LRMS-ESI: Calcd for $C_{30}H_{56}NO_7Si$: m/z=570.4 $[M+H]^+$; Found: 570.4 [M+H]+. $^1$H NMR (400 MHz, CDCl$_3$, ppm) $\delta_H$ 7.40-7.28 (overlap, 5H), 4.90 (br, 1H), 4.58 (s, 2H), 3.99 (m, 1H), 3.72 (q, 2H), 3.56-3.49 (overlap, 8H), 3.35-3.27 (overlap, 6H), 1.48-1.41 (overlap, 30H).

Example 1.3. Synthesis of Compound A6

(Pd/C, 200 mg). The reaction flask was purged with hydrogen and then stirred overnight before the mixture was extracted with 50 mL of EtOAc and 3 times with 50 mL of 1% LiCl solution. The organic layer was collected, concentrated, and purified by column chromatography to yield compound A6 (260 mg, 0.53 mmol). LRMS-ESI: Calcd for $C_{23}H_{50}NO_7Si$: m/z=480.3 [M+H]+; Found: 480.2 [M+H]+. $^1$H NMR (400 MHz, CDCl$_3$, ppm) $\delta_H$ 4.96 (br, 1H), 3.87-3.80 (overlap, 4H), 3.73-7.63 (overlap, 4H), 3.63-3.54 (overlap, 4H), 3.54-3.46 (overlap, 3H), 3.32-3.25 (br, 2H), 2.92 (br, 1H), 1.06-1.02 (overlap, 30H).

Example 1.4. Synthesis of Compound A8

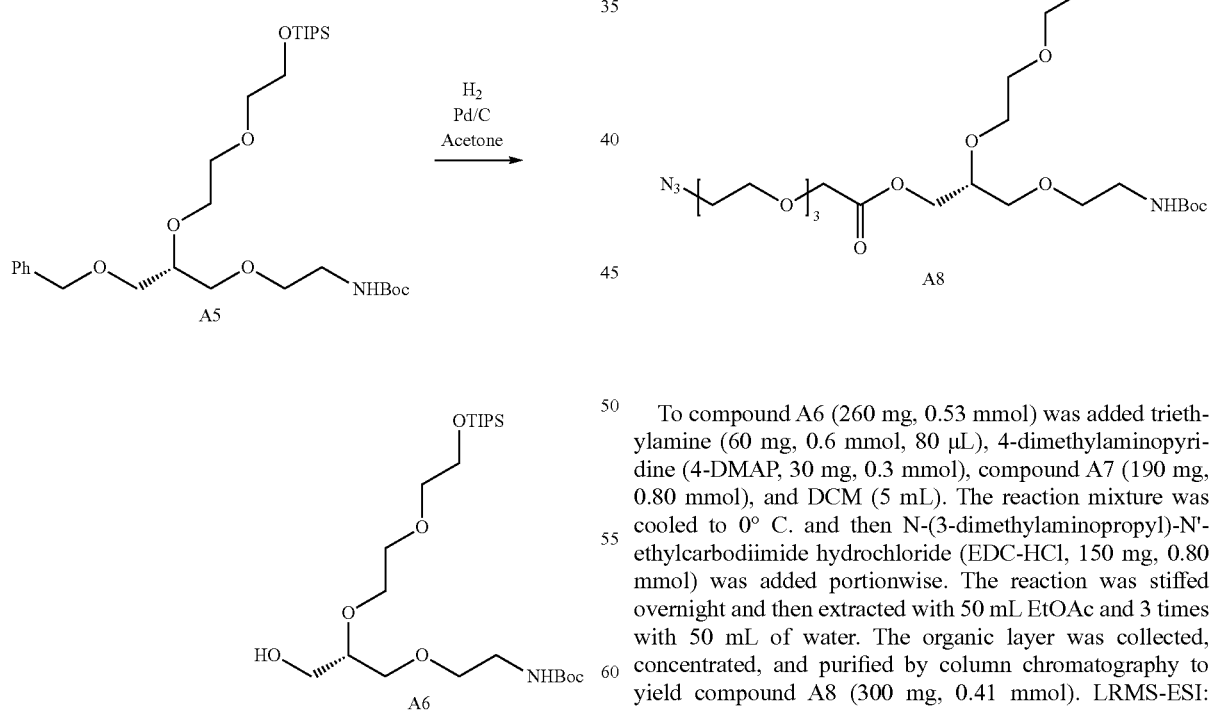

To a solution of compound A5 (900 mg, 1.6 mmol) in Acetone (15 mL) was added 10 wt % palladium on carbon To compound A6 (260 mg, 0.53 mmol) was added triethylamine (60 mg, 0.6 mmol, 80 μL), 4-dimethylaminopyridine (4-DMAP, 30 mg, 0.3 mmol), compound A7 (190 mg, 0.80 mmol), and DCM (5 mL). The reaction mixture was cooled to 0° C. and then N-(3-dimethylaminopropyl)-N'-ethylcarbodiimide hydrochloride (EDC-HCl, 150 mg, 0.80 mmol) was added portionwise. The reaction was stirred overnight and then extracted with 50 mL EtOAc and 3 times with 50 mL of water. The organic layer was collected, concentrated, and purified by column chromatography to yield compound A8 (300 mg, 0.41 mmol). LRMS-ESI: Calcd for $C_{31}H_{63}N_4O_{11}Si$: m/z=695.4 $[M+H]^+$; Found: 695.5 [M+H]+. $^1$H NMR (400 MHz, CDCl$_3$, ppm) $\delta_H$ 4.99 (br, 1H), 4.32 (dd, 1H), 4.22 (dd, 1H), 4.19 (s, 2H), 3.84 (t, 2H), 3.76-3.64 (overlap, 16H), 3.59 (t, 2H), 3.55-3.51 (overlap, 3H), 3.40 (t, 2H), 3.30 (br, 2H), 1.08-1.04 (overlap, 30H).

Example 1.5. Synthesis of Compound A9

Example 1.6. Synthesis of Compound A10

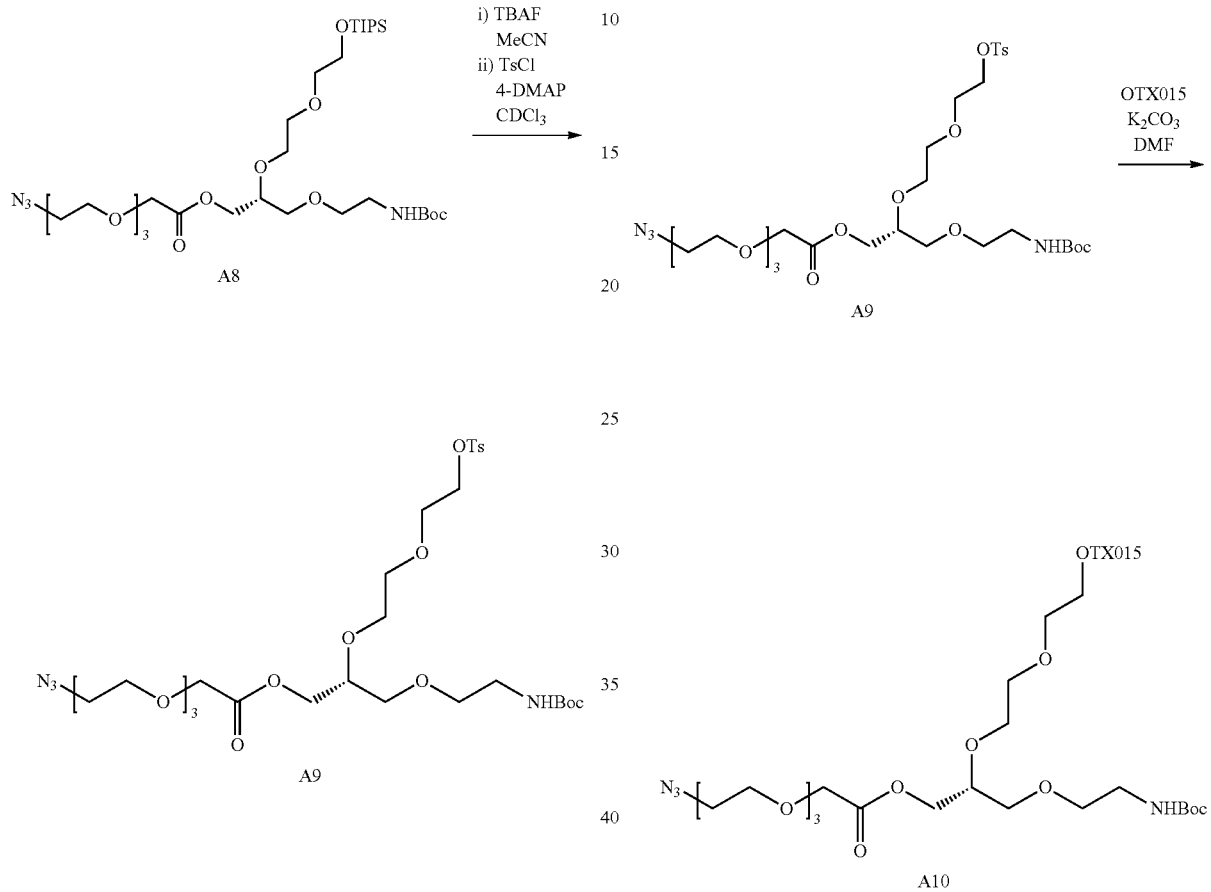

Compound 5 (300 mg, 0.41 mmol) was dissolved in ACN (2 mL) and cooled to 0° C. Then, TBAF (1M in THF, 410 µL) was added dropwise to the reaction mixture. After warming to room temperature and stirring for 1 hour, the mixture was concentrated under reduced pressure and the crude mixture was purified by column chromatography. The resulting deprotected product (100 mg, 0.18 mmol) was then added to a mixture of 4-DMAP (40 mg, 0.4 mmol), and DCM (1 mL). Then, tosyl chloride (50 mg, 0.3 mmol) was added and the mixture was stirred at room temperature overnight. Water (1 mL) was added to quench the reaction and mixture was extracted with 10 mL EtOAc and 10 mL of 50% brine solution. The organic layer was collected, concentrated, and purified by column chromatography to yield compound A9 (130 mg, 0.18 mmol). LRMS-ESI: Calcd for $C_{29}H_{49}N_4O_{13}S$: m/z=693.3 $[M+H]^+$; Found: 693.3 $[M+H]^+$. $^1H$ NMR (400 MHz, CDCl$_3$, ppm) $\delta_H$ 7.80 (d, 2H), 7.35 (d, 2H), 4.97 (br, 1H), 4.29 (dd, 1H), 4.20-4.16 (overlap, 3H), 4.14 (t, 2H), 3.75-3.66 (overlap, 15H), 3.59-3.55 (overlap, 2H), 3.53-3.48 (overlap, 4H), 3.39 (t, 2H), 3.28 (br, 2H), 2.44 (s, 3H), 1.43 (s, 9H).

To compound A9 (130 mg, 0.18 mmol) was added OTX015 (100 mg, 0.18 mmol), K$_2$CO$_3$ (38 mg, 0.27 mmol), and DMF (1.8 mL). The reaction was heated to 85° C. and after 1 day, DMF was removed under reduced pressure. The mixture was extracted with DCM and 50% saturated brine. The organic layer was collected, concentrated, and purified by column chromatography to yield compound A10 (42 mg, 0.041 mmol). LRMS-ESI: Calcd for $C_{47}H_{62}ClN_7O_{12}S$: m/z=983.4 $[M-N_2]^+$; Found: 983.6 $[M-N_2]^+$. $^1H$ NMR (400 MHz, CDCl$_3$, ppm) $\delta_H$ 7.45 (d, 2H), 7.40 (d, 2H), 7.32 (d, 2H), 6.84 (d, 2H), 5.00 (br, 1H), 4.63 (m, 1H), 4.32-4.27 (overlap, 2H), 4.21-4.14 (overlap, 5H), 4.07 (t, 2H), 3.81 (t, 2H), 3.77-3.64 (overlap, 12H), 3.54-3.45 (overlap, 6H), 3.40-3.36 (overlap, 3H), 3.30-3.25 (br, 2H), 2.66 (s, 3H), 2.39 (s, 3H), 1.66 (s, 3H), 1.42 (s, 9H).

Example 1.7. Synthesis of Compound A12
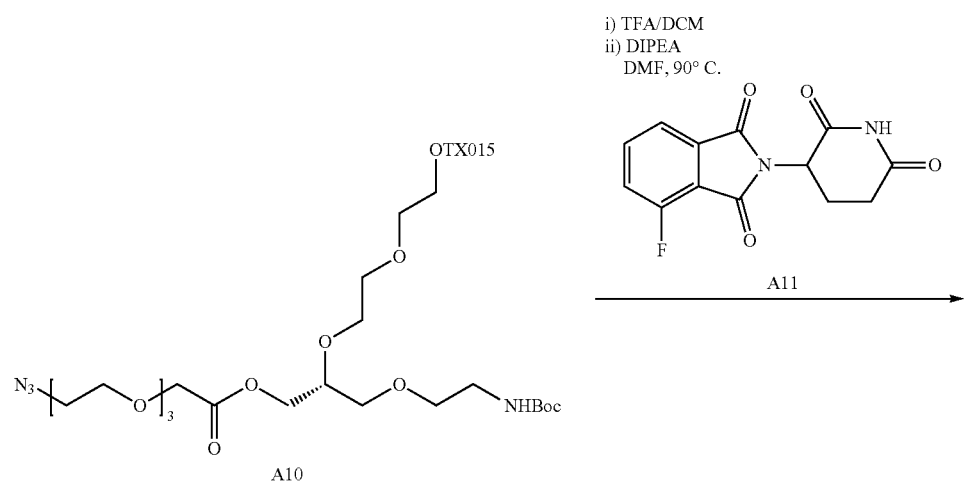
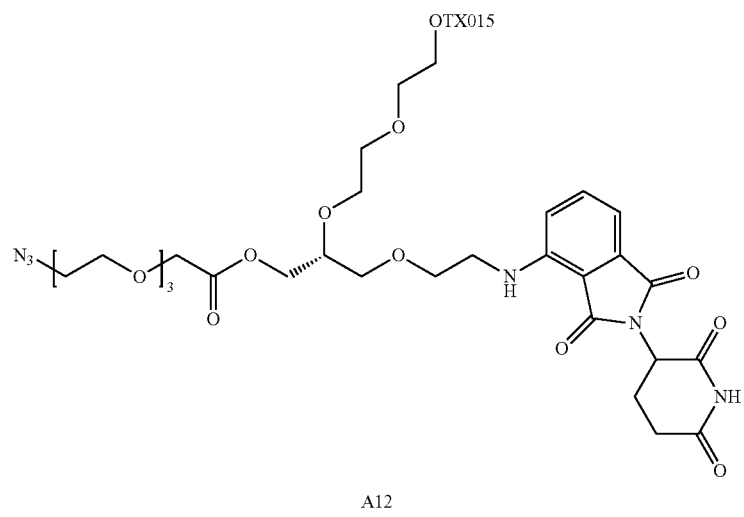

A 50/50 mixture of TFA/DCM (1 mL) was added to compound A10 (40 mg, 0.040 mmol) and the reaction was stirred for 1 hour. Then, TFA and DCM were removed under reduced pressure and N,N-diisopropylethylamine (26 mg, 0.20 mmol, 34 µL) and DMF (0.4 mL) were added to the crude mixture, followed by compound A11 (44 mg, 0.16 mmol). The solution was heated to 85° C. and stirred overnight. Afterwards, the solution was concentrated under reduced pressure and the crude mixture was purified by column chromatography to yield compound A12 (13 mg, 0.012 mmol). LRMS-ESI: Calcd for $C_{55}H_{62}ClN_7O_{12}S$: m/z=1139.4 $[M-N_2]^+$; Found: 1139.1 $[M-N_2]^+$. $^1$H NMR (400 MHz, CDCl$_3$, ppm) $\delta_H$ 8.68 (d, 1H), 7.51-7.40 (overlap, 6H), 7.34 (d, 2H), 7.11 (dd, 1H), 6.92 (dd, 1H), 6.83 (d, 2H), 6.44 (q, 1H), 4.91 (m, 1H), 4.64 (m, 1H), 4.35 (m, 1H), 4.25-4.14 (overlap, 5H), 4.07 (t, 2H), 3.81 (t, 2H), 3.79-3.65 (overlap, 12H), 3.61-3.58 (overlap, 2H), 3.50-3.48 (overlap, 9H), 3.41-3.37 (overlap, 4H), 2.68 (s, 3H), 2.40 (s, 3H), 1.67 (s, 3H).

Example 1.8. Synthesis of Macromonomer A13

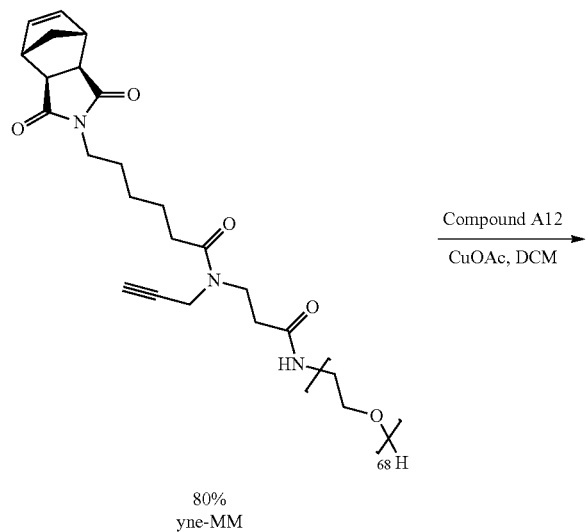

80%
yne-MM

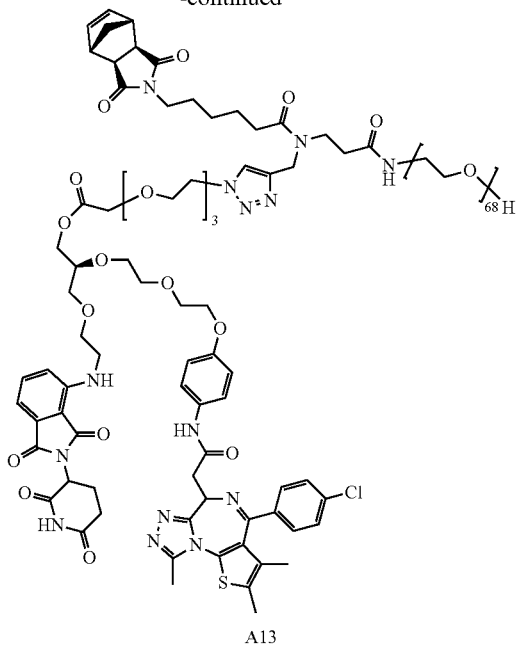

A13

To a solution of yne-MM (18.42 mg, 5.468 µmol, 1.0 eq.), compound A12 (6.5 mg, 6.015 µmol, 1.2 eq.), and DCM (0.3 mL) was added a pinch of Copper(I) acetate (CuOAc). The reaction mixture was stirred under N$_2$ for ~1 hour. The reaction mixture was filtered through a 0.45 µm filter (Nalgene). The crude mixture was concentrated under vacuum, redissolved in chloroform, and subjected to recycling preparative HPLC, affording the pure product macromonomer A13, also referred to as compound 9, as an off-white solid (19.43 mg, 80% yield).

Example 1.9. Synthesis of Compound B3

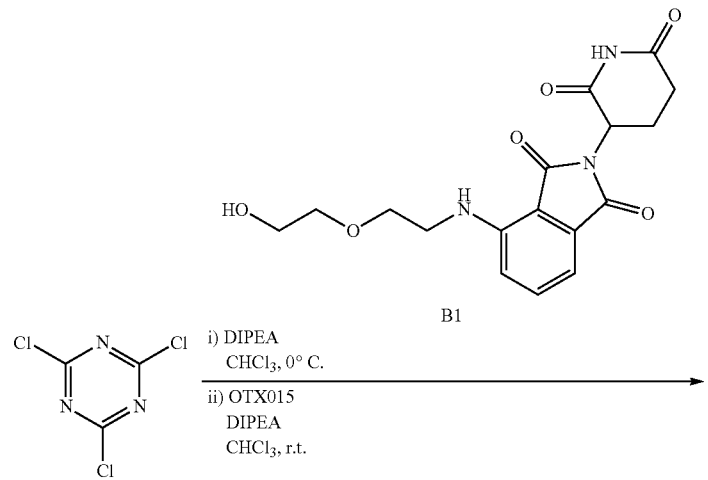

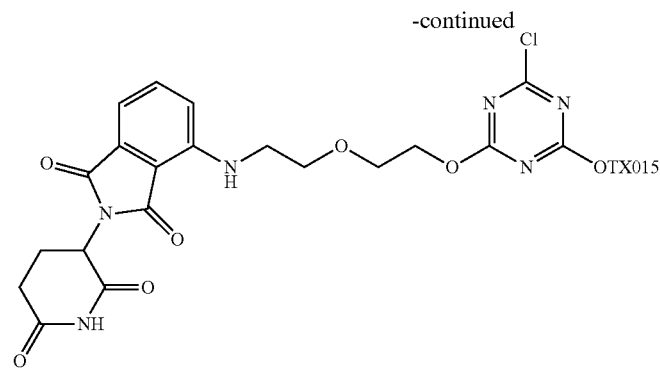

B2

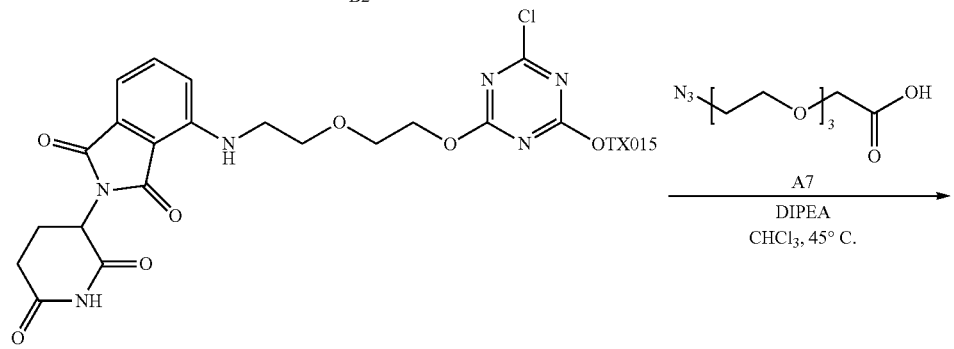

B2

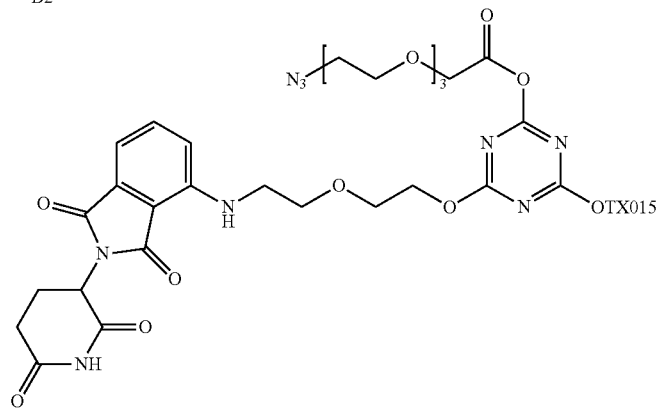

B3

To a solution of cyanuric chloride (11 mg, 0.060 mmol) in Chloroform (15 mL) was added DIPEA (7.2 mg, 0.060 mmol). The solution was cooled to 0° C. and compound B1 (22 mg, 0.060 mmol) was added portionwise. The reaction flask was left to react at 0° C. for 2 hours. Additional DIPEA (7.2 mg, 0.060 mmol) was then added into the solution. OTX015 (30 mg, 0.060 mmol) was then added in portionwise and the reaction mixture was allowed to warm to room temperature. Formation of compound B2 was confirmed by crude $^1$H NMR and LRMS. N-methylmorpholine (6.1 mg, 0.060 mmol) was then added to the solution. Compound A7 (32 mg, 0.12 mmol) was then slowly injected into the reaction mixture. After allowing the mixture to stir for 1 hour at room temperature, the reaction was warmed to 45° C. and left to react overnight. The reaction mixture was extracted with 50 mL of EtOAc and 2 times with 50 mL of 1% LiCl solution. The organic layer was collected, concentrated, and purified by column chromatography to yield compound B3 (5 mg, 0.005 mmol). $^1$H NMR (400 MHz, CDCl$_3$, ppm) $\delta_H$ 8.69 (d, 1H), 7.58-7.45 (overlap, 6H), 7.38 (d, 2H), 7.20 (dd, 1H), 6.94 (dd, 1H), 6.80 (d, 2H), 6.49 (q, 1H), 4.45 (t, 2H), 3.85 (t, 2H), 3.81-3.65 (overlap, 14H), 3.52-3.45 (overlap, 10H), 3.39 (br, 2H), 2.68 (s, 3H), 2.40 (s, 3H), 1.67 (s, 3H).

Example 1.10. Synthesis of BBP-10

To a solution of compound A13 (14.51 mg, 3.26 µmol, 10.0 eq.) in THF (48.9 µL) was added a solution of Ru (16.3 µL, 0.33 µmol, 1.0 eq., 0.005 M in THF). The reaction mixture was stirred for 1 hour at room temperature and quenched with a drop of ethyl vinyl ether. The reaction mixture was transferred to a Spectrum® 8kD Molecular weight cut-off (MWCO) in 2 mL nanopure water, and the solution was dialyzed against water (500 mL×3, solvent exchange every 6 h). The dialyzed solution was then concentrated to the desired concentration via centrifugation with a filter tube (3 kDa MWCO, Millipore Sigma). The resulting polymer (BBP-10, degree of polymerization of 10) was characterized by GPC, revealing a high MM-to-brush conversion (≥95%, Đ=1.137), and DLS, revealing a hydrodynamic diameter ($D_h$) of ~8.0 nm.

Example 2. Cellular Degradation of BRD4 in KMS27, KMS12BM, MM1S, and MOLP Cells

Gel electrophoresis of cell lysate revealed cellular degradation of BRD4 in CRBN-sensitive cell lines.

Example 3. In Vitro Cell Viability in KMS11, MM1S, KMS12BM, KMS18 KMS27, MM1R, OPM2, and U266 Cells In vitro cell viability assay was performed on both compound 9 and BBP-10 on various cell lines, revealing comparable in vitro toxicity compared to the unmodified PROTAC.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Wurz, R. P.; Dellamaggiore, K.; Dou, H.; Javier, N.; Lo, M.-C.; McCarter, J. D.; Mohl, D.; Sastri, C.; Lipford, J. R.; Cee, V. J., *J. Med. Chem.* 2018, 61, 2, 453.

What is claimed is:

1. A compound of the formula:

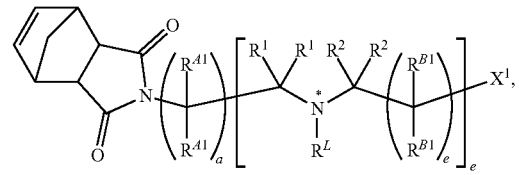

or a salt thereof, wherein:
  each instance of $R^{A1}$ is hydrogen;
  a is an integer between 1 and 20, inclusive;
  each instance of $R^{B1}$ is hydrogen;
  b is an integer between 1 and 20, inclusive;
  each instance of $R^1$ and $R^2$ is hydrogen, or two instances of $R^1$ attached to the same carbon atom are taken together to form oxo, or two instances of $R^2$ attached to the same carbon atom are taken together to form oxo;
  $R^L$ is of the formula:

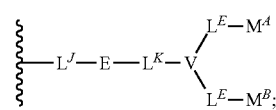

e is 1;

X$^1$ is —C(=O)OR$^C$ or —C(=O)N(R$^C$)$_2$;

each instance of R$^C$ is independently hydrogen or

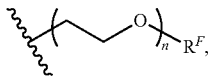

wherein each instance of n is independently an integer from 30 to 100, inclusive, and each instance of R$^F$ is independently hydrogen or unsubstituted C$_{1-6}$ alkyl, provided that at least one instance of R$^C$ is

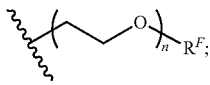

L$^J$ is unsubstituted C$_1$-C$_6$ alkylene or unsubstituted C$_1$-C$_6$ heteroalkylene, wherein the C$_1$-C$_6$heteroalkylene is C$_1$-C$_6$alkylene that further comprises one oxygen atom inserted between adjacent carbon atoms or placed at one terminal position of the parent chain;

E is triazole, a bond, —O—, —C(=O)NR$^A$—, or —NR$^A$C(=O)—, wherein R$^A$ is hydrogen or methyl;

L$^K$ is of the formula:

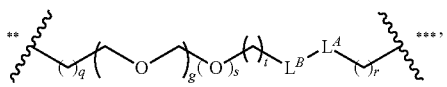

wherein:
q is an integer from 1 to 12, inclusive;
g is 0 or an integer from 1 to 12, inclusive;
s is 0 or 1;
t is 0 or an integer from 1 to 10, inclusive;
-L$^B$-L$^A$- is —C(=O)O— or —OC(=O)O—;
r is 0 or an integer from 1 to 12, inclusive;
"**" is attached to E; and
"***" is attached to V;
V is CH;

each instance of L$^E$ is independently of the formula:

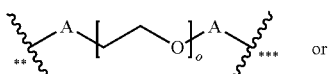
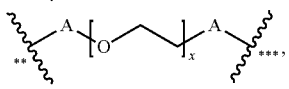

wherein:
each instance of A is independently a single bond or —CH$_2$—;
each instance of o is independently an integer between 1 and 30, inclusive;
each instance of x is independently an integer between 1 and 30, inclusive;
"**" is attached to V; and
"***" is attached to M$^A$ or M$^B$;

M$^A$ is of the formula:

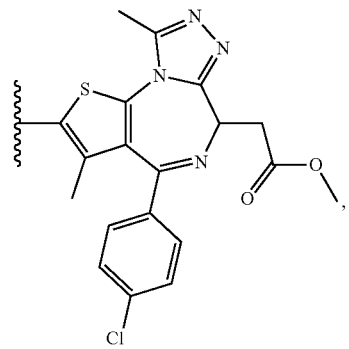

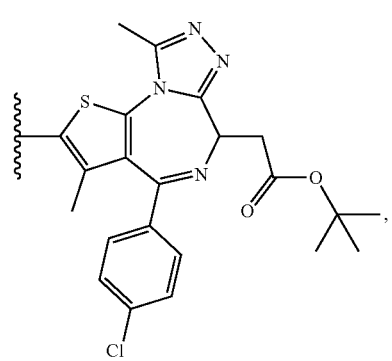

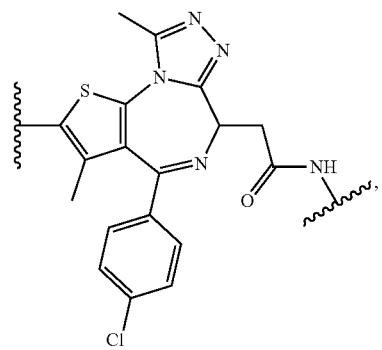

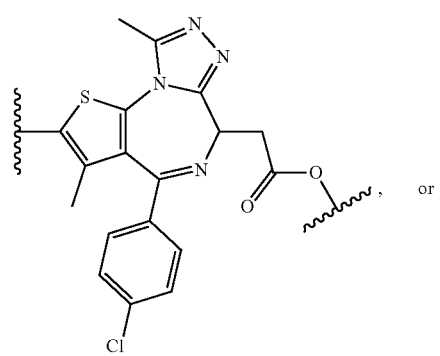

or

-continued (TL-I)

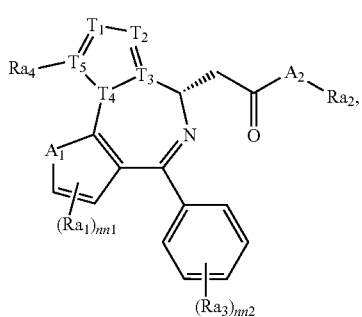

wherein:

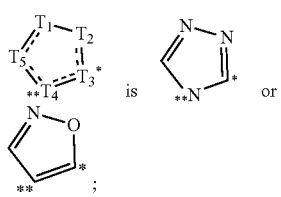 is  or $A_1$ is S;
$A_2$ is $NRa_5$ or O;
nn1 is 0, 1, or 2;
each $Ra_1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, $C(O)NRa_5L$, OL, $NRa_5L$, or L;
$Ra_2$ is H, $C_1$-$C_6$ alkyl, $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is optionally substituted with $C_1$-$C_3$ alkyl, L, or C(O)L, and wherein the phenyl is optionally substituted with $C_1$-$C_3$ alkyl, CN, halogen, OH, $C_1$-$C_3$ alkoxy, or L;
nn2 is 0, 1, 2, or 3;
each $Ra_3$ is independently $C_1$-$C_3$ alkyl, $(CH_2)_{0-3}$—CN, $(CH_2)_{0-3}$-halogen, L, or $C(O)NRa_5L$;
$Ra_4$ is $C_1$-$C_3$ alkyl or hydrogen;
$Ra_5$ is H or $C_1$-$C_3$ alkyl; and
L is a Linker of Formula L0:

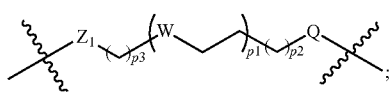

(L0)

p1 is an integer selected from 0 to 12;
p2 is an integer selected from 0 to 12;
p3 is an integer selected from 1 to 6;
each W is independently absent, $CH_2$, O, S, NH, or $NR_{19}$;
$Z_1$ is absent, $CH_2C(O)NH$, $OCH_2C(O)NH$, $OCH_2C(O)NR_{19}$, C(O)NH, $C(O)NR_{19}$, NHC(O), $NR_{19}C(O)$, $CH_2$, O, NH, or $NR_{19}$;
each $R_{19}$ is independently $C_1$-$C_3$ alkyl;
Q is absent or $NHC(O)CH_2$; and the Linker of Formula L0 is covalently bonded to an instance of $L^E$ via the

next to Q;
provided that Formula TL-I comprises only one L; and
$M^B$ is of the formula:

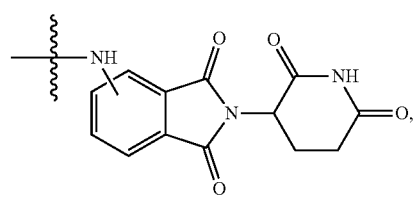

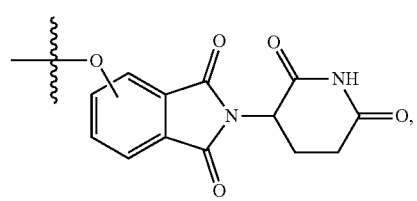

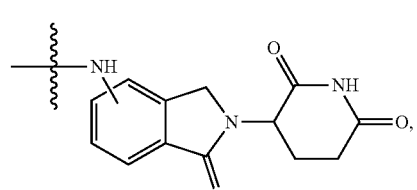

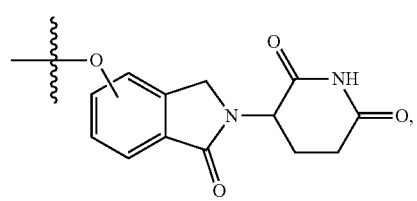

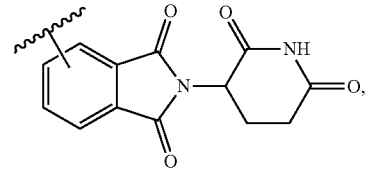

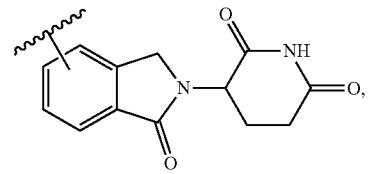

-continued

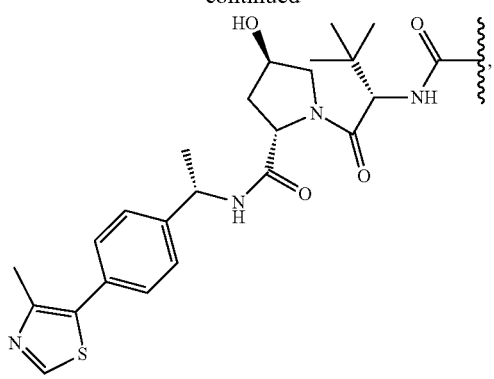

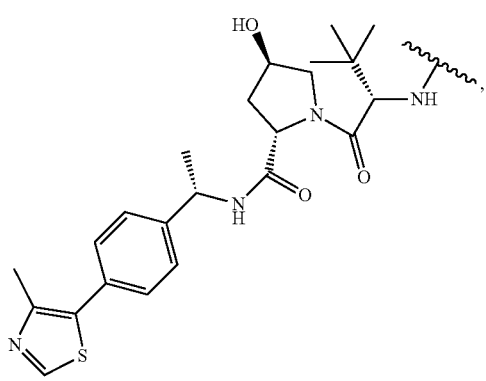

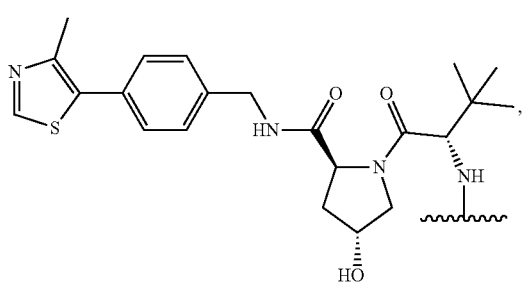

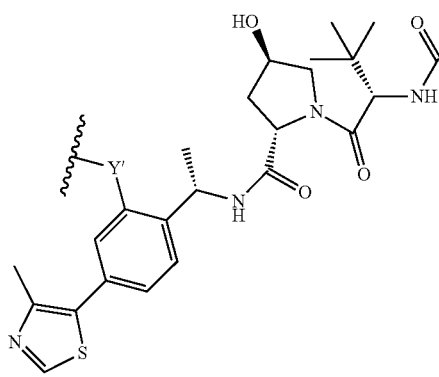

-continued

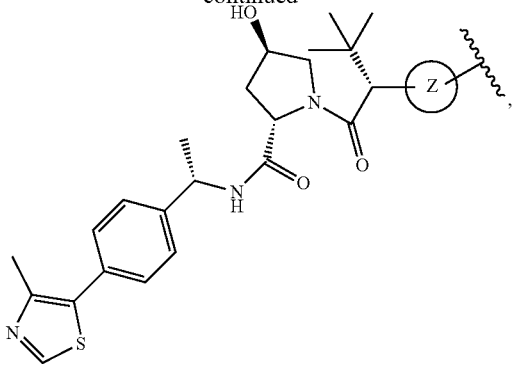

wherein:
Y' is a single bond, —NH—, —O—, or —CH₂—; and

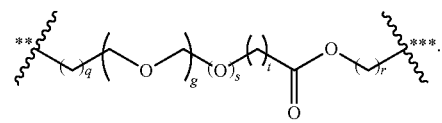 is substituted or unsubstituted carbocyclylene, substituted or unsubstituted heterocyclylene, substituted or unsubstituted arylene, or substituted or unsubstituted heteroarylene.

2. A kit comprising:
a compound of claim 1, or a salt thereof; and
instructions for using the compound, or a salt thereof.

3. The compound of claim 1, or a salt thereof, wherein a is 2, 3, 4, 5, or 6.

4. The compound of claim 1, or a salt thereof, wherein two instances of $R^1$ attached to the same carbon atom are taken together to form oxo.

5. The compound of claim 1, or a salt thereof, wherein $L^J$ is unsubstituted $C_1$-$C_6$ alkylene.

6. The compound of claim 1, or a salt thereof, wherein E is triazole.

7. The compound of claim 1, or a salt thereof, wherein $L^K$ is of the formula:

8. The compound of claim 1, or a salt thereof, wherein -$L^J$-E-$L^K$- is of the formula:

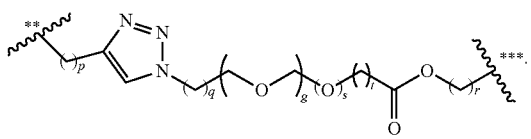

wherein:
p is an integer from 1 to 12, inclusive.

9. The compound of claim 8, or a salt thereof, wherein -$L^J$-E-$L^K$- is of the formula:

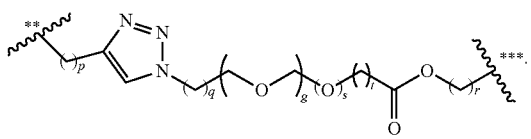

10. The compound of claim 1, or a salt thereof, wherein

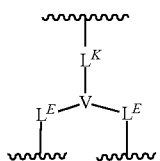

is

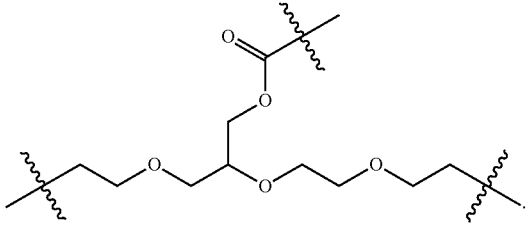

11. The compound of claim 1, or a salt thereof, wherein $M^A$ is of Formula TL-I.

12. The compound of claim 1, or salt thereof, wherein $M^B$ is of the formula:

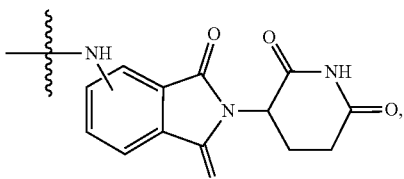

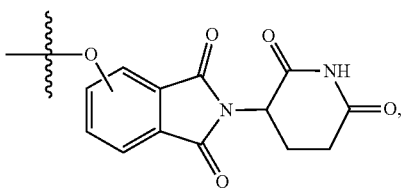

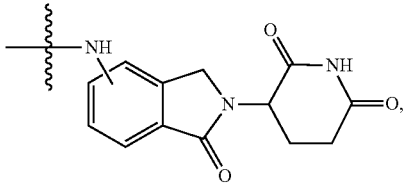

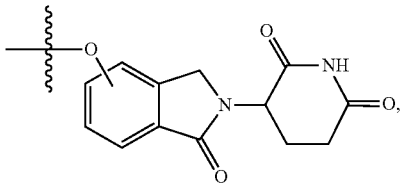

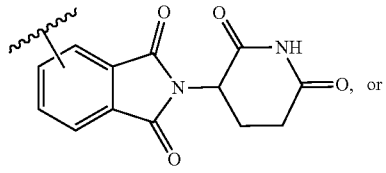

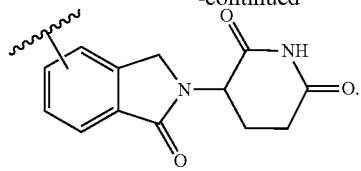

13. The compound of claim 1, or a salt thereof, wherein each instance of $R^2$ is hydrogen.

14. The compound of claim 1, or a salt thereof, wherein b is 1, 2, 3, 4, 5, or 6.

15. The compound of claim 1, or a salt thereof, wherein $X^1$ is —C(=O)N(R$^C$)$_2$.

16. The compound of claim 15, or a salt thereof, wherein: one instance of $R^C$ is of the formula:

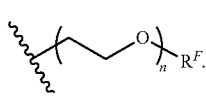

17. The compound of claim 1, or a salt thereof, wherein the compound is of the formula:

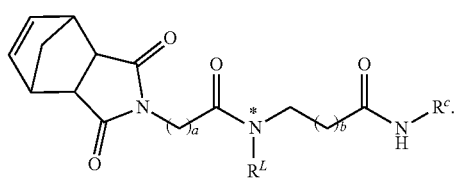

18. The compound of claim 1, or a salt thereof, wherein the compound is of the formula:

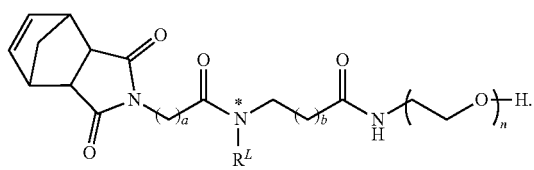

19. The compound of claim 1, or a salt thereof, wherein $M^A$ is of the formula:

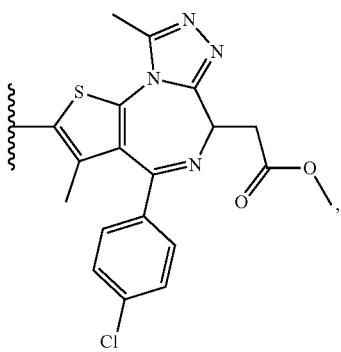

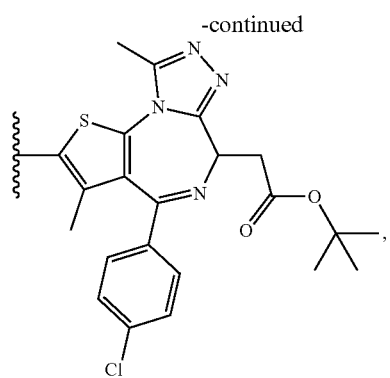
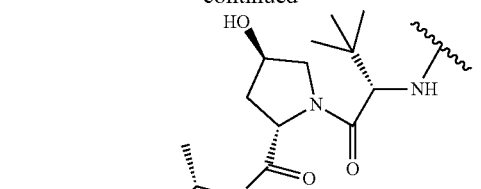
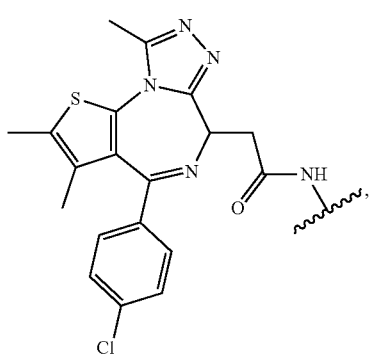
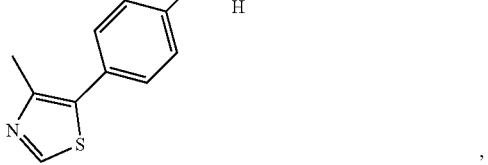
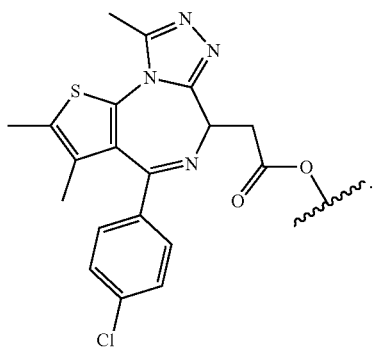
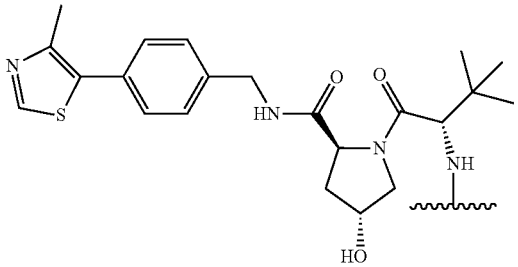
20. The compound of claim 1, or a salt thereof, wherein $M^B$ is of the formula:
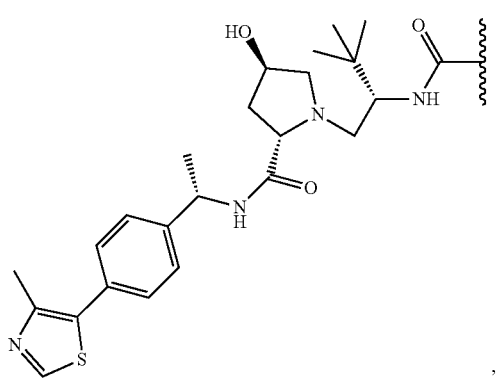
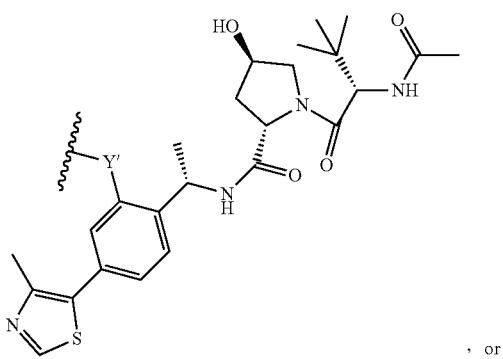
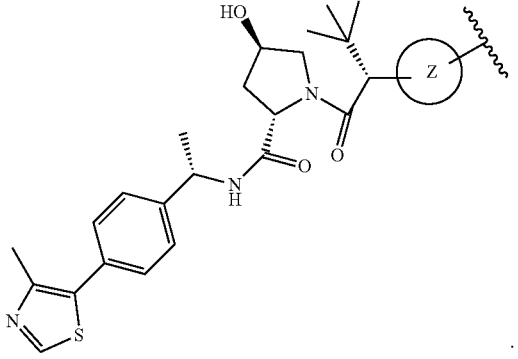

21. The compound of claim 1, or a salt thereof, wherein the compound is of the formula:
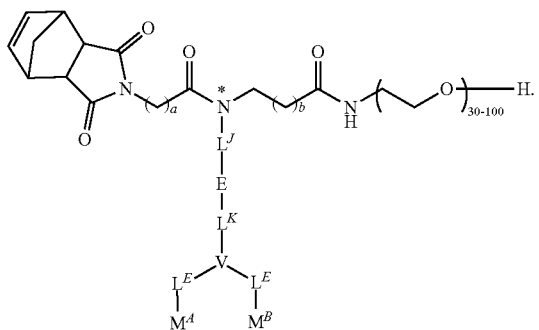
22. The compound of claim 1, or a salt thereof, wherein the compound is of the formula:
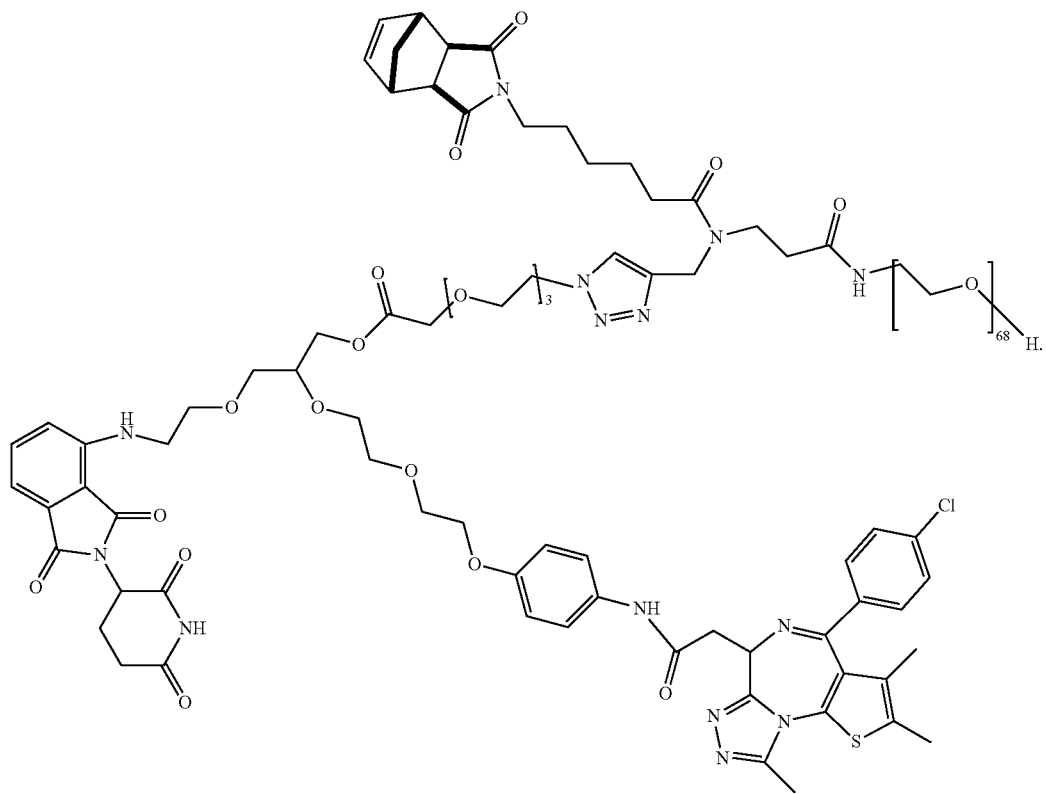

23. The compound of claim 1, or a salt thereof, wherein E is a bond, —O—, —C(=O)NR$^A$—, or —NR$^A$C(=O)—.
24. The compound of claim 11, or a salt thereof, wherein M$^A$ is of Formula TL-I1:
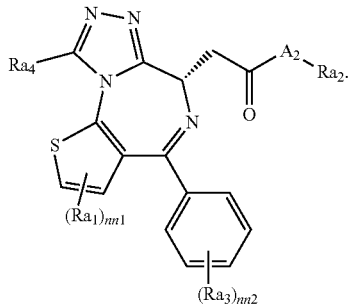
(TL-I1)
* * * * *

UNITED STATES PATENT AND TRADEMARK OFFICE
CERTIFICATE OF CORRECTION

PATENT NO. : 12,042,513 B2
APPLICATION NO. : 17/093832
DATED : July 23, 2024
INVENTOR(S) : Jeremiah A. Johnson et al.

Page 1 of 4

It is certified that error appears in the above-identified patent and that said Letters Patent is hereby corrected as shown below:

In the Claims

In Claim 1, at Column 172, Lines 42-48, the formula:

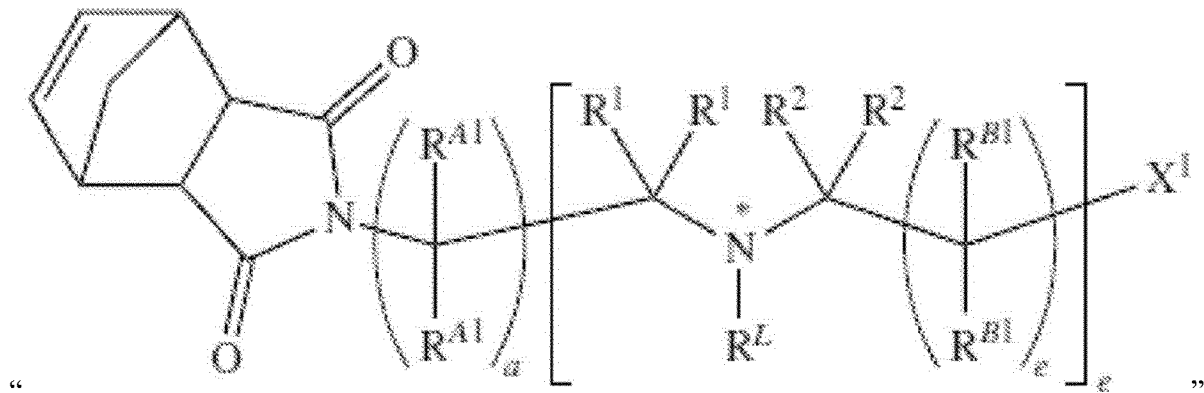

"

Should be replaced with the formula:

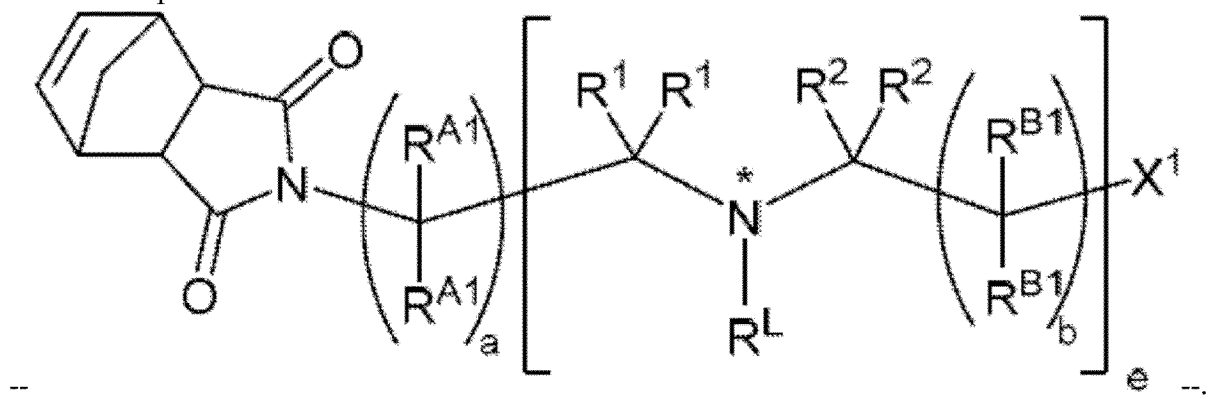

--.

Signed and Sealed this
Twenty-fifth Day of March, 2025

Coke Morgan Stewart
*Acting Director of the United States Patent and Trademark Office*

In Claim 1, at Column 174, Lines 36-49, the formula:
"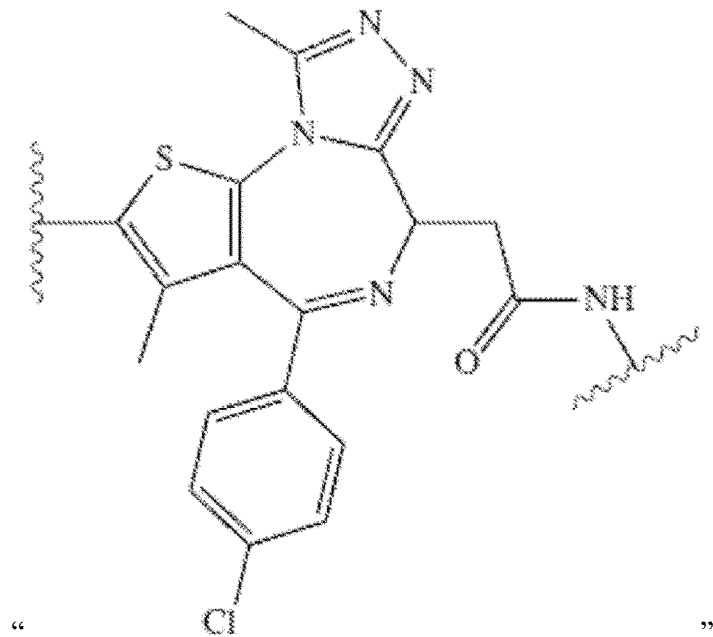"
Should be replaced with the formula:
--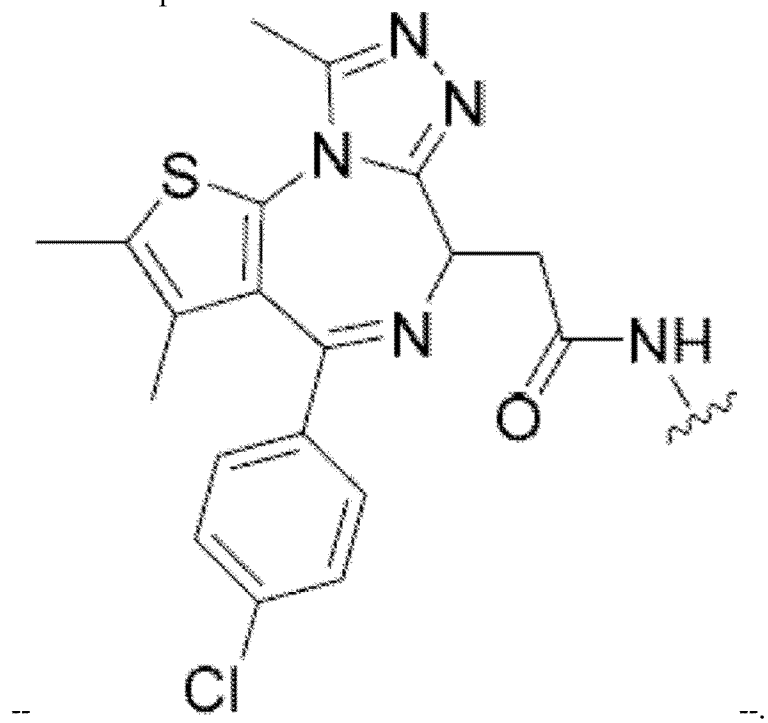--.

In Claim 1, at Column 174, Lines 53-66, the formula:
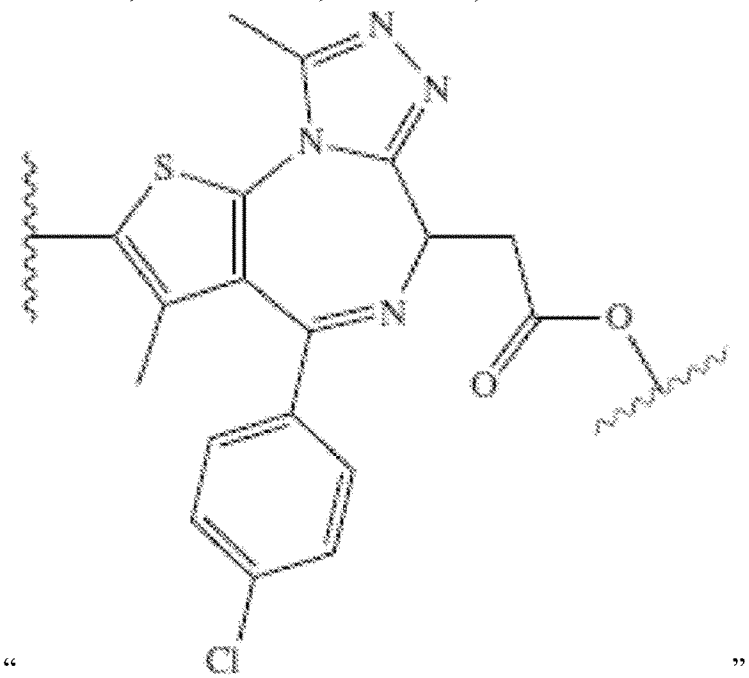
"  "
Should be replaced with the formula:
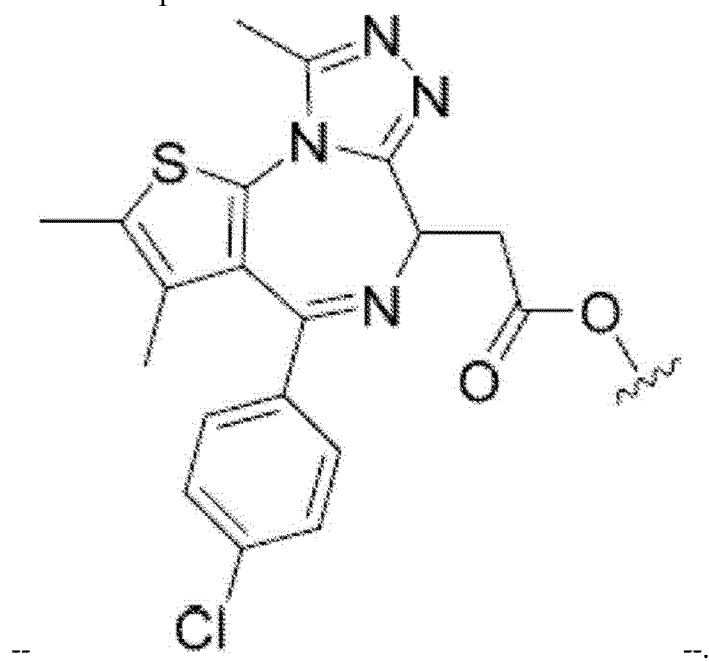
-- --.
In Claim 1, at Column 175, Lines 62-63, the text:
"$OCH_2C(O)NR_1g$"
Should be replaced with the text:
-- $OCH_2C(O)NR_{19}$ --.

CERTIFICATE OF CORRECTION (continued)
U.S. Pat. No. 12,042,513 B2

In Claim 20, at Column 181, Lines 52-66, the formula:

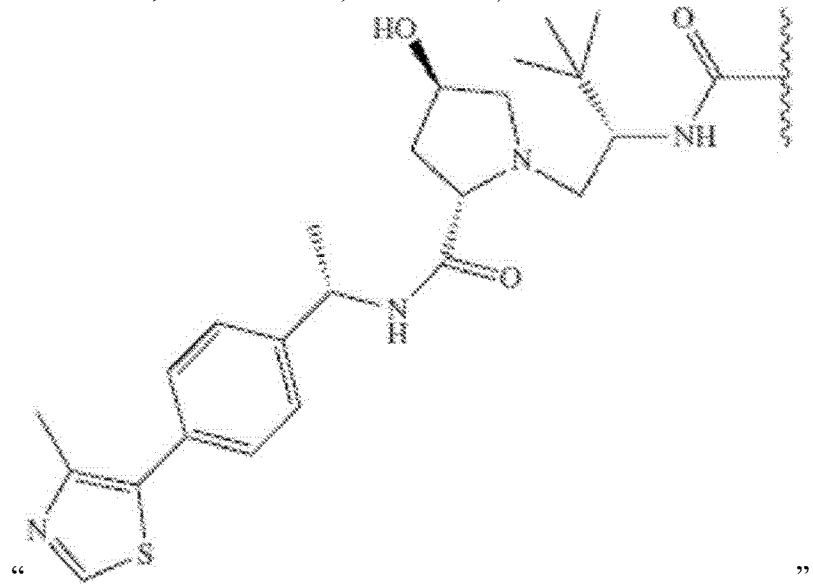

"

Should be replaced with the formula:

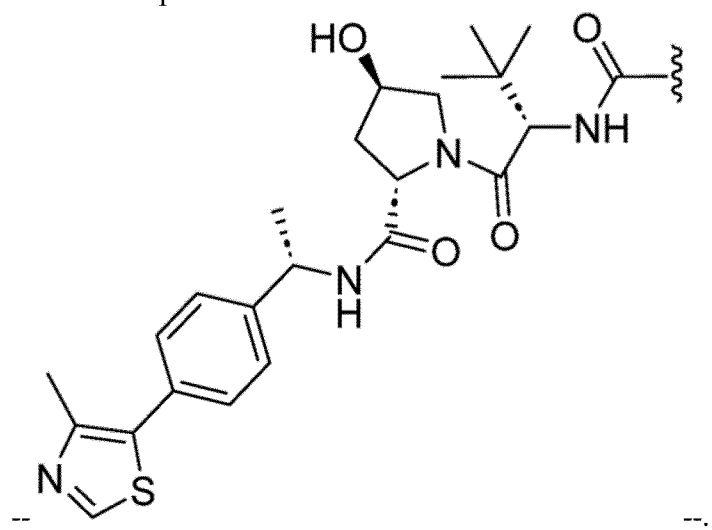

--.